US012617805B2

(12) United States Patent
Shou et al.

(10) Patent No.: US 12,617,805 B2
(45) Date of Patent: May 5, 2026

(54) CODRUG THAT DISINTEGRATES IN INTESTINE, PREPARATION THEREFOR, AND USE THEREOF

(71) Applicants: ENNOVABIO (ZHEJIANG) PHARMACEUTICALS CO., LTD., Shaoxing (CN); SHANGHAI ENNOVABIO PHARMACEUTICALS CO., LTD., Shanghai (CN)

(72) Inventors: Jianyong Shou, Shanghai (CN); Xiang Ao, Shanghai (CN); Lei Jiang, Shanghai (CN); Shengyang Liu, Shanghai (CN); Xudong Mao, Shanghai (CN); Zhi Qiao, Shanghai (CN); Xiaoping Xie, Shanghai (CN); Jianhua Zhang, Shanghai (CN)

(73) Assignees: Ennovabio (Zhejiang) Pharmaceuticals Co., Ltd., Zhejiang (CN); Shanghai Ennovabio Pharmaceuticals Co., Ltd, Shanghai (CN)

( * ) Notice: Subject to any disclaimer, the term of this patent is extended or adjusted under 35 U.S.C. 154(b) by 621 days.

(21) Appl. No.: 18/016,532

(22) PCT Filed: Jul. 19, 2021

(86) PCT No.: PCT/CN2021/107208

§ 371 (c)(1),
(2) Date: Jan. 17, 2023

(87) PCT Pub. No.: WO2022/012693

PCT Pub. Date: Jan. 20, 2022

(65) Prior Publication Data

US 2023/0271982 A1 Aug. 31, 2023

(30) Foreign Application Priority Data

Jul. 17, 2020 (CN) ........................ 202010694145.1

(51) Int. Cl.

| | |
|---|---|
| ***C07D 519/00*** | (2006.01) |
| ***A61K 31/519*** | (2006.01) |
| ***A61K 31/5377*** | (2006.01) |
| ***A61K 47/54*** | (2017.01) |
| ***A61K 47/55*** | (2017.01) |
| ***A61K 47/65*** | (2017.01) |
| ***A61P 1/00*** | (2006.01) |
| ***C07D 309/02*** | (2006.01) |
| ***C07H 15/26*** | (2006.01) |

(52) U.S. Cl.
CPC .......... *C07D 519/00* (2013.01); *A61K 31/519* (2013.01); *A61K 31/5377* (2013.01); *A61K 47/549* (2017.08); *A61K 47/55* (2017.08); *A61K 47/65* (2017.08); *A61P 1/00* (2018.01); *C07D 309/02* (2013.01); *C07H 15/26* (2013.01)

(58) Field of Classification Search
CPC ......... C07D 519/00; C07H 15/26; A61P 1/00; A61K 47/55; A61K 47/65; A61K 47/54; A61K 47/549
See application file for complete search history.

(56) References Cited

FOREIGN PATENT DOCUMENTS

| | | | |
|---|---|---|---|
| CN | 107613768 | A | 1/2018 |
| CN | 108272802 | A | 7/2018 |
| EP | 2651864 | B1 | 7/2016 |
| TW | 201742863 | A | 12/2017 |
| WO | 9520567 | A1 | 8/1995 |
| WO | 2017201069 | A1 | 11/2017 |

OTHER PUBLICATIONS

English translation International Search Report mailed Nov. 3, 2021 corresponding to PCT/CN2021/107208, 4 pages.
Das, N. et al., "Codrug: An efficient approach for drug optimization", European Journal of Pharmaceutical Sciences, vol. 41, Oct. 1, 2010, 1 introduction, figure 3 54-56, table 3.
Aljuffali, Ibrahim A. et al., "Expert Opinion on Drug Delivery", The codrug approach for facilitating drug delivery and bioactivity, May 9, 2016, ISSN: 1744-7593, abstract, 1 introduction.

*Primary Examiner* — Alicia L Otton
(74) *Attorney, Agent, or Firm* — Ice Miller LLP

(57) ABSTRACT

The present invention relates to a codrug that cleaved in the gut, preparation therefor, and a use thereof. Specifically, provided is a codrug compound in formula I. Also provided are a method of using the present compound for the treatment of gastrointestinal tract autoimmune diseases, inflammatory diseases, and cancers, as well as a method and an intermediate for preparing the present compound.

14 Claims, 3 Drawing Sheets

CODRUG THAT DISINTEGRATES IN INTESTINE, PREPARATION THEREFOR, AND USE THEREOF

FIELD OF THE INVENTION

The invention relates to a codrug compound that is cleaved in gut. The invention also relates to pharmaceutical compositions comprising such compounds; methods of using such compounds for treating gastrointestinal autoimmune diseases, inflammatory diseases and cancers; and methods and intermediates for the preparation of such compounds.

BACKGROUND OF THE INVENTION

JAK family (JAK1, JAK2, JAK3 and TYK2) inhibitors such as tofacitinib have been approved for the treatment of certain patients suffering from moderate to severe active rheumatoid arthritis (RA) and moderate to severe ulcerative colitis (UC). In many clinical trials of JAK family inhibitors, a large number of adverse events mediated by systemic drug exposure have been reported, including severe infections, opportunistic infections, and laboratory abnormalities, such as lymphopenia, neutropenia, elevated liver enzymes, elevated lipid and elevated serum creatinine. All of JAK inhibitors currently approved in the market carry black-box warnings of safety risks such as serious infections, malignancies, and thrombosis. Therefore, development of next generation of safer JAK family inhibitor drugs may require limiting their systemic exposure in the treatment of local inflammatory diseases. For example, increasing the distribution of the JAK family inhibitors in the gastrointestinal tract, while minimizing the systemic exposure of drugs in the treatment of UC.

Berberine, also known as berberinum, is an isoquinoline alkaloid extracted from plants such as *Coptis chinensis*. Berberine is well documented and has been used in the traditional Chinese medicine for more than a thousand years. It is of low bioavailability. Berberine is mainly used in the treatment of gastrointestinal diseases in clinical practice, such as diarrhea and intestinal infection. Studies in recent years have also found certain therapeutic potential of berberine for cardiovascular diseases, as well as glucose and lipid metabolism regulation. Berberrubine is the major in vivo metabolite of berberine. Studies in animal models have shown that berberrubine have similar therapeutic effects to berberine in ulcerative colitis. However, up to date, there has been no effective way to improve the therapeutic effect of berberine or its analogs in the art.

Inflammation bowel disease (IBD) mainly includes ulcerative colitis and Crohn's disease. These chronic intestinal inflammatory diseases have long-term disease course, recurrent attacks, and excessive chronic inflammation which may raise the risk of cancers. The incidence rate of IBD has been on the rise in recent years. It is currently believed that the pathogenesis of IBD may relate to genetic, environmental, immunity, and microorganisms, but the exact etiology has not been fully understood. Current clinical treatment mainly involves the use of salicylic acid derivatives, adrenal glucocorticoids and immunosuppressants, all of which have certain adverse effects such as gastrointestinal discomfort and anaphylaxes. Our previous work has shown that the combination of JAK inhibitors and berberine analogs can achieve synergistic effects and lead to better treatment for gastrointestinal inflammatory diseases. In the present invention, a codrug compound linking berberine analog and JAK inhibitor is designed, it will be cleaved into two effective molecules in intestine and enrich within gastrointestinal tract, while reducing the systemic exposure in the whole body to achieve a better safety profile. The synergistic effects of the two drug molecules would provide better therapeutic effects.

SUMMARY OF THE INVENTION

In one aspect, the present invention provides a codrug which is formed by a berberine analog as a first therapeutic agent (preferably Berberrubine) linked to a JAK family inhibitor (preferably Tofacitinib, Upadacitinib, SHR0302) as a second therapeutic agent, via a covalent linkage which can be cleaved. The codrug is designed to release the JAK family inhibitor and the first therapeutic agent in the gastrointestinal tract, thereby increasing the content of JAK family inhibitor and the first therapeutic agent in the inflammation site of gastrointestinal tract, and minimize the systemic exposure in the whole body.

In the first aspect of the present invention, a codrug compound shown in the formula I is provided. The codrug compound is formed by the first drug molecule, the second drug molecule and a linker precursor:

$$D_1\text{-linker-}D_2; \quad \text{I}$$

wherein, $D_1$ is the first drug group; and the first drug group is a structural fragment in the first drug molecule which can be connected to the linker (i.e., the fragment of the first drug molecule can be attached to the linker through coupling or condensing reactions with the linker precursor, and the linker moiety is not included this fragment);

$D_2$ is the second drug group; and the second drug group is the structural fragment in the second drug molecule which can be connected to the linker (i.e., the fragment of the second drug molecule can be attached to the linker through coupling or condensing reactions with the linker precursor, and the linker moiety is not included this fragment); and the first drug molecule and the second drug molecule are drug molecules that have synergistic effects;

wherein the covalent connection can be a covalent connection formed by losing a hydrogen atom, or a covalent connecting to the linker by other way, such as a covalent connection formed by the condensation reaction of reactive groups such as hydroxyl, carboxyl, amino;

and the linker has a structure selected from the group (a), (b) or (c), in each formula, $J_1$ connects to the first drug group, and $J_2$ connects to the second drug group;

(a)

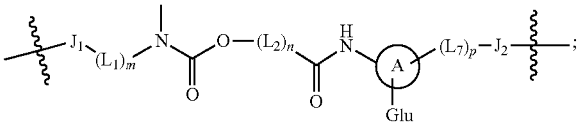

the Glu has a structure selected from the group consisting of:

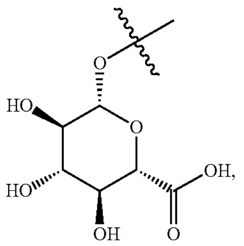

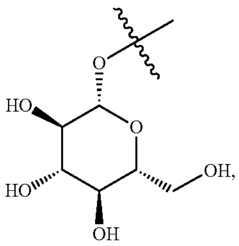

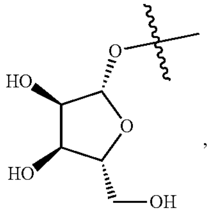

,

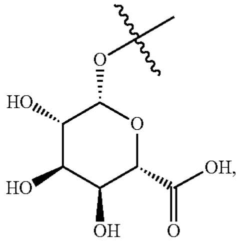

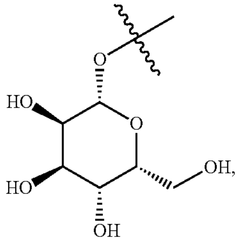

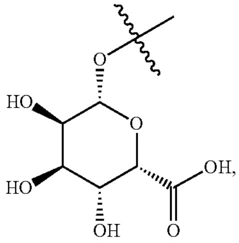

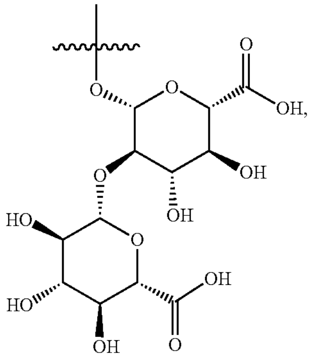

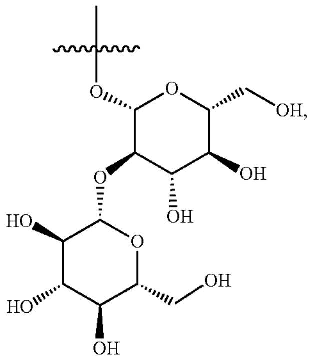

-continued

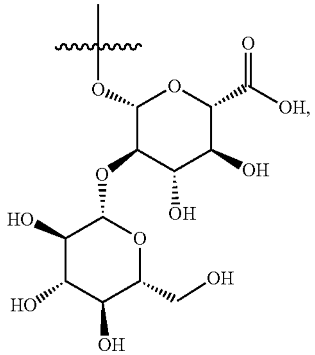

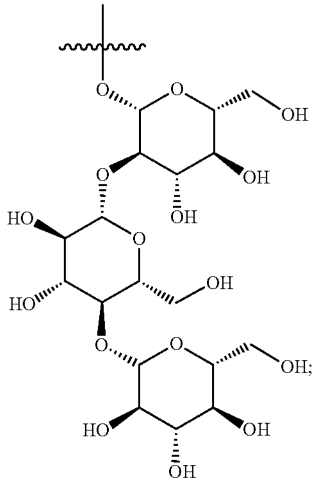

wherein the A ring is selected from the group consisting of $C_6$-$C_{10}$ aryl, 5-10 membered heteroaryl, and 3-12 membered heterocyclic group;

(b)

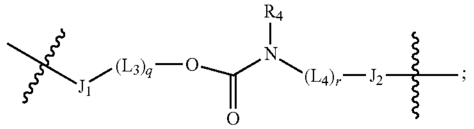

wherein, $R_4$ is selected from the group consisting of H, $C_{1-6}$ alkyl, and $C_{1-6}$ alkyoxy-$C_{1-4}$ alkylene-, $C_{3-12}$ cycloalkyl, $C_{3-12}$ cycloalkyl-$C_{1-4}$ alkylene-;

(c)

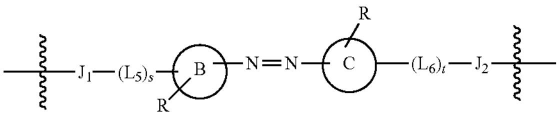

wherein, the B-ring and C-ring are independently selected from the group consisting of $C_6$-$C_{10}$ aryl, 5-10 membered heteroaryl, 3-12 membered heterocyclic group; In the above formula (a), (b) and (c), the $J_1$ and $J_2$ are each independently as —$(Y)_z$—, and each Y is selected from the group consisting of —NH—, —C(O)—, —C(O)O—, —NHC(O)NH—, —CH═CH—, —NH$(CH_2)$—, —NHC(O)—, —$CH_2$—, —$OCH_2CH_2O$—, —O—, —S—, —$P(O)_2O$—, —$S(O)_2$—, —S(O)—, —C(O)NH—, —N═N—; and Y can be substituted by one or more R, with the proviso that the combination of each Y forms a chemically stable structure;

each $L_1$, $L_2$, $L_3$, $L_4$, $L_5$, $L_6$ and $L_7$ are independently selected from the group consisting of $C_1$-$C_8$ alkylene, $C_{1-6}$ alkylene-O—$C_{1-4}$ alkylene (—$CH_2$—O—$CH_2$—), $C_{2-6}$ alkenyl, $C_{2-6}$ alkynyl, $C_{3-6}$ cycloalkyl, $C_6$-$C_{10}$ arylidene, 5-10 membered heteroarylidene, 3-12 membered heterocyclylene group, or a group selected from: —NH—, —C(O)—, —CH═CH—, —NH($CH_2$)—, —NHC(O)—, —$CH_2$—, —$OCH_2CH_2O$—, —O—, —S—, —$P(O)_2O$—, —$S(O)_2$—, —S(O)—, —C(O)NH—, —C(O)O—, —NHC(O)NH—, —N═N—, —C(O)NH$(CH_2)_{(1-4)}$—NHC(O)—; with the proviso that the combination of $L_1$, $L_2$, $L_3$, $L_4$, $L_5$, $L_6$ and $L_7$ forms a stable divalent structure;

and the Y, $L_1$, $L_2$, $L_3$, $L_4$, $L_5$, $L_6$ and $L_7$ are optionally substituted by one or more R, and the R is selected from the group consisting of H, —OH, $C_1$-$C_4$ alkyl, halogen, cyano, nitro, —$OR_4$, $C_{1-6}$ haloalkyl, sulfonate group, $C_0$-$C_4$ alkyl-$S(O)_2$—$C_1$-$C_4$ alkyl, formyl, carboxyl, —$COOR_4$; with the proviso that each Y, $L_1$, $L_2$, $L_3$, $L_4$, $L_5$, $L_6$ and $L_7$ together form a chemically stable structure;

m, n, p, q, r, s and t each independently selected from 0, 1, 2, 3, 4, 5, 6, 7, 8, 9, 10, 11, 12, 13, 14, 15 or 16;

z is selected from the group consisting of 0, 1, 2, 3, 4, 5 and 6; preferably, z is selected from 1, 2 or 3.

In another preferred embodiment, the connection comprises: a connection site formed by losing structural fragments in the drug molecule, or connection through coordination bond.

In another preferred embodiment, in the above formula (a), (b) and (c), the $J_1$ and $J_2$ are each independently as —$(Y)_z$—, and each Y is selected from the group consisting of —NH—, —C(O)—, —C(O)O—, —NHC(O)NH—, —CH═CH—, —NH($CH_2$)—, —NHC(O)—, —$CH_2$—, —$OCH_2CH_2O$—, —O—, —S—, —$P(O)_2O$—, —$S(O)_2$—, —S(O)—, —C(O)NH—, —N═N—; the Y can be substituted by one or more R, with the proviso that the combination of each Y forms a chemically stable structure;

each $L_1$, $L_2$, $L_3$, $L_4$, $L_5$, $L_6$ and $L_7$ is independently selected from the group consisting of $C_1$-$C_8$ alkylene, $C_{1-6}$ alkylene-O—$C_{1-4}$ alkylene (—$CH_2$—O—$CH_2$—), $C_{2-6}$ alkenyl, $C_{2-6}$ alkynyl, $C_{3-6}$ cycloalkyl, $C_6$-$C_{10}$ arylidene, 5-10 membered heteroarylidene, 3-12 membered heterocyclylene group, or a group selected from: —NH—, —C(O)—, —CH═CH—, —NH($CH_2$)—, —NHC(O)—, —$CH_2$—, —$OCH_2CH_2O$—, —O—, —S—, —$P(O)_2O$—, —$S(O)_2$—, —S(O)—, —C(O)NH—, —C(O)O—, —NHC(O)NH—, —N═N—, —C(O)NH$(CH_2)_{(1-4)}$—NHC(O)—; with the proviso that the combination of $L_1$, $L_2$, $L_3$, $L_4$, $L_5$, $L_6$ and $L_7$ forms a stable divalent structure;

and the Y, $L_1$, $L_2$, $L_3$, $L_4$, $L_5$, $L_6$ and $L_7$ are optionally substituted by one or more R, and the R is selected from the group consisting of H, —OH, $C_1$-$C_4$ alkyl, halogen, cyano, nitro, —$OR_4$, $C_{1-6}$ haloalkyl, sulfonate group, $C_0$-$C_4$ alkyl-$S(O)_2$—$C_1$-$C_4$ alkyl, formyl, carboxyl, —$COOR_4$; with the proviso that each Y, $L_1$, $L_2$, $L_3$, $L_4$, $L_5$, $L_6$ and $L_7$ together form a chemically stable structure;

and m, n, p, q, r, s and t are each independently selected from 0, 1, 2, 3, 4, 5, 6, 7 or 8.

z is selected from the group consisting of 0, 1, 2, 3, 4, 5 and 6; preferably, z is selected from 1, 2 or 3.

In another preferred embodiment, in the above formula (a), (b), and (c), the $J_1$ and $J_2$ are independently selected from the group consisting of —NH—, —C(O)—, —C(O)O—, —NHC(O)NH—, —CH═CH—, —NH($CH_2$)—, —NHC(O)—, —$CH_2$—, —$OCH_2CH_2O$—, —O—, —S—, —$P(O)_2$ O—, —$S(O)_2$—, —S(O)—, —C(O)NH—, —N═N—.

In another preferred embodiment, the $J_1$ and $J_2$ are independently selected from the group consisting of methylene,

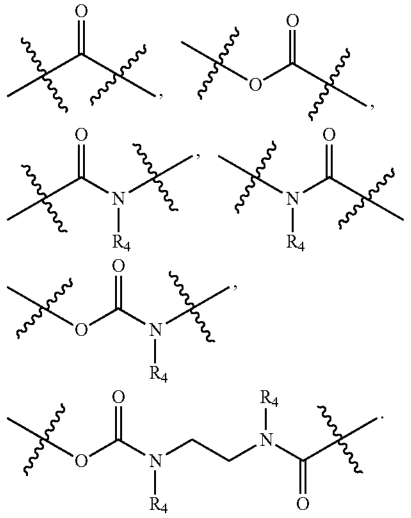

In another preferred embodiment, the $J_1$ is selected from the group consisting of methylene,

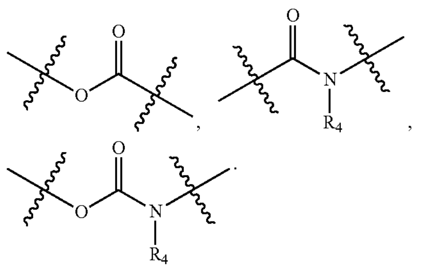

In another preferred embodiment, the $J_2$ is selected from the group consisting of methylene,

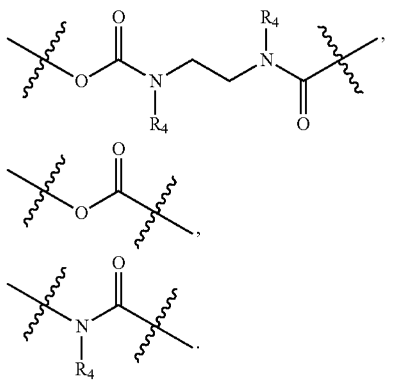

In another preferred embodiment, the first drug molecule is selected from the group consisting of berberine, berberrubine, and analogs thereof.

In another preferred embodiment, the second drug molecule is a JAK family inhibitor or analogs thereof.

In another preferred embodiment, the linker is of the following structure:

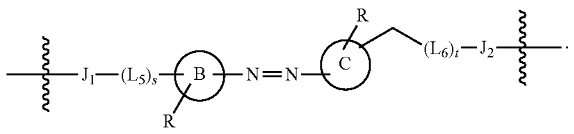

In another preferred embodiment, the first drug molecule is a drug molecule of the following formula II, formula III or formula IV:

formula II

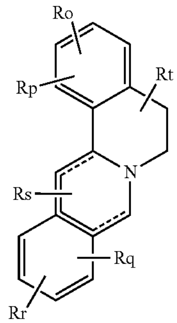

formula III

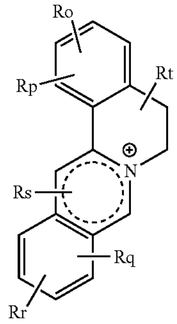

formula IV

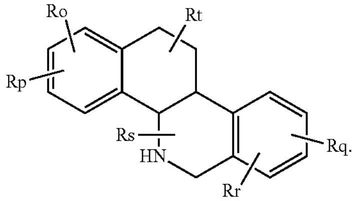

wherein,

Ro, Rp, Rq, Rr, Rs and Rt are each independently selected from the group consisting of H, substituted or unsubstituted $C_1$-$C_4$ alkyl, substituted or unsubstituted $C_1$-$C_4$ alkoxy; or Ro, Rp, Rq, Rr, Rs and Rt on two adjacent atoms together with the atom to which they are attached form a 5-7 membered heterocyclic ring; wherein said substitution means that one or more hydrogen atoms of the group are replaced by substituents selected from halogen, $C_1$-$C_4$ alkyl or phenyl.

In another preferred embodiment, the JAK family inhibitors and analogs thereof are selected from the following group: Tofacitinib, Ruxolitinib, Oclacitinib, Baricitinib, Peficitinib, Abrocitinib, Filgotinib, Upadacitinib, Delgocitinib, Itacitinib, Fedratinib, Decernotinib, SHR-0302, AZD-4205, ASN-002, BMS-986165, PF-06700841, PF-06651600, R-348, INCB-52793, ATI-501, ATI-502, NS-018, KL-130008, and deuterated derivatives of the above molecules.

In another preferred embodiment, the first drug group is selected from the following group:

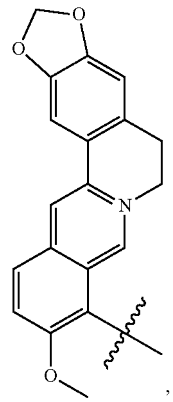
,
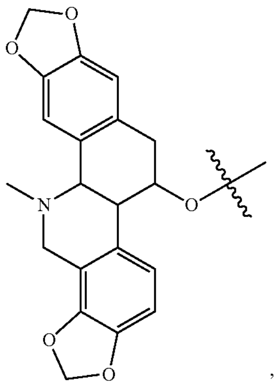
,
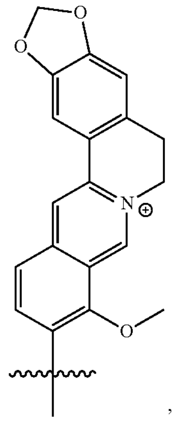
,
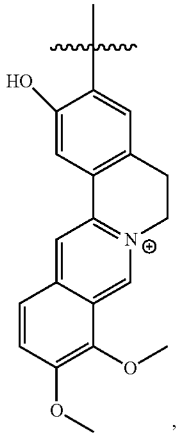
,
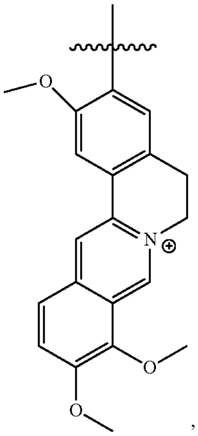
,
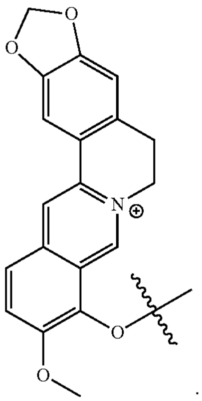
.

or the first drug group is a group formed by losing one hydrogen atom in the drug molecular selected from the following group:

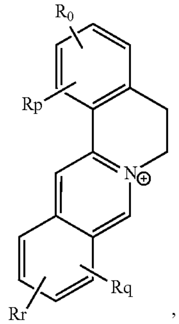
,
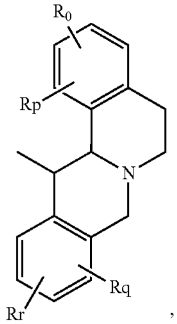
,
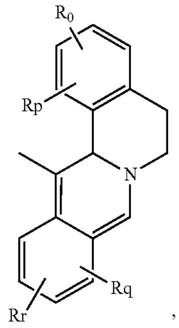
,
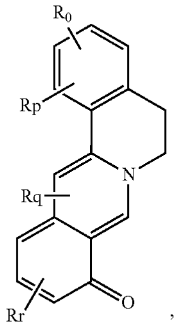
,
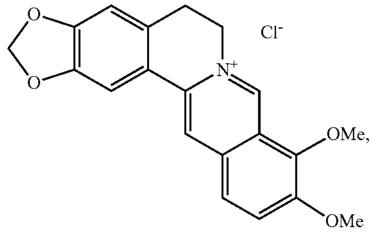
,
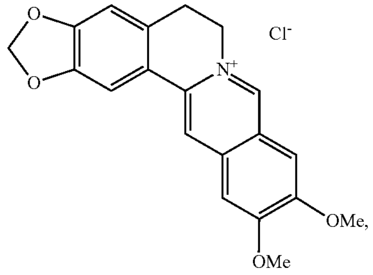
,
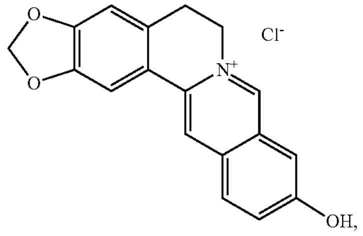
,
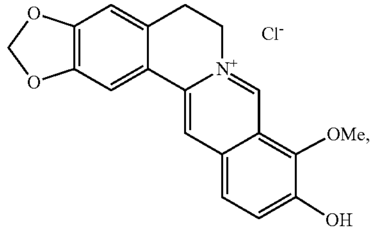
,
-continued
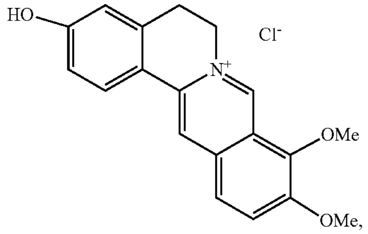
,
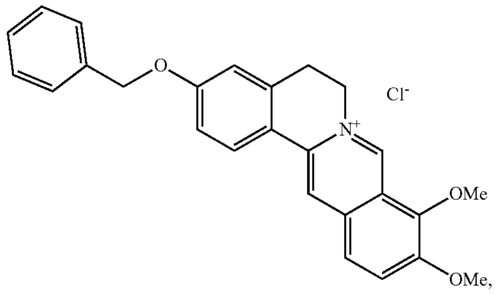
,
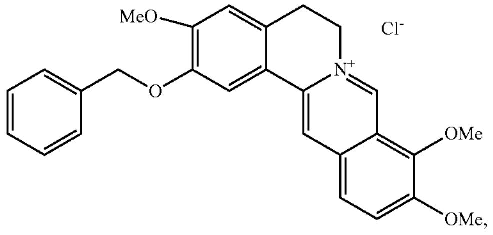
,
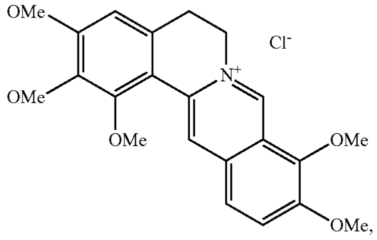
,
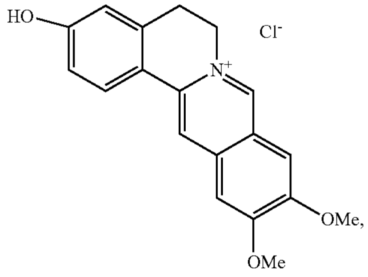
,
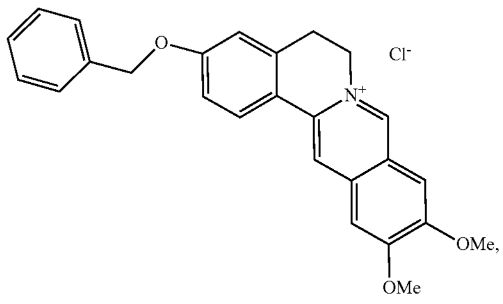
, -continued
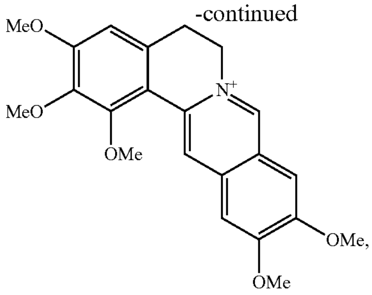
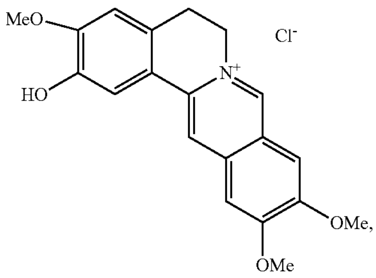
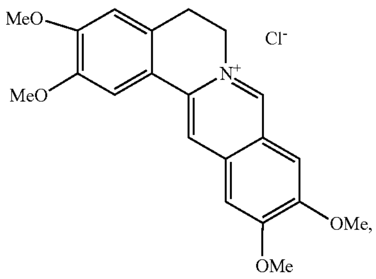
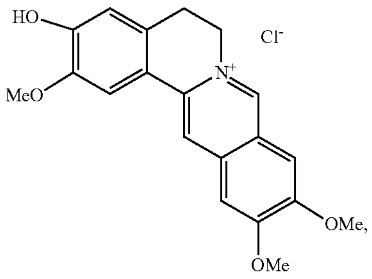
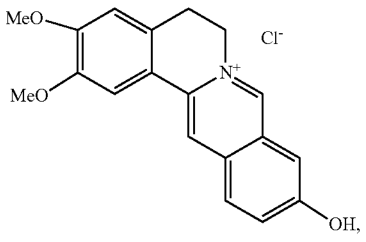
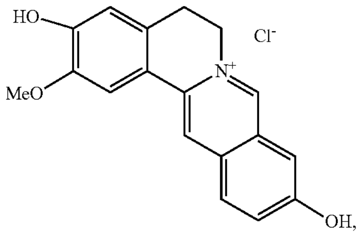
-continued
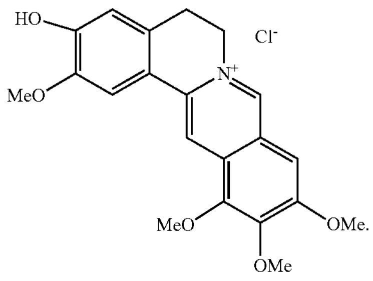
In another preferred embodiment, the first drug group has the structure of the following formula:
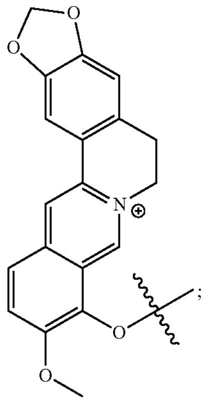 [SMILES: *Oc1c(OC)ccc2cc3[n+](cc12)CCc1cc2c(cc1-3)OCO2]
In another preferred embodiment, the second drug group is selected from the group consisting of:
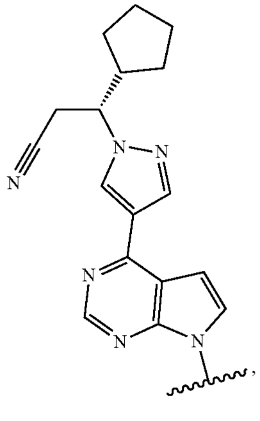
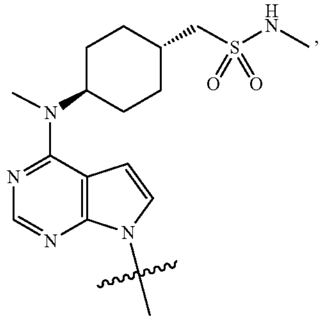

-continued
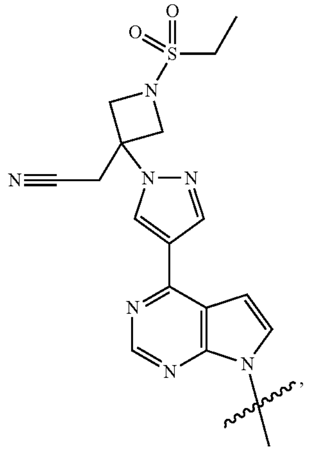
,
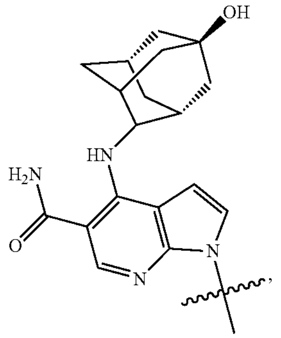
,
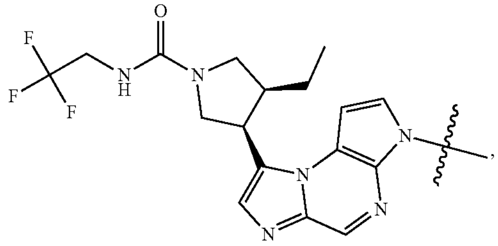
,
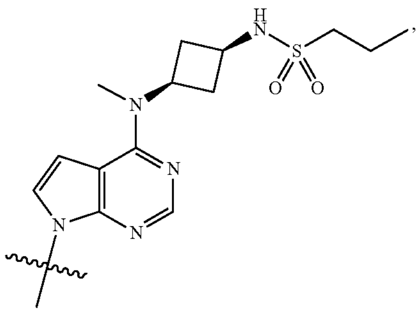
,
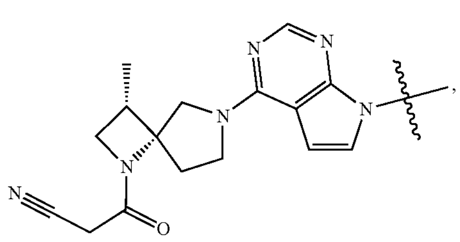
,
-continued
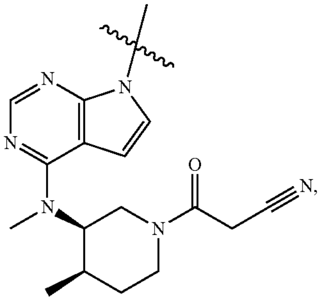
,
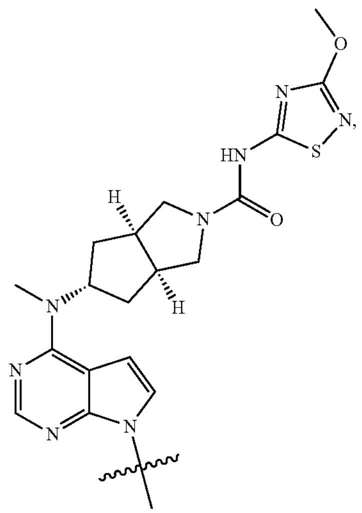
,
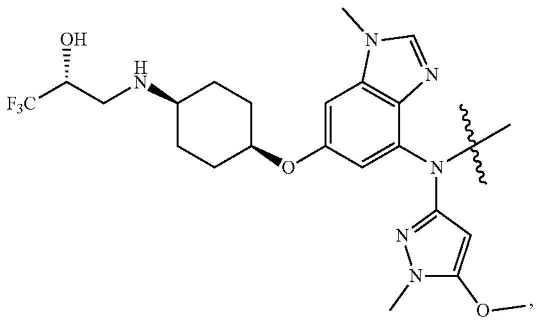
,
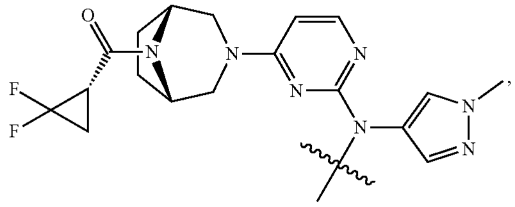
,
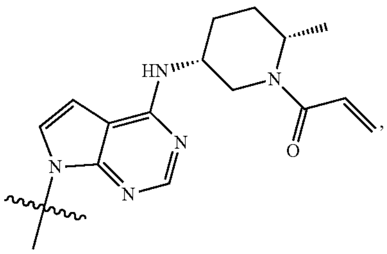
, -continued
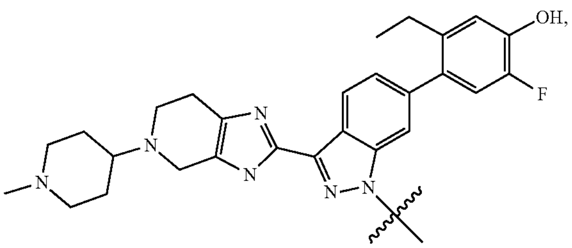
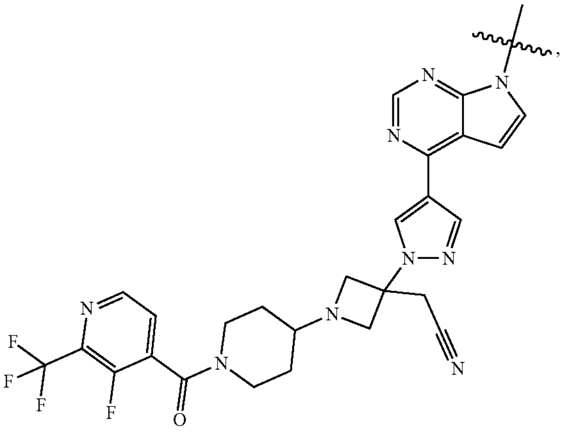
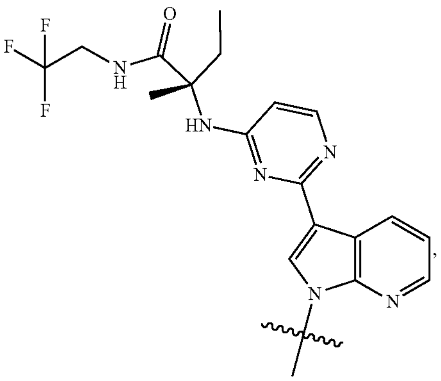
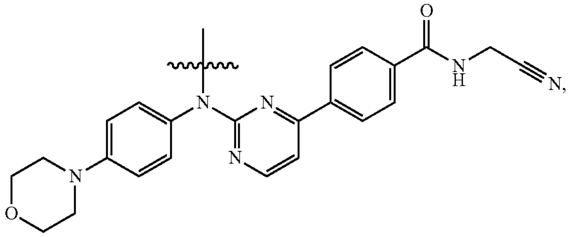
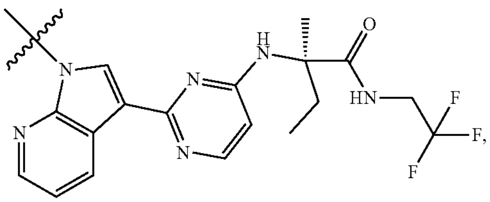
-continued
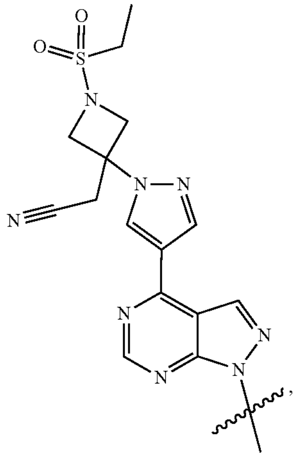
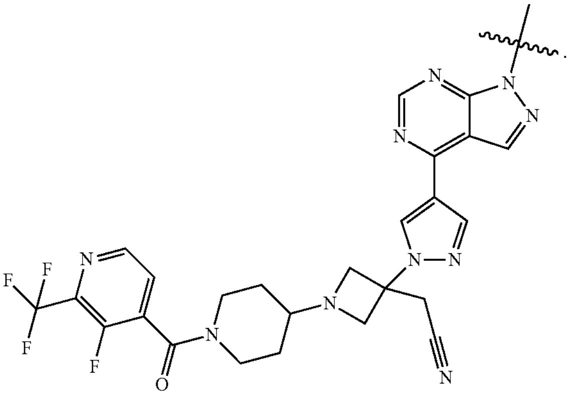
In another preferred embodiment, the second drug group is selected from the group consisting of
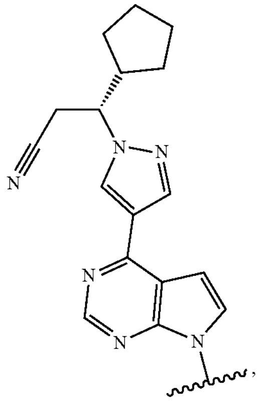
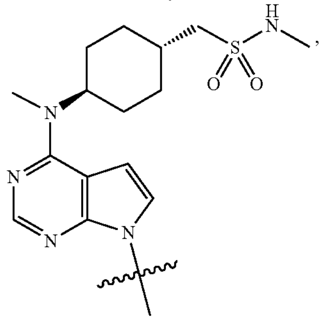

-continued
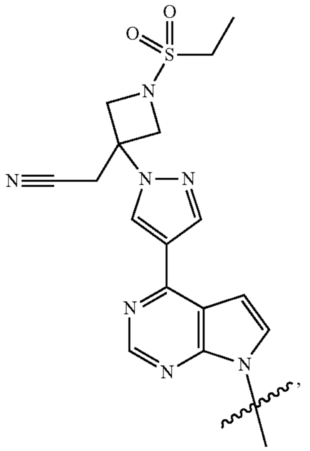
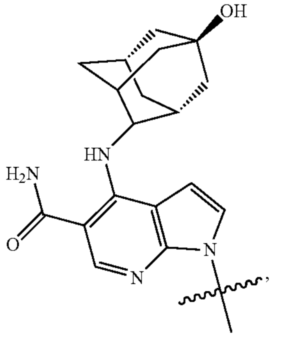
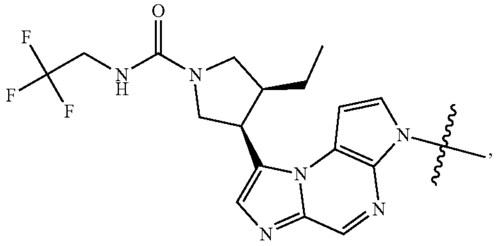
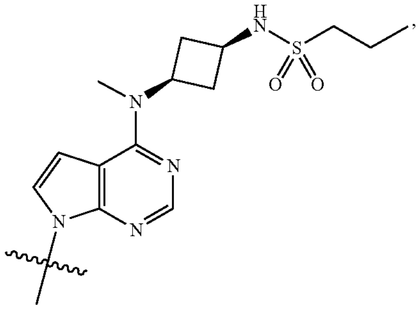
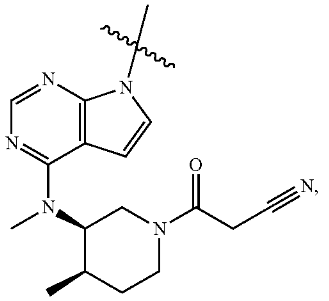
-continued
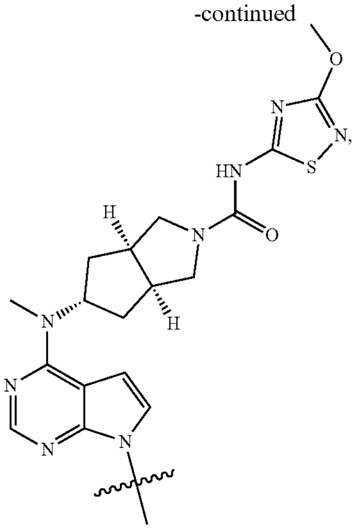
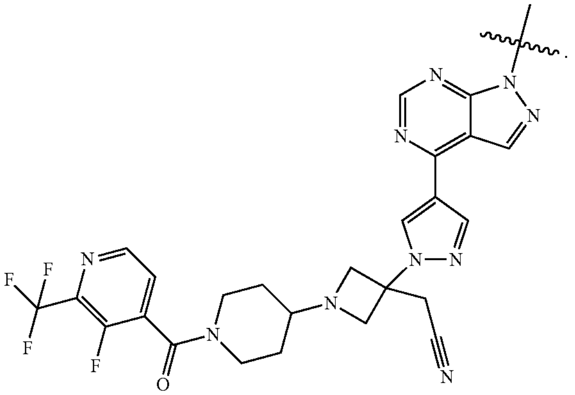
In another preferred embodiment, the first drug group is
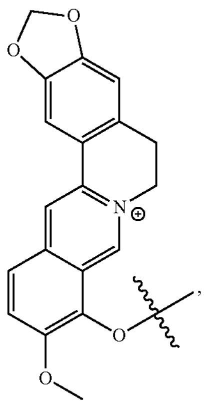 [SMILES: *Oc1c(OC)ccc2cc3[n+](cc12)CCc1cc2c(cc1-3)OCO2]
and the second drug group is
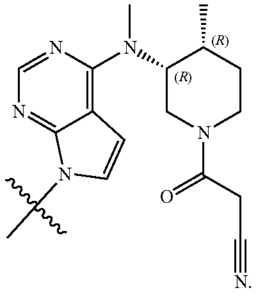

In another preferred embodiment, the A-$(L_7)_p$-$J_2$- has the structure shown in the formula:

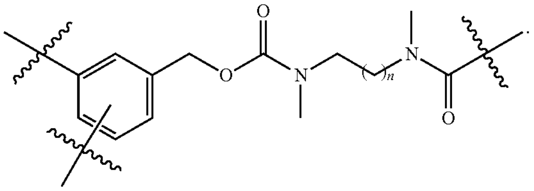

In another preferred embodiment, the -A(Glu)-$(L_7)_p$-$J_2$- has the structure shown in the formula:

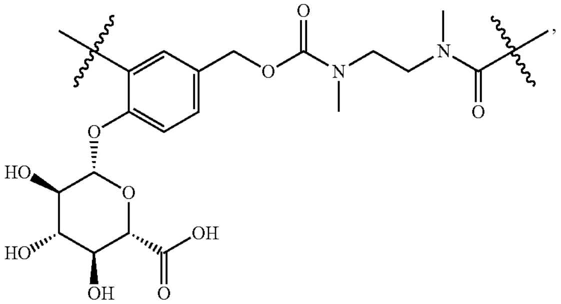

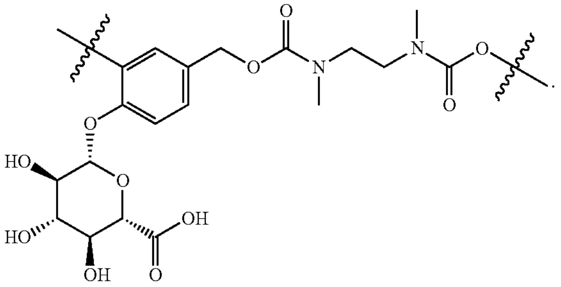

In another preferred embodiment, the -$(L_1)_m$- and -$(L_2)_n$- are independently of the following formula:

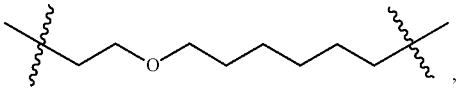

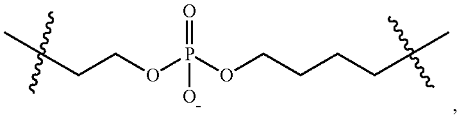

-continued

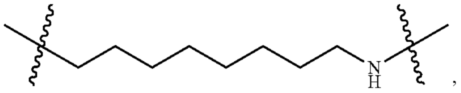

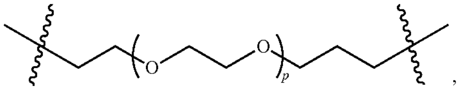

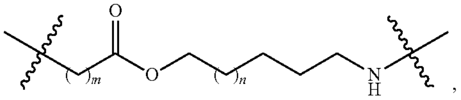

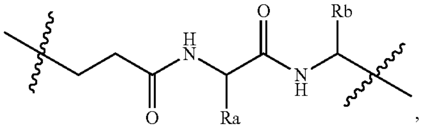

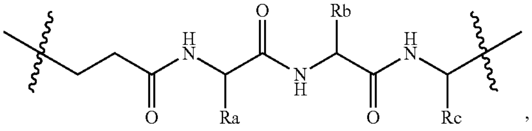

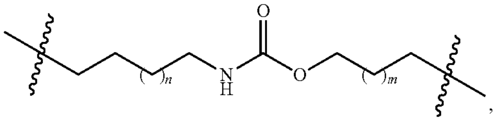

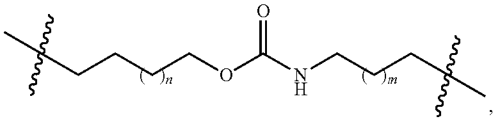

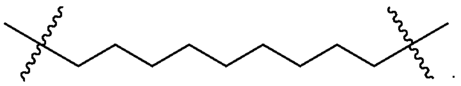

in the above formulas,

Ra, Rb and Rc are each independently a group formed by losing one hydrogen atom in an amino acid selected from the group consisting of: Glycine, Alanine, Valine, Leucine, Isoleucine, Phenylalanine, Tryptophan, Tyrosine, Aspartate, Histidine, Asparagine, Glutamate, Lysine, Glutamine, Methionine, Arginine, Serine, Threonine, Cysteine, and Proline.

In another preferred embodiment, the linker is selected from the following (A), (B) or (C) group:

Group (A) has a structure of -$L_a$-L-, where the $L_a$ has a structure selected from the group consisting of:

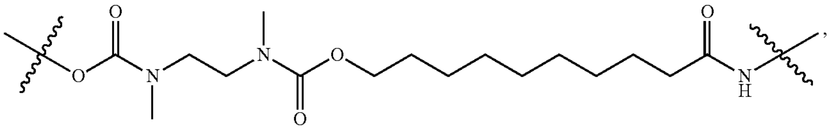

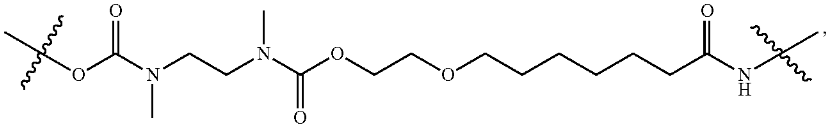

-continued
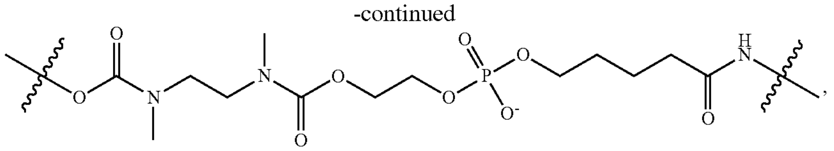
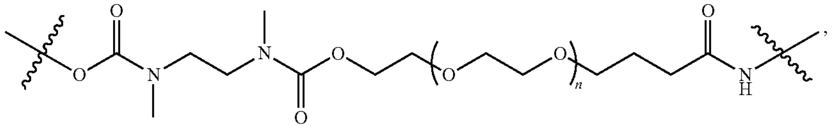
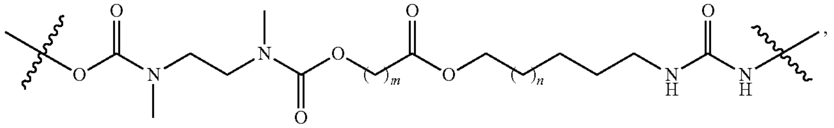
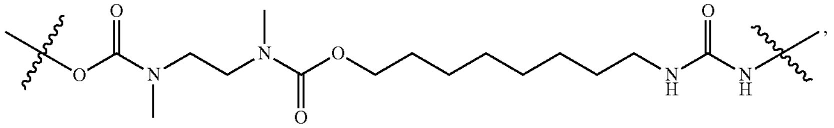
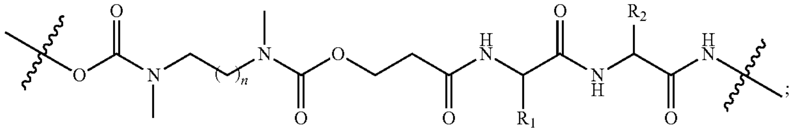
and the L has the structure shown below, wherein * is the connection site of L to $L_a$:
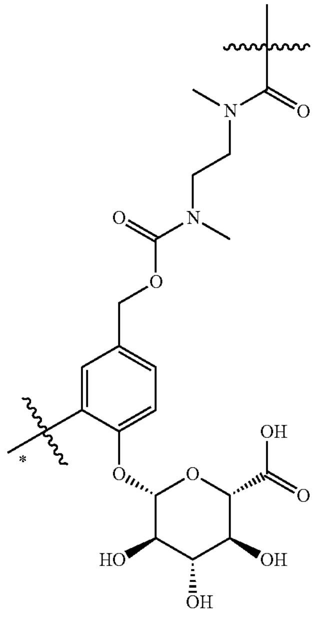 [SMILES: *C(=O)N(C)CCN(C)C(=O)OCc1ccc(O[C@@H]2O[C@H](C(=O)O)[C@@H](O)[C@H](O)[C@H]2O)c(*)c1]
Group (B):
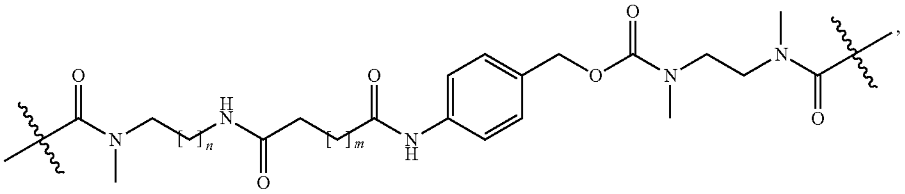

-continued
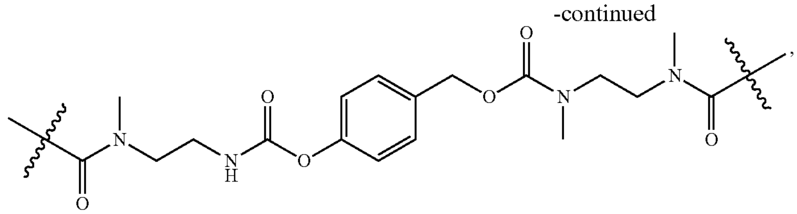
,
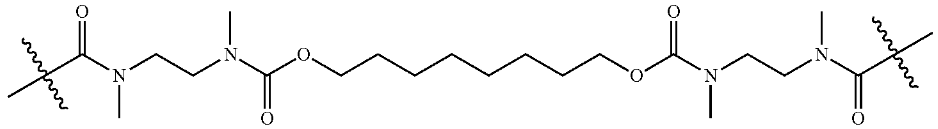
,
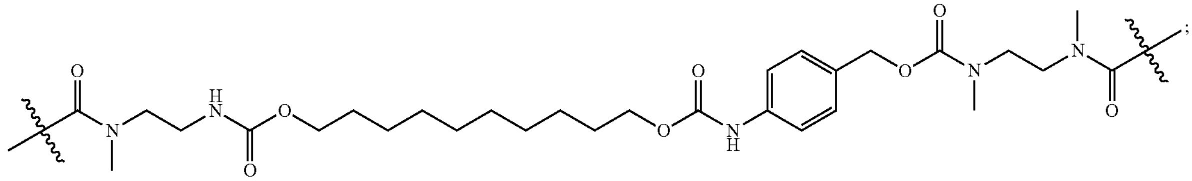
;
Group (C):
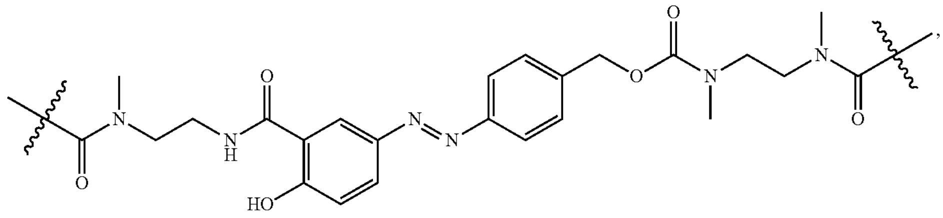
,
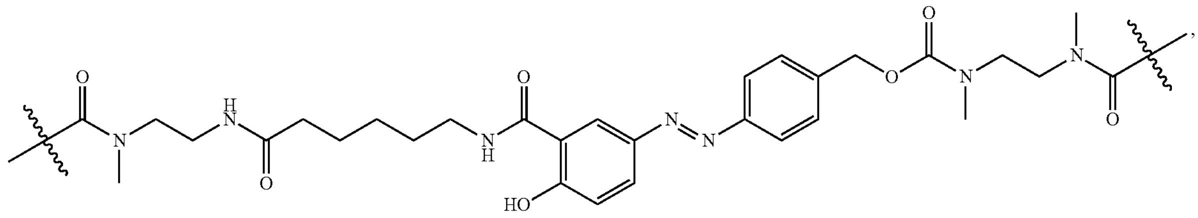
,
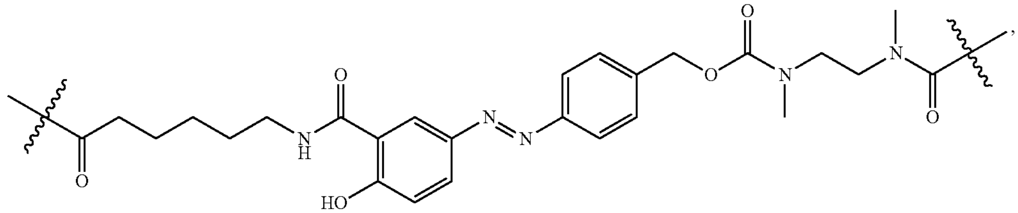
,
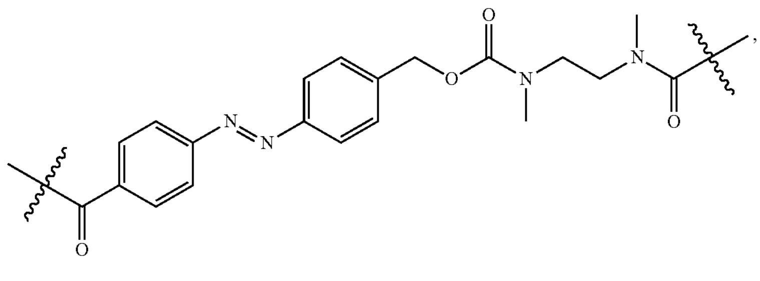
, -continued
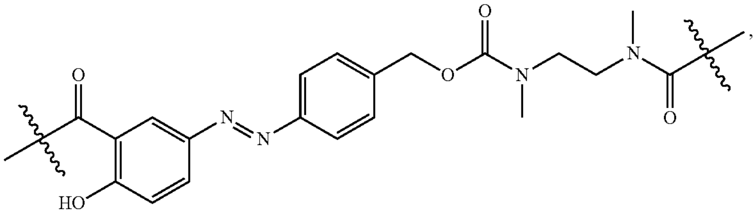
,
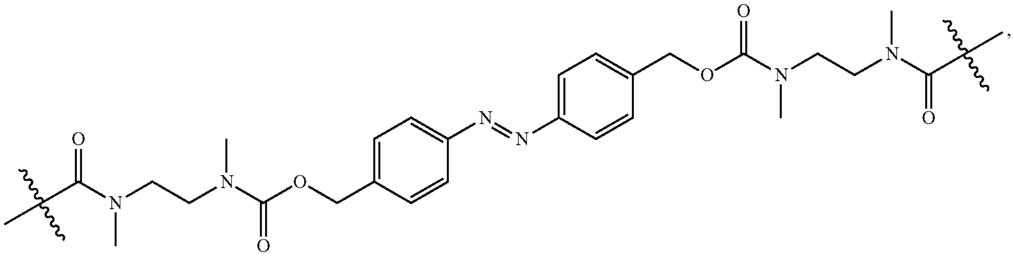
,
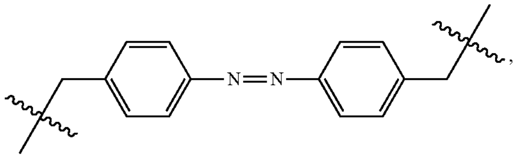
,
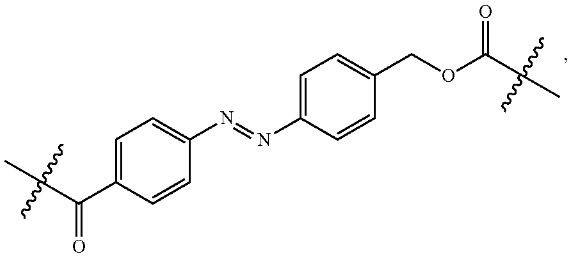
,
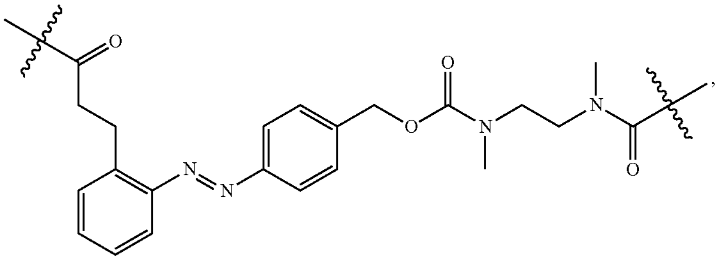
,
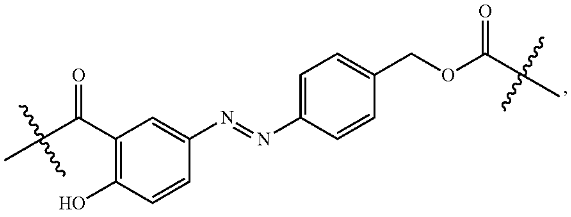
,
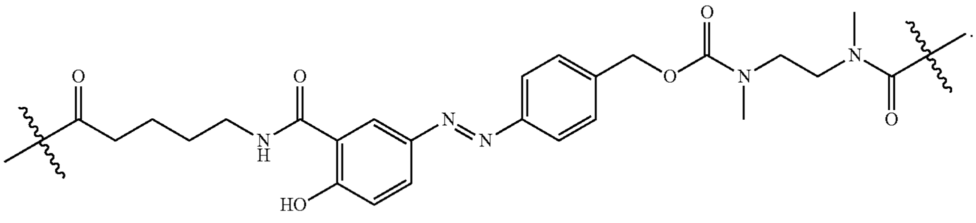
.

In another preferred embodiment, the compound is selected from the group consisting of:
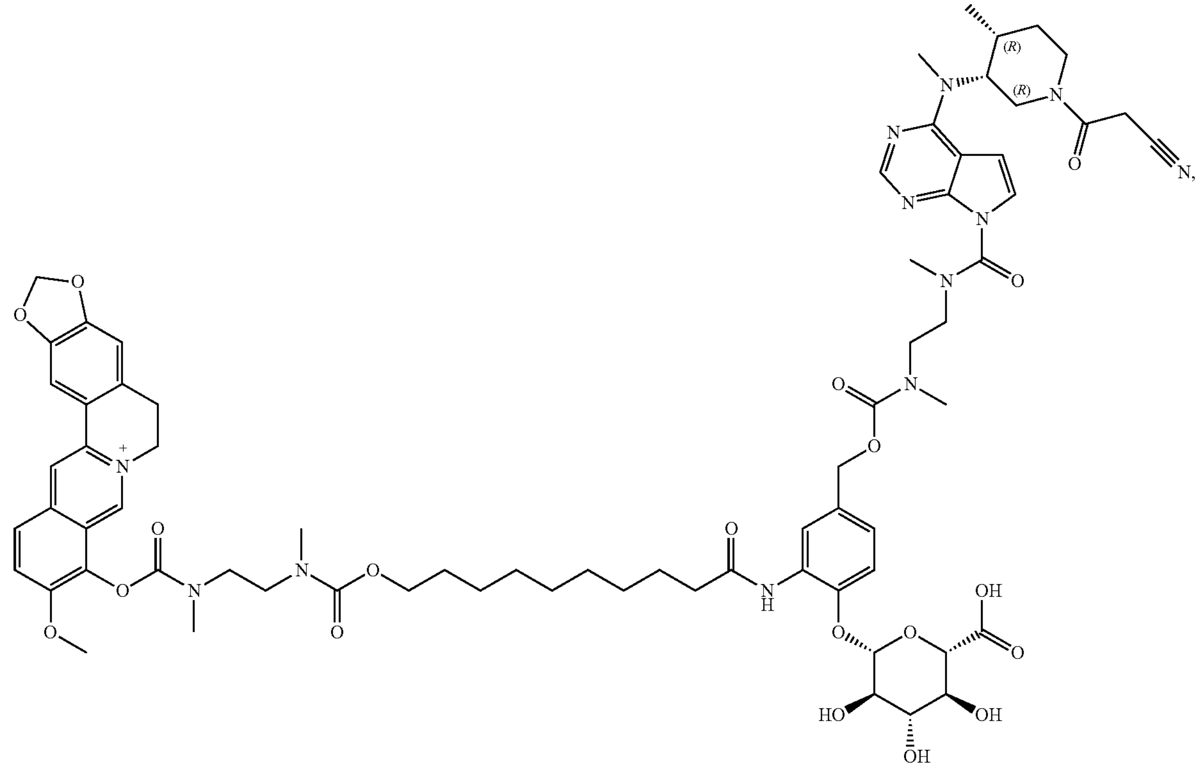
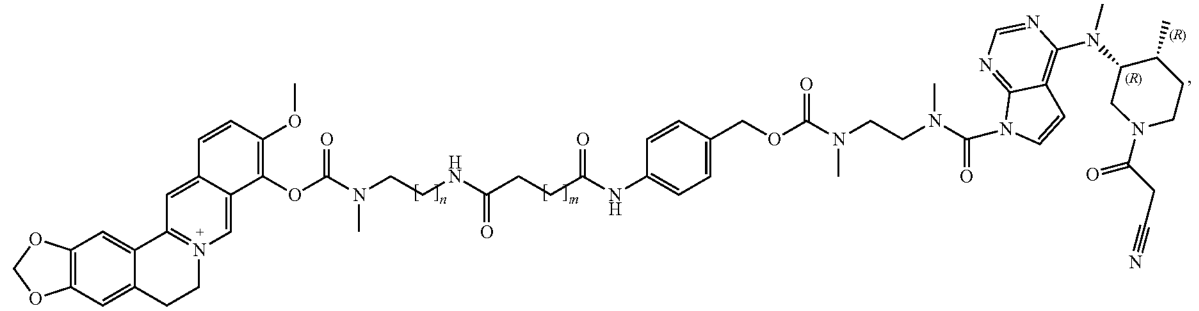
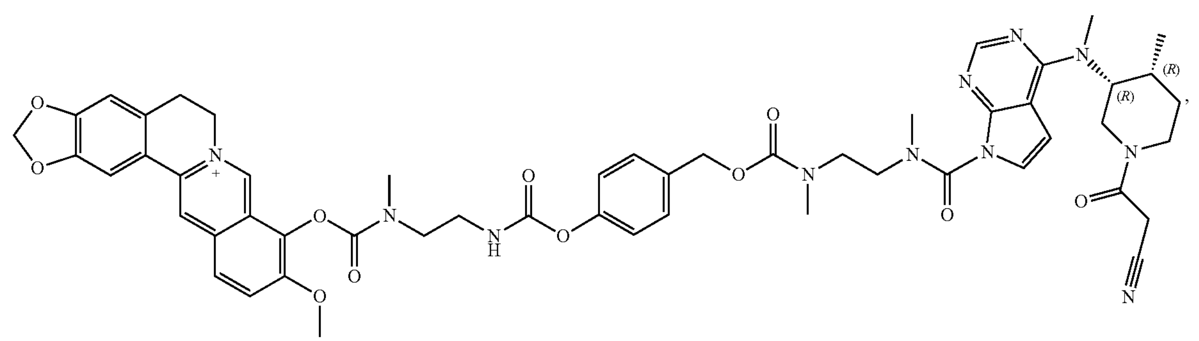

-continued
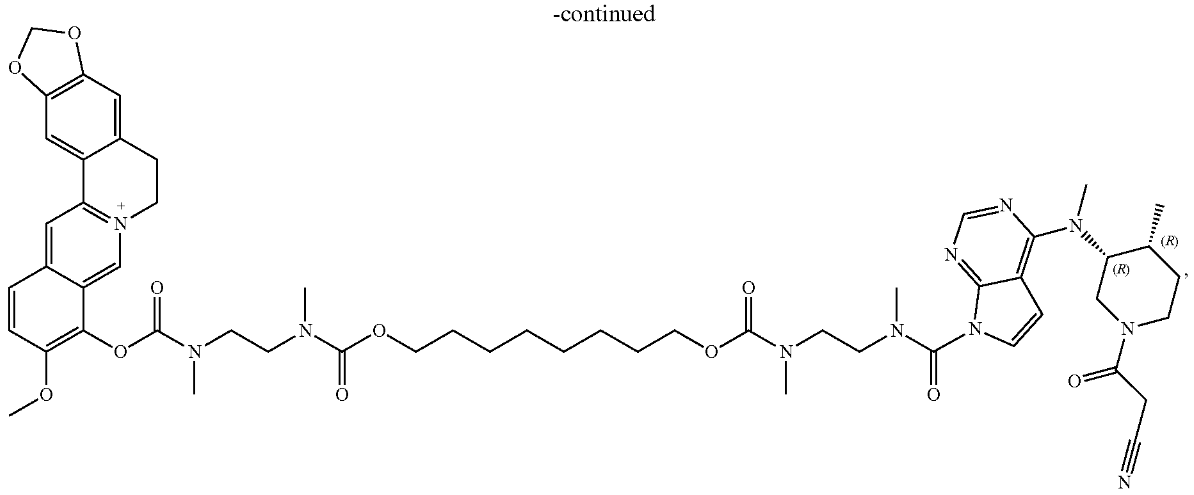
,
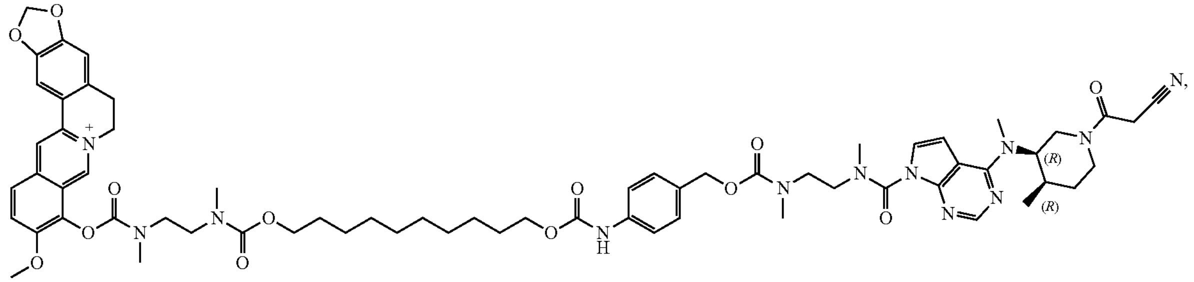
,
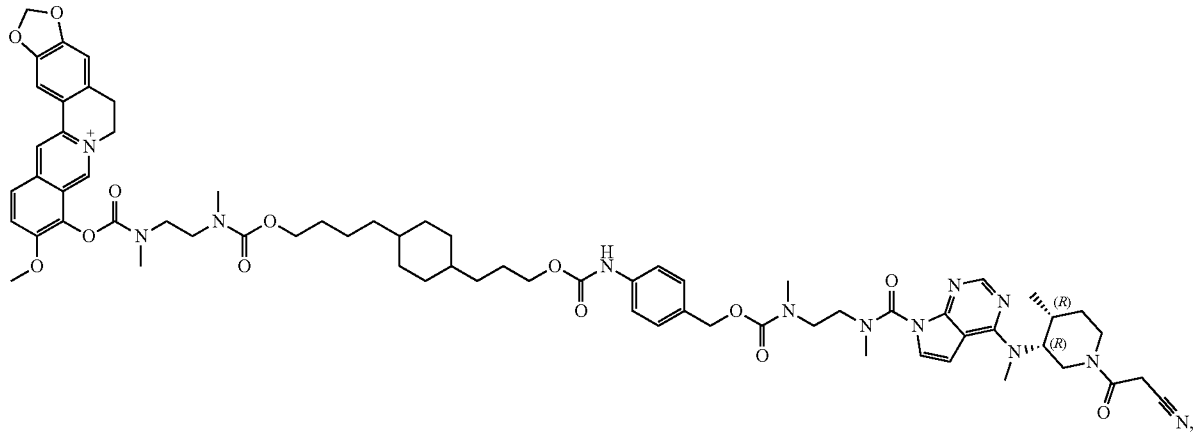
,
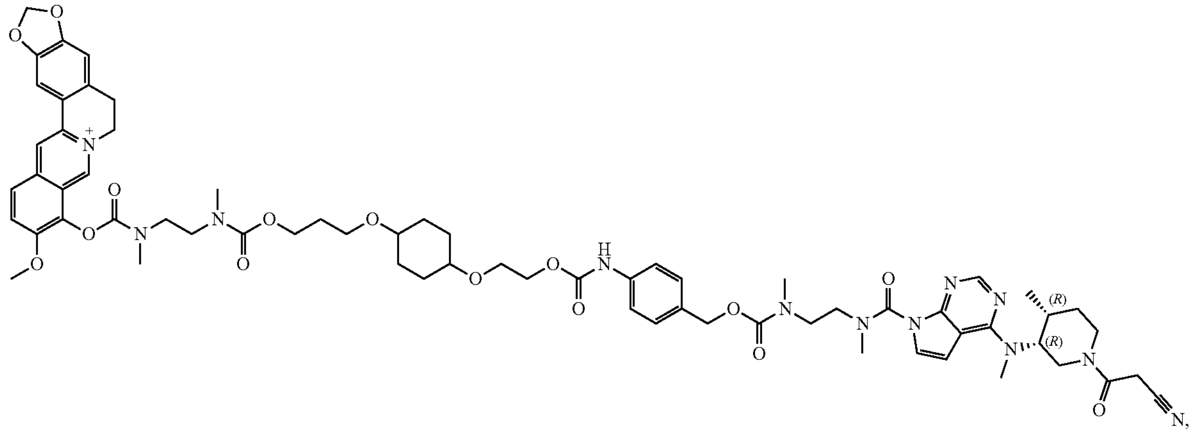
,

-continued
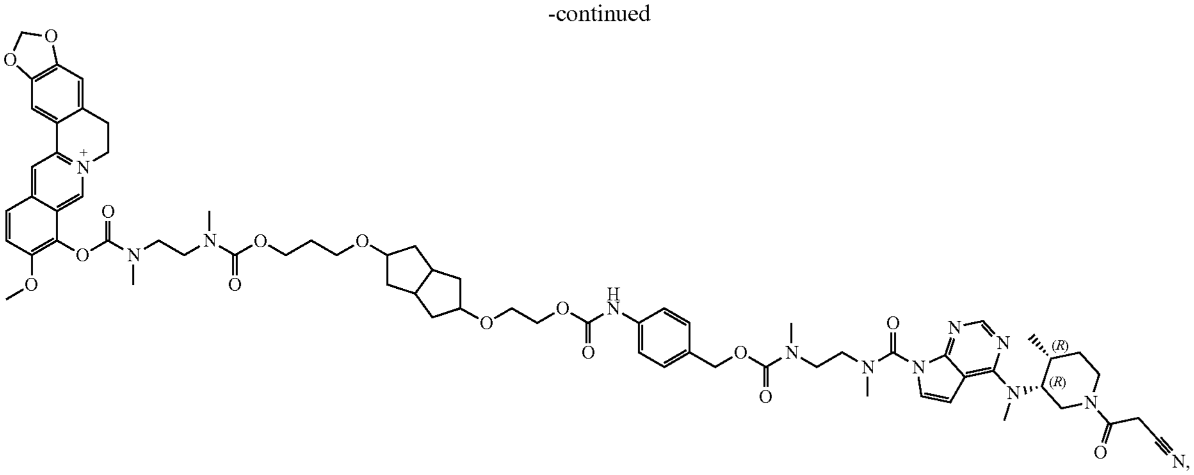
,
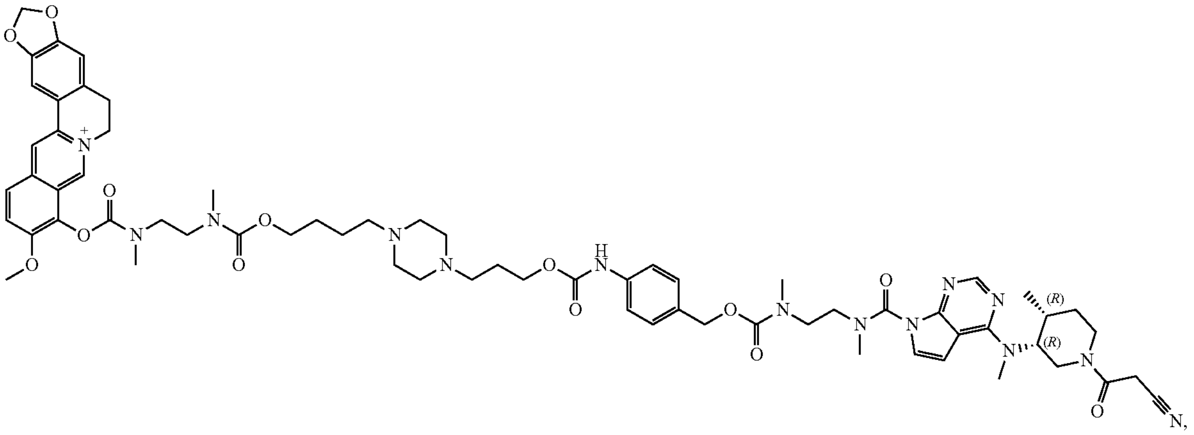
,
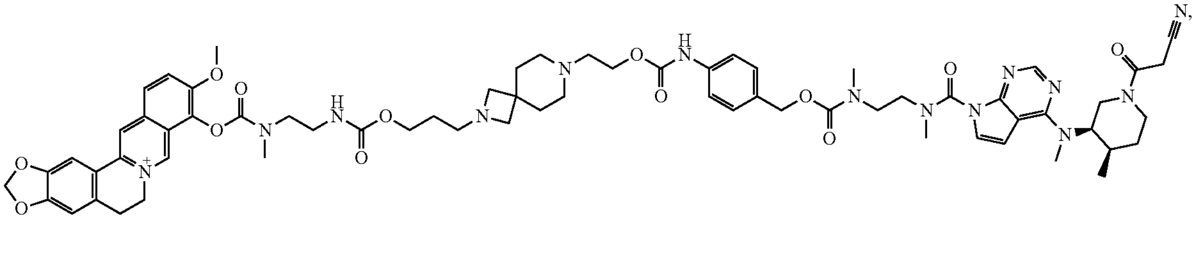
,
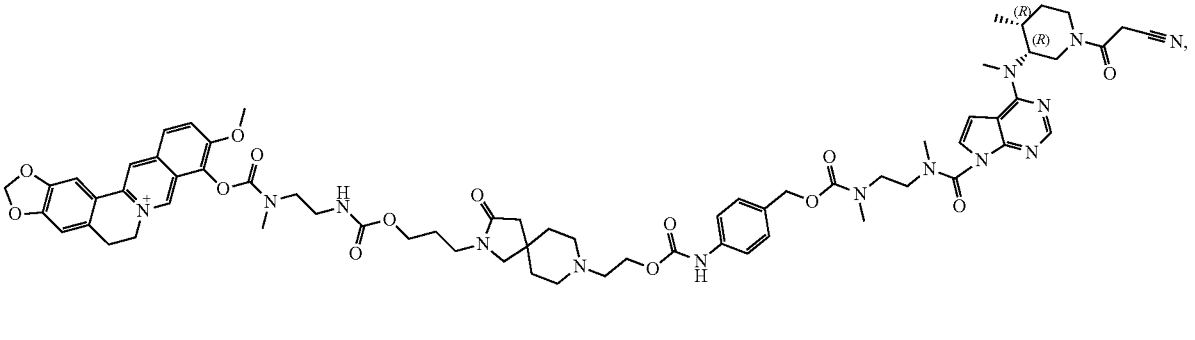
,

-continued
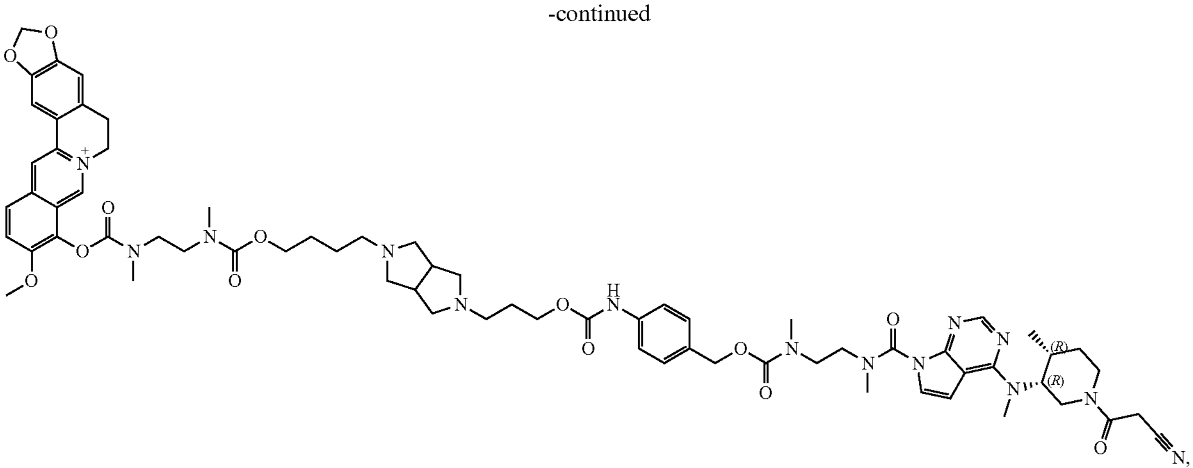
,
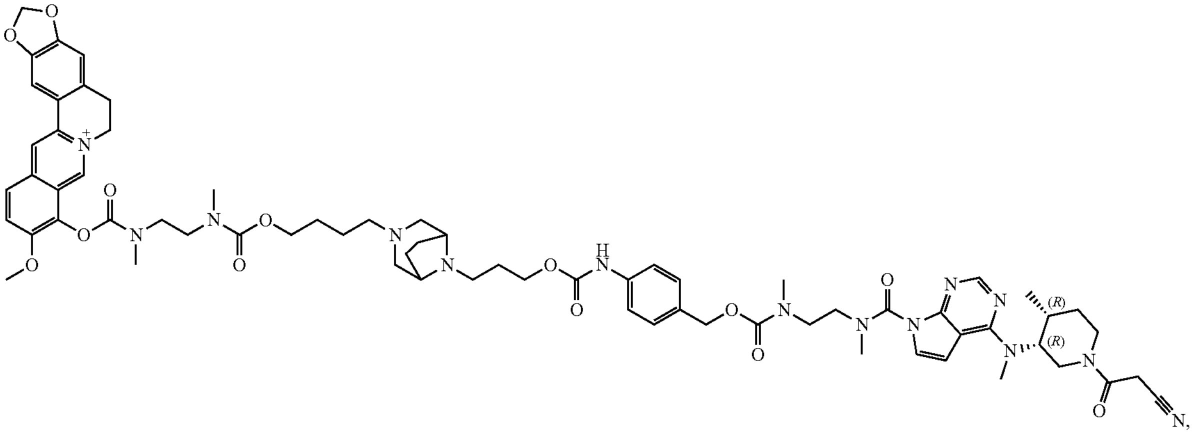
,
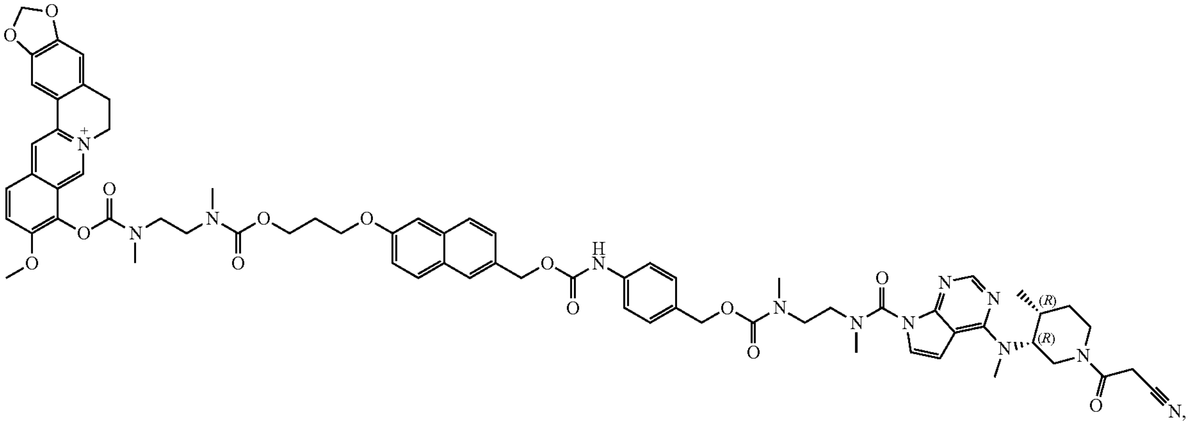
,
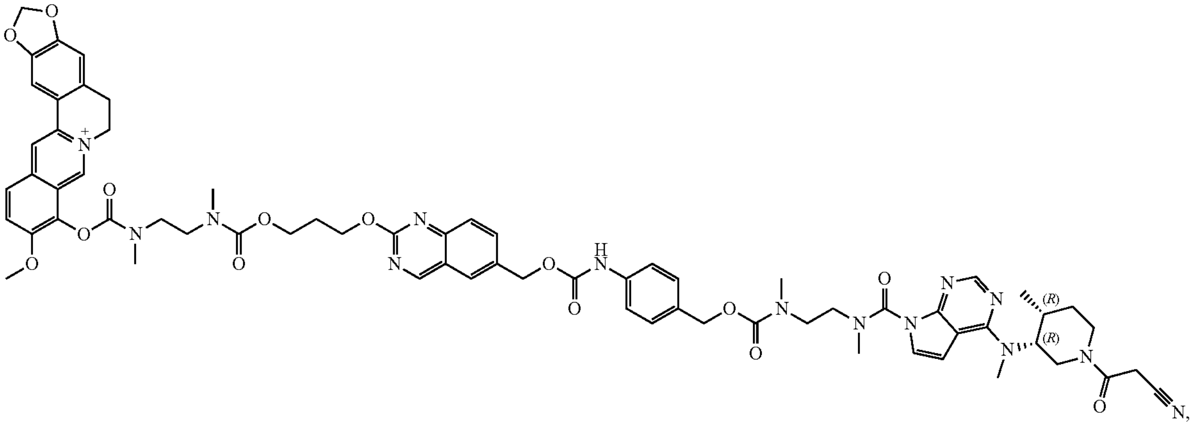
,

-continued
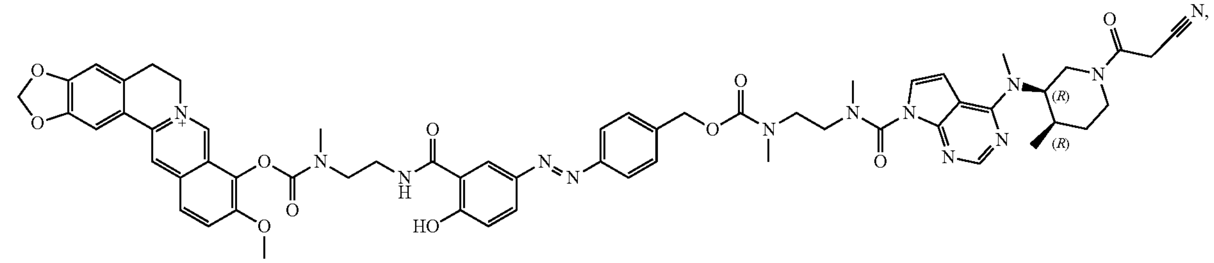
,
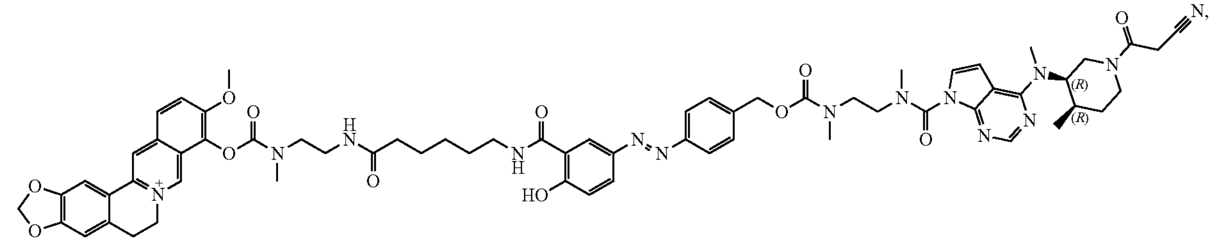
,
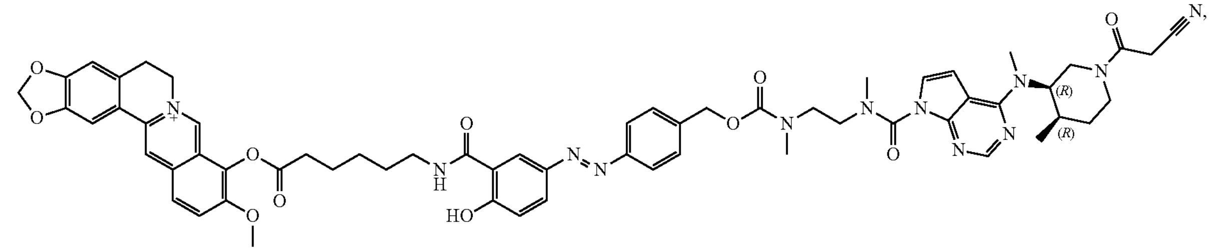
,
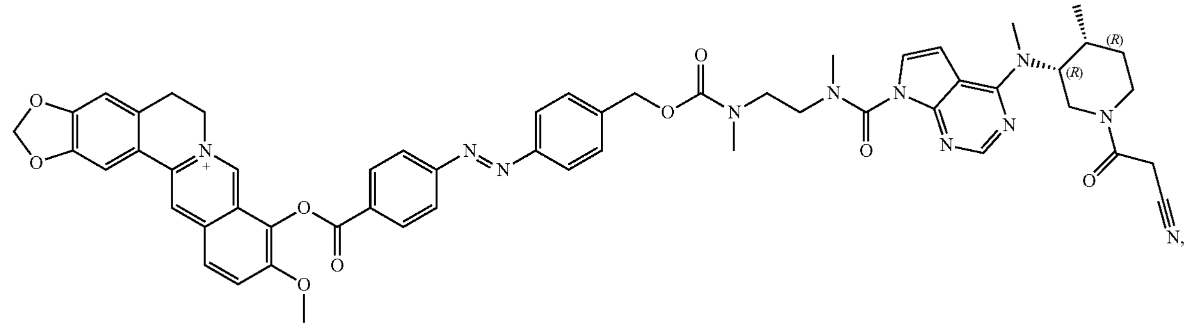
,
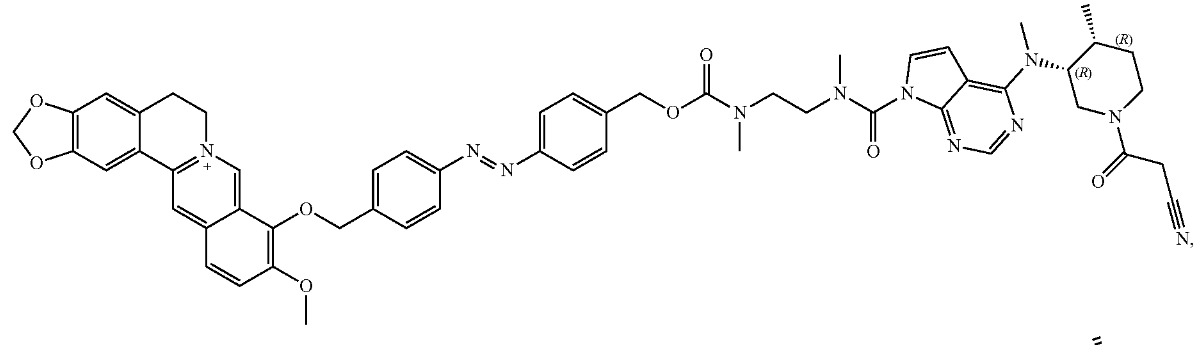
,
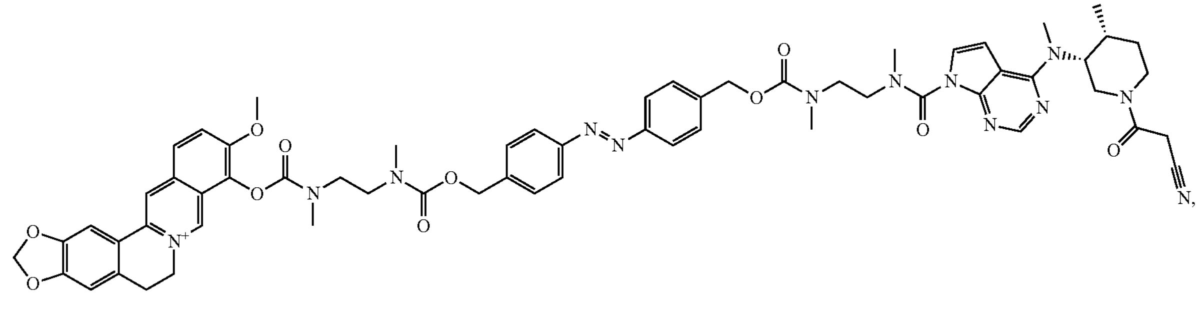
, -continued
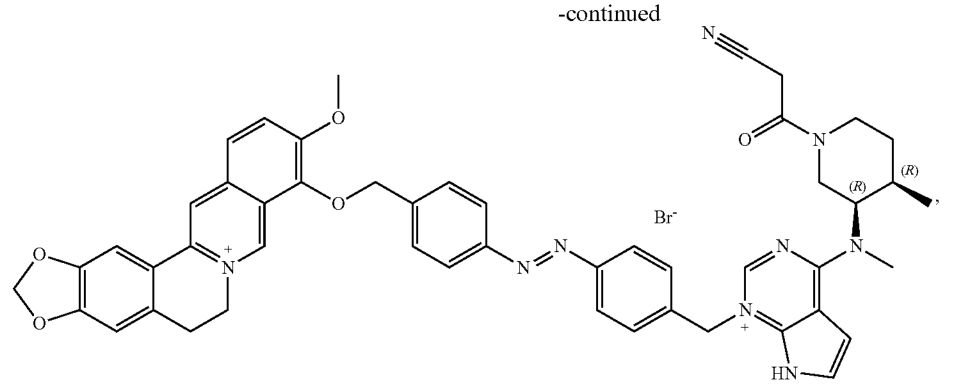
,
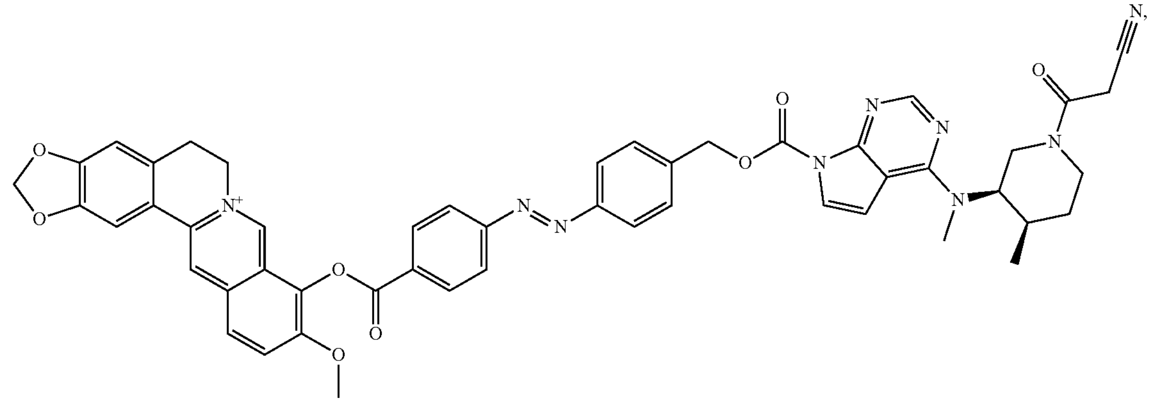
,
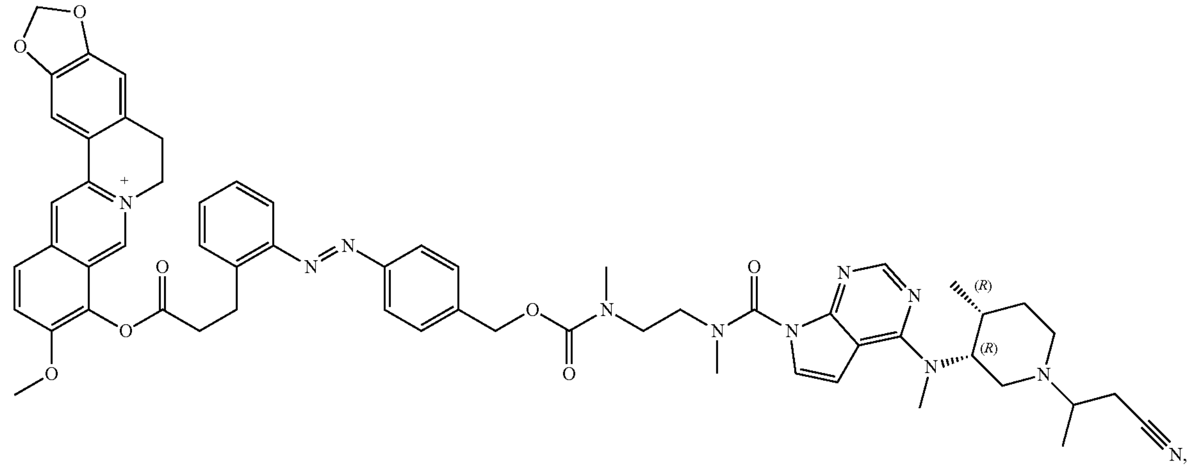
,
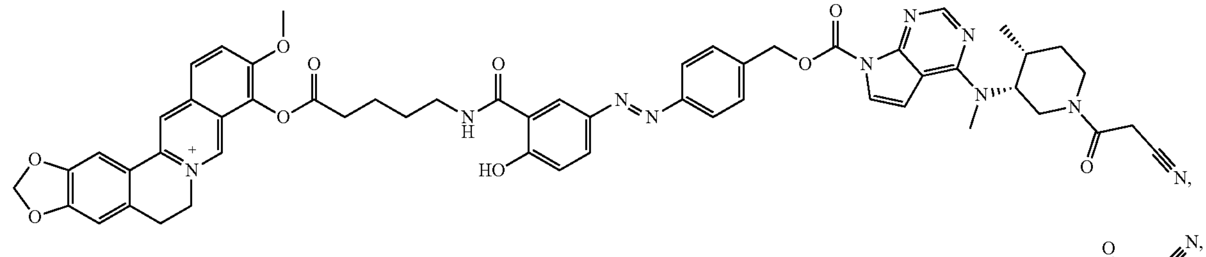
,
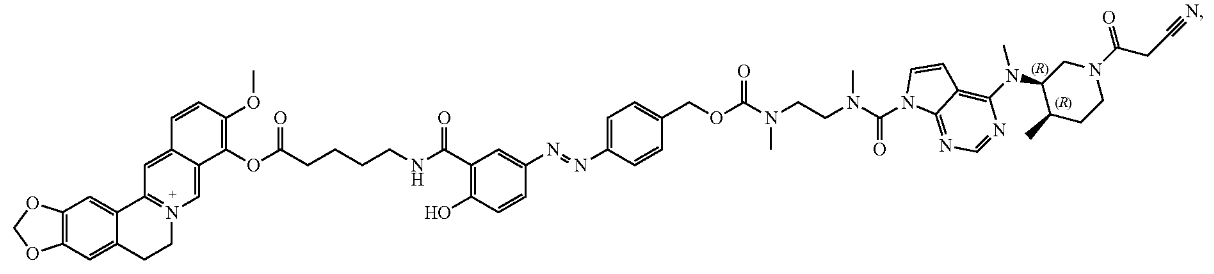

-continued
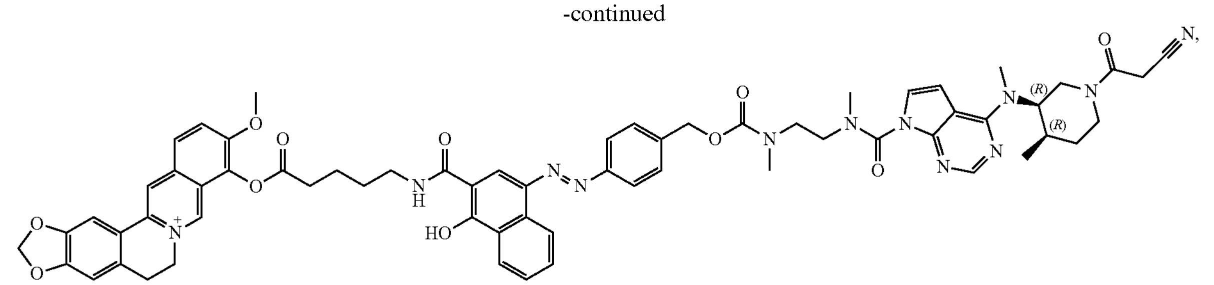
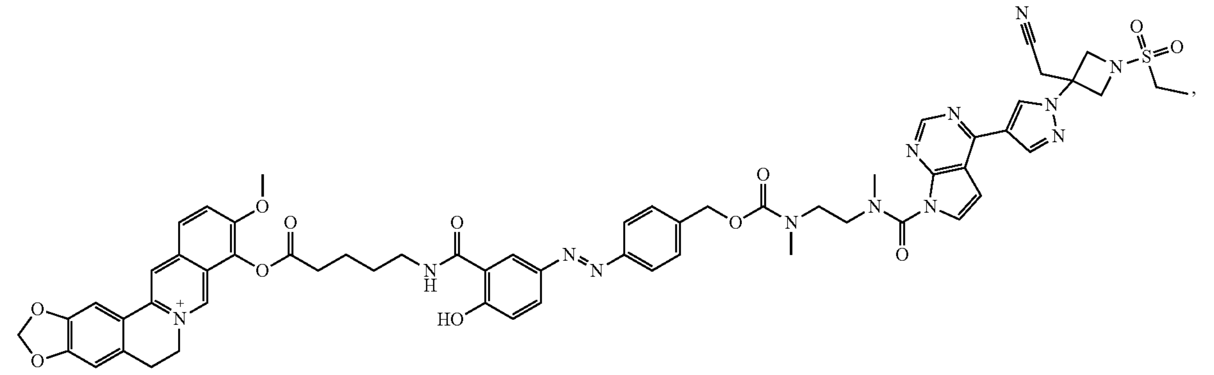
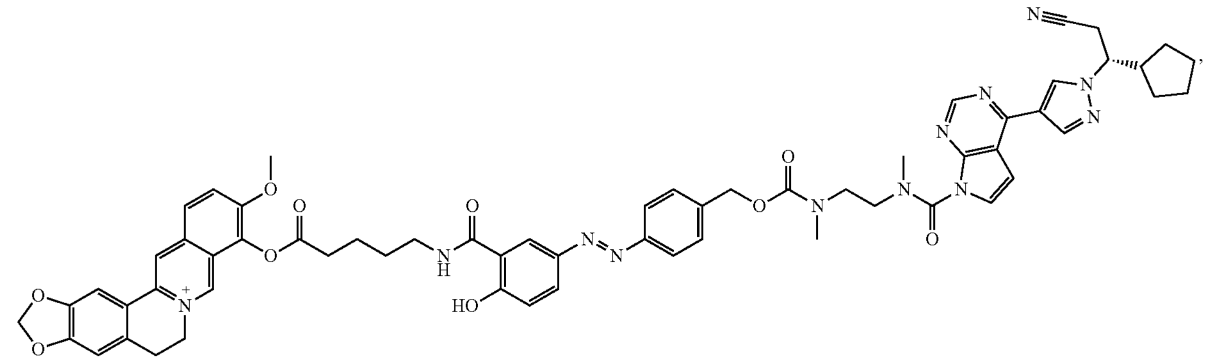
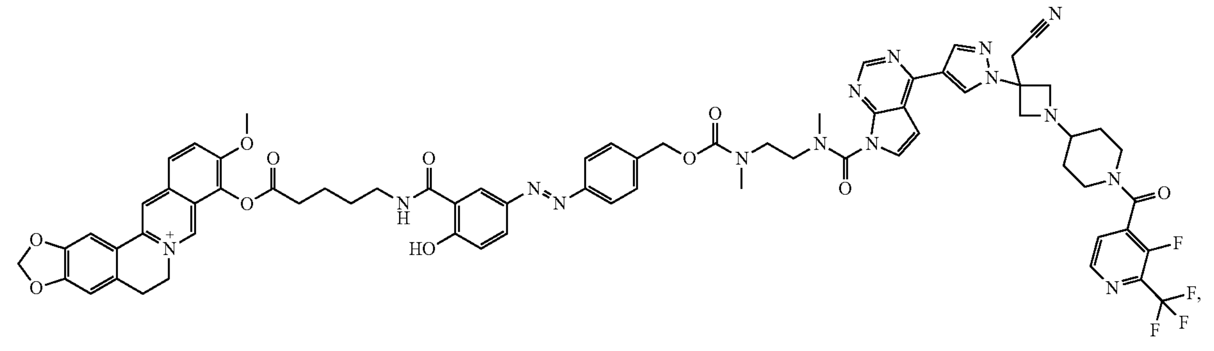
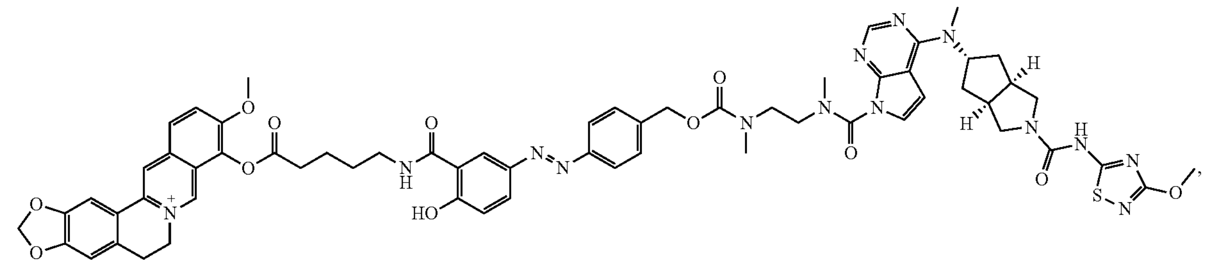

-continued
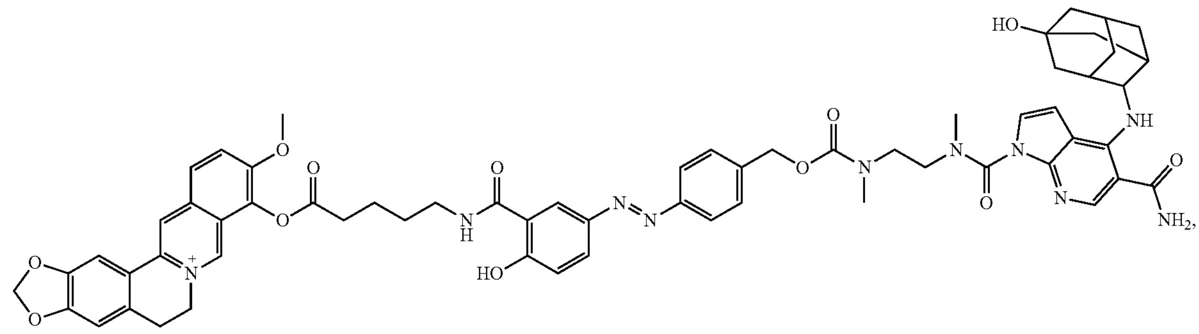
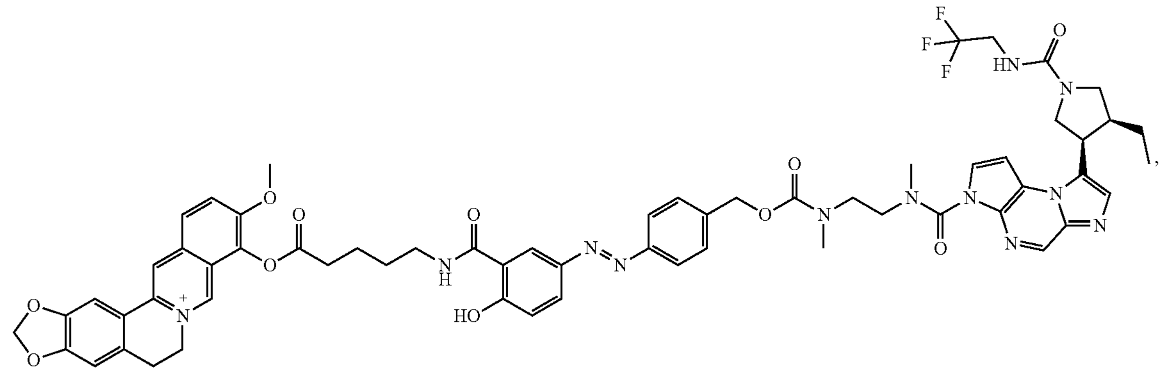
, and
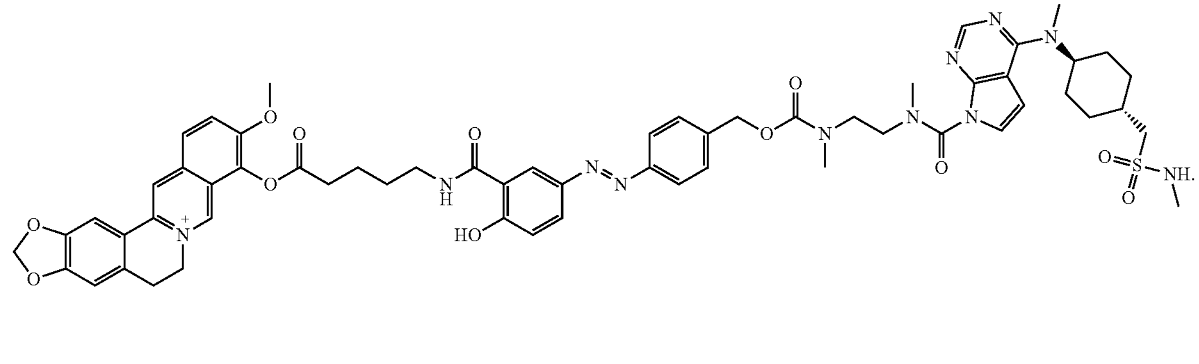

In another preferred embodiment, the compound is selected from the following structures:
| No. | Compound structure |
|---|---|
| 1 | 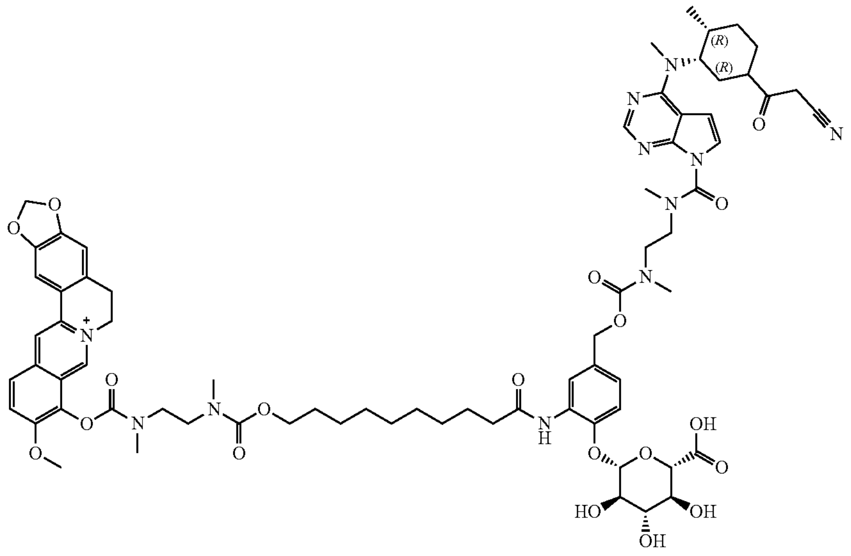 |
| 2 | 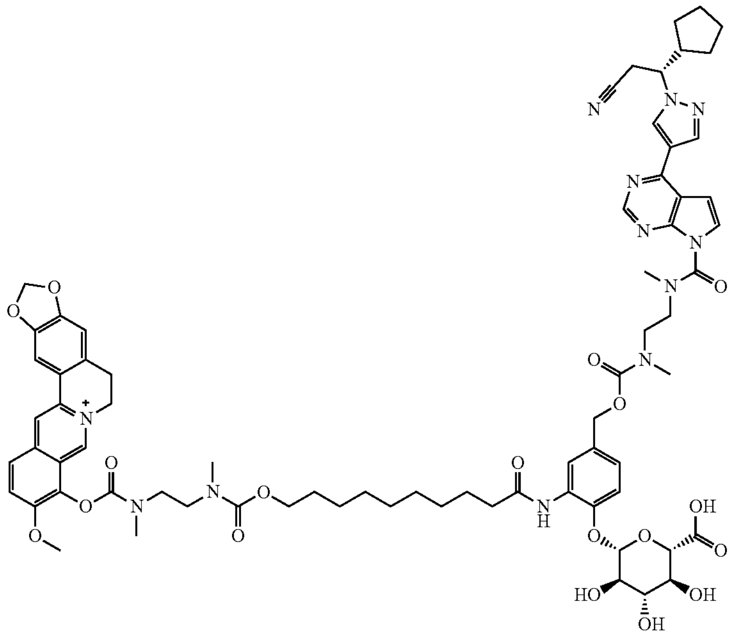 [SMILES: COc1ccc2cc3[n+](cc2c1OC(=O)N(C)CCN(C)C(=O)OCCCCCCCCCC(=O)Nc1cc(COC(=O)N(C)CCN(C)C(=O)n2ccc4c(-c5cnn([C@H](CC#N)C6CCCC6)c5)ncnc42)ccc1O[C@@H]1O[C@H](C(=O)O)[C@@H](O)[C@H](O)[C@H]1O)CCc1cc2c(cc1-3)OCO2] |

-continued
| No. | Compound structure |
| --- | --- |
| 3 | 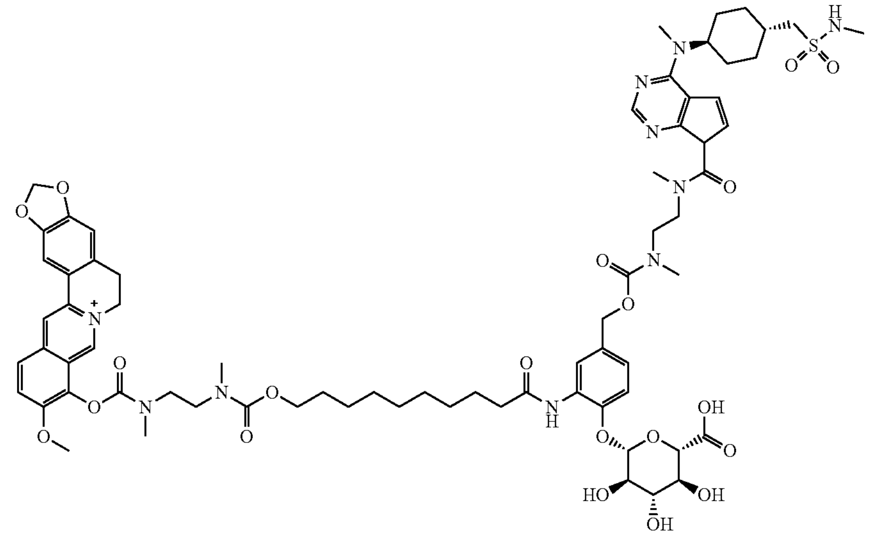 [SMILES: CNS(=O)(=O)C[C@H]1CC[C@H](N(C)c2ncnc3c2C=CC3C(=O)N(C)CCN(C)C(=O)OCc2ccc(O[C@@H]3O[C@H](C(=O)O)[C@@H](O)[C@H](O)[C@H]3O)c(NC(=O)CCCCCCCCCOC(=O)N(C)CCN(C)C(=O)Oc3c(OC)ccc4cc5[n+](cc34)CCc3cc4c(cc3-5)OCO4)c2)CC1] |
| 4A | 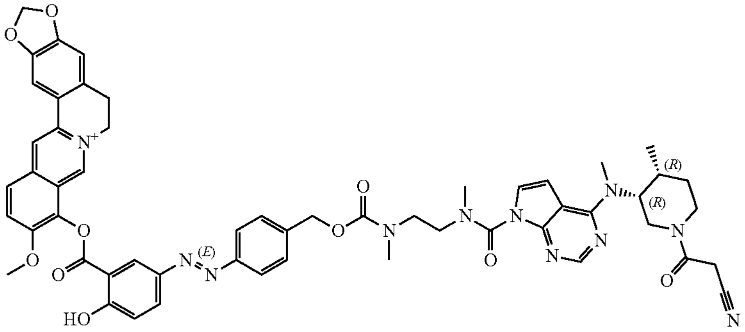 |
| 4B | 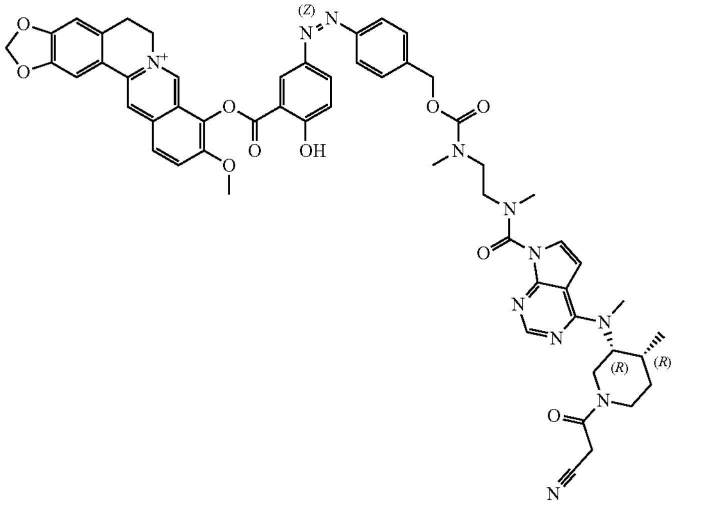 |

-continued
| No. | Compound structure |
| --- | --- |
| 5 | 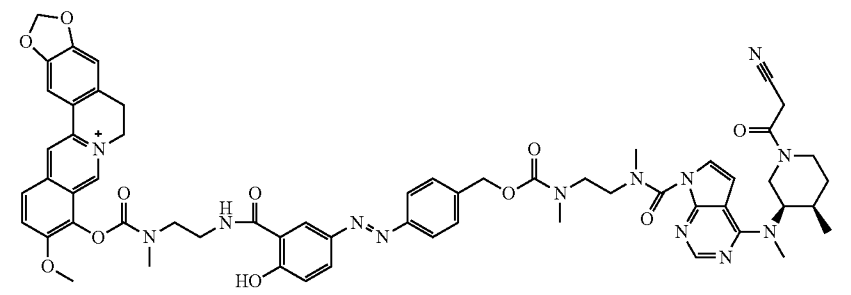 [SMILES: COc1ccc2cc3[n+](cc2c1OC(=O)N(C)CCNC(=O)c1cc(/N=N/c2ccc(COC(=O)N(C)CCN(C)C(=O)n4ccc5c(N(C)[C@H]6CN(C(=O)CC#N)CC[C@H]6C)ncnc54)cc2)ccc1O)CCc1cc2c(cc1-3)OCO2] |
| 6 | 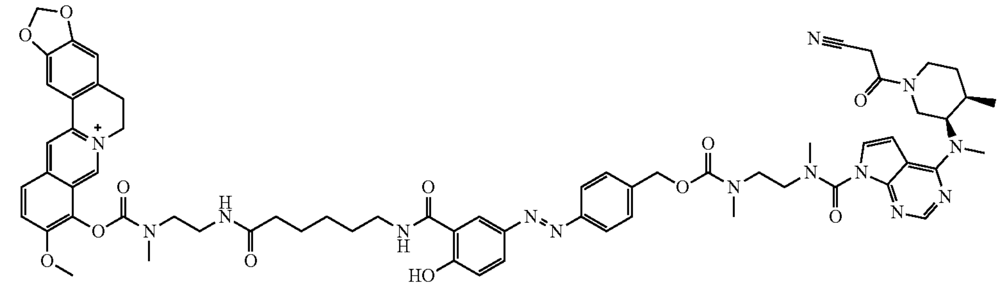 [SMILES: COc1ccc2cc3[n+](cc2c1OC(=O)N(C)CCNC(=O)CCCCCNC(=O)c1cc(/N=N/c2ccc(COC(=O)N(C)CCN(C)C(=O)n4ccc5c(N(C)[C@H]6CN(C(=O)CC#N)CC[C@H]6C)ncnc54)cc2)ccc1O)CCc1cc2c(cc1-3)OCO2] |
| 7 | 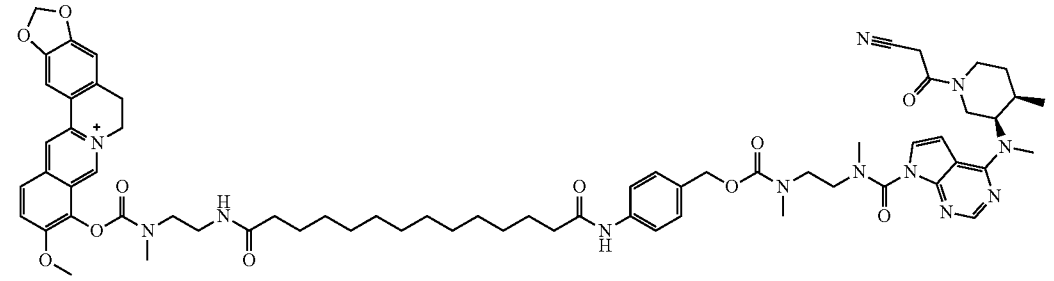 [SMILES: COc1ccc2cc3[n+](cc2c1OC(=O)N(C)CCNC(=O)CCCCCCCCCCCCC(=O)Nc1ccc(COC(=O)N(C)CCN(C)C(=O)n2ccc4c(N(C)[C@H]5CN(C(=O)CC#N)CC[C@H]5C)ncnc42)cc1)CCc1cc2c(cc1-3)OCO2] |
| 8 | 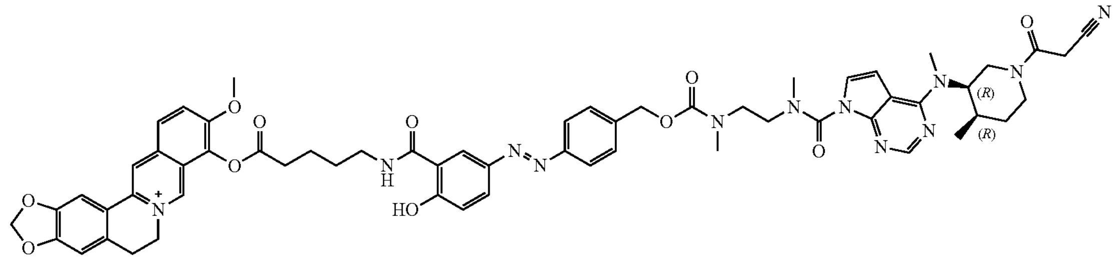 |
| 9 | 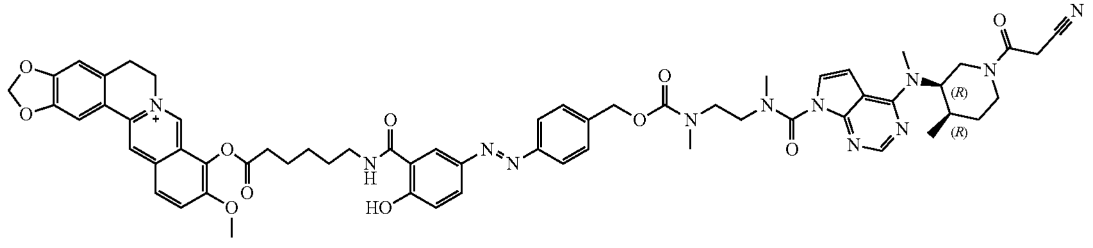 |

-continued
| No. | Compound structure |
|---|---|
| 10 | 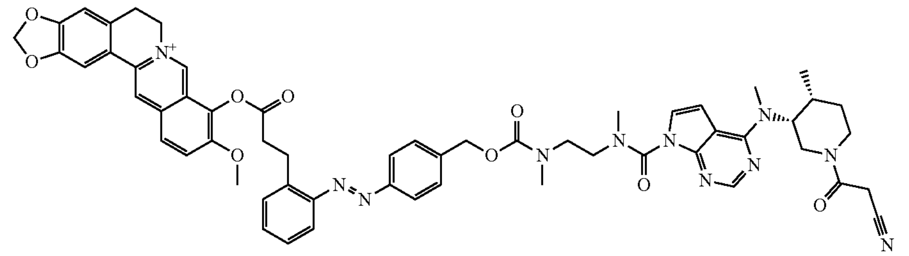 [SMILES: COc1ccc2cc3[n+](cc2c1OC(=O)CCc1ccccc1/N=N/c1ccc(COC(=O)N(C)CCN(C)C(=O)n2ccc4c(N(C)[C@H]5CN(C(=O)CC#N)CC[C@H]5C)ncnc42)cc1)CCc1cc2c(cc1-3)OCO2] |
| 11 | 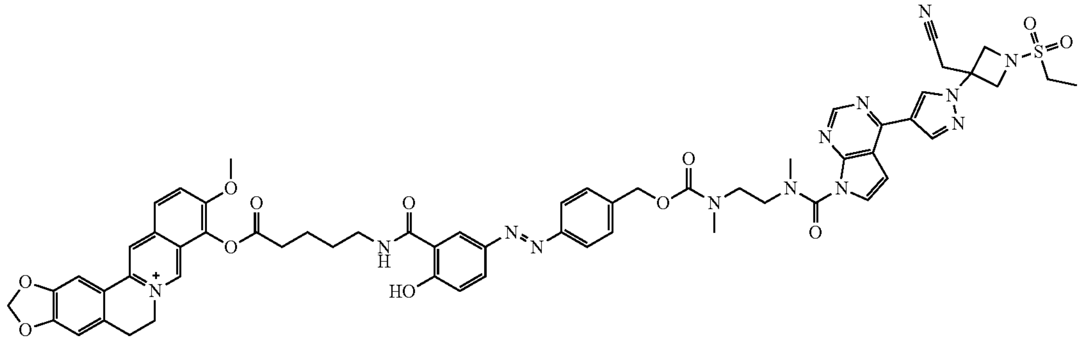 [SMILES: CCS(=O)(=O)N1CC(CC#N)(n2cc(-c3ncnc4c3ccn4C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)cn2)C1] |
| 12 | 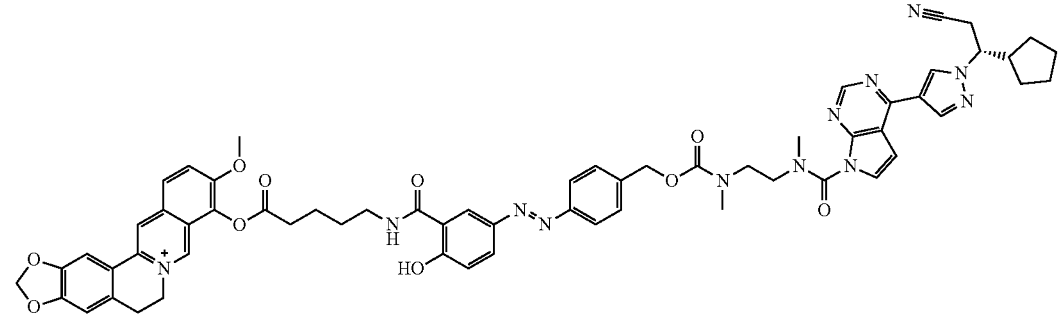 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn([C@H](CC#N)C7CCCC7)c6)ncnc54)cc2)ccc1O)CCc1cc2c(cc1-3)OCO2] |
| 13 | 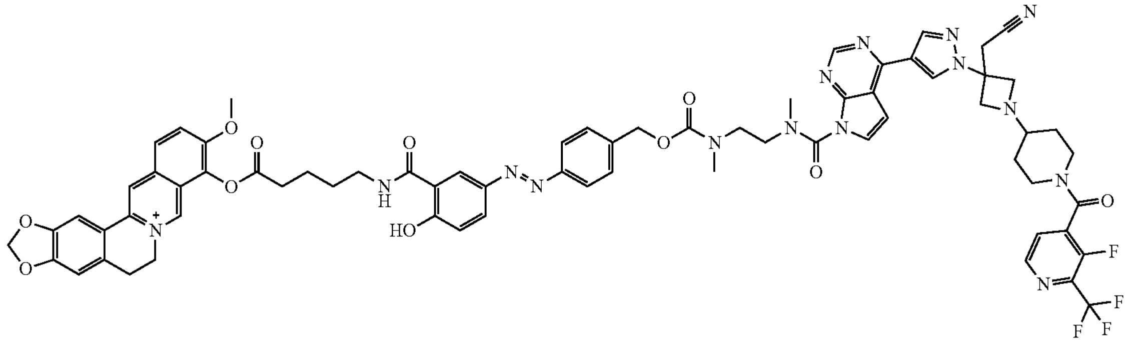 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn(C7(CC#N)CN(C8CCN(C(=O)c9ccnc(C(F)(F)F)c9F)CC8)C7)c6)ncnc54)cc2)ccc1O)CCc1cc2c(cc1-3)OCO2] |
| 14 | 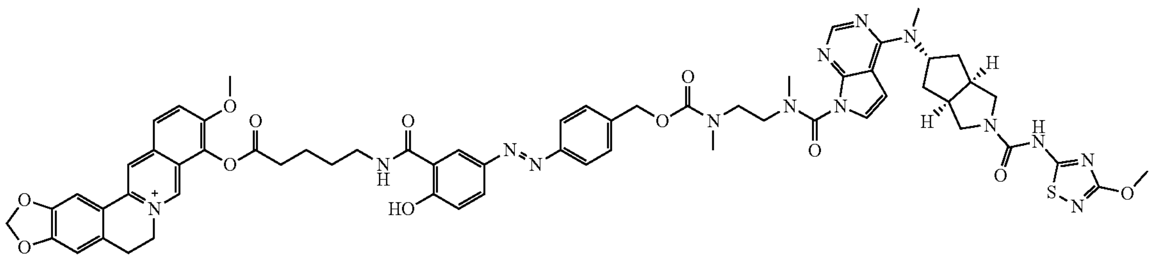 [SMILES: COc1nsc(NC(=O)N2C[C@H]3C[C@H](N(C)c4ncnc5c4ccn5C(=O)N(C)CCN(C)C(=O)OCc4ccc(/N=N/c5ccc(O)c(C(=O)NCCCCC(=O)Oc6c(OC)ccc7cc8[n+](cc67)CCc6cc7c(cc6-8)OCO7)c5)cc4)C[C@H]3C2)n1] |

-continued

| No. | Compound structure |
| --- | --- |
| 15 | 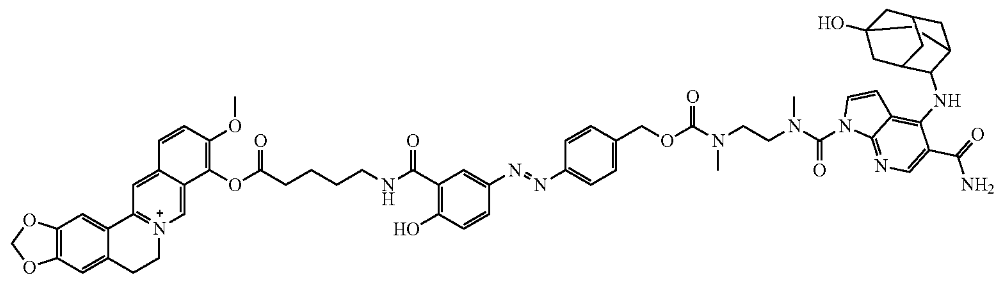 [SMILES: COc1ccc2cc3[n+](cc2c1OC(=O)CCCCNC(=O)c1cc(/N=N/c2ccc(COC(=O)N(C)CCN(C)C(=O)n4ccc5c(NC6C7CC8CC6CC(O)(C8)C7)c(C(N)=O)cnc54)cc2)ccc1O)CCc1cc2c(cc1-3)OCO2] |
| 16 | 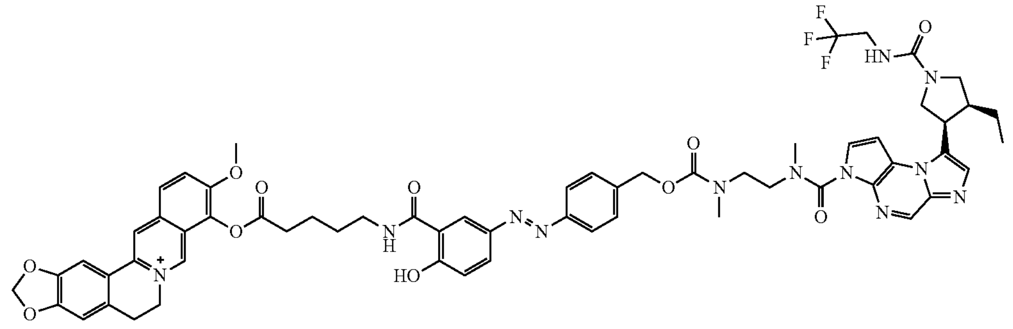 [SMILES: CC[C@@H]1CN(C(=O)NCC(F)(F)F)C[C@@H]1c1cnc2cnc3c(ccn3C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)n12] |
| 17 | 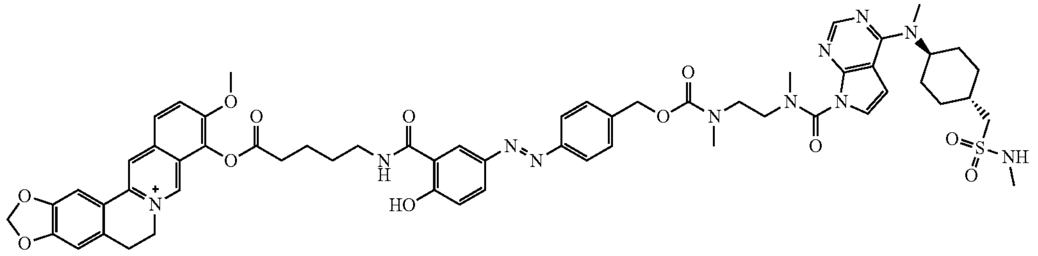 [SMILES: CNS(=O)(=O)C[C@H]1CC[C@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)CC1] |
| 18 | 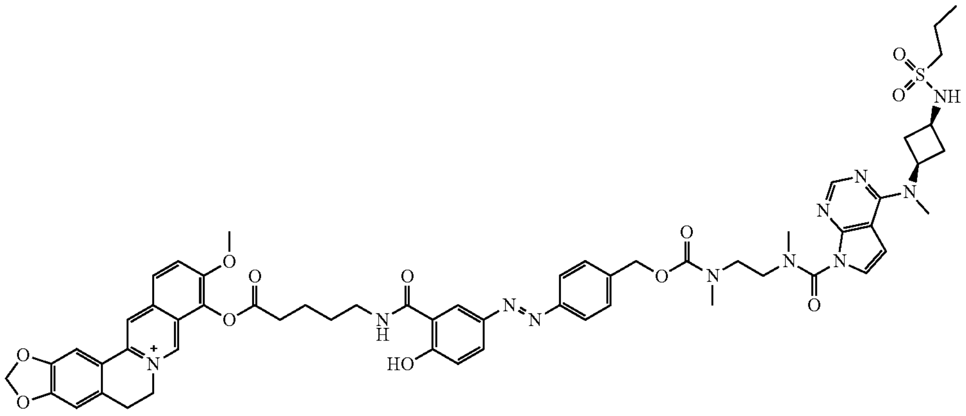 [SMILES: CCCS(=O)(=O)N[C@H]1C[C@@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)C1] |

In the second aspect of the present invention, a pharmaceutical composition is provided, comprising a therapeutically effective amount of a compound according to the first aspect of the present invention, or a stereoisomer, a racemate, or a pharmaceutically acceptable salt thereof, and pharmaceutically acceptable excipients.

In another preferred embodiment, the pharmaceutical composition is an enteric-coated preparation.

In another preferred embodiment, the pharmaceutical composition is used for the treatment of a disease selected from the group consisting of gastrointestinal inflammatory diseases (such as ulcerative colitis, Crohn's disease, colitis associated with immune checkpoint inhibitor therapy, collagenous colitis, lymphocytic colitis, pouchitis, acute/chronic gastritis, acute/chronic appendicitis), gastroenteritis caused by radiotherapy or chemotherapy, gastrointestinal autoimmune diseases (e.g., graft-versus-host disease, celiac sprue, autoimmune bowel disease), peptic ulcer, irritable bowel syndrome, gastric cancer, esophageal cancer and colon cancer.

In the third aspect of the present invention, the use of the compound or the pharmaceutically acceptable salts as described in the first aspect of the present invention, or the pharmaceutical composition described in the second aspect of the invention for the prevention and treatment of gastrointestinal functional disorders is provided.

In another preferred embodiment, the gastrointestinal functional disorders are gastrointestinal inflammatory diseases.

In another preferred embodiment, the gastrointestinal inflammatory disease is selected from the group consisting of ulcerative colitis, Crohn's disease, and colitis associated with immune checkpoint inhibitor therapy.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
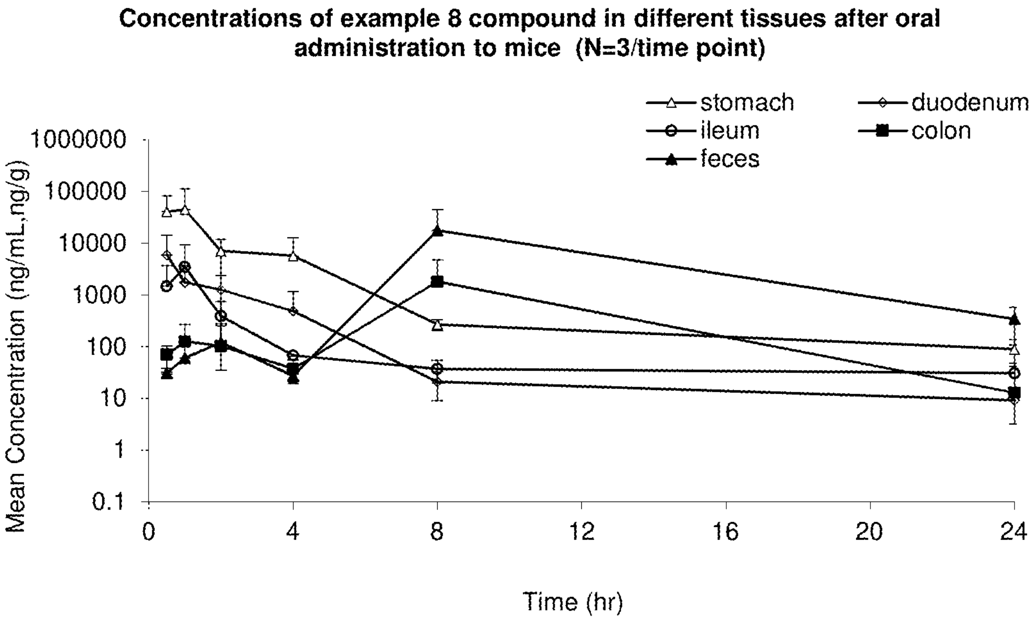
FIG. 1 shows the curve of the concentration of compound 8 vs time in different tissues after the mice were orally administered with compound of example 8.
Figure 2:
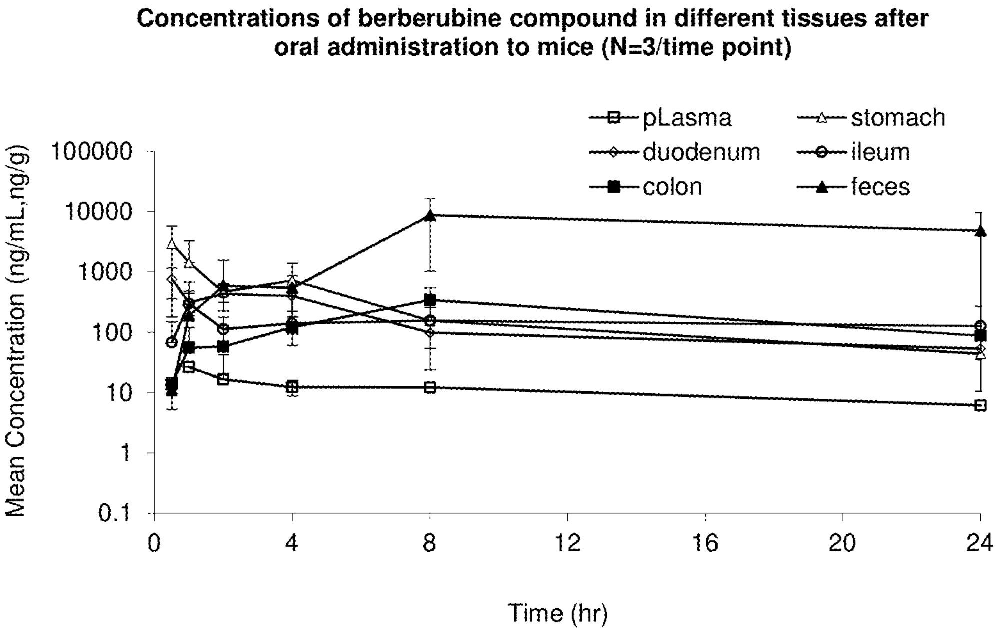
FIG. 2 shows the curve of the concentration of berberrubine vs time in different tissues after the mice orally administered with compound of example 8.
Figure 3:
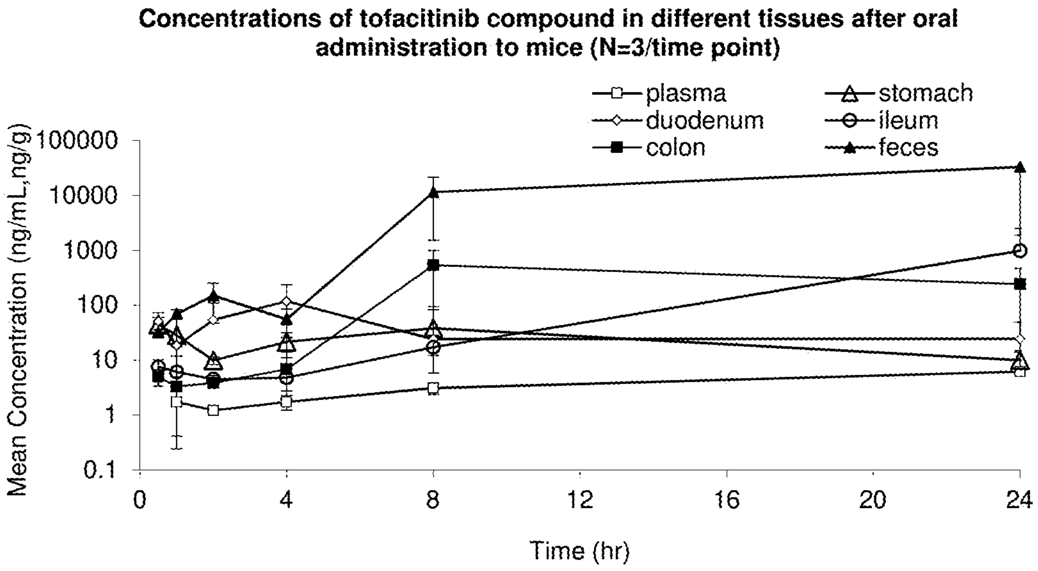
FIG. 3 shows the curve of the concentration of tofacitinib vs time in different tissues after the mice were orally administered with compound of example 8.
Figure 4:
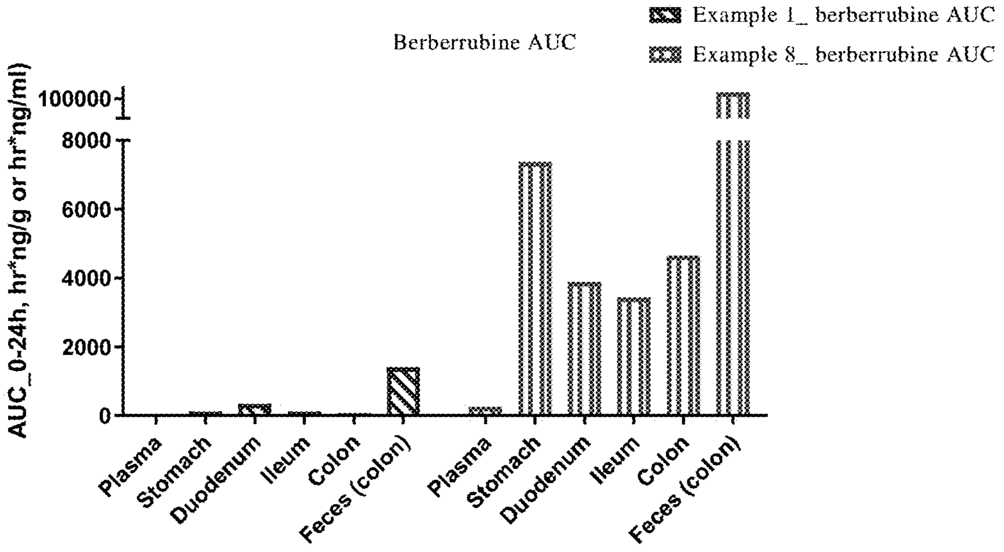
FIG. 4 shows the $AUC_{0\text{-}24\ h}$ of berberrubine in different tissues after the mice were orally administered with compounds of example 1 and 8.
Figure 5:
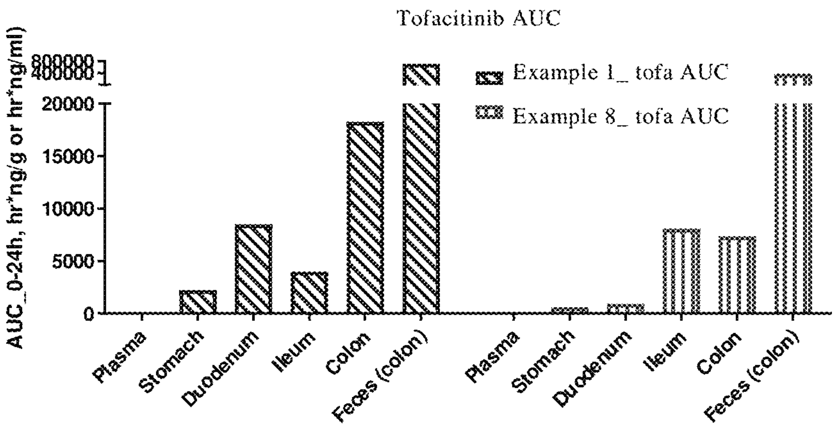
FIG. 5 shows the $AUC_{0\text{-}24\ h}$ of tofacitinib in different tissues after the mice were orally administered with compound of example 1 and 8.

Through long-term and in-depth research, the inventor found that when the JAK family inhibitor and berberine analogs were prepared into a codrug for administration, better effects would be achieved in the treatment of gastrointestinal diseases compared with single doses using the same amount. Moreover, the design of codrug molecules can lead to site-directed local release of the drugs. The present invention is completed on this basis.

Terms

Unless otherwise defined, all technical and scientific terms used herein have the same meaning as commonly understood by one of ordinary skill in the art to which this invention belongs.

As used herein, the terms "containing" or "including (comprising)" may be an open-ended form, semi-close ended form, or close ended form. In other words, the terms also include situations such as "essentially consisting of . . . " or "consisting of . . . ."

In the present application, as a group or part of another group, the term "alkyl" means a fully saturated straight or branched hydrocarbon chain group which consists only of carbon atoms and hydrogen atoms, and has, for example, 1 to 12 (preferably 1 to 8, more preferably 1 to 6) carbon atoms, and is bonded to the rest of the molecule by a single bond, for example, including but not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, decyl and decyl. For the present invention, the term "$C_1$-$C_6$ alkyl" refers to an alkyl containing from 1 to 6 carbon atoms.

In this application, as a group or part of another group, the term "6-10 membered aromatic ring" means an aromatic ring having 6-10 carbon ring atoms. The aromatic ring may be monocyclic or bicyclic, for example, benzene ring, naphthalene ring, or the like.

In the present application, as part of a group or other group, the term "5-10 membered heteroaryl" means a hetero aromatic ring having 5-10 ring members, and at least 1 (which may be 1, 2 or 3) ring atom is a heteroatom selected from nitrogen, oxygen and sulfur. The heteroaryl may be monocyclic or bicyclic, for example, pyrimidopyrazole ring, pyrazinoimidazole ring, pyridopyrazole ring, pyridoimidazole ring, pyridopyrimidine ring, and pyridopyridine ring.

In the present application, as a group or part of another group, the term "heterocyclyl" means a stable 3- to 20-membered non-aromatic cyclic group consisted of 3 to 14 carbon atoms and 1 to 6 heteroatoms selected from the group consisting of nitrogen, phosphorus, oxygen and sulfur. Unless otherwise specifically indicated in the specification, a heterocyclic group may be a ring system with monocyclic, bicyclic, tricyclic or ever more rings, which may include fused ring system, bridged ring system or spiro ring system; the nitrogen, carbon or sulfur atom may optionally be oxidized; the nitrogen atom may optionally be quaternized; and the heterocyclic group may be partially or fully saturated. The heterocyclic group may be bonded to the rest part of the molecule via a carbon atom or a hetero atom through a single bond. In the heterocyclic group containing a fused ring, one or more of the rings may be aryl or heteroaryl group as defined hereinafter, provided that the point of attachment to the rest part of the molecule is a non-aromatic ring atom. For the purpose of the present invention, the heterocyclic group is preferably a stable 4 to 11 membered non-aromatic single ring containing 1 to 3 heteroatoms selected from nitrogen, oxygen or sulfur.

Codrug

In the present application, "codrug", "co-loaded drug" or "interactive drug" can be used interchangeably to refer to a drug molecule which can be metabolized in vivo and form two pharmaceutical molecules with different pharmacological effects. In the present application, a typical codrug is the compound shown in formula I.

The codrugs can be metabolized in vivo and form a variety of different therapeutic agents. In the present invention, a preferred first therapeutic agent is berberine or analogs thereof, and the second therapeutic agent is the JAK family inhibitor.

First Drug Molecule

In the present application, the "first therapeutic agent" and "first drug molecule" can be used interchangeably, both of which refer to the first drug molecule which can be used in the codrug of the invention. The first drug molecule can form a first drug group and link to the connecting site of the codrug molecule after losing any reactive functional group in the molecule.

In the present invention, berberine or analogs thereof can be used as the first treatment agent of codrug. Preferred first drug molecules are shown in the following types of II, III, or IV.

formula II

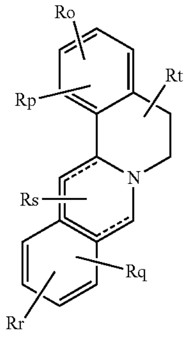

formula III

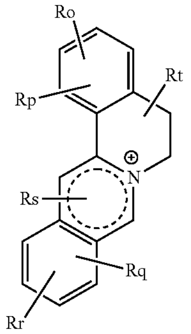

formula IV

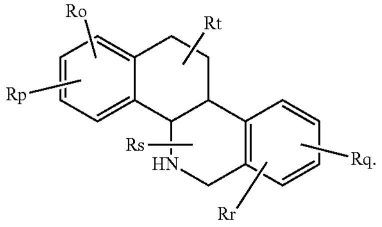

Second Drug Molecule

As used herein, the "second therapeutic agent" and "second drug molecule" can be used interchangeably, which both refer to the second drug molecule which can be used in the codrug of the invention. The second drug molecule can form a second drug group and link to the connecting site of the codrug molecule after losing any hydrogen atom in the molecule.

A preferred second drug molecule is JAK family inhibitors, which can be used for the treatment of intestinal diseases in clinical practice, such as intestinal inflammatory diseases. The JAK family inhibitor can be a JAK inhibitor known in the art, or compound that has not been validated for JAK inhibitory activity. The exemplary second drug group formed by a JAK inhibitor is selected from the group consisting of:

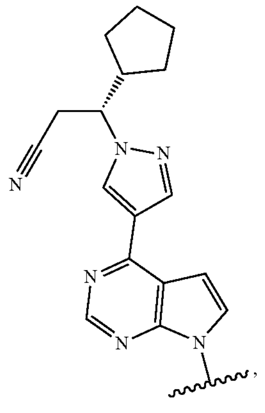

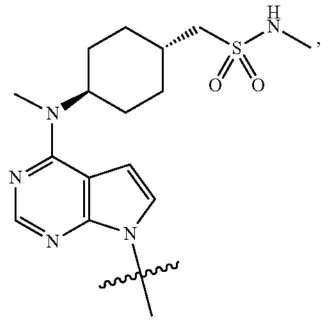

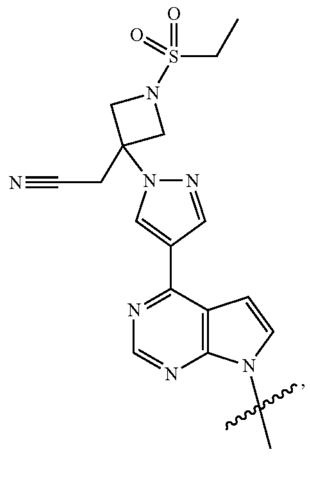

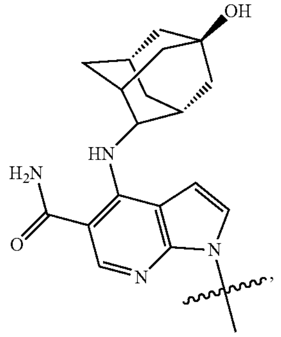

-continued
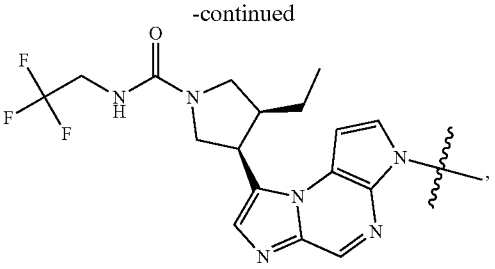
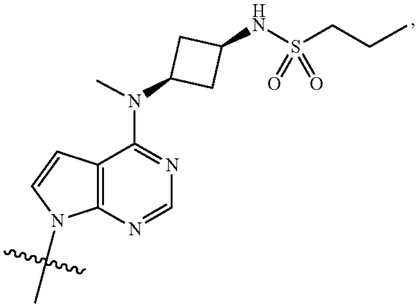
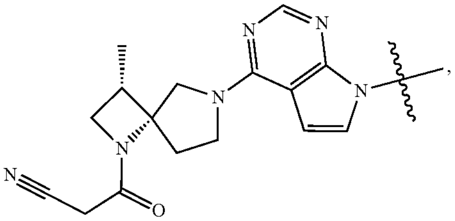
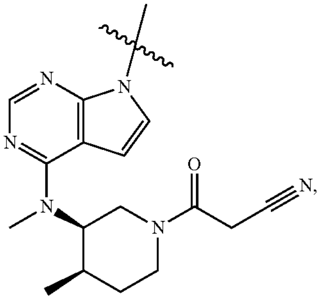
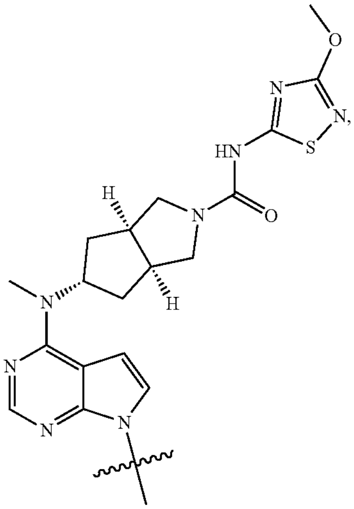
-continued
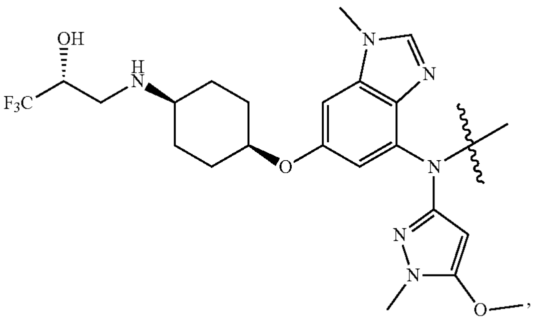
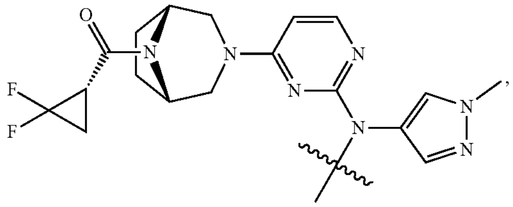
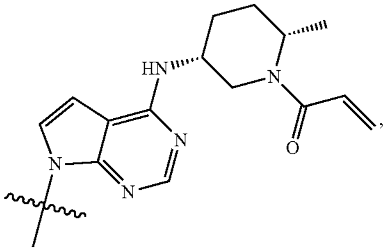
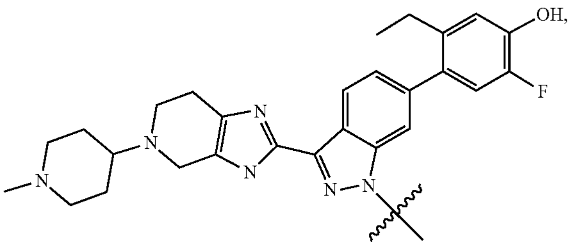
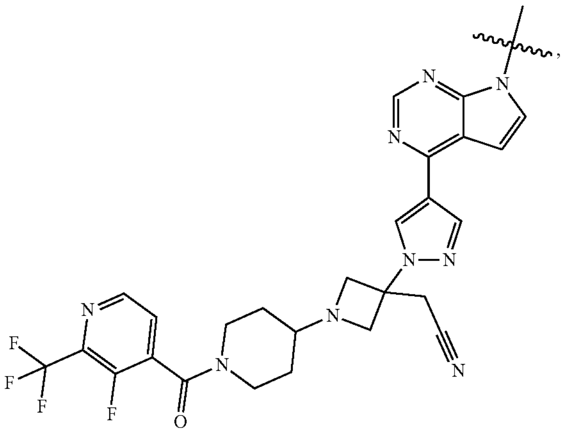

-continued

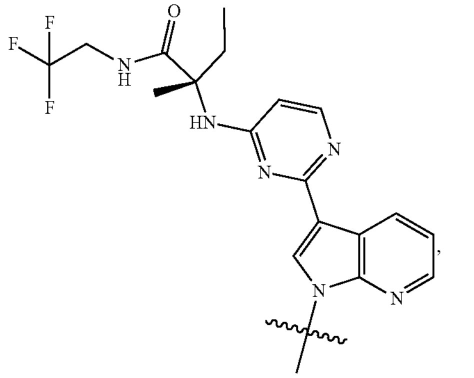

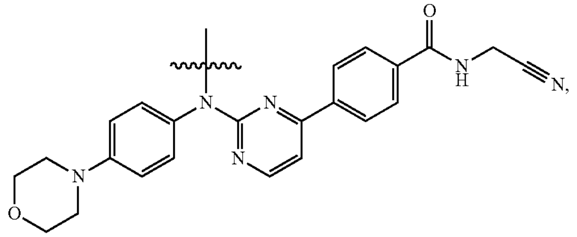

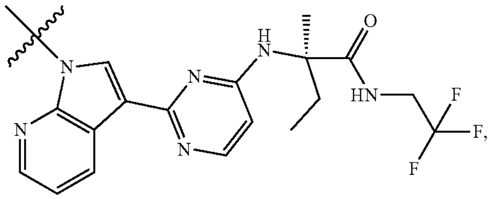

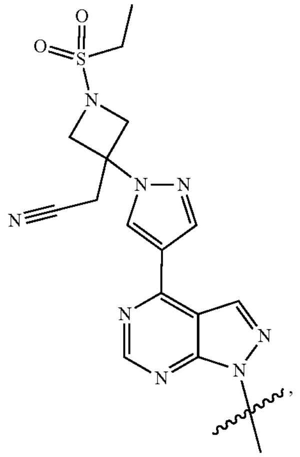

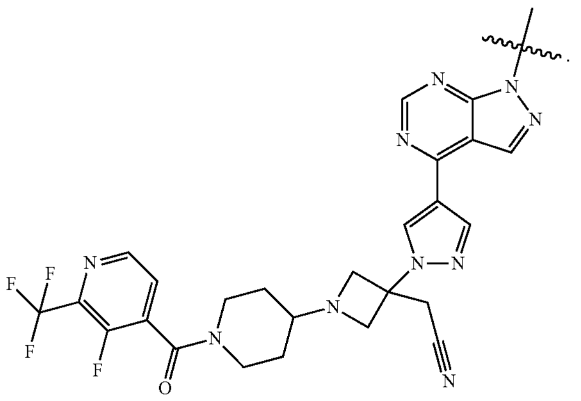

The Compound of the Present Invention

The compound of the present invention is a compound shown in the formula I, or stereoisomers or racemates thereof, or pharmaceutically acceptable salts thereof.

The compounds of the invention may contain one or more chiral carbon atoms and, thus, may produce enantiomers, diastereomers, and other stereoisomeric forms. Each chiral carbon atom can be defined as (R)- or (S)-based on stereochemistry. The invention is intended to include all possible isomers, as well as racemic and optically pure forms thereof. Racemates, diastereomers or enantiomers may employ as starting materials or intermediates for the preparation of the compounds of the invention. Optically active isomers can be prepared by chiral synthons or chiral reagents, or resolved using conventional techniques, such as by crystallization and chiral chromatography.

Conventional techniques for the preparation/isolation of individual isomers include chiral synthesis from a suitable optically pure precursor, or resolution of the racemate (or racemic form of a salt or derivative) using, for example, chiral high performance liquid chromatography. For example, see Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

The term "pharmaceutically acceptable salt" includes pharmaceutically acceptable acid addition salts and pharmaceutically acceptable base addition salts.

"Pharmaceutically acceptable acid addition salt" means a salt formed with an inorganic or organic acid capable of maintaining the bioavailability of the free base without other side effects. Inorganic acid salts include, but are not limited to, hydrochlorides, hydrobromides, sulfates, nitrates, phosphates, and the like; and organic acid salts include, but are not limited to, formate, acetate, 2,2-dichloroacetate, trifluoroacetate, propionate, hexanoate, octoate, decanoate, undecylenate, glycolate, gluconate, lactate, sebacate, adipates, glutaric acid salts, malonates, oxalates, maleates, succinates, fumarates, tartrates, citrates, palmitates, stearates, oleates, cinnamate, laurate, malate, glutamate, pyroglutamate, aspartate, benzoate, methanesulfonate, besylate, p-toluenesulfonate, alginate, ascorbate, salicylate, 4-aminosalicylate, naphthalene disulfonate, and the like. These salts can be prepared by methods known in the art.

"Pharmaceutically acceptable base addition salt" means a salt formed with an inorganic or organic base capable of maintaining the bioavailability of the free acid without other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium, sodium, potassium, calcium and magnesium salts. Salts derived from organic bases include, but are not limited to, the following salts: primary amines, secondary amines and tertiary amines, substituted amines, including naturally substituted amines, cyclic amines, and basic ion exchange resins. For example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline, and caffeine. These salts can be prepared by methods known in the art.

Preparation Method

The following reaction scheme exemplarily illustrates a method for preparing a compound of formula I, a stereoisomer, or racemate thereof, or a pharmaceutically acceptable salt thereof, wherein each group is as described in the above. It should be understood that in the following reaction schemes, combinations of substituents and/or variables in the general formula are only permissible if such combinations result in stable compounds. It should also be understood that other general formulas can be prepared by those skilled in the art of organic chemistry through the methods disclosed herein (by applying appropriately substituted starting materials and modifying the synthesis parameters corresponding to the need) or methods known by those skilled in the art.

In various aspects and embodiments, the present invention involves tofacitinib glucuronide or a pharmaceutical acceptable salt thereof; pharmaceutical compositions comprising such compounds; methods of using such compounds in the treatment of gastrointestinal inflammatory diseases; and methods and intermediates for the preparation of such compounds.

The compounds described herein may contain one or more chiral centers. In such cases, the depiction or designation of a particular stereoisomer means that the indicated stereocenter has the indicated stereochemistry. It should be understood that, unless otherwise specified, minor amount of other stereoisomers may also present, as far as the utility of the depicted or named compound is not eliminated by the presence of another stereoisomer.

In addition, as used herein, unless otherwise specified, the terms including "the compound of the present invention" and the "formula I compound" (or similar terms) are also intended to include pharmaceutically acceptable salts.

Application

Since the codrug of the present invention has an excellent intestine-targeted release effect, the compound of the present invention and its various crystal forms, pharmaceutically acceptable inorganic or organic salts, hydrates or solvates, and a pharmaceutical composition containing the compound of the invention as the main active ingredient can be used for the prevention and/or treatment of intestinal functional diseases, preferably inflammatory diseases of the gastrointestinal tract.

In the present application, terms "pharmaceutical composition" refers to a formulation of a compound of the invention and a medium generally accepted in the art for the delivery of a biologically active compound to a mammal, such as a human. The medium comprises pharmaceutically acceptable carriers. The purpose of the pharmaceutical composition is to promote the administration to an organism, thus facilitating the absorption of the active ingredients and thereby exerting the biological activity.

The term "pharmaceutically acceptable" as used herein, refers to a substance (such as a carrier or diluent) that does not affect the biological activities or properties of the compound of the invention, and is relatively non-toxic, i.e., the substance can be administered to an individual without causing undesirable biological reactions, or interacting with any of the components contained in the composition in an undesirable manner.

"Pharmaceutically acceptable excipients" as used herein include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant government authorities for acceptable use in humans or domestic animals.

The "tumor" of the present invention includes, but is not limited to, glioma, sarcoma, melanoma, articular chondrocarcinoma, cholangiocarcinoma, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanin tumor, kidney cancer, oral cancer and other diseases.

"Prevention", "preventing" and "prevented" as used herein include reducing the possibility of the occurrence or progression of a disease or condition in a patient.

The term "treatment" and other similar synonyms as used herein includes the following meanings:

(i) preventing the occurrence of a disease or condition in a mammal, particularly when such a mammal is susceptible to the disease or condition, but has not been diagnosed as having the disease or condition;

(ii) inhibiting a disease or condition, i.e., inhibiting its development;

(iii) alleviating the disease or condition, i.e., degrading the condition of the disease or illness; or (iv) alleviating the symptoms caused by the disease or condition.

The term "effective amount", "therapeutically effective amount", or "pharmaceutically effective amount" as used herein, refers to an amount of at least one agent or compound that, after administration, is sufficient to alleviate one or more symptoms of the disease or condition being treated to some extent. The result can be the reduction and/or alleviation of signs, symptoms or causes, or any other desired changes in the biological system. For example, an "effective amount" for the treatment is an amount of a composition comprising a compound disclosed herein that is required to provide significant condition-relieving effects in clinic. An effective amount suitable for any individual case can be determined using techniques such as dose escalation testing.

The terms "take", "administrate", "apply" and the like as used herein refers to a method of delivering a compound or composition to a desired site for biological action. These methods include, but are not limited to, oral, duodenal, parenteral injection (including intravenous, subcutaneous, intraperitoneal, intramuscular, intraarterial injection or infusion), topical administration, and rectal administration. The techniques of administration of the compounds and methods described herein are well known to those skilled in the art, for example, those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

The terms "pharmaceutical combination", "drug combination", "combination", "administering other treatments", "administering other therapeutic agents" and the like as used herein, refer to a pharmaceutical treatment obtained by mixing or combining more than one active ingredient, which includes both fixed and unfixed combinations of active ingredients.

The term "fixed combination" refers to simultaneously administrating at least one compound described herein and at least one synergistic agent to a patient in the form of a single entity or a single dosage form. The term "unfixed combination" refers to simultaneous administrating, administrating in combination or sequentially administrating in variable interval time at least one of the compounds described herein and at least one synergistic formulation to a patient in the form of separate entities. These can also be applied to cocktail therapy, for example, administrating three or more active ingredients.

Compared with the Prior Art, the Main Advantages of the Present Invention are 1. The codrug compound of the present invention themselves is gut-restricted and cannot be effectively absorbed. It releases two pharmaceutical components in the targeted intestine segments so as to enrich the effective ingredients in the gastrointestinal tract for therapy and reduce the systemic drug exposure.
2. The compounds of the present invention can effectively release the JAK inhibitor (such as Tofacitinib) and berberrubine or its analogs so as to synergistically treat gastrointestinal autoimmune inflammatory diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless otherwise specified, parts and percentage are calculated by weight.

EXAMPLES

In each examples:

Analytic Method I

LCMS instrument: Waters Acquity UPLC-MS, UV detector: Acquity UPLC

Column: Acquity UPLC HSS T3 1.8 UM, column temperature 40° C.

mobile phases: A: $H_2O$ (0.1% TFA), B: acetonitrile, gradient elution

Intermediate A: (10-methoxy-9-((methyl(2-(methyl(((10-oxo-10-((5-(4,7,10,10-tetramethyl-3,8-dioxo-2,9-dioxa-4,7-diazaundecyl)-2-(((2S,3R,4S,5S,6S)-3,4,5-triacetoxy-6-(methoxycarbonyl)tetrahydro-2H-pyran-2-yl)oxy)phenyl)amino)decyl)oxy)carbonyl)amino)ethyl)carbamoyl)oxy)-5,6-dihydro-[1,3]dioxolo[4,5-g]isoquinolino[3,2-a]isoquinolin-7-ium) was Prepared According to the Procedure Shown in the Following Scheme

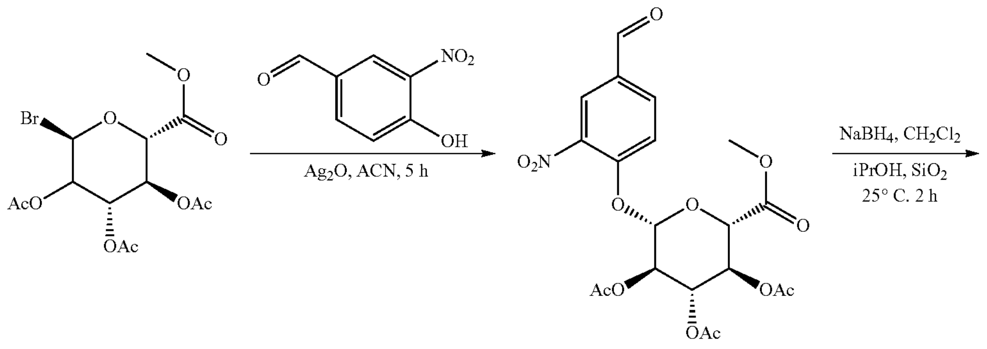

A-1

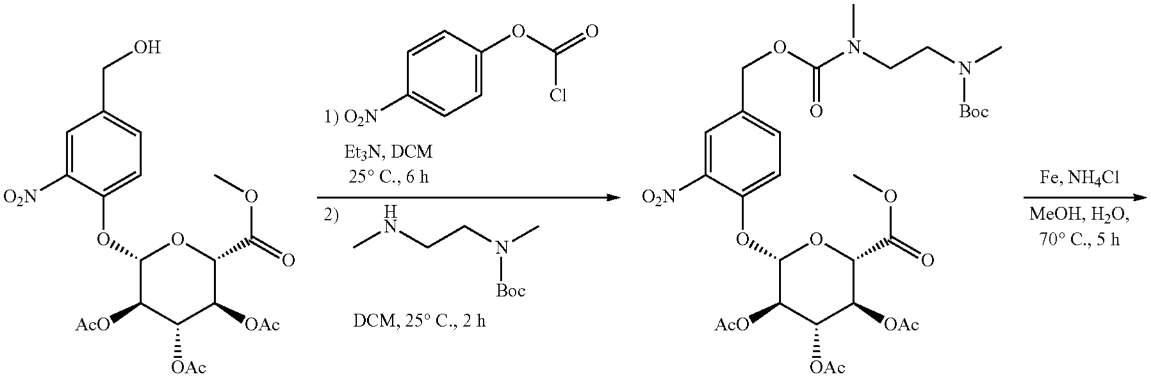

A-2

A-3

-continued
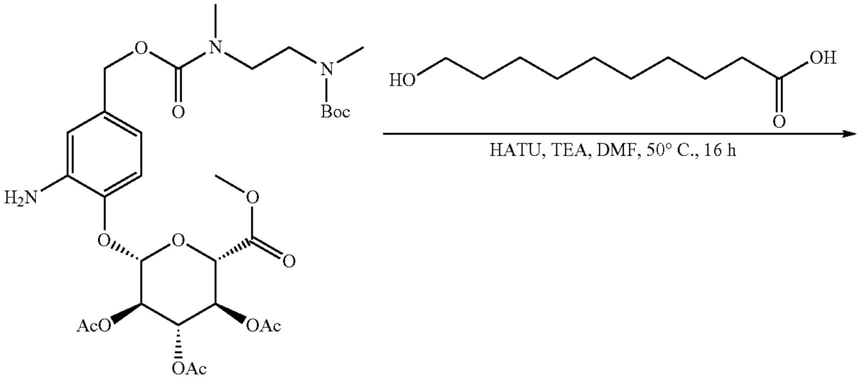
A-4
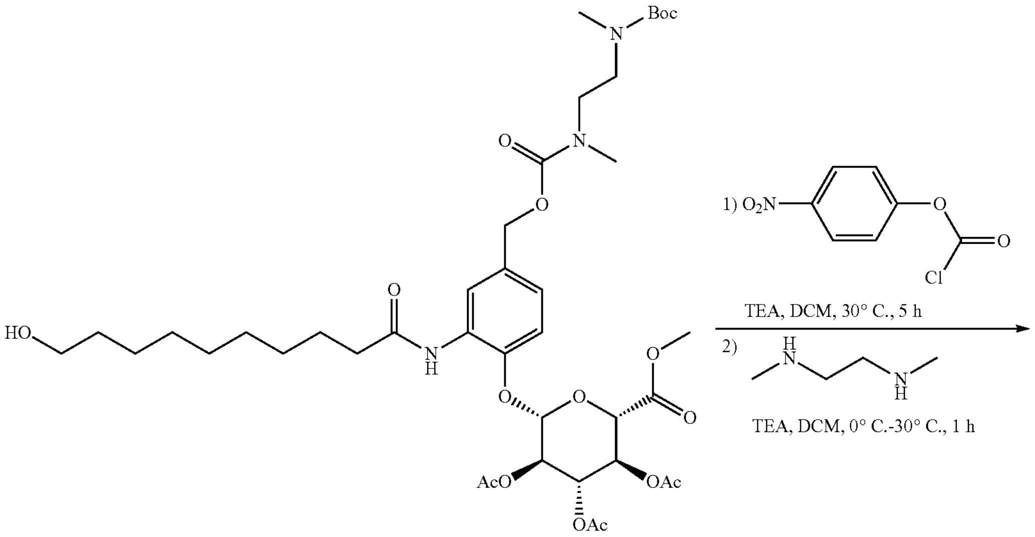
A-5
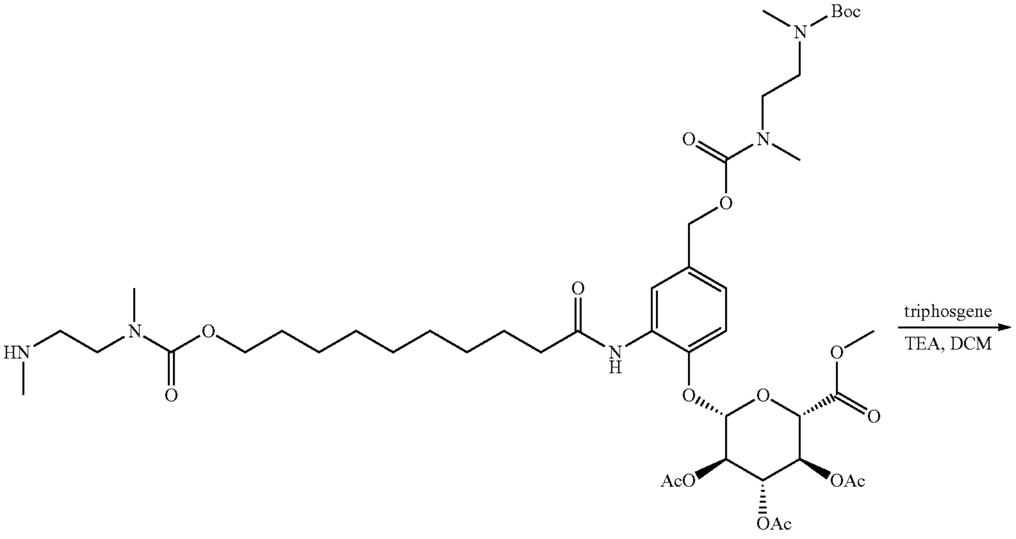
A-6

-continued
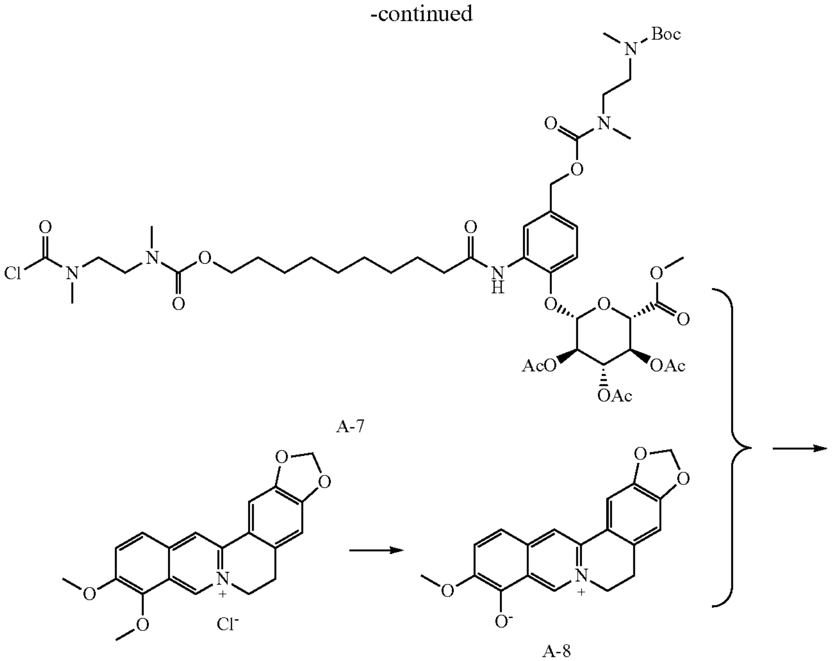
A-7
A-8
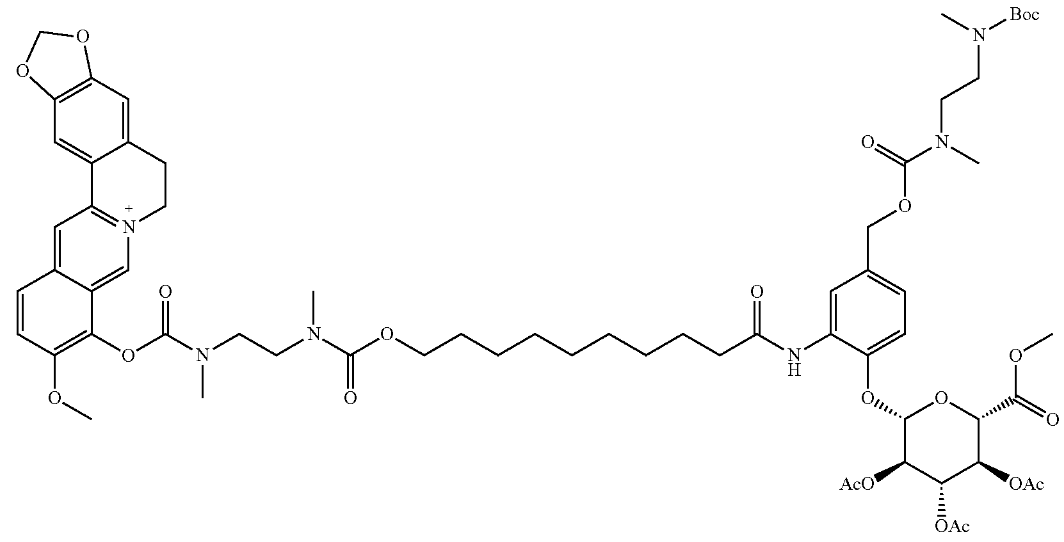
A

Intermediate A-1: (2S,3R,4S,5S,6S)-2-(4-formyl-2-nitrophenoxy)-6-(methoxycarbonyl)tetrahydro-2H-pyran-3,4,5-triyl triacetate

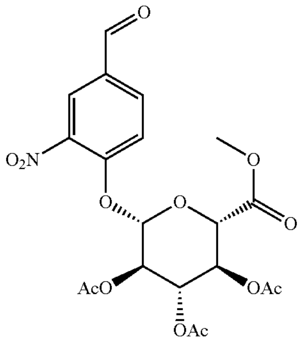 [SMILES: COC(=O)[C@H]1O[C@@H](Oc2ccc(C=O)cc2[N+](=O)[O-])[C@H](OC(C)=O)[C@@H](OC(C)=O)[C@@H]1OC(C)=O]

(2R,3R,4S,5S,6S)-2-bromo-6-(methoxycarbonyl)tetrahydro-2H-pyran-3,4,5-triyl triacetate (300 g, 755 mmol), 4-hydroxyl-3-nitrobenzaldehyde (214.6 g, 1284 mmol) and silver oxide (788 g, 3400 mmol) were added into 4 L of acetonitrile. The mixture was stirred at 25-30° C. for 5 h under light-protected conditions. LCMS indicated that starting materials were completely consumed. The reaction mixture was filtered, and the resulting filtrate was concentrated under reduced pressure to provide a crude product. The crude product was dissolved with ethyl acetate, filtered out the insoluble substance, and the resulting filtrate was washed with saturated sodium bicarbonate aqueous solution and saturated brine successively. The organic phase was separated and was dried over anhydrous sodium sulfate. Organic phase was concentrated under reduced pressure to provide the title compound (295 g, 81%) as a yellow solid.

MS (ESI): m/z=506.1 $[M+Na]^+$.

Intermediate A-2: (2S,3R,4S,5S,6S)-2-(4-(hydroxymethyl)-2-nitrophenoxy)-6-(methoxycarbonyl)tetrahydro-2H-pyran-3,4,5-triyl triacetate

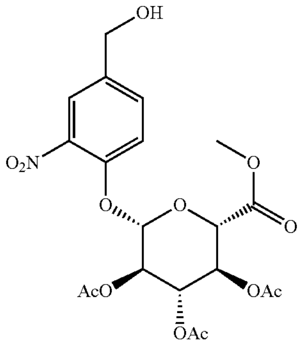 [SMILES: COC(=O)[C@H]1O[C@@H](Oc2ccc(CO)cc2[N+](=O)[O-])[C@H](OC(C)=O)[C@@H](OC(C)=O)[C@@H]1OC(C)=O]

Intermediate A-1 (46.5 g, 96 mmol) and 19 g of silica gel were added into the mixture of dichloromethane (450 mL) and isopropyl (90 mL). The reaction was cooled to 0° C., and 5.5 g of sodium borohydride was added slowly. The reaction mixture was stirred at 0° C. for 2 h. LCMS indicated that starting materials were completely consumed. The reaction mixture was filtered, and saturated ammonium chloride solution (200 ml) was added to the resulting filtrate. After separation, the organic phase was washed twice with saturated brine (300 ml) and dried over anhydrous sodium sulfate. And then it was concentrated under reduced pressure to give the crude product. The crude product was triturated in MTBE to give the title compound (340 g, 72.9%) as a white solid.

MS (ESI): m/z=508.1 $[M+Na]^+$.

Intermediate A-3: (2S,3S,4S,5R,6S)-2-(methoxycarbonyl)-6-(2-nitro-4-(4,7,10,10-tetramethyl-3,8-dioxo-2,9-dioxa-4,7-diazaundecyl)phenoxy)tetrahydro-2H-pyran-3,4,5-triyl triacetate

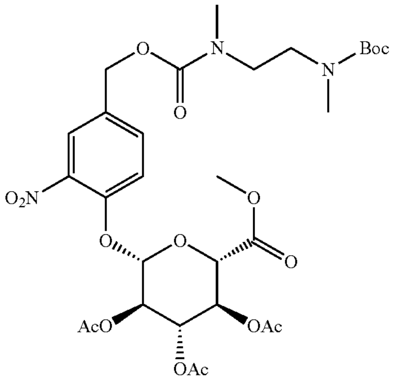 [SMILES: COC(=O)[C@H]1O[C@@H](Oc2ccc(COC(=O)N(C)CCN(C)C(=O)OC(C)(C)C)cc2[N+](=O)[O-])[C@H](OC(C)=O)[C@@H](OC(C)=O)[C@@H]1OC(C)=O]

Intermediate A-2 (150 g, 310 mmol), and triethylamine (62.4 g, 620 mmol) were added into 1.5 L of dichloromethane. 4-nitrophenyl carbonochloridate (71.6 g, 350 mmol) was dissolved in 300 ml of dichloromethane, and added dropwise to the reaction mixture under nitrogen protection at 0° C. After addition, the reaction mixture was stirred at 25° C. for 6 h. LCMS indicated that starting materials were completely consumed. The tert-butylmethyl(2-(methylamino)ethyl)carbamate (75.8 g, 400 mmol) was added dropwise to the reaction mixture at 0° C. After addition, the reaction mixture was stirred at 25° C. for 16 h. LCMS indicated that starting materials were completely consumed. The reaction mixture was cooled to 0° C., 1 L of saturated sodium bicarbonate aqueous solution was added, and the organic phase was collected by separation. The organic phase was washed with saturated sodium carbonate aqueous solution (800 ml*8) and saturated brine (800 ml), dried over sodium sulfate and filtered. The organic phase was concentrated under reduced pressure to provide the target compound (200 g, 92%).

MS (ESI): m/z=722.2 $[M+Na]^+$.

Intermediate A-4: (2S,3R,4S,5S,6S)-2-(2-amino-4-(4,7,10,10-tetramethyl-3,8-dioxo-2,9-dioxa-4,7-diazaundecyl)phenoxy)-6-(methoxycarbonyl)tetrahydro-2H-pyran-3,4,5-triyl triacetate

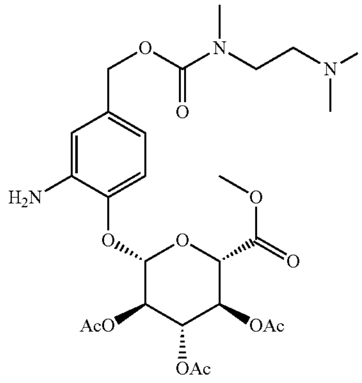

Intermediate A-3 (200 g, 285.8 mmol) was dissolved in 2 L of methanol and 550 ml of water, and the iron powder (80 g, 1429.1 mmol) and ammonium chloride (153 g, 2858.1 mmol) were added slowly. The reaction mixture was stirred at 70° C. for 5 h under nitrogen protection. LCMS indicated that starting materials were completely consumed. The reaction mixture was filtered, and the filter cake was washed with 2 L of ethyl acetate. The organic phase in the filtrate was concentrated under reduced pressure to provide a crude product. The crude product was partitioned into 2 L of ethyl acetate and 1.5 L of water. The organic phase was separated and washed with saturated brine (500 mL*3). After separation, the organic phase was dried over anhydrous sodium sulfate and concentrated under reduced pressure to provide a crude product. The crude product was purified by silica gel column (dichloromethane:methanol=40:1) to obtain the target compound (100 g, 52%) as a yellow oil.

MS (ESI): m/z=670.2 $[M+H]^+$.

$^1$HNMR (400 MHz, DMSO-$d_6$) δ 6.83 (d, J 8.2 Hz, 1H), 6.66 (s, 1H), 6.50 (d, J 8.2 Hz, 1H), 5.52-5.43 (m, 2H), 5.12-5.03 (m, 2H), 4.86 (s, 2H), 4.68 (d, J 10.0 Hz, 3H), 3.64 (s, 3H), 3.31-3.25 (m, 3H), 2.79 (dd, J 38.7, 13.2 Hz, 7H), 2.02 (d, J 12.9 Hz, 9H), 1.36 (s, 9H).

Intermediate A-5: (2S,3R,4S,5S,6S)-2-(2-(10-hydroxydecanamido)-4-(4,7,10,10-tetramethyl-3,8-dioxo-2,9-dioxa-4,7-diazaundecyl)phenoxy)-6-(methoxycarbonyl)tetrahydro-2H-pyran-3,4,5-triyl triacetate

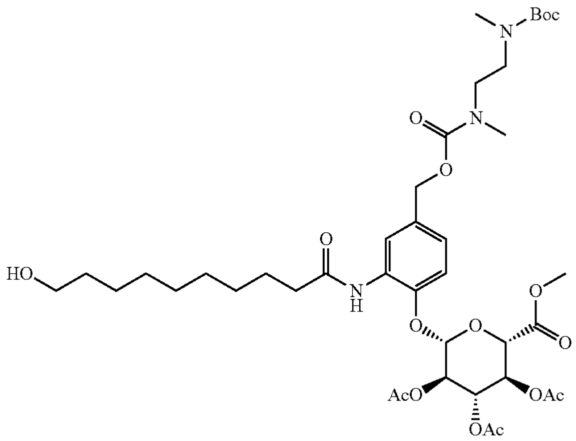 [SMILES: COC(=O)[C@H]1O[C@@H](Oc2ccc(COC(=O)N(C)CCN(C)C(=O)OC(C)(C)C)cc2NC(=O)CCCCCCCCCO)[C@H](OC(C)=O)[C@@H](OC(C)=O)[C@@H]1OC(C)=O]

To a mixture of Intermediate A-4 (100 g, 150 mmol) in N,N-dimethylformamide (600 mL), triethylamine (51.8 mL, 0.37 mmol) and the 10-hydroxydecanoic acid (39.3 g, 210 mmol) were added, and then 2-(7-azabenzotriazol-1-yl)-N,N,N',N'-tetramethyluronium hexafluorophosphate (79.5 g, 210 mmol) was slowly added. After addition, the reaction mixture was stirred at 50° C. for 16 h under the protection of nitrogen. The reaction was diluted with 2 L of ethyl acetate. The diluted reaction mixture was washed with water (1.5 L*8) and brine (1.5 L*2), dried over sodium sulfate, and concentrated to obtain a crude product. The crude product was purified by silica gel column (dichloromethane:methanol=20:1) to obtain the title compound (47.0 g, 37%) as a yellow oil.

MS (ESI): m/z=862.2 $[M+Na]^+$.

Intermediate A-6: (2S,3S,4S,5R,6S)-2-(methoxycarbonyl)-6-(2-(10-((methyl(2-(methylamino)ethyl)carbamoyl)oxy)decanamido)-4-(4,7,10,10-tetramethyl-3,8-dioxo-2,9-dioxa-4,7-diazaundecyl)phenoxy)tetrahydro-2H-pyran-3,4,5-triyl triacetate

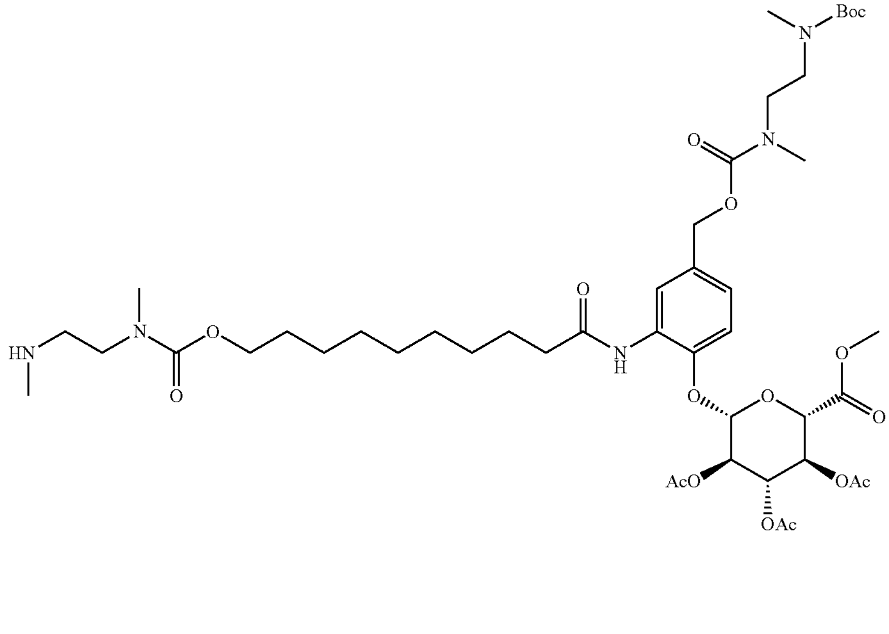 [SMILES: CNCCN(C)C(=O)OCCCCCCCCCC(=O)Nc1cc(COC(=O)N(C)CCN(C)C(=O)OC(C)(C)C)ccc1O[C@@H]1O[C@H](C(=O)OC)[C@@H](OC(C)=O)[C@H](OC(C)=O)[C@H]1OC(C)=O]

Intermediate A-5 (46.0 g, 57.7 mmol) and triethylamine (15.2 mL, 109.8 mmol) were dissolved in 400 mL of dichloromethane, and a solution of 4-nitrophenyl carbonochloridate (14.3 g, 71.2 mmol) in dichloromethane (60 mL) was added dropwise to the reaction mixture at 0° C. under nitrogen protection. After addition, the reaction mixture was stirred at 25-30° C. for 16 h. LCMS indicated that starting materials were consumed. Triethylamine (22.8 ml, 164.4 mmol) was added to the reaction mixture obtained from the previous step. Then N,N'-dimethylethylene-1,2-diamine (14.5 g, 164.4 mmol) was added dropwise to the reaction mixture obtained from the previous step at 0° C. under nitrogen protection. After addition, the mixture was stirred at 25-30° C. for 4 h. LCMS indicated that the reaction was completed, and the reaction mixture was diluted with dichloromethane (800 ml). The diluted organic phase was washed with saturated sodium bicarbonate aqueous solution (600 ml*3) and brine (700 ml), dried over sodium sulfate, and concentrated under reduced pressure to obtain a crude product. The crude product was purified by normal silica gel column chromatography (dichloromethane:methanol=10:1) to provide title compound (36.0 g, 68%) as a yellow oil.

MS (ESI): m/z=954.5 $[M+H]^+$.

Intermediate A-7: (2S,3R,4S,5S,6S)-2-(2-(10-(((2-((chlorocarbonyl)(methyl)amino)ethyl)(methyl)carbamoyl)oxy)decanamido)-4-(4,7,10,10-tetramethyl-3,8-dioxo-2,9-dioxa-4,7-diazaundecyl)phenoxy)-6-(methoxycarbonyl)tetrahydro-2H-pyran-3,4,5-triyl triacetate

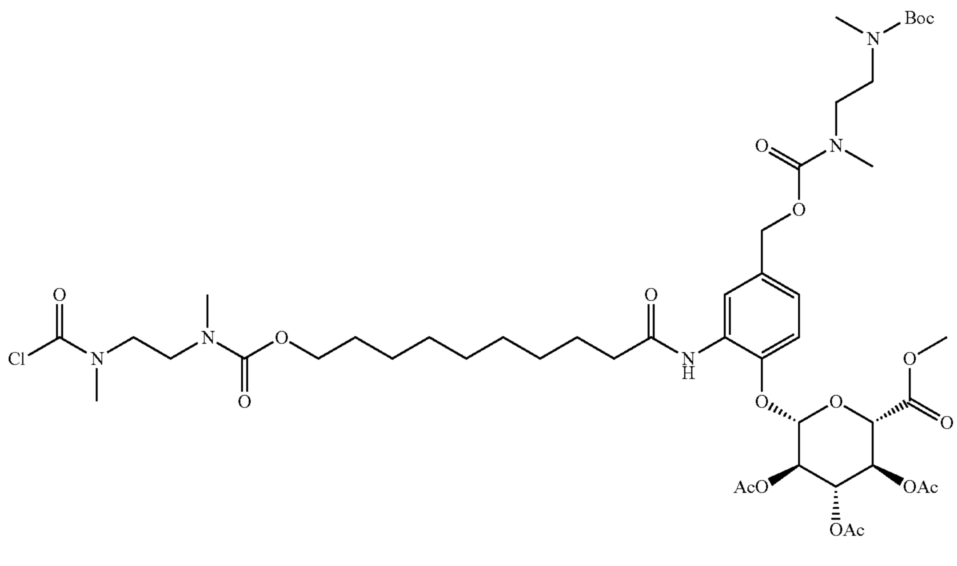 [SMILES: COC(=O)[C@H]1O[C@@H](Oc2ccc(COC(=O)N(C)CCN(C)C(=O)OC(C)(C)C)cc2NC(=O)CCCCCCCCCOC(=O)N(C)CCN(C)C(=O)Cl)[C@H](OC(C)=O)[C@@H](OC(C)=O)[C@@H]1OC(C)=O]

To a mixture of triphosgene (11.2 g, 37.7 mmol) in 100 mL dichloromethane in a three-necked flask, Intermediate A-6 (36.0 g, 37.7 mmol) in 300 mL dichloromethane was added dropwise at 0° C. under nitrogen protection. After addition, the reaction mixture was stirred at room temperature for 10 min, and then triethylamine (15.7 mL, 113.2 mmol) was added dropwise to the reaction mixture at 0° C. under nitrogen protection. After addition, the reaction mixture was stirred at 25-30° C. for 3 h. LCMS indicated that starting materials were completely consumed. The reaction mixture was cooled to 0° C., and quenched with saturated sodium bicarbonate aqueous solution (300 mL), the organic layer was separated. The organic phase was washed with saturated sodium carbonate aqueous solution (300 ml*2) and saturated brine (200 ml), and dried over sodium sulfate, and the target compound (46.0 g of crude product) was obtained by concentration under reduced pressure, and directly used for the next step without further purification.

MS (ESI): m/z=1038.3 $[M+Na]^+$.

Intermediate A-8: 10-methoxy-5,6-dihydro-[1,3]dioxolo[4,5-g]isoquinolino[3,2-a]isoquinolin-7-ium-9-olate

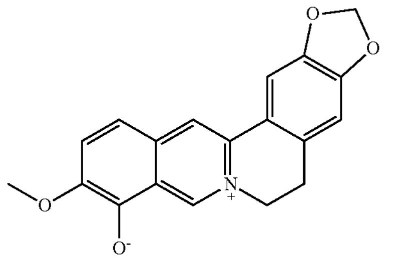

Berberine hydrochloride (35.0 g, 94.3 mmol) was added into a round bottom flask, and it was vacuumed by an oil pump then it was heated to 180° C. for 4 h. After cooling down to room temperature, the crude product was triturated in ethanol, filtered and the resulting cake was dried to give the title compound (23.0 g, 73%) as a red solid.

MS (ESI): m/z=322.1 $[M]^+$.

Intermediate A: 10-methoxy-9-((methyl(2-(methyl(((10-oxo-10-((5-(4,7,10,10-tetramethyl-3,8-dioxo-2,9-dioxa-4,7-diazaundecyl)-2-(((2S,3R,4S,5S,6S)-3,4,5-triacetoxy-6-(methoxycarbonyl)tetrahydro-2H-pyran-2-yl)oxy)phenyl)amino)decyl)oxy)carbonyl)amino)ethyl)carbamoyl)oxy)-5,6-dihydro-[1,3]dioxolo[4,5-g]isoquinolino[3,2-a]isoquinolin-7-ium

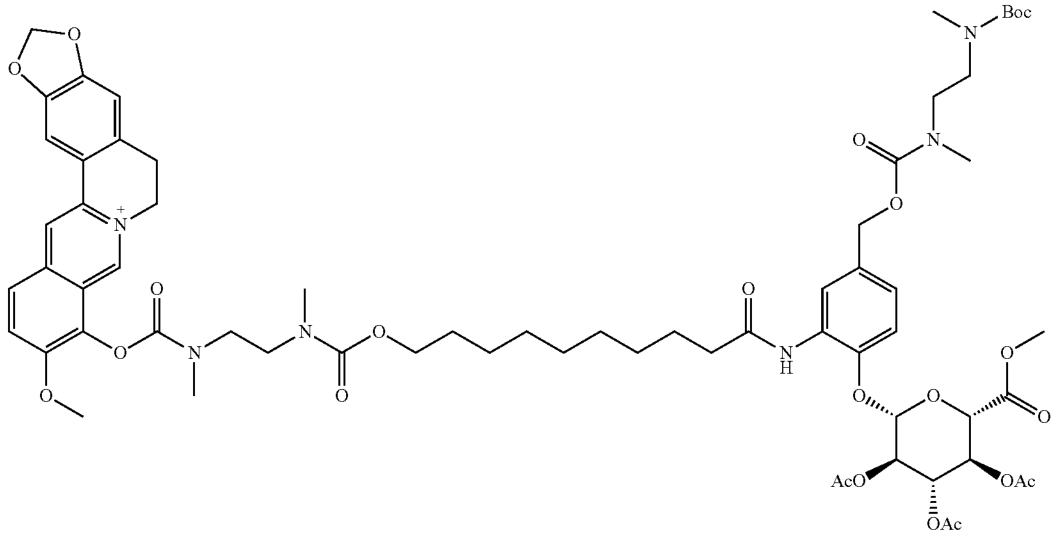

To a mixture of Intermediate A-8 (9.6 g, 30.0 mmol) in 100 mL of pyridine in a three-necked flask, Intermediate A-7 (46.0 g, 45.0 mmol) in 300 mL pyridine was added dropwise at 0° C. under nitrogen protection. The reaction mixture was stirred at 25° C. for 16 h. LCMS indicated that starting materials were consumed. The reaction mixture was concentrated, and the resulting residue was purified by the silica gel column (dichloromethane:methanol=10:1) to provide a crude product as a black solid. The crude product was purified by normal column chromatography (dichloromethane:methanol=3:2) to obtain the title compound (11.0 g, 22%).

MS (ESI): m/z=601.6 (M−100+H/2)+.

$^1$HNMR (400 MHz, $CDCl_3$) δ 11.24-10.55 (m, 1H), 8.45 (s, 2H), 7.83 (dd, J=35.6, 27.7 Hz, 3H), 7.42 (d, J=20.4 Hz, 1H), 7.21-6.74 (m, 3H), 6.27 (d, J=4.1 Hz, 0H), 6.08 (s, 2H), 5.78 (s, OH), 5.57-5.23 (m, 6H), 5.06 (d, J=11.4 Hz, 2H), 4.23-3.95 (m, 5H), 3.78 (d, J=18.4 Hz, 3H), 3.54-2.73 (m, 20H), 2.34 (t, J=23.9 Hz, 2H), 2.09 (dt, J=9.8, 4.0 Hz, 8H), 1.88-0.86 (m, 27H).

Intermediate B: 2-hydroxy-5-((4-(4,7,10,10-tetramethyl-3,8-dioxo-2,9-dioxa-4,7-diazaundecyl)phenyl)diazenyl) benzoic acid

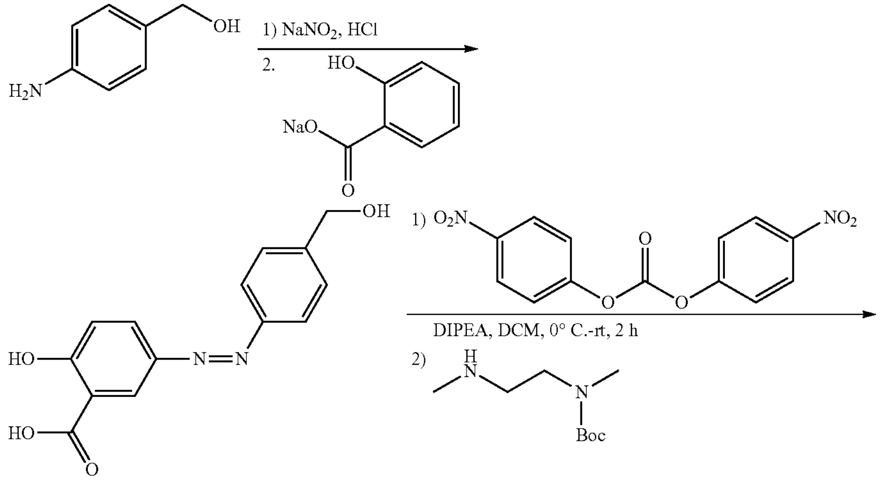

B-1

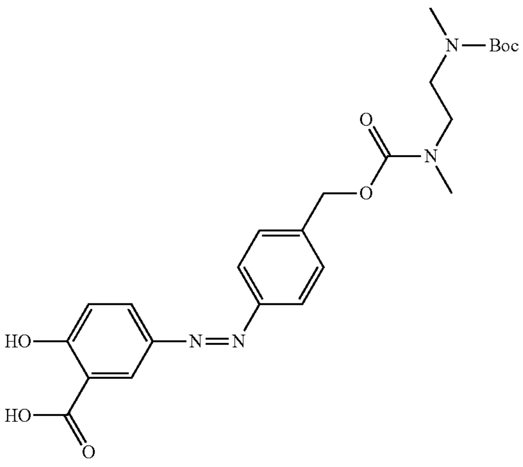

B

Intermediate B-1: 2-hydroxy-5-((4-(hydroxymethyl) phenyl)diazenyl)benzoic Acid

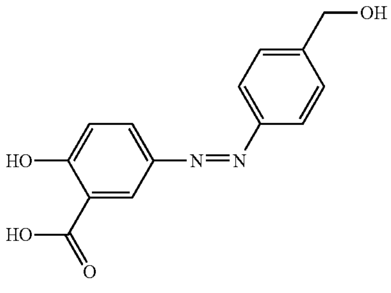 [SMILES: O=C(O)c1cc(N=Nc2ccc(CO)cc2)ccc1O]

A suspension of 4-aminobenzyl alcohol (2.0 g, 16.2 mmol) in water (30 mL) at 0° C. was treated with 3.4 mL of concentrated hydrochloric acid, then an ice-cold $NaNO_2$ aqueous solution was slowly added (1.2 g, 17.0 mmol, 8 mL). The mixture was stirred at 0° C. for another 1 h, the above reaction solution was added to an aqueous solution (25 mL) of sodium 2-hydroxybenzoate (2.72 g, 0.35 mmol) and potassium carbonate (3.2 g, 22.7 mmol). Throughout the dropwise addition, the pH of the reaction solution was maintained at 13-14 by adding sodium hydroxide aqueous dropwise. The mixture was stirred at room temperature for 1 h. The pH was adjusted to 4-5 with hydrochloric acid (2 N) and the product was precipitated, filtered and the cake was washed with water (50 mL). The resulting cake was dried under vacuum to give the title compound (4.0 g, 90%) as a red solid.

MS (ESI): m/z=272.8 $[M+H]^+$.

Intermediate B: 2-hydroxy-5-((4-(4,7,10,10-tetramethyl-3,8-dioxo-2,9-dioxa-4,7-diazaundecyl)phenyl)diazenyl)benzoic Acid

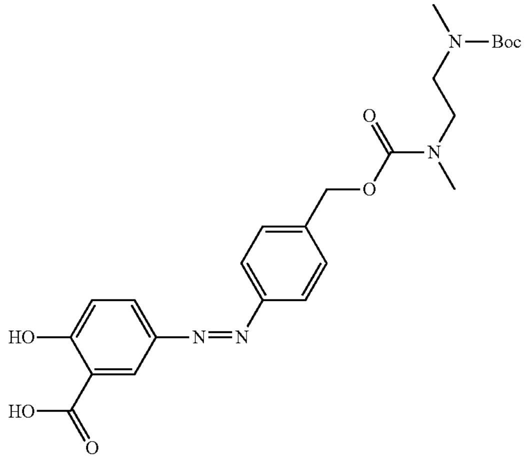 [SMILES: CN(CCN(C)C(=O)OC(C)(C)C)C(=O)OCc1ccc(N=Nc2ccc(O)c(C(=O)O)c2)cc1]

To a mixture of Intermediate B-1 (200 mg, 0.73 mmol) and diisopropylethylamine (114 mg, 0.88 mmol) in 5 mL of dichloromethane, bis(4-nitrophenyl)carbonate (268 mg, 0.88 mmol) was added. The reaction mixture was stirred for 48 h at room temperature. tert-Butyl methyl(2-(methylamino)ethyl)carbamate (165 mg, 0.88 mmol) and diisopropylethylamine (114 mg, 0.88 mmol) were added dropwise to the reaction mixture obtained from the previous step at 0° C. After addition, the reaction mixture was stirred at 25° C. for 2 h. LCMS indicated that starting materials were completely consumed. The reaction mixture was concentrated under reduced pressure, and the resulting residue was purified by reverse-phase column chromatography to provide title compound (195 mg, 55%) as a red solid.

MS (ESI): m/z=508.9 $[M+Na]^+$.

$^1H$ NMR (400 MHz, $CDCl_3$) δ 8.29 (d, J=2.4 Hz, 1H), 8.04 (dd, $J_1$=2.4 Hz, $J_2$=8.8 Hz, 1H), 7.82 (d, J=8.4 Hz, 2H), 7.50 (d, J=8.0 Hz, 2H), 7.11 (d, J=9.2 Hz, 1H), 5.10 (s, 2H), 3.35-3.32 (m, 4H), 2.88-2.82 (m, 3H), 2.73-2.68 (m, 3H), 1.32 (s, 9H).

Intermediate C: 9-(((2-aminoethyl)(methyl)carbamoyl)oxy)-10-methoxy-5,6-dihydro-[1,3]dioxolo[4,5-g]isoquinolino[3,2-a]isoquinolin-7-ium

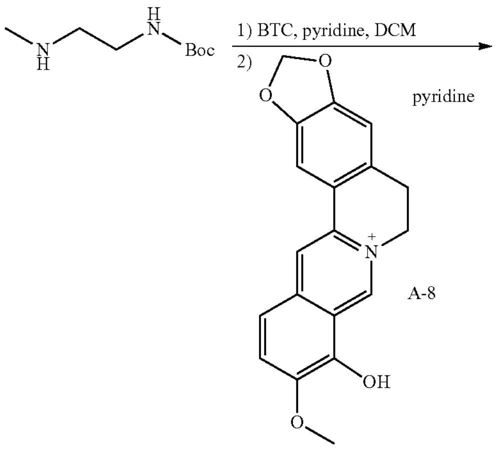

-continued

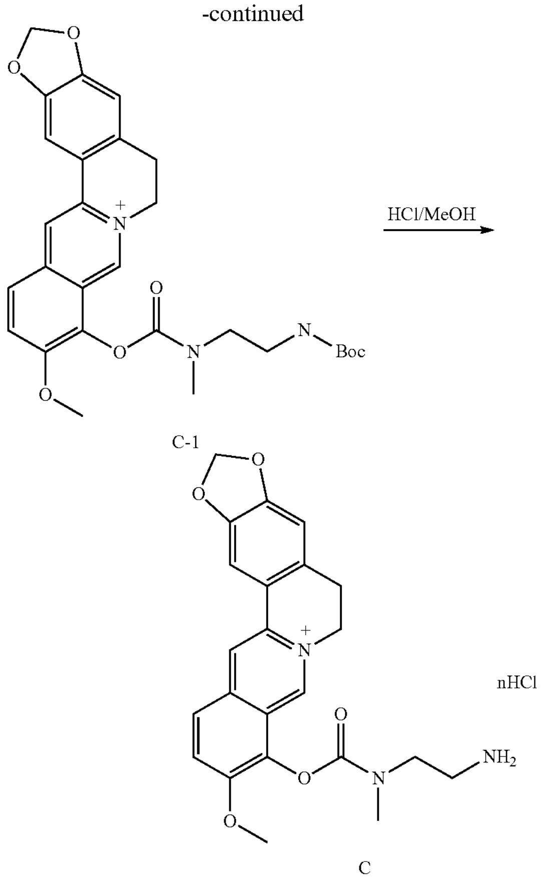

Intermediate C-1: 9-(((2-((tert-butoxycarbonyl)amino)ethyl)(methyl)carbamoyl)oxy)-10-methoxy-5,6-dihydro-[1,3]dioxolo[4,5-g]isoquinolino[3,2-a]isoquinolin-7-ium

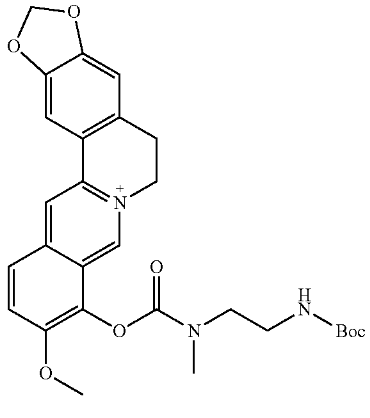

To a mixture of tert-butyl (2-(methylamino)ethyl)carbamate (15.0 g, 86.0 mmol) in dichloromethane (200 mL), triphosgene (25.6 g, 86.0 mmol) and pyridine (20.0 g, 258 mmol) were slowly added successively under ice-bath. The reaction mixture was stirred at room temperature (15° C.) for 1 hour. TLC indicated that the starting material was consumed. The reaction mixture was washed with water (200 ml), and the aqueous phase was extracted with dichloromethane (100 ml*2). The combined organic phase was washed with saturated brine, dried over sodium sulfate, filtered and concentrated under reduced pressure to obtain an intermediate. The intermediate was dissolved in pyridine (20 ml), and added into the mixture of Intermediate A-8 (27.7 g, 86.0 mmol) in pyridine (30 ml) under ice bath. Then the mixture was warmed to room temperature (15° C.) and stirred for 16 h. LCMS indicated that starting materials were consumed. The reaction solution was concentrated, and the resulting residue was purified by normal phase column chromatography (dichloromethane:methanol=10:1) to obtain the product as a yellow solid (6.5 g, 14%).

MS (ESI): m/z=522.1[M]$^+$.

Intermediate C: 9-(((2-aminoethyl)(methyl)carbamoyl)oxy)-10-methoxy-5,6-dihydro-[1,3]dioxolo[4,5-g]isoquinolino[3,2-a]isoquinolin-7-ium

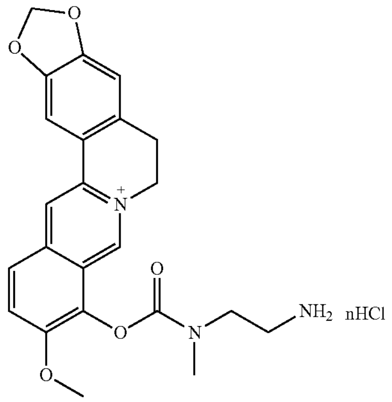

The intermediate C-1 (4.5 g, 8.6 mmol) was mixed into the hydrochloric methanol solution (2 mol/L, 100 ml), and stirred at room temperature (15° C.) overnight. LCMS indicated that the reaction was completed. The mixture was concentrated under reduced pressure to provide title compound (3.6 g, 100%) as a brown solid.

MS (ESI): m/z=422.1 [M]$^+$.

Intermediate D: 9-((4-hydroxybenzyl)oxy)-10-methoxy-5,6-dihydro-[1,3]dioxolo[4,5-g]isoquinolino[3,2-a]isoquinolin-7-ium

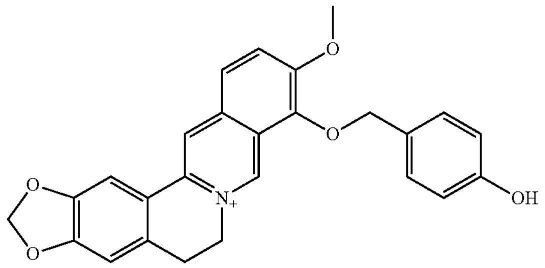

To a solution of Intermediate A-8 (300 mg, 0.93 mmol) in acetonitrile (3 mL), was added 4-(chloromethyl)phenyl acetate (257 mg, 1.4 mmol) and potassium carbonate (257 mg, 1.86 mmol). The reaction mixture was heated to 80° C. and stirred for 16 h. The reaction mixture was diluted with dichloromethane (50 mL), filtered, the filter cake was washed with water (50 mL) and the filter cake was purified by normal phase column chromatography (dichloromethane: methanol=10:1) to give the title compound (97 mg, 24%) as a dark red solid.

MS (ESI): m/z=428.1 [M]$^+$.

Preparation of Codrug Compounds

Example 1: 9-(((2-((((10-((2-(((2S,3R,4S,5S,6S)-6-carboxyl-3,4,5-trihydroxyl tetrahydro-2H-pyran-2-yl)oxo)-5-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido <ethylenediamine>)ethyl)(methyl)carbamoyl)oxo)methyl)phenyl)amino)-10-carbonyldecyl)oxo)carbonyl)(methyl)amino)ethyl)(methyl)carbamoyl)oxo)-10-methoxy-5,6-dihydro-[1,3]dioxolo[4,5-g]isoquinolo[3,2-a] isoquinolin-7-ium

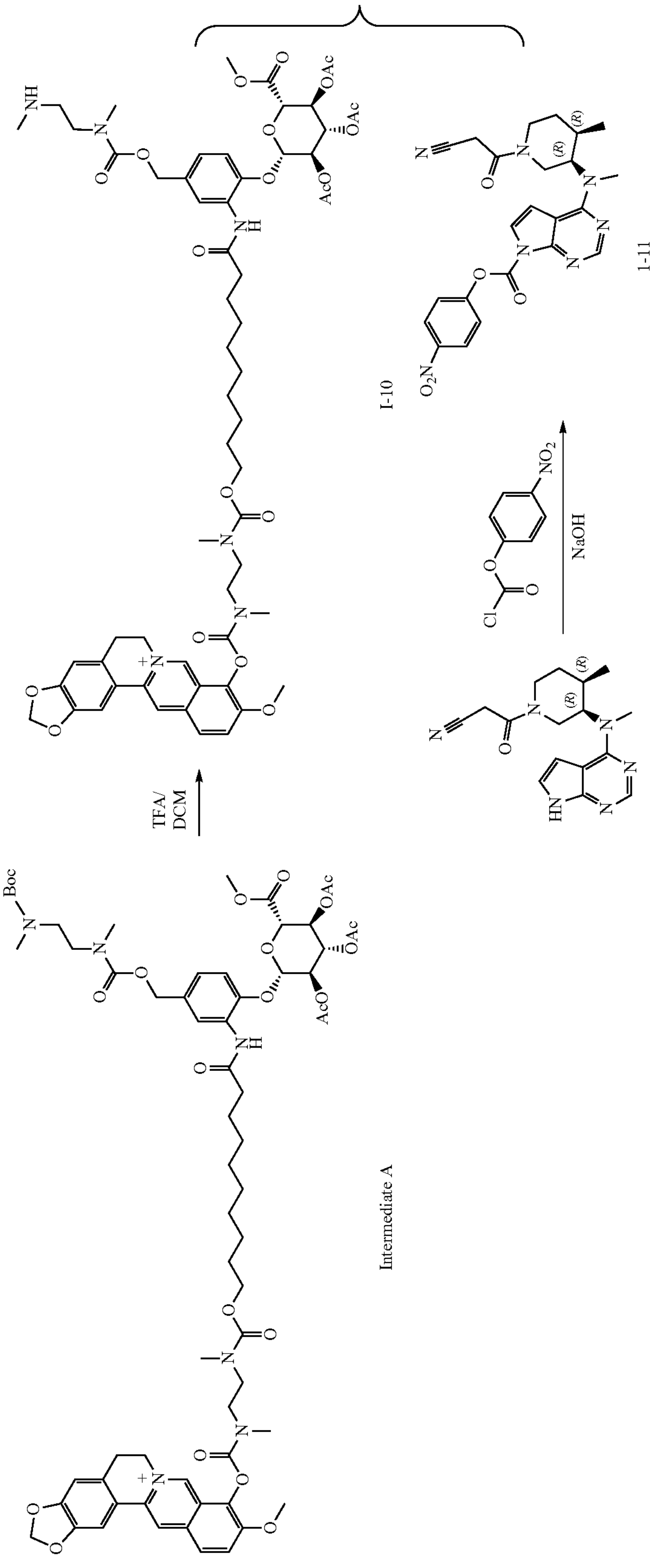
Intermediate A
I-10
1-11

-continued
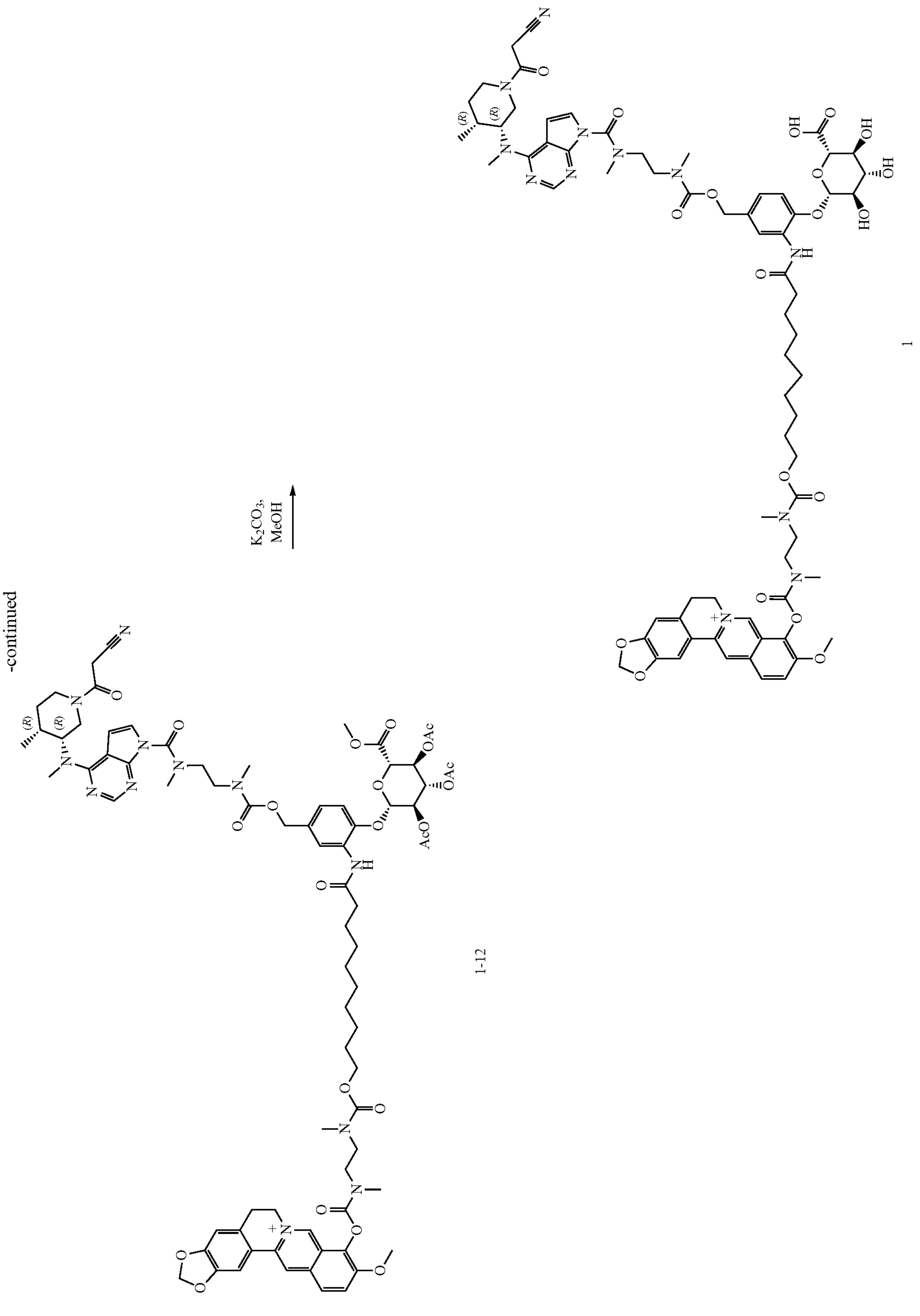
1-12
1

Example 1-11: 4-nitrophenyl-4-(((3R,4R)-1-(2-cyanoacetyl)-4-methylpiperidin-3-yl)(methyl)amino)-7H-pyrrolo[2,3-d]pyrimidine-7-carboxylate

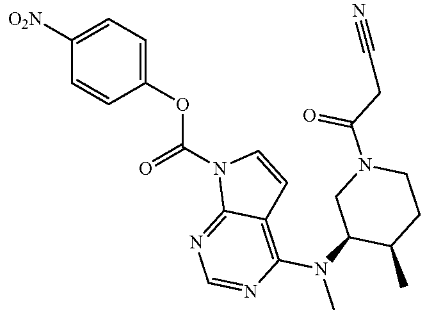 [SMILES: C[C@@H]1CCN(C(=O)CC#N)C[C@@H]1N(C)c1ncnc2c1ccn2C(=O)Oc1ccc([N+](=O)[O-])cc1]

To a mixture of Tofacitimb (8.9 g, 28.6 mmol) in dichloromethane (140 mL) was added an aqueous solution (48 mL) of sodium hydroxide (3.4 g, 85.6 mmol) and tetrabutylammonium bromide (920 mg, 2.86 mmol) in water (48 mL). A solution of p-nitrophenyl chloroformate (11.5 g, 57.1 mmol) in dichloromethane (48 mL) was added slowly to the above reaction mixture dropwise. After addition, the reaction mixture was stirred at room temperature for 4 h. LCMS indicated that starting materials were completely consumed. The mixture was added with 500 ml dichloromethane, washed with saturated aqueous ammonium chloride (200 ml), and filtered through a pad of celite. The filtrate was separated, and the organic phase was washed with 200 ml of saturated brine. The organic phase was dried over anhydrous sodium sulfate, filtered and concentrated under reduced pressure. The crude product was triturated for 5 times in the solvent of dichloromethane and petroleum ether to afford the title compound (16.3 g, 85%) as a yellow foamy solid.

MS (ESI): m/z=478.1 $[M+H]^+$.

Example 1-10: 10-methoxy-9-((methyl(2-(methyl(((10-((5-(((methyl(2-(methylamino)ethyl)carbamoyl)oxy)methyl)-2-(((2S,3R,4S,5S,6S)-3,4,5-triacetoxy-6-(methoxycarbonyl)tetrahydro-2H-pyran-2-yl)oxy)phenyl)amino)-10-oxodecyl)oxy)carbonyl)amino)ethyl)carbamoyl)oxy)-5,6-dihydro-[1,3]dioxolo[4,5-g]isoquinolino[3,2-a]isoquinolin-7-ium

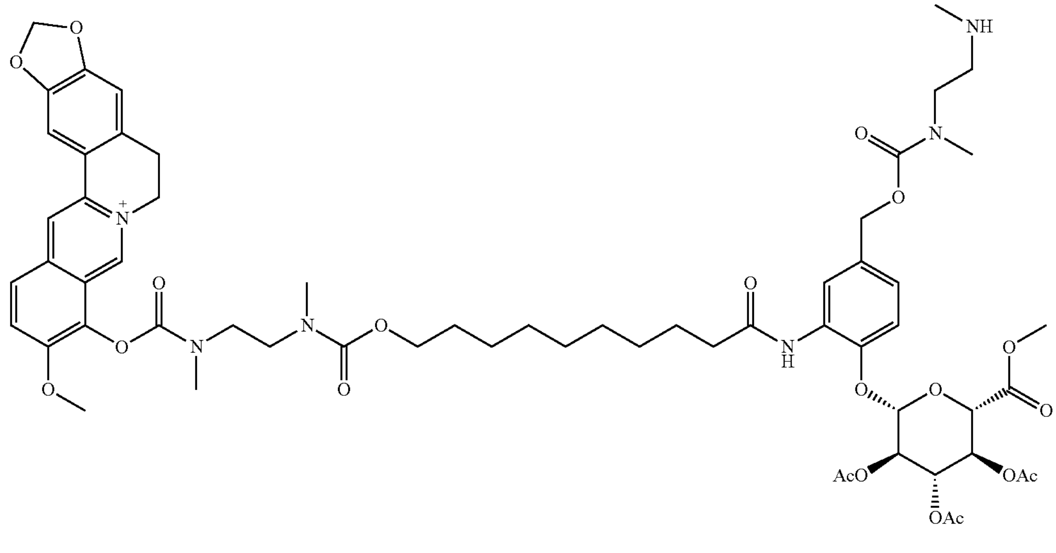

To a solution of Intermediate A (4.8 g, 3.7 mmol) in dichloromethane (40 mL) was added trifluoroacetic acid (10 mL). The reaction mixture was stirred at room temperature for 1 h. LCMS indicated that the reaction was completed. The reaction solution was concentrated under reduced pressure, dissolved with dichloromethane (30 mL), concentrated again under reduced pressure to remove trifluoroacetic acid as much as possible and dried in vacuum by oil pump to give the title compound (4.43 g, 100%), as a yellow oil.

MS (ESI): m/z=601.4 $[M/2]^+$.

Example 1-12: 9-(((2-((((10-((5-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-(((2S,3R,4S,5S,6S)-3,4,5-diacetoxy-6-(methoxycarbonyl)tetrahydro-2H-pyran-2-yl)oxy)phenyl)amino)-10-oxodecyl)oxy)carbonyl)(methyl)amino)ethyl)(methyl)carbamoyl)oxy)-10-methoxy-5,6-dihydro-[1,3]dioxolo[4,5-g]isoquinolino[3,2-a]isoquinolin-7-ium

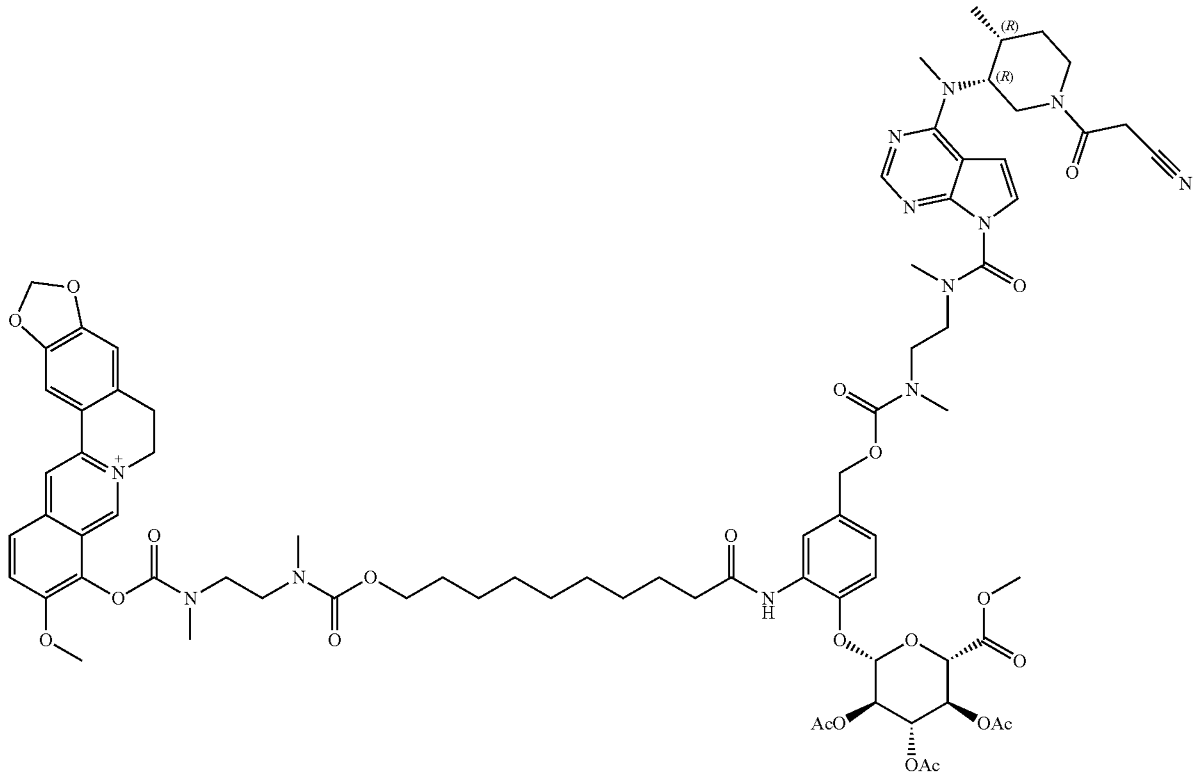

A solution of Example 1-10 (4.4 g, 3.7 mmol) in dichloromethane (100 mL) was cooled to 0° C., and N,N-diisopropylethylamine (1.56 g, 12 mmol) and Examples 1-11 (1.76 g, 3.69 mmol) were added and stirred at room temperature for 1 h. LCMS indicated that the reaction was completed. The reaction solution was diluted with 300 mL of dichloromethane and washed successively with water, saturated brine, and the washed organic phase was dried over anhydrous sodium sulfate and concentrated under reduced pressure. The crude product was purified by normal phase column chromatography (eluted by dichloromethane with 7-9% methanol) to give the title compound (2.83 g, 53%) as a yellow foamy solid.

MS (ESI): m/z=770.7 [M/2]$^+$.

Example 1: 9-(((2-((((10-((2-(((2S,3R,4S,5S,6S)-6-carboxy-3,4,5-trihydroxytetrahydro-2H-pyran-2-yl)oxy)-5-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)amino)-10-oxodecyl)oxy)carbonyl)(methyl)amino)ethyl)(methyl)carbamoyl)oxy)-10-methoxy-5,6-dihydro-[1,3]dioxolo[4,5-g]isoquinolino[3,2-a]isoquinolin-7-ium

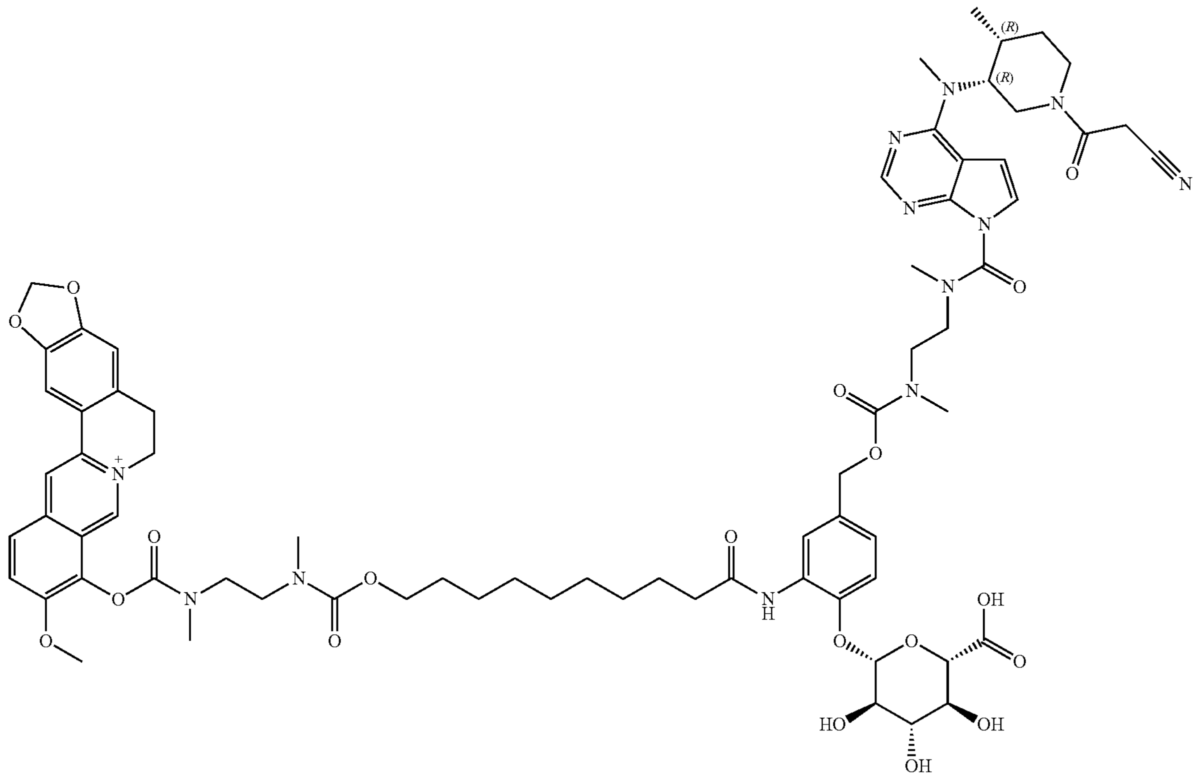

A mixture of Example 1-12 (163 mg, 0.105 mmol) in methanol (4 ml) was cooled to 0° C., and an aqueous solution of potassium carbonate (1 mmol/ml, 1 ml) was added. The mixture was stirred at 0° C. for 2 h. LCMS indicated that the reaction was completed. The reaction solution was adjusted to pH 5 with acetic acid and then concentrated under reduced pressure. The crude product was separated by prep-HPLC (gradient eluted by acetonitrile/water) to afford title compound (35.7 mg, 24%) as a yellow solid.

MS (ESI): m/z=1399.5 $[M]^+$.

$^1H$ NMR: (400 MHz, $CD_3OD$) δ 10.06-9.59 (m, 1H), 8.71-8.61 (m, 1H), 8.15-7.98 (m, 4H), 7.60-7.50 (m, 1H), 7.26-7.17 (m, 1H), 6.95-6.72 (m, 3H), 6.72-6.66 (m, 1H), 6.05 (s, 2H), 5.05-4.90 (m, 4H), 4.78-4.59 (m, 2H), 4.21-4.08 (m, 2H), 4.04 (s, 3H), 3.96-3.35 (m, 18H), 3.21-2.95 (m, 13H), 2.29-1.84 (m, 3H), 1.84-1.02 (m, 20H).
The following compounds were obtained by replacing the corresponding starting materials using a method similar to that of Example 1.
| No. | Compound structure | LCMS, HNMR |
|---|---|---|
| 2 | 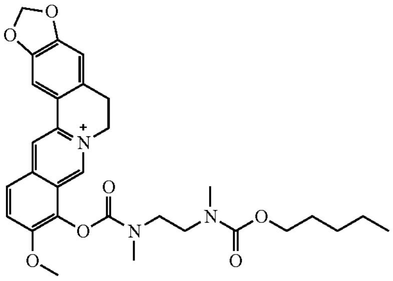 | MS(ESI): m/z = 697.5 $[M/2]^+$. $^1H$ NMR: (400 MHz, $CD_3OD$) δ 9.73-9.52 (m, 1H), 8.66-8.64 (m, 2H), 8.34-8.28 (m, 2H), 8.12-8.04 (m, 2H), 7.56-7.54 (m, 1H), 7.26-6.85 (m, 6H), 6.04 (s, 2H), 4.66-4.41 (m, 10H), 4.12-4.03 (m, 3H), 3.75-3.45 (m, 9H), 3.18-2.87 (m, 12H), 2.54-1.89 (m, 7H),1.73-1.07 (m, 24H). |
| | 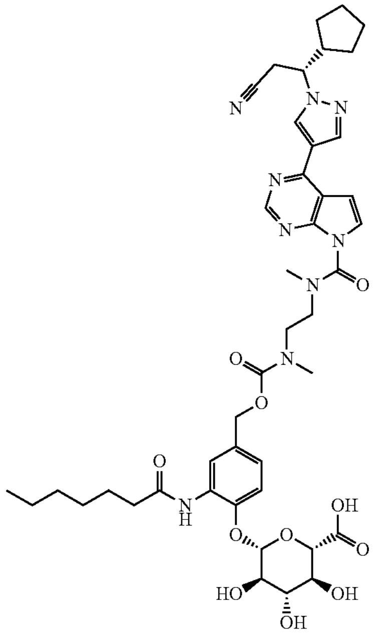 | |

-continued

| No. | Compound structure | LCMS, HNMR |
|---|---|---|
| 3 | 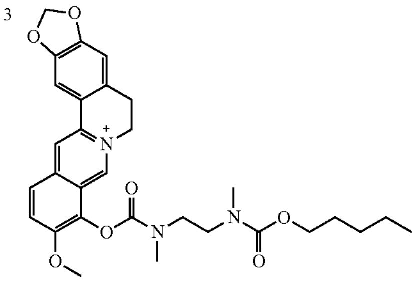 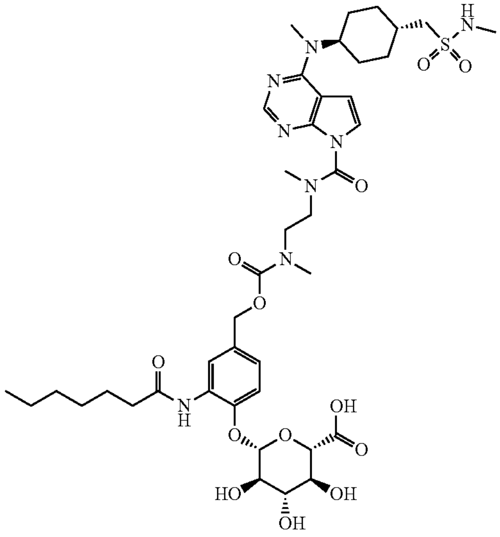 | MS(ESI): m/z = 713.0 [M/2]$^+$. $^1$H NMR: (400 MHz, $CD_3OD$) δ 10.07-9.59 (m, 1H), 8.72-8.69 (m, 1H), 8.50 (br, 1H), 8.38-8.28 (m, 3H), 7.60-7.55 (m, 1H), 7.27-7.18 (m, 1H), 6.96-6.66 (m, 4H), 6.05 (s, 2H), 5.07-4.91 (m, 2H), 4.78-4.60 (s, 2H), 4.17-4.08 (m, 2H), 4.05 (s, 3H), 3.72-3.45 (m, 11H), 3.19-2.95 (m, 15H), 2.68 (s, 3H), 2.33-1.09 (m, 32H). |

Example 4A: 9-((5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzoyl)oxy)-10-methoxy-5,6-dihydro-[1,3]dioxolo[4,5-g]isoquinolino[3,2-a]isoquinolin-7-ium Example 4B: 9-((5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzoyl)oxy)-10-methoxy-5,6-dihydro-[1,3]dioxolo[4,5-g]isoquinolino[3,2-a]isoquinolin-7-ium

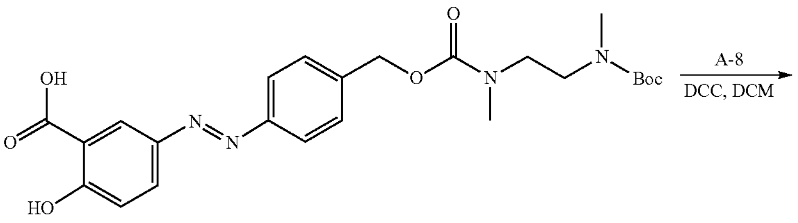

Intermediate B

-continued
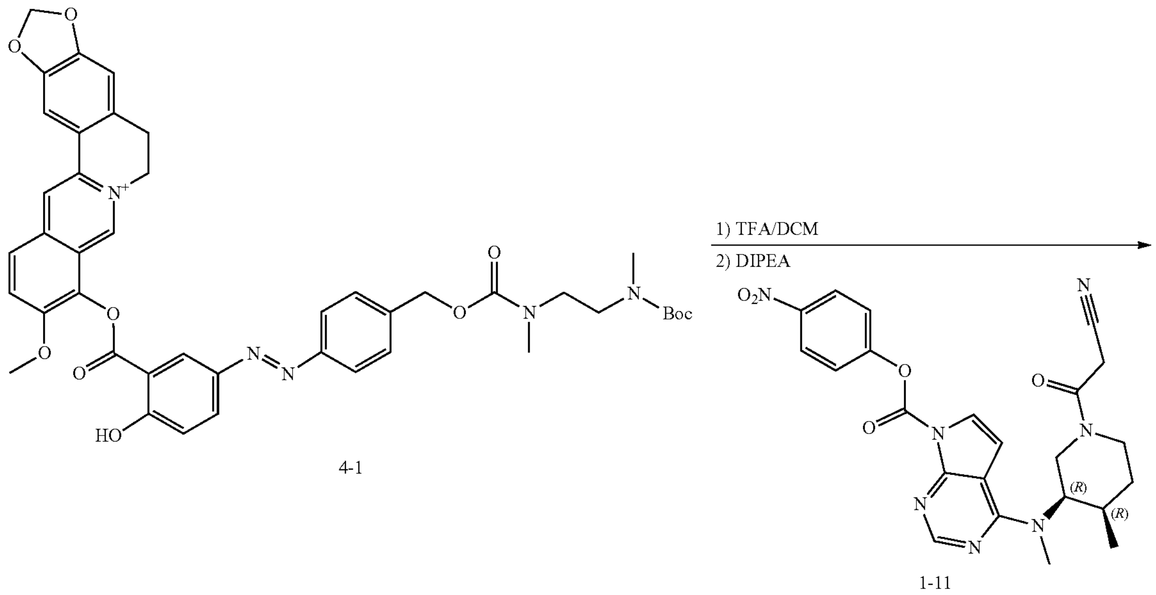
4-1
1-11
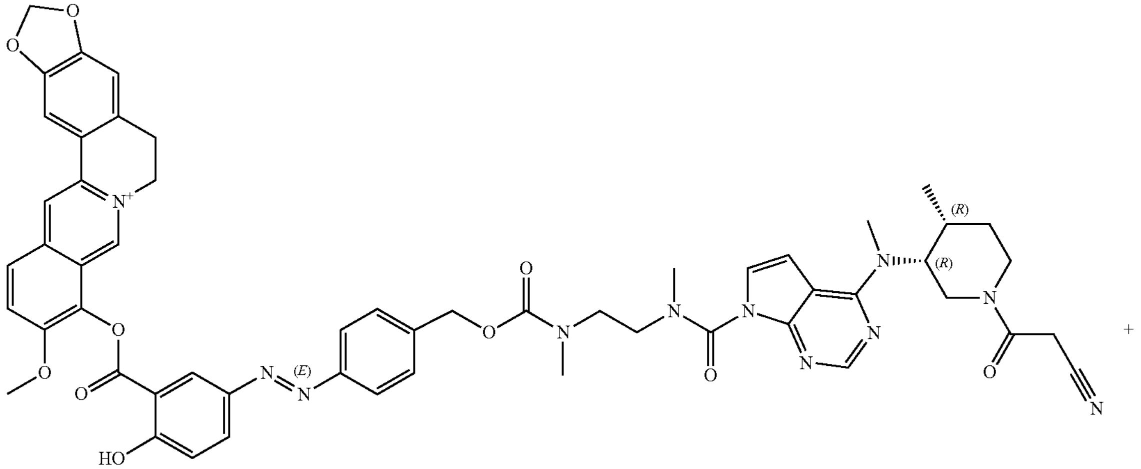
4A

-continued

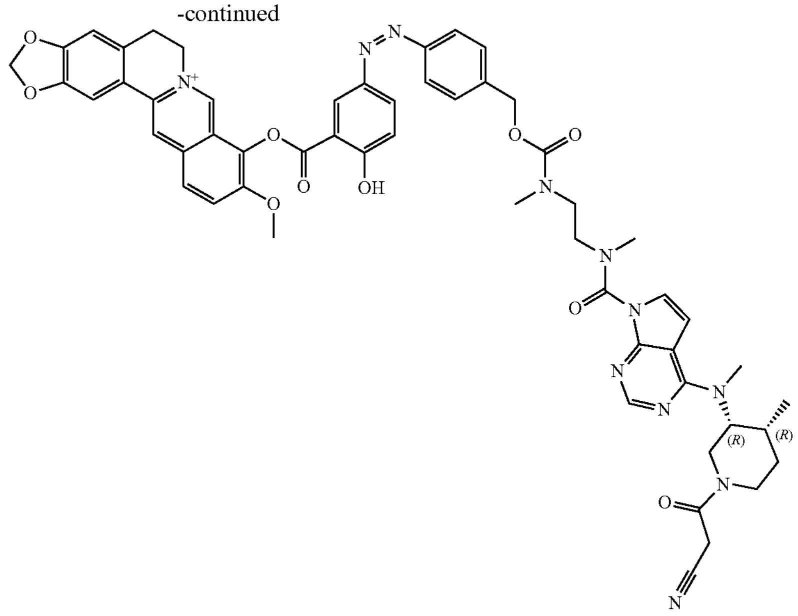

4B

Example 4-1: (E)-9-((2-hydroxy-5-((4-(4,7,10,10-tetramethyl-3,8-dioxo-2,9-dioxa-4,7-diazaundecyl)phenyl)diazenyl)benzoyl)oxy)-10-methoxy-5,6-dihydro-[1,3]dioxolo[4,5-g]isoquinolino[3,2-a]isoquinolin-7-ium

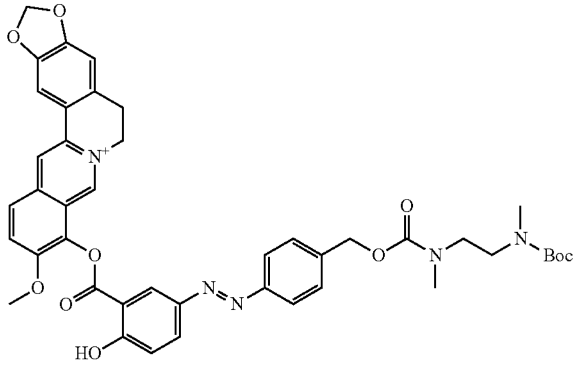

To a mixture of Intermediate B (486 mg, 1.0 mmol), Intermediate A-8 (322 mg, 1.0 mmol) and dicyclohexylcarbodiimide (247 mg, 1.2 mmol) in a single-necked flask, dichloromethane (10 mL) was added. The mixture was stirred at room temperature for 1 h. LCMS indicated that the reaction was completed, then the reaction mixture was filtered and concentrated under reduced pressure. The crude product was purified by reverse-phase column chromatography to obtain the title compound (156 mg, 19.7%) as a brown oil.

MS (ESI): m/z=790.1 $[M]^+$.

Example 4A: 9-((5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzoyl)oxy)-10-methoxy-5,6-dihydro-[1,3]dioxolo[4,5-g]isoquinolino[3,2-a]isoquinolin-7-ium and Example 4B: 9-((5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzoyl)oxy)-10-methoxy-5,6-dihydro-[1,3]dioxolo[4,5-g]isoquinolino[3,2-a]isoquinolin-7-ium

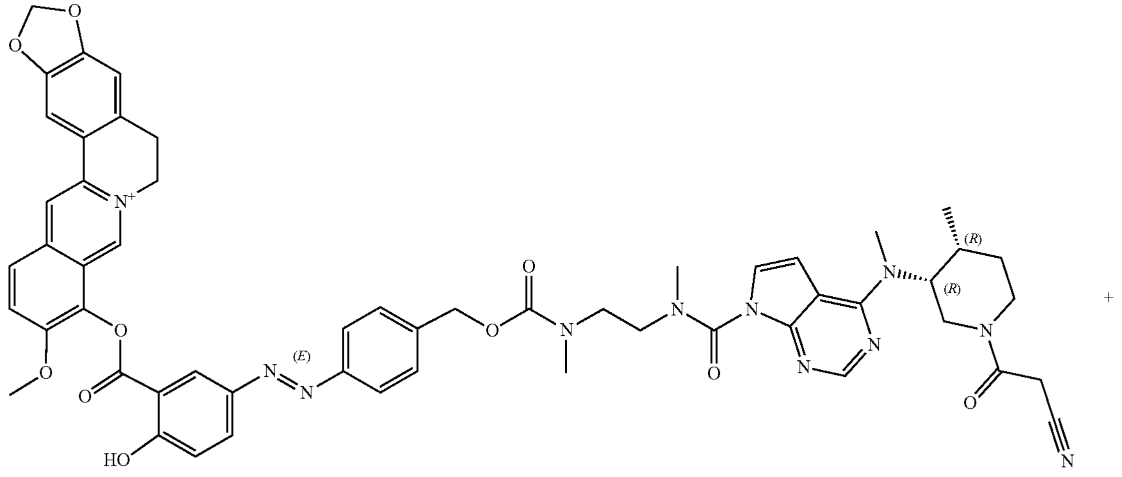

4A

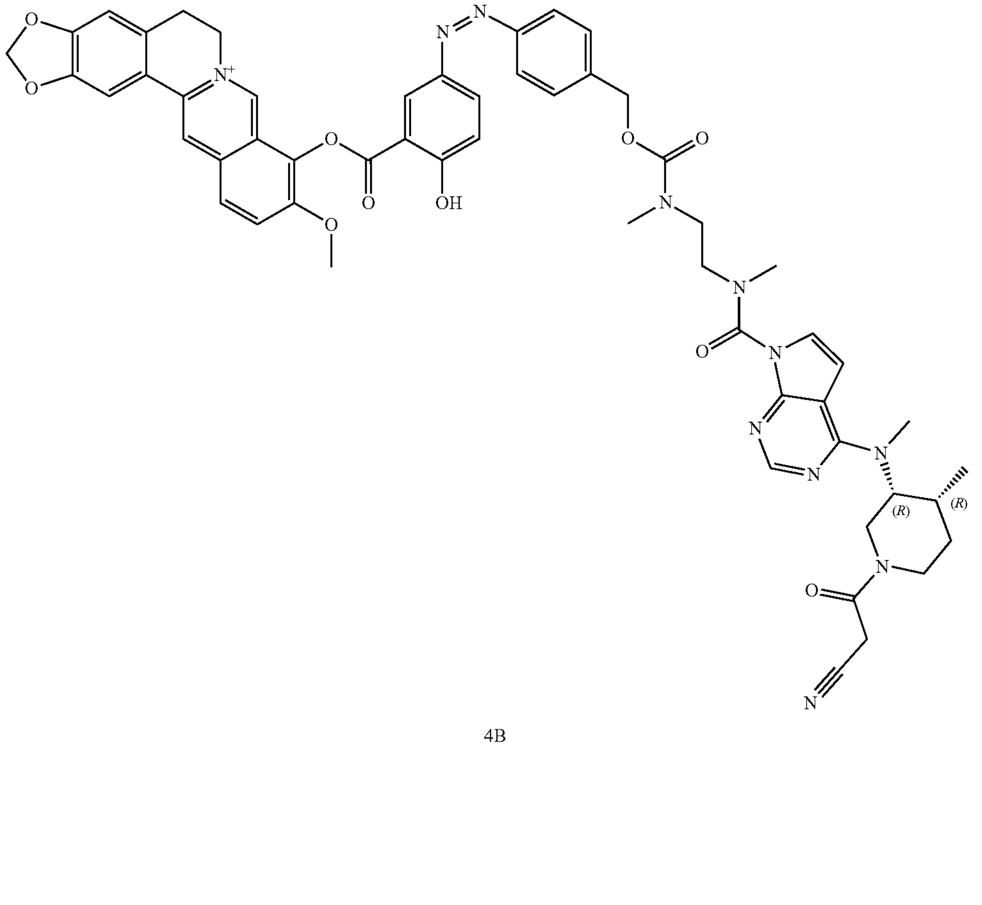

4B

To a mixture of Example 4-1 (156 mg, 0.19 mmol) in dichloromethane (2 mL) was added trifluoroacetic acid (0.4 mL). The mixture was stirred for 20 minutes at room temperature. LCMS indicated that the reaction was completed. The reaction mixture was concentrated under reduced pressure, dried in vacuum by oil pump and redissolved in dichloromethane (2 mL) and cooled to 0° C. N,N-Diisopropylethylamine (101 mg, 0.78 mmol) and Example 1-11 (94 mg, 0.19 mmol) were added and the resulting mixture was stirred at room temperature for 1 h. LCMS indicated that the reaction was completed. The reaction mixture was concentrated, and the crude product was purified by prep-HPLC (gradient eluted by acetonitrile/water (including 0.1% trifluoroacetic acid)) to obtain the title compound 4A (6.0 mg, 3%) as a yellow solid; 4B (6.0 mg, 3.0%) as a yellow solid.

MS (ESI): m/z=1028.4[M]$^+$.

Example 5: 9-(((2-(5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzamido)ethyl)(methyl)carbamoyl)oxy)-10-methoxy-5,6-dihydro-[1,3]dioxolo[4,5-g]isoquinolino[3,2-a]isoquinolin-7-ium

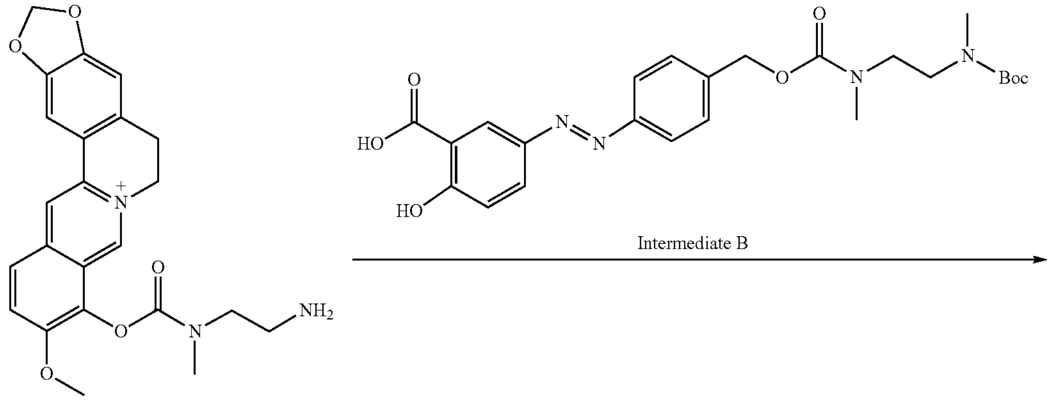

Intermediate C

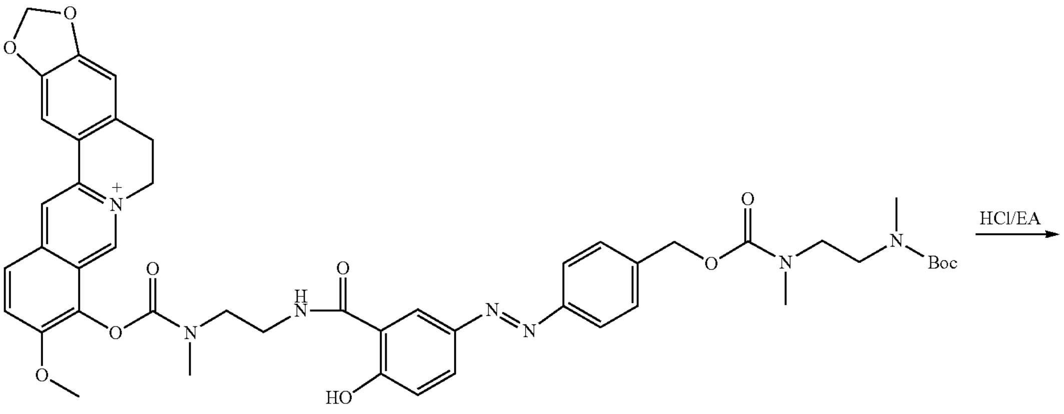

5-1

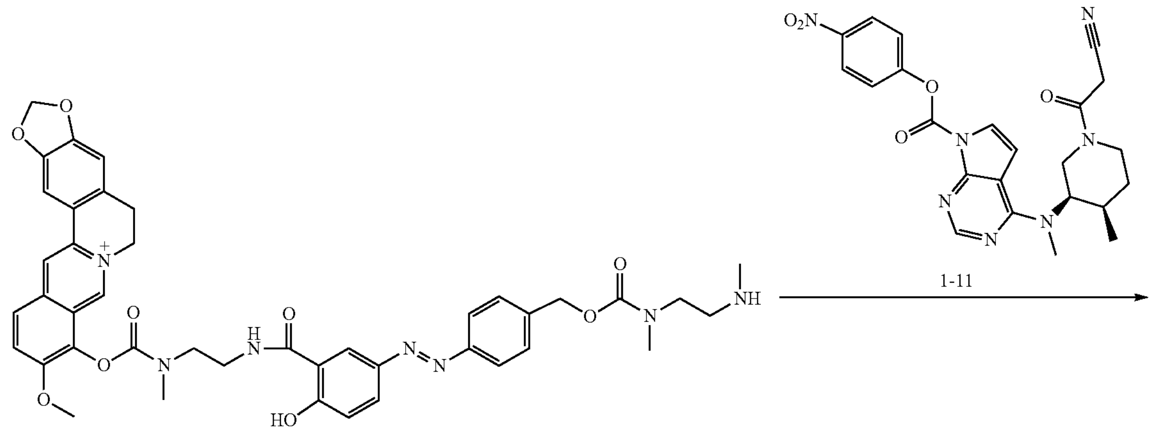

5-2

-continued

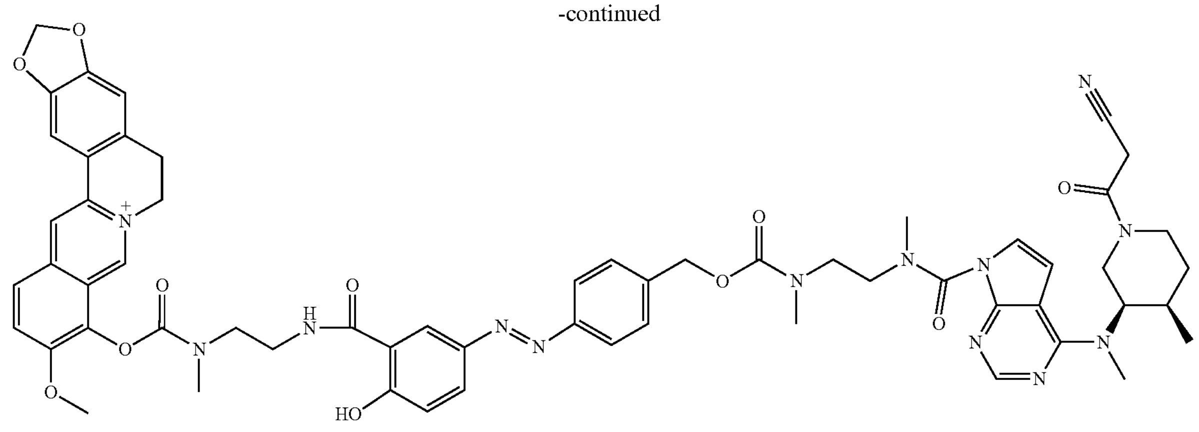

Example 5-1: (E)-9-(((2-(2-hydroxy-5-((4-(4,7,10,10-tetramethyl-3,8-dioxo-2,9-dioxa-4,7-diazaundecyl)phenyl)diazenyl)benzamido)ethyl)(methyl)carbamoyl)oxy)-10-methoxy-5,6-dihydro-[1,3]dioxolo[4,5-g]isoquinolino[3,2-a]isoquinolin-7-ium

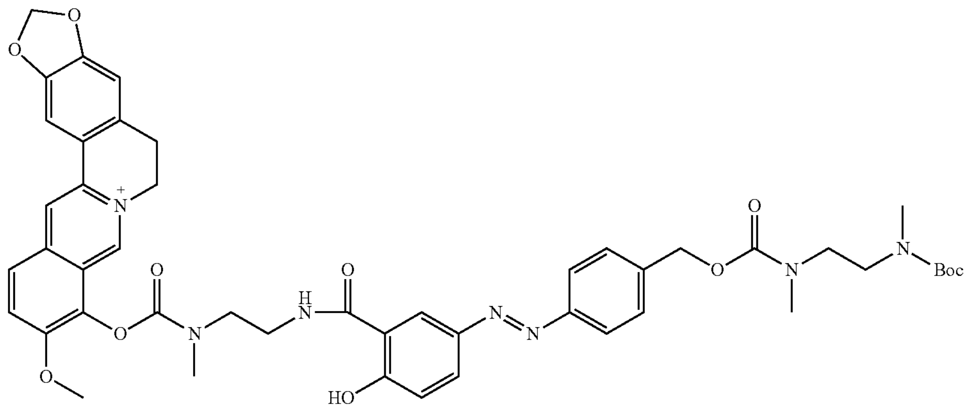

To a mixture of Intermediate C (700 mg, 1.65 mmol), Intermediate B (782 mg, 1.65 mmol) and 1-(3-dimethylaminopropyl)-3-ethylcarbodiimide hydrochloride (477 mg, 2.48 mmol) in a single-necked flask, N,N-dimethylformamide (5 mL) and 4-dimethylaminopyridine (50 mg, 0.41 mmol) were added. The mixture was stirred at room temperature for 1 h, then diisopropylethylamine (427 mg, 3.31 mmol) was added. The reaction solution was stirred at room temperature for 5 h. After the reaction was completed as monitored by LCMS, the reaction mixture was quenched by adding hydrochloric acid (1 N), and the reaction solution was directly purified by reversed-phase column to obtain the title compound (470 mg, 32%) as a yellow solid.

MS (ESI): m/z=890.3 $[M]^+$.

Example 5-2: (E)-9-(((2-(2-hydroxy-5-((4-(((methyl (2-(methylamino)ethyl)carbamoyl)oxy)methyl)phenyl)diazenyl)benzamido)ethyl)(methyl)carbamoyl) oxy)-10-methoxy-5,6-dihydro-[1,3]dioxolo[4,5-g] isoquinolino[3,2-a]isoquinolin-7-ium

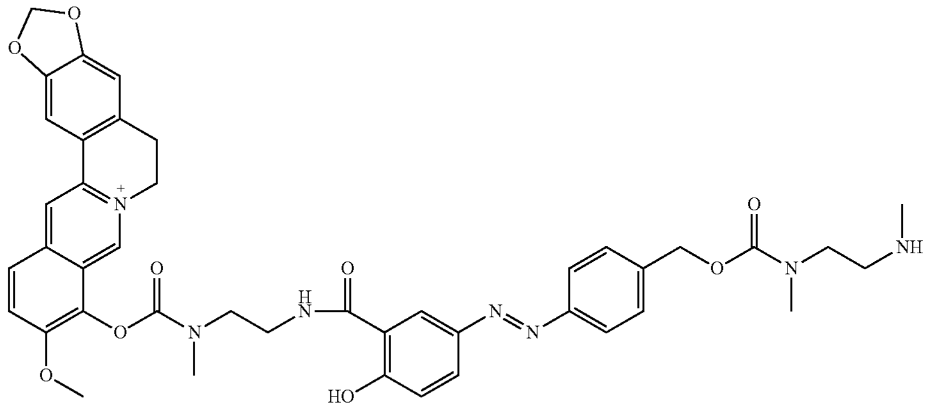

To a mixture of Example 5-1 (470 mg, 0.53 mmol) in methanol (2 mL) was added hydrochloride ethyl acetate solution (4 mol/L, 2 mL) and stirred at room temperature for 1 h. LCMS indicated that the reaction was completed. The reaction solution was concentrated under reduced pressure, the residue was redissolved in dichloromethane (10 mL), concentrated again under reduced pressure, repeat the desolvation-concentration process one more time, and then dried in vacuo with an oil pump to provide the title compound (390 mg, 93.5%) as a yellow solid.

MS (ESI): m/z=790.2 $[M+H]^+$.

Example 5: 9-(((2-(5-((E)-(4-((((2-(4-(((3R,4R)-1-(2-cyanoacetyl)-4-methylpiperidin-3-yl)(methyl) amino)-N-methyl-7H-pyrrolo[2,3-d]pyrimidine-7-carboxamido)ethyl)(methyl)carbamoyl)oxy)methyl) phenyl)diazenyl)-2-hydroxybenzamido)ethyl) (methyl)carbamoyl)oxy)-10-methoxy-5,6-dihydro-[1,3]dioxolo[4,5-g]isoquinolino[3,2-a]isoquinolin-7-ium

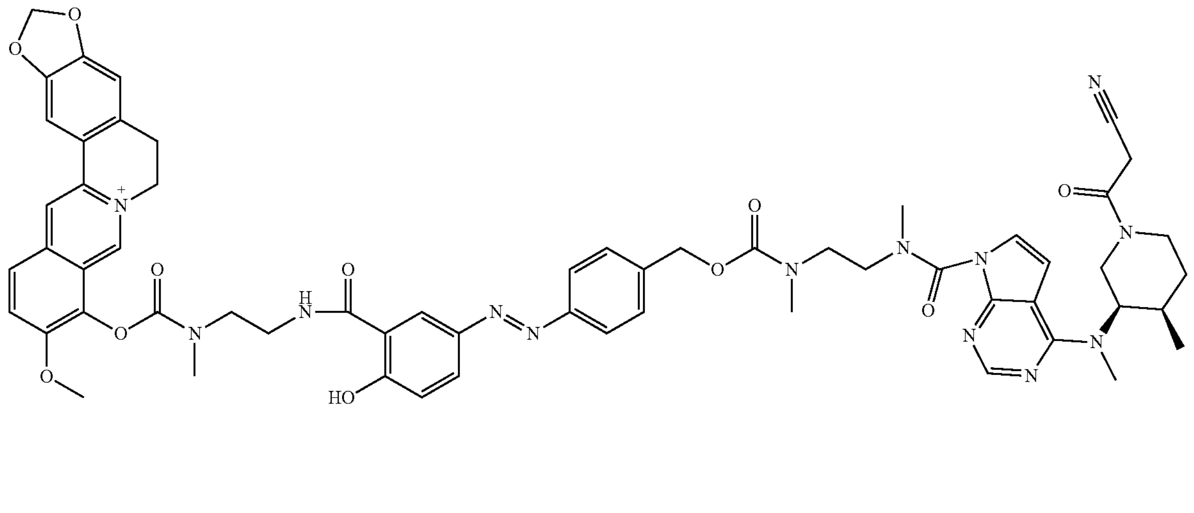

A mixture of Example 5-2 (390 mg, 0.49 mmol) in dichloromethane (5 mL) was cooled to 0° C., and N,N-diisopropylethylamine (254 mg, 1.97 mmol) and Example 1-11 (235 mg, 0.49 mmol) were added. The mixture was stirred at room temperature for 1. LCMS indicated that the reaction was completed. The reaction mixture was diluted with dichloromethane (50 mL), washed with water (50 mL) and saturated brine (50 mL) successively, dried over anhydrous sodium sulfate, and concentrated under reduced pressure. The crude product was purified by normal phase column chromatography (eluted by 0.1% formic acid in dichloromethane and methanol) to afford the title compound (114 mg, 20%) as a yellow solid.

MS (ESI): m/z=1128.4 $[M+H]^+$.

$^1H$ NMR: (400 MHz, $CD_3OD$) δ 9.79-9.59 (m, 1H), 8.59-7.87 (m, 7H), 7.65-7.40 (m, 4H), 7.03-6.83 (m, 3H), 6.70-6.44 (m, 1H), 6.08 (s, 2H), 5.32-4.94 (m, 3H), 3.91-3.72 (m, 6H), 3.62-3.43 (m, 9H), 3.35 (s, 3H), 3.22-2.66 (m, 13H), 2.41-2.26 (m, 1H), 1.84-1.52 (m, 2H), 1.36-1.26 (m, 4H), 1.03-0.85 (m, 3H).

Example 6: 9-(((2-(6-(5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzamido)hexanamido)ethyl)(methyl)carbamoyl)oxy)-10-methoxy-5,6-dihydro-[1,3]dioxolo[4,5-g]isoquinolino[3,2-a]isoquinolin-7-ium

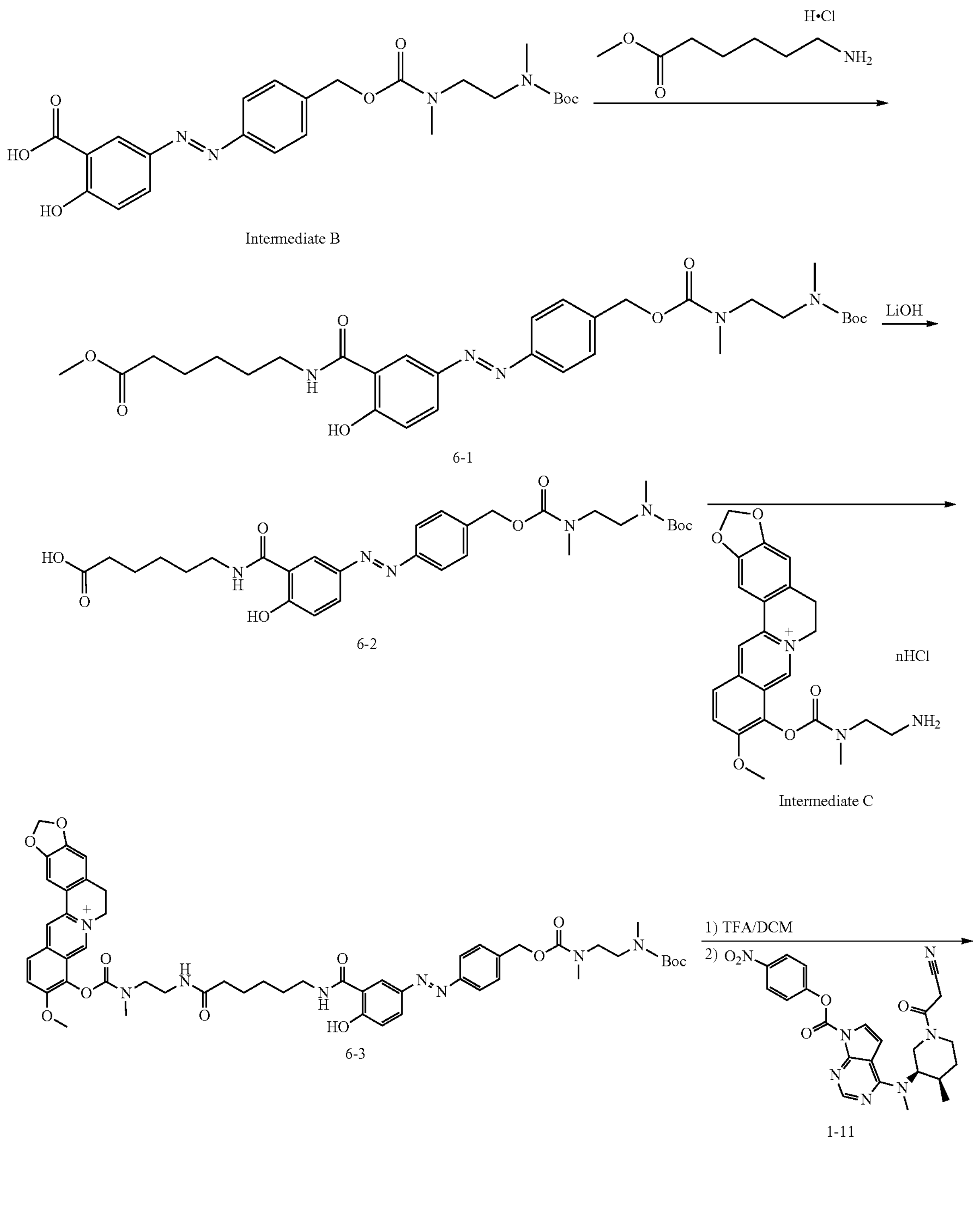

Intermediate B 6-1

6-2

Intermediate C 6-3

1-11

-continued

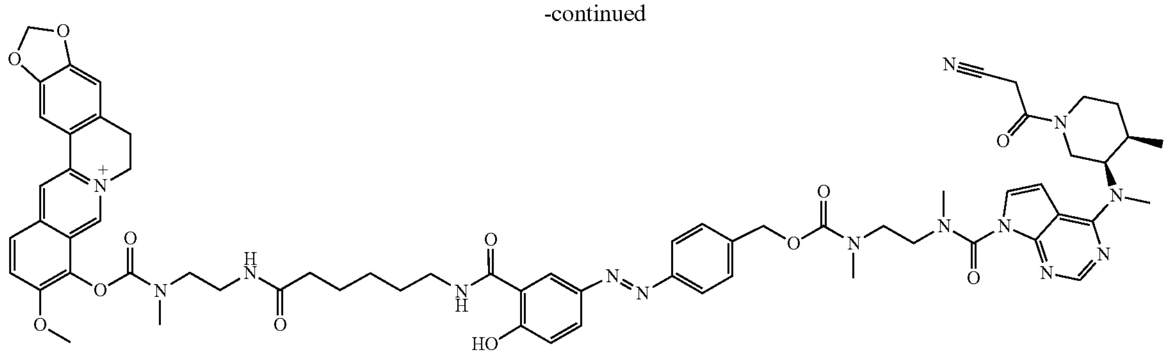

6

Example 6-1: Methyl-(E)-6-(2-hydroxy-5-((4-(4,7,10,10-tetramethyl-3,8-dioxo-2,9-dioxa-4,7-diazaundecyl)phenyl)diazenyl)benzamido)hexanoate

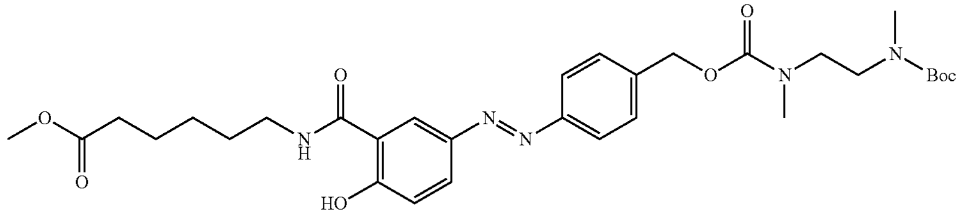 [SMILES: COC(=O)CCCCCNC(=O)c1cc(/N=N/c2ccc(COC(=O)N(C)CCN(C)C(=O)OC(C)(C)C)cc2)ccc1O]

To a mixture of Intermediate B (1900 mg, 3.9 mmol), methyl 6-aminohexanoate hydrochloride (849 mg, 4.6 mmol) and diisopropylethylamine (2017 mg, 15.6 mmol) in N,N-dimethylformamide (19 mL), 0-(7-azabenzotriazole)-N,N,N,N-tetramethyluronium hexafluorophosphate (2228 mg, 5.86 mmol) was added. The reaction mixture was stirred at 30° C. for 3 h. After the reaction was completed as monitored by LCMS, the reaction mixture was diluted with ethyl acetate (150 mL), washed with water (100 mL) for four times and saturated brine (100 mL), dried over anhydrous sodium sulfate, filtered and concentrated under reduced pressure. The crude product was purified by normal phase column chromatography (petroleum ether:ethyl acetate=2:1) to obtain the title compound (870 mg, 36.3%) as a yellow solid.

MS (ESI): m/z=636.2 $[M+Na]^+$.

Example 6-2: (E)-6-(2-hydroxy-5-((4-(4,7,10,10-tetramethyl-3,8-dioxo-2,9-dioxa-4,7-diazaundecyl)phenyl)diazenyl)benzamido)hexanoic Acid

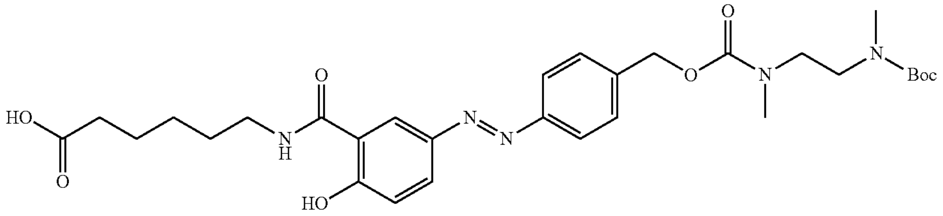 [SMILES: CN(CCN(C)C(=O)OC(C)(C)C)C(=O)OCc1ccc(/N=N/c2ccc(O)c(C(=O)NCCCCCC(=O)O)c2)cc1]

To a mixture of Example 6-1 (800 mg, 1.3 mmol) in methanol (5 ml) and water (2 ml), lithium hydroxide monohydrate (247 mg, 6.5 mmol) was added. The reaction mixture was stirred at 65° C. for 1 h. After the reaction was completed as monitored by LCMS, the reaction solution was cooled to room temperature, neutralized with dilute hydrochloric acid to pH 4-5, and extracted with 100 mL of ethyl acetate. The organic phase was washed with saturated brine, dried over anhydrous sodium sulfate, and concentrated under reduced pressure to afford title compound (784 mg, 100%) as a yellow solid.

MS (ESI): m/z=622.2 $[M+Na]^+$.

Example 6-3: (E)-9-(((2-(6-(2-hydroxy-5-((4-(4,7,10,10-tetramethyl-3,8-dioxo-2,9-dioxa-4,7-diazaundecyl)phenyl)diazenyl)benzamido)hexanamido)ethyl) (methyl)carbamoyl)oxy)-10-methoxy-5,6-dihydro-[1,3]dioxolo[4,5-g]isoquinolino[3,2-a]isoquinolin-7-ium

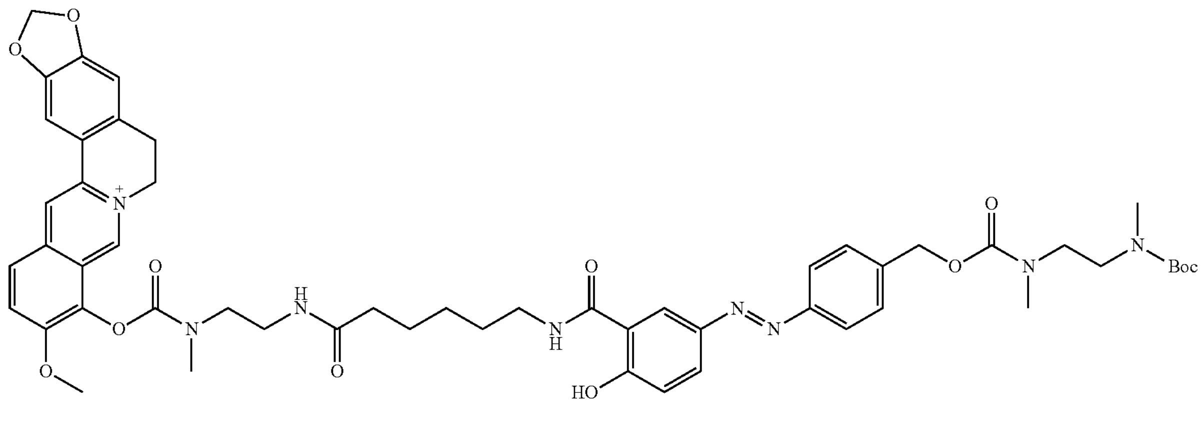

To a mixture of Example 6-2 (820 mg, 1.37 mmol), Intermediate C (693 mg, 1.64 mmol) in DMF (1 mL), were added O-(7-azabenzotriazole)-N,N,N,N-tetramethyluronium hexafluorophosphate (780 mg, 2.05 mmol) and diisopropylethylamine (706 mg, 5.47 mmol) successively. After addition, the mixture was stirred at room temperature for 0.5 h. After the reaction was completed as monitored by LCMS, the reaction mixture was diluted with dichloromethane (100 mL), washed with water (50 mL*4) and brine (50 mL*2), dried over anhydrous sodium sulfate, and concentrated under reduced pressure to obtain a crude product. The crude product was purified by silica gel column chromatography (methanol:dichloromethane=1:12 (containing 0.1% formic acid)) to afford the title compound (525 mg, 38%) as a yellow solid.

MS (ESI): m/z=1003.3 $[M]^+$.

Example 6: 9-(((2-(6-(5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzamido)hexanamido)ethyl)(methyl)carbamoyl)oxy)-10-methoxy-5,6-dihydro-[1,3]dioxolo[4,5-g]isoquinolino[3,2-a]isoquinolin-7-ium

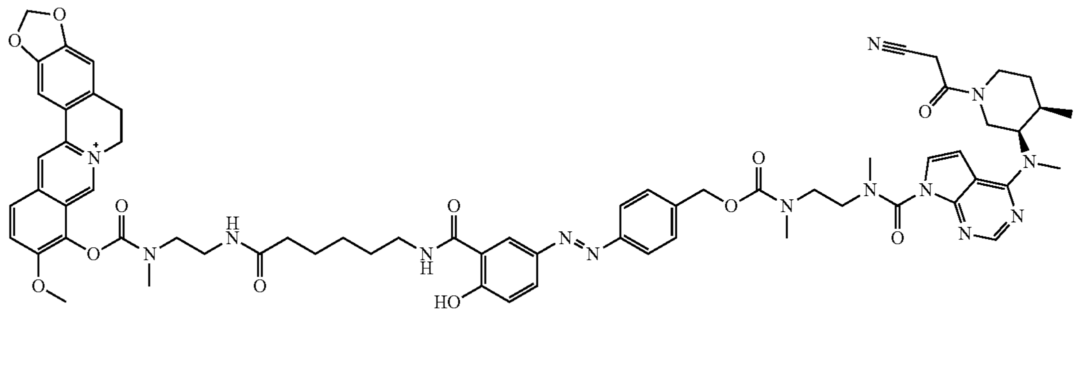 [SMILES: COc1ccc2cc3[n+](cc2c1OC(=O)N(C)CCNC(=O)CCCCCNC(=O)c1cc(/N=N/c2ccc(COC(=O)N(C)CCN(C)C(=O)n4ccc5c(N(C)[C@H]6CN(C(=O)CC#N)CC[C@H]6C)ncnc54)cc2)ccc1O)CCc1cc2c(cc1-3)OCO2]

To a solution of Example 6-3 (525 mg, 0.52 mmol) in dichloromethane (2 mL) was added trifluoroacetic acid (0.4 mL). The mixture was stirred at room temperature for 1 h. LCMS monitored that the reaction was completed. The reaction mixture was concentrated under reduced pressure, dried in vacuum by oil pump and redissolved in dichloromethane (2 mL) and then cooled to 0° C. N,N-Diisopropylethylamine (270 mg, 2.09 mmol) and Example 1-11 (249 mg, 0.52 mmol) were added. The resulting mixture was stirred at room temperature for 0.5 h. LCMS indicated that the reaction was completed. The reaction solution was concentrated, and the crude product was purified by prep-HPLC (gradient eluted by acetonitrile/water (containing 0.1% trifluoroacetic acid)) to afford the title compound (135 mg, 21%) as a yellow solid.

MS (ESI): m/z=1241.8[M]$^+$.

$^1$H NMR: (400 MHz, $CD_3OD$) δ 9.89-9.59 (m, 1H), 8.59-8.47 (m, 2H), 8.37-8.31 (m, 1H), 8.12-7.93 (m, 2H), 7.70-7.61 (m, 2H), 7.51-7.43 (m, 2H), 6.75-6.73 (m, 1H), 6.05 (s, 2H), 5.17-4.90 (m, 4H), 3.98 (s, 3H), 3.79-3.25 (m, 14H), 3.23-3.06 (m, 9H), 2.32-2.27 (m, 3H), 1.72-1.21 (m, 11H), 0.99-0.87 (m, 4H).

Example 7: 9-(((2-(14-((4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)amino)-14-oxotetradecanamido)ethyl)(methyl)carbamoyl)oxy)-10-methoxy-5,6-dihydro-[1,3]dioxolo[4,5-g]isoquinolino[3,2-a]isoquinolin-7-ium

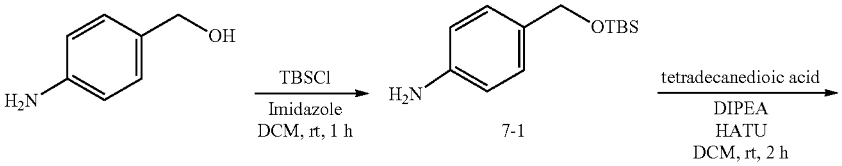

7-1

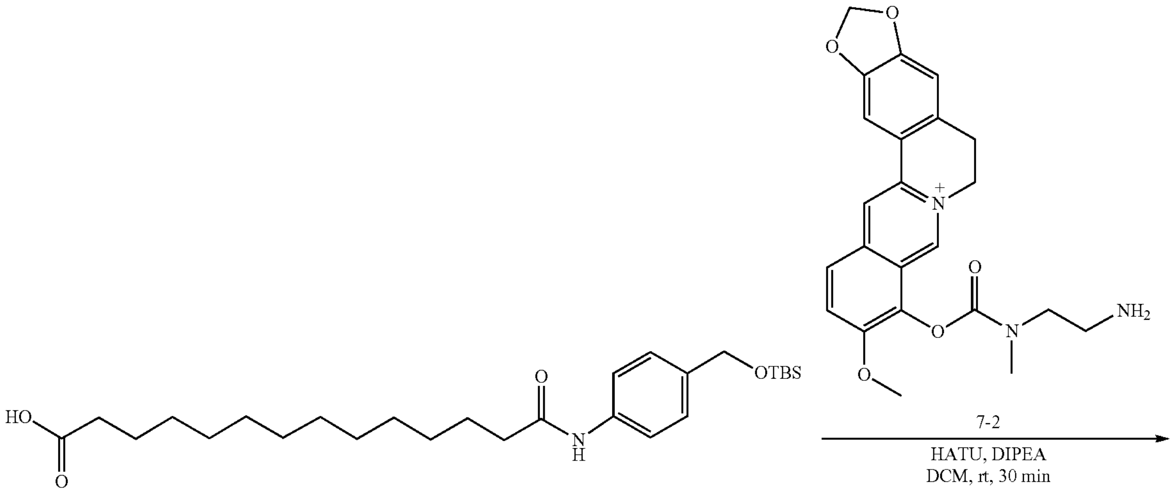

7-2

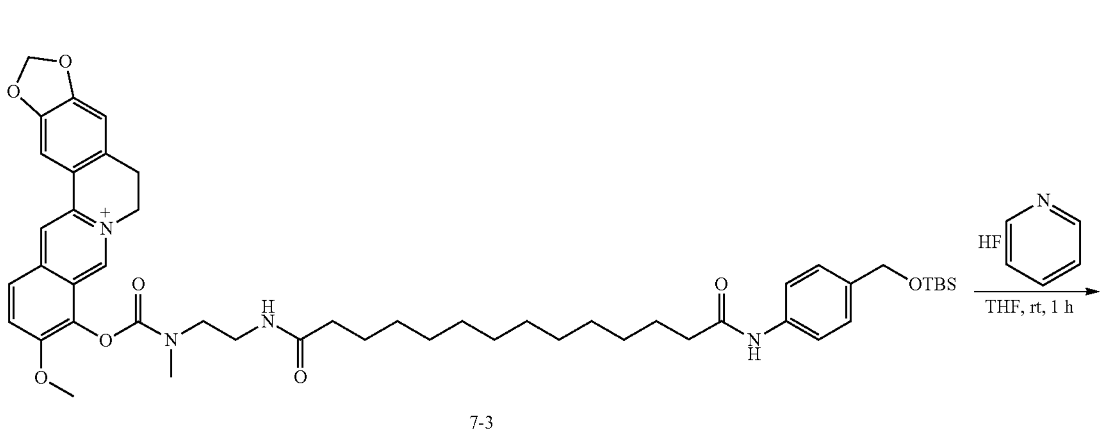

7-3

-continued

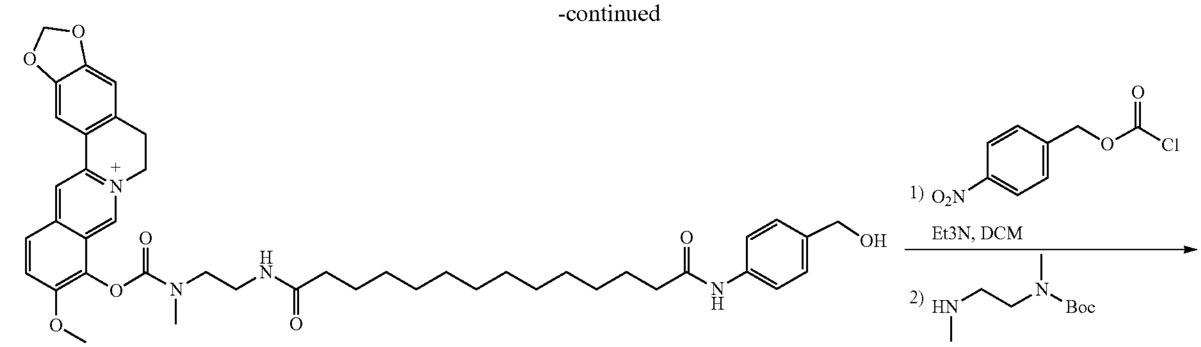

7-4

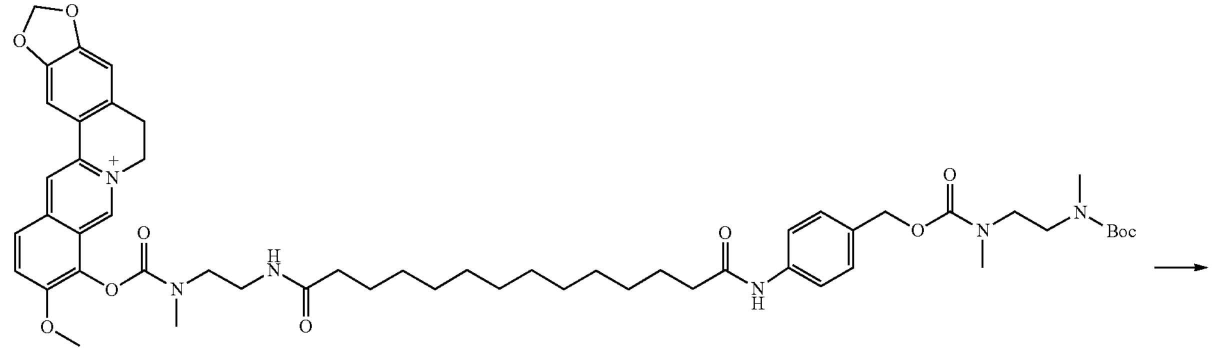

7-5

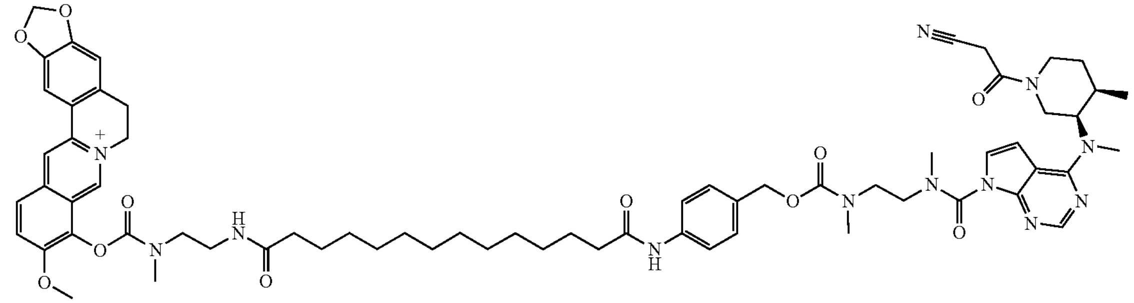

7

Example 7-1: 4-(((tert-Butyldimethylmethylsilyl) oxo)methyl)aniline

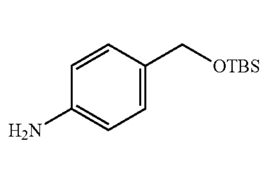 [SMILES: CC(C)(C)[Si](C)(C)OCc1ccc(N)cc1]

To a mixture of (4-aminophenyl)methanol (5.0 g, 40.6 mmol) and imidazole (3.04 g, 44.66 mmol) in dichloromethane (70 mL) was added tert-butyldimethylchlorosilane (6.12 g, 40.6 mmol). The mixture was reacted at room temperature for 1 h. Ethyl acetate (200 mL) was added to the reaction mixture. The organic phase was washed with water (400 mL), dried over anhydrous sodium sulfate and concentrated under reduced pressure. The residue was purified by normal phase column (petroleum ether:ethyl acetate=5:1) to afford the title compound (9.3 g, 95%) as a pale yellow liquid.

MS (ESI): m/z=238.1 $[M+H]^+$.

Example 7-2: 14-((4-(((tert-butyldimethylsilyl)oxy) methyl)phenyl)amino)-14-oxotetradecanoic Acid

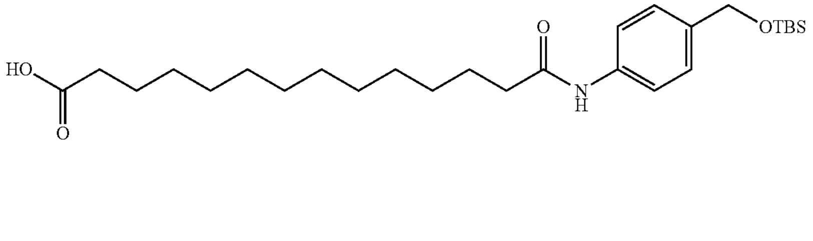 [SMILES: CC(C)(C)[Si](C)(C)OCc1ccc(NC(=O)CCCCCCCCCCCCC(=O)O)cc1]

To a mixture of Example 7-1 (4280 mg, 18.06 mmol) and tetradecanedioic acid (6989 mg, 27.09 mmol) in dichloromethane (43 mL) was added N,N-diisopropylethylamine (4659 mg, 36.12 mmol). The reaction mixture was cooled to 0° C. and stirred for 20 min. To the reaction mixture was added 2-(7-azabenzotriazole)-N,N,N',N'-tetramethyluronium hexafluorophosphate (10.3 g, 27.09 mmol). The reaction was warmed to room temperature and stirred for 16 h. The reaction solution was diluted with dichloromethane (20 mL) and washed with water (40 mL), the organic phase was dried over anhydrous sodium sulfate and concentrated under reduced pressure. The residue was purified by normal phase column (petroleum ether:ethyl acetate=1:1) to afford the title compound (6.7 g, 79%) as a pale yellow solid.

MS (ESI): m/z=500.2 [M+Na]$^+$.

Example 7-3: 9-(((2-(14-((4-(((tert-butyldimethylsilyl)oxy)methyl)phenyl)amino)-14-oxotetradecanamido)ethyl)(methyl)carbamoyl)oxy)-10-methoxy-5,6-dihydro-[1,3]dioxolo[4,5-g]isoquinolino[3,2-a]isoquinolin-7-ium

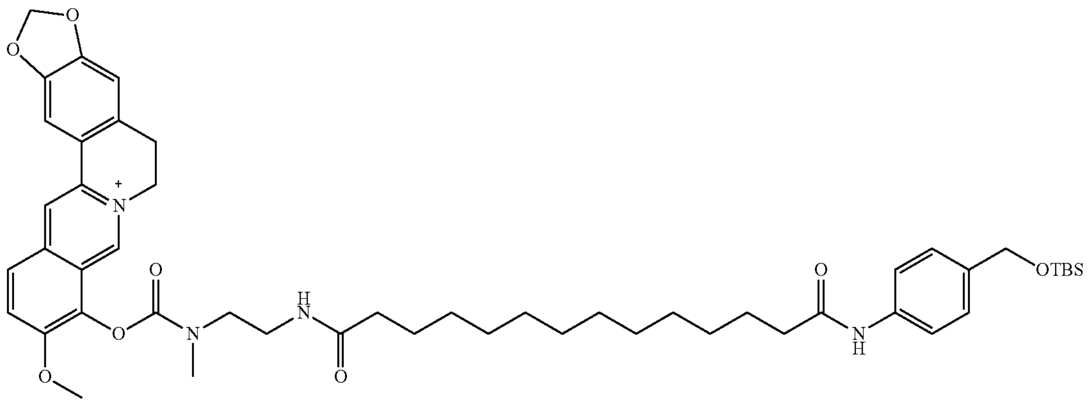 [SMILES: COc1ccc2cc3[n+](cc2c1OC(=O)N(C)CCNC(=O)CCCCCCCCCCCCC(=O)Nc1ccc(CO[Si](C)(C)C(C)(C)C)cc1)CCc1cc2c(cc1-3)OCO2]

To a mixture of Example 7-2 (1800 mg, 3.77 mmol) and Intermediate C (1592 mg, 3.77 mmol) in dichloromethane (20 mL) in a single-necked flask was added N,N-diisopropylethylamine (1947 mg, 15.09 mmol) at 0° C. After stirring for 20 min, 2-(7-azabenzotriazole)-N,N,N',N'-tetramethyluronium hexafluorophosphate (2870 mg, 7.55 mmol) was added. The reaction mixture was warmed to room temperature and stirred for 40 min. The reaction mixture was washed with water (40 mL), the organic phase was dried over anhydrous sodium sulfate and concentrated under reduced pressure. The residue was purified by normal phase column chromatography (ethyl acetate:petroleum ether=1:1) to afford the target compound (2200 mg, 66.2%) as a white solid.

MS (ESI): m/z=881.4 [M]$^+$.

Example 7-4: 9-(((2-(14-((4-(hydroxymethyl)phenyl)amino)-14-oxotetradecanamido)ethyl)(methyl)carbamoyl)oxy)-10-methoxy-5,6-dihydro-[1,3]dioxolo[4,5-g]isoquinolino[3,2-a]isoquinolin-7-ium

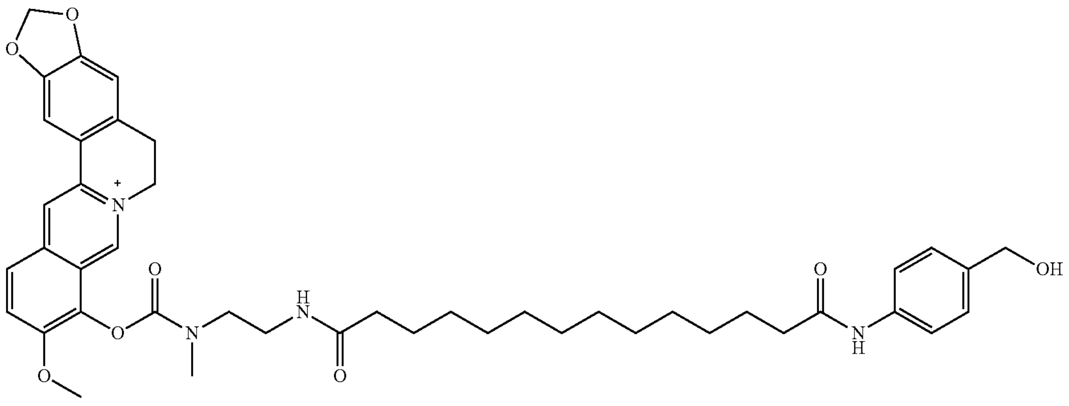 [SMILES: COc1ccc2cc3[n+](cc2c1OC(=O)N(C)CCNC(=O)CCCCCCCCCCCCC(=O)Nc1ccc(CO)cc1)CCc1cc2c(cc1-3)OCO2]

To a mixture of Example 7-3 (2100 mg, 2.38 mmol) in tetrahydrofuran (30 mL) was added pyridine hydrofluoride (753 mg, 9.53 mmol). The reaction was stirred at room temperature for 16 h. LCMS indicated the reaction was completed. The mixture was diluted with dichloromethane (30 mL). The organic phase was washed with water, dried over anhydrous sodium sulfate and concentrated under reduced pressure to afford the target compound (1360 mg, 74.3%) as a white solid.

MS (ESI): m/z=767.3 $[M]^+$.

Example 7-5: 10-methoxy-9-((methyl(2-(14-oxo-14-((4-(4,7,10,10-tetramethyl-3,8-dioxo-2,9-dioxa-4,7-diazaundecyl)phenyl)amino)tetradecanamido)ethyl)carbamoyl)oxy)-5,6-dihydro-[1,3]dioxolo[4,5-g]isoquinolino[3,2-a]isoquinolin-7-ium

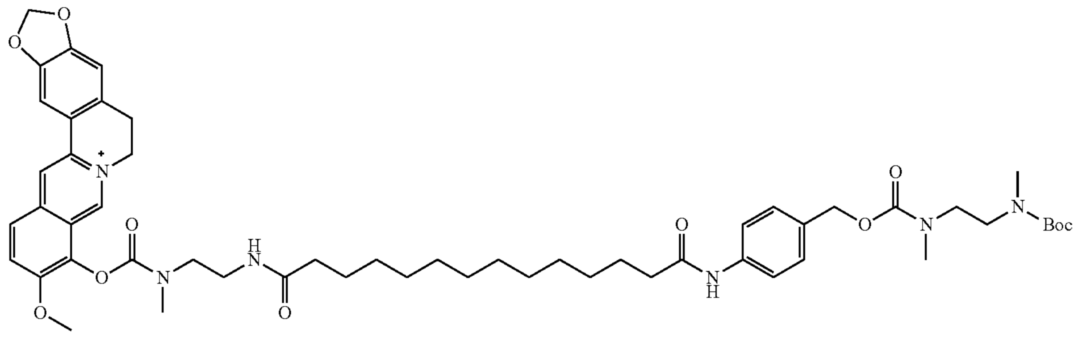 [SMILES: COc1ccc2cc3[n+](cc2c1OC(=O)N(C)CCNC(=O)CCCCCCCCCCCCC(=O)Nc1ccc(COC(=O)N(C)CCN(C)C(=O)OC(C)(C)C)cc1)CCc1cc2c(cc1-3)OCO2]

To a mixture of Example 7-4 (675 mg, 0.88 mmol) in dichloromethane (10 mL) was added triethylamine (267 mg, 2.64 mmol) slowly at 0° C. A solution of 4-nitrophenyl carbonochloridate (265 mg, 1.32 mmol) in dichloromethane (1 mL) was added slowly dropwise. The reaction was stirred at room temperature for 1 h. The reaction mixture was cooled to 0° C., and a solution of tert-butylmethyl (2-(methylamino)ethyl)carbamate (249 mg, 1.32 mmol) in dichloromethane (1.32 mL) was added slowly dropwise, and then the reaction mixture was stirred at room temperature for 1 h. The reaction mixture was washed with water (20 mL*2), and dried over anhydrous sodium sulfate and concentrated under reduced pressure. The residue was purified by silica gel column (ethyl acetate:petroleum ether=1:1) to afford the target compound (240 mg, 28%) as an orange-yellow oil.

MS (ESI): m/z=981.5 $[M]^+$.

Example 7: 9-(((2-(14-((4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)amino)-14-oxotetradecanamido)ethyl)(methyl)carbamoyl)oxy)-10-methoxy-5,6-dihydro-[1,3]dioxolo[4,5-g]isoquinolino[3,2-a]isoquinolin-7-ium

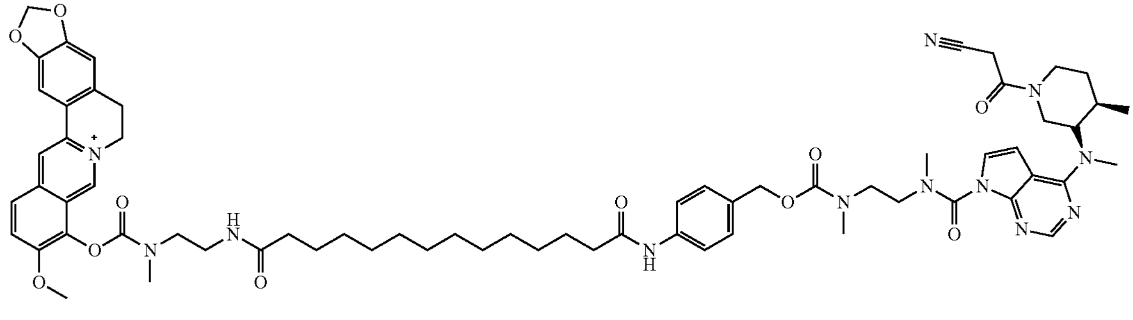

To a mixture of Example 7-5 (210 mg, 0.214 mmol) in dichloromethane (2 mL) in a single-necked flask, trifluoroacetic acid (0.4 mL) was added. The reaction mixture was stirred at room temperature for 15 min. After the reaction was completed as monitored by LCMS, the reaction mixture was concentrated under reduced pressure. Then dichloromethane (1 mL), N,N-diisopropylethylamine (0.1 mL, 0.64 mmol), and Example 1-11 (102 mg, 0.21 mmol) were added. And the resulting mixture was stirred at room temperature for 15 min. The reaction mixture was concentrated under reduced pressure, and the resulting residue was dissolved with N,N-dimethylformamide (2 mL). The mixture was purified by Prep-HPLC (gradient eluted by acetonitrile/water (containing 0.1% trifluoroacetic acid)) to afford the target compound (15.2 mg, 5.8%) as a yellow solid.

MS (ESI): m/z=1219.7 $[M]^+$.

$^1$HNMR (400 MHz, $CD_3OD$) δ 10.039-9.792 (m, 1H), 8.76-8.73 (m, 1H), 8.53 (s, 1H), 8.15 (m, 3H), 7.64-7.62 (m, 1H), 7.51-7.50 (m, 1H), 7.46-7.44 (m, 1H), 7.29-7.27 (m, 1H), 6.93-6.91 (m, 1H), 6.78-6.66 (m, 2H), 6.082 (s, 2H), 5.00-4.99 (m, 5H), 4.06 (s, 3H), 3.96-3.87 (m, 4H), 3.68 (s, 3H), 3.57-3.55 (m, 2H), 3.48-3.44 (m, 4H), 3.23-3.21 (m, 3H), 3.08 (s, 2H), 2.42-2.40 (m, 1H), 2.33-2.29 (t, J=8.0 Hz, 3H), 2.25-2.17 (m, 3H), 1.71-1.54 (m, 7H), 1.28-1.20 (m, 21H), 1.09-0.99 (m, 5H).

Example 8: 9-((5-(5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzamido)pentanoyl)oxy)-10-methoxy-5,6-dihydro-[1,3]dioxolo[4,5-g]isoquinolino[3,2-a]isoquinolin-7-ium

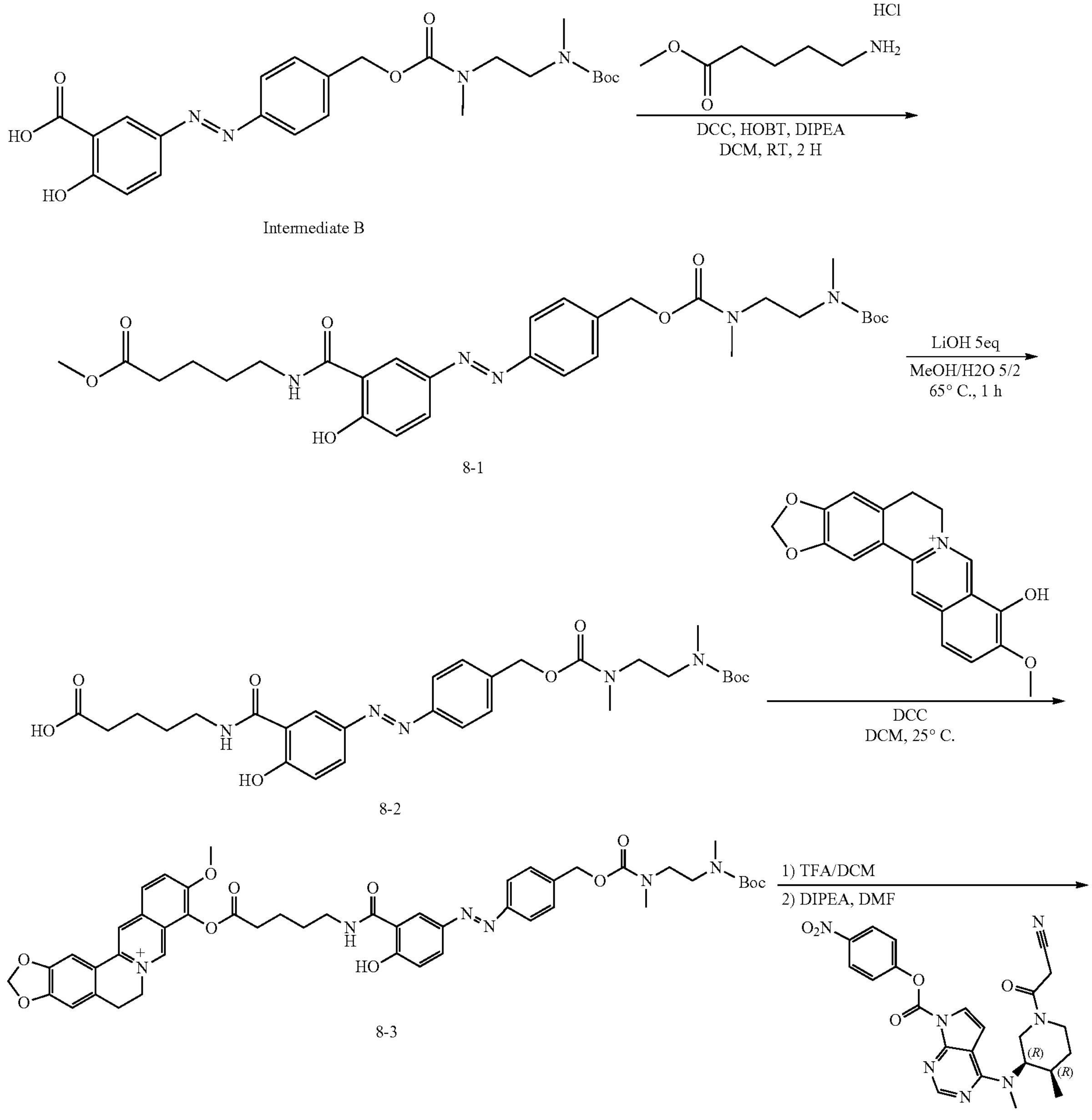

Intermediate B 8-1

8-2

8-3

1-11

-continued

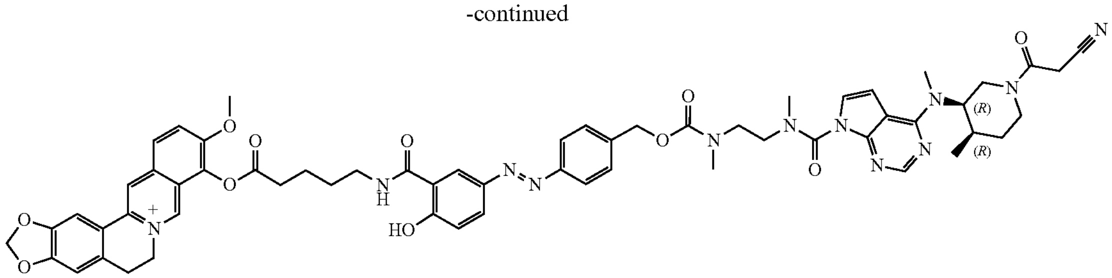

8

Example 8-1: Methyl-(E)-5-(2-hydroxy-5-((4-(4,7,10,10-tetramethyl-3,8-dioxo-2,9-dioxa-4,7-diazaundecyl)phenyl)diazenyl)benzamido)pentanoate

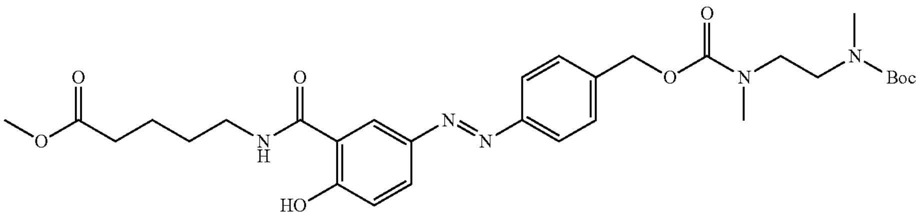 [SMILES: COC(=O)CCCCNC(=O)c1cc(/N=N/c2ccc(COC(=O)N(C)CCN(C)C(=O)OC(C)(C)C)cc2)ccc1O]

A mixture of Intermediate B (3.0 g, 6.17 mmol), 1-hydroxybenzotriazole (1.001 g, 7.41 mmol), dicyclohexylcarbodiimide (1.783 g, 8.64 mmol) in dichloromethane (20 mL) was stirred at 0° C. for 20 min, then methyl 5-aminopentanoate hydrochloride (1.212 g, 7.41 mmol), N,N-diisopropylethylamine (1.752 g, 13.6 mmol) were added. The mixture was warmed to room temperature and stirred for 2 h. The reaction was completed as monitored by LCMS, the reaction mixture was filtered and the resulting filtrate was concentrated under reduced pressure. The residue was purified by normal phase column (petroleum ether:ethyl acetate=1:1) to afford the title compound (3.34 g, 91%) as a red solid.

MS (ESI): m/z=622.2 $[M+Na]^+$.

Example 8-2: (E)-5-(2-hydroxy-5-((4-(4,7,10,10-tetramethyl-3,8-dioxo-2,9-dioxa-4,7-diazaundecyl)phenyl)diazenyl)benzamido)pentanoic Acid

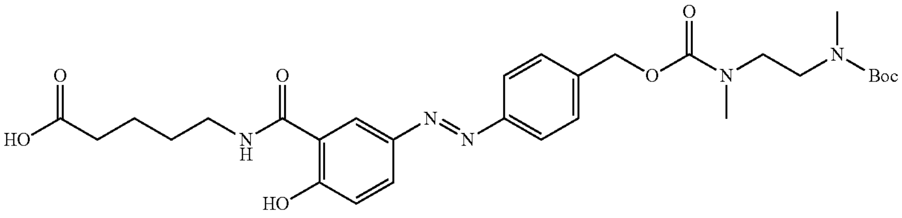 [SMILES: CN(CCN(C)C(=O)OC(C)(C)C)C(=O)OCc1ccc(/N=N/c2ccc(O)c(C(=O)NCCCCC(=O)O)c2)cc1]

To mixture of Example 8-1 (3300 mg, 5.51 mmol) in methanol (30 mL) and water (15 mL), lithium hydroxide monohydrate (1157 mg, 27.5 mmol) was added. The reaction mixture was heated to reflux at 65° C. for 1 h. After cooling down, the reaction mixture was adjusted to pH 5 with dilute hydrochloric acid. The mixture was extracted with ethyl acetate (100 mL) for 3 times, the organic phase was combined and dried over anhydrous sodium sulfate and concentrated under reduced pressure to afford the title compound (3000 mg, 93.1%) as an orange solid.

MS (ESI): m/z=608.2 $[M+Na]^+$.

Example 8-3: (E)-9-((5-(2-hydroxy-5-((4-(4,7,10,10-tetramethyl-3,8-dioxo-2,9-dioxa-4,7-diazaundecyl)phenyl)diazenyl)benzamido)pentanoyl)oxy)-10-methoxy-5,6-dihydro-[1,3]dioxolo[4,5-g]isoquinolino[3,2-a]isoquinolin-7-ium

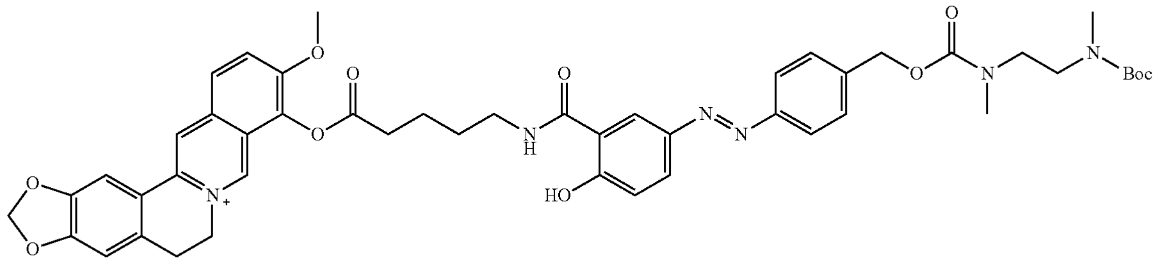 [SMILES: COc1ccc2cc3[n+](cc2c1OC(=O)CCCCNC(=O)c1cc(/N=N/c2ccc(COC(=O)N(C)CCN(C)C(=O)OC(C)(C)C)cc2)ccc1O)CCc1cc2c(cc1-3)OCO2]

To a mixture of Example 8-2 (1500 mg, 2.56 mmol) in dichloromethane (20 mL) in a single neck flask were added dicyclohexylcarbodiimide (792 mg, 3.84 mmol) and Intermediate A-8 (908 mg, 2.82 mmol). The reaction mixture was stirred at room temperature for 2 h. After the reaction was completed as monitored by LCMS, the reaction mixture was washed with water (60 mL) for 3 times, and the organic phase was dried over anhydrous sodium sulfate and concentrated under reduced pressure. The residue was purified by normal phase column chromatography (dichloromethane: methanol=10:1) to give the title compound (367 mg, 16.1%) as an orange oil.

MS (ESI): m/z=889.4 $[M]^+$.

Example 8: 9-((5-(5-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)-2-hydroxybenzamido)pentanoyl)oxy)-10-methoxy-5,6-dihydro-[1,3]dioxolo[4,5-g]isoquinolino[3,2-a]isoquinolin-7-ium

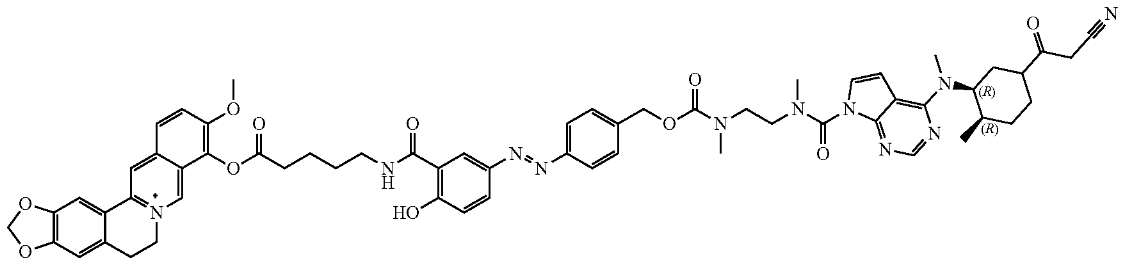

To a mixture of Example 8-3 (300 mg, 0.34 mmol) in dichloromethane (2.5 ml) was added trifluoroacetic acid (0.5 mL). The reaction mixture was stirred at room temperature for 15 min, and the mixture was concentrated under reduced pressure. Then N,N-dimethylformamide (2 mL), N,N-diisopropylethylamine (95.8 mg, 0.74 mmol) and Example 1-11 (193 mg, 0.4 mmol) were added. The reaction mixture was stirred at room temperature for 15 min. After the reaction was completed as monitored by LCMS, the reaction was quenched by hydrochloric acid (1 N). The reaction mixture was purified by Prep-HPLC (gradient eluted by acetonitrile/water (containing 0.1% trifluoroacetic acid)) to afford the target compound (62.0 mg, 16%) as a yellow solid.

MS (ESI): m/z=1127.5 $[M]^+$.

$^1$H NMR (400 MHz, $CD_3OD$) δ 9.63-9.60 (m, 1H), 8.70-8.62 (m, 1H), 8.39-8.35 (m, 1H), 8.11-8.02 (m, 3H), 7.91-7.89 (m, 1H), 7.68-7.66 (m, 2H), 7.59-7.56 (m, 2H), 7.46-7.40 (m, 2H), 7.01-6.85 (m, 3H), 6.09 (s, 2H), 5.18-5.16 (m, 2H), 4.03-4.02 (m, 3H), 3.92-3.91 (m, 3H), 3.81-3.73 (m, 3H), 3.65-3.59 (m, 2H), 3.56-3.52 (m, 4H), 3.46-3.39 (m, 2H), 3.24-3.18 (m, 5H), 3.17-3.16 (m, 3H), 2.94-2.91 (m, 4H), 2.36-2.28 (m, 1H), 1.99-1.94 (m, 2H), 1.91-1.86 (m, 2H), 1.68-1.60 (m, 5H), 0.94-0.92 (m, 2H).

The following compound was obtained by replacing the corresponding starting materials using a method similar to that of Example 8.

| | | |
|---|---|---|
| 9 | Compound structure | 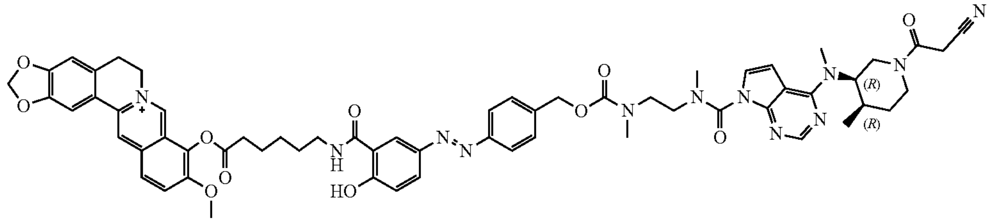 |
| | LCMS, $^1H$ NMR | MS (ESI): m/z = 1141.4 $[M]^+$. $^1H$ NMR (400 MHZ, DMSO-$d_6$) δ 9.57-9.54 (m, 1H), 8.60-8.53 (m, 1H), 8.25-8.18 (m, 2H), 8.05-7.90 (m, 2H), 7.82-7.78 (m, 1H), 7.65-7.58 (m, 2H), 7.53-7.49 (m, 2H), 7.39-7.28 (m, 2H), 7.15-7.02 (m, 1H), 6.92-6.84 (m, 2H), 6.08 (s, 2H), 3.95-3.92 (m, 6H), 3.68-3.63 (m, 3H), 3.54-3.51 (m, 4H), 3.46-3.40 (m, 2H), 3.24-3.14 (m, 5H), 3.17-3.14 (m, 3H), 3.03-3.01 (m, 5H), 2.87-2.84 (m, 3H), 2.37-2.29 (m, 1H), 1.96-1.89 (m, 2H), 1.82-1.80 (m, 3H), 1.74-1.60 (m, 6H), 0.98-0.94 (m, 2H). |

Example 10: 9-((3-(2-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)phenyl)propanoyl)oxy)-10-methoxy-5,6-dihydro-[1,3]dioxolo[4,5-g]isoquinolino[3,2-a]isoquinolin-7-ium

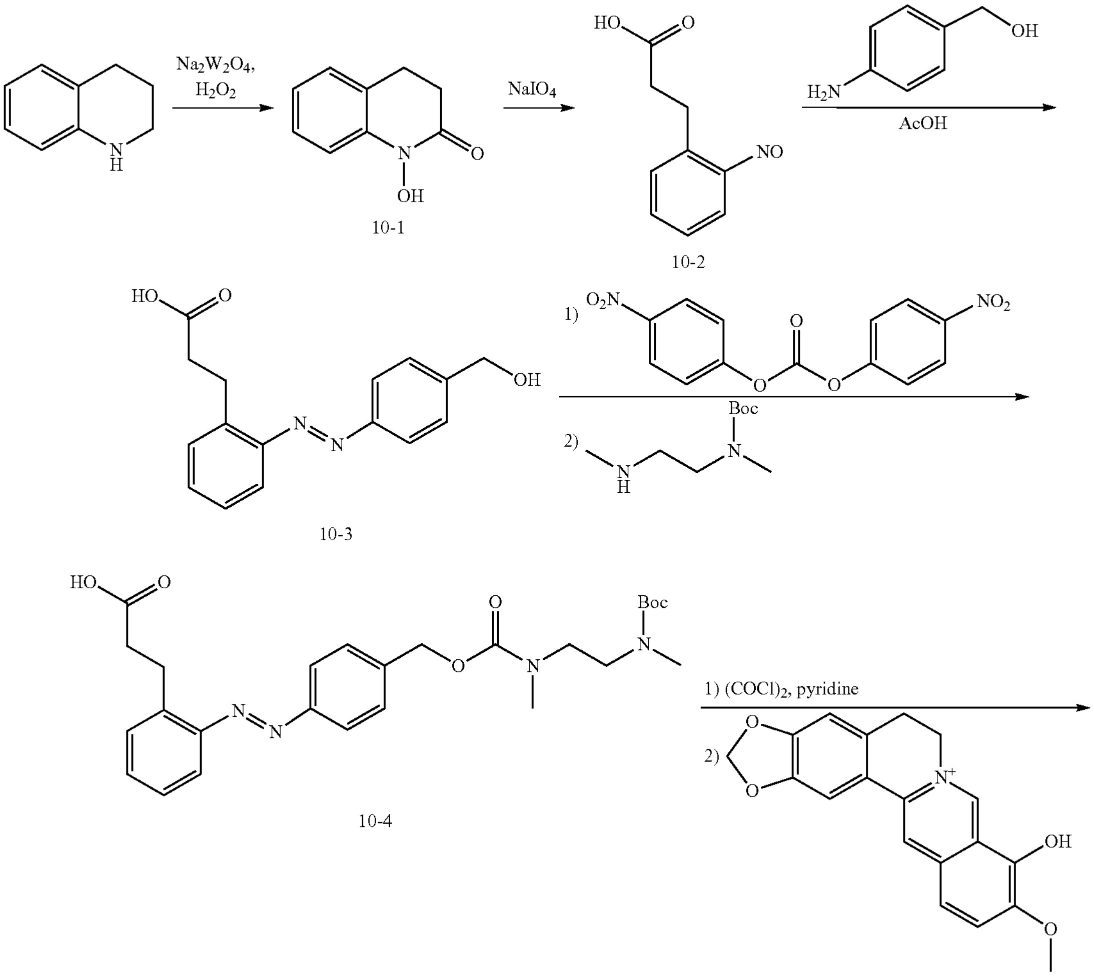

10-1
10-2
10-3
10-4
A-8

-continued

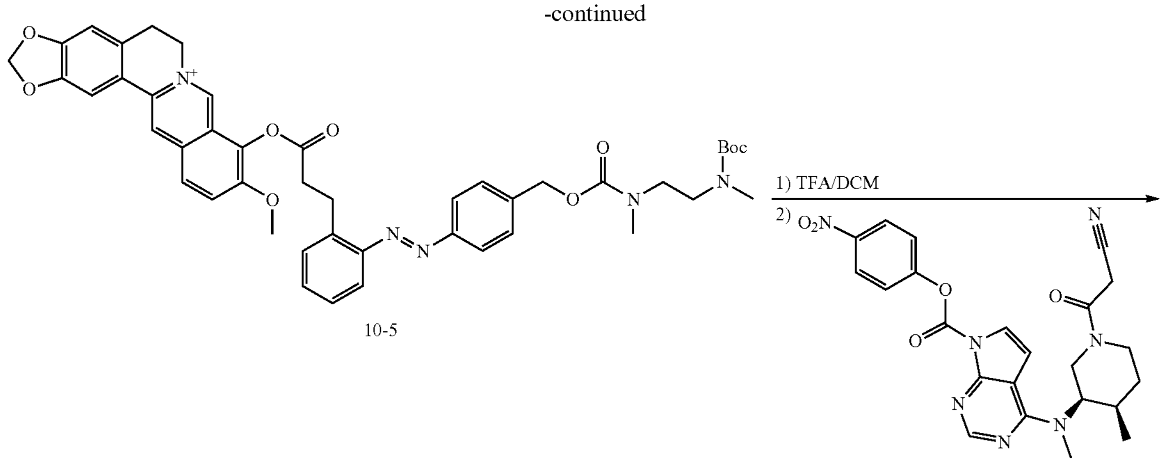

10-5

1-11

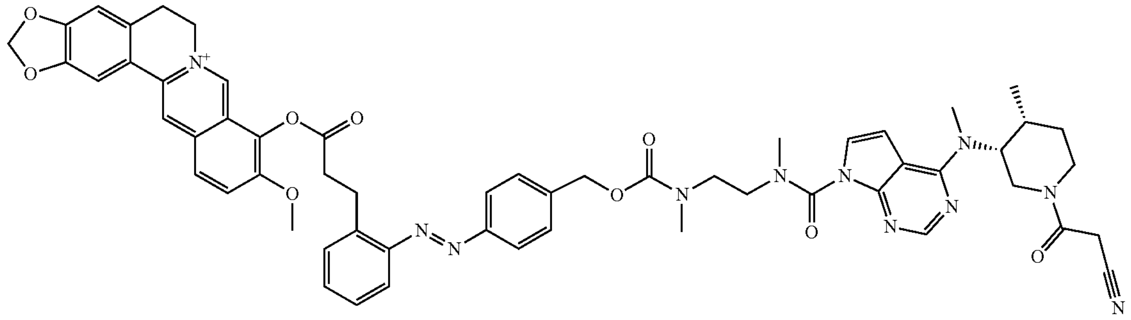

10

Example 10-1: 1-Hydroxy-3,4-dihydroquinolin-2(1H)-one

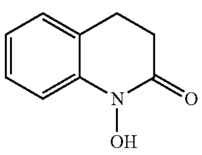 [SMILES: O=C1CCc2ccccc2N1O]

Hydrogen peroxide (35%, 22 mL) was added dropwise to a mixture of 1,2,3,4-tetrahydroquinoline (10.0 g, 75 mmol) and sodium tungstate dihydrate (1.9 g, 3.7 mmol) in methanol (200 mL). After addition, the mixture was stirred at room temperature overnight. The reaction mixture was concentrated under reduced pressure. The residue was dissolved in water (200 mL) and extracted with dichloromethane (100 mL*2). The organic phases were combined, dried over anhydrous sodium sulfate, filtered, and the filtrate was concentrated under reduced pressure to obtain the crude product. The crude product was triturated in dichloromethane/methanol (1:1, 100 mL) and filtered. The filter cake was dried to give the title compound (8.8 g, 72%) as a brownish-yellow solid.

MS (ESI): m/z=164.1 $[M+H]^+$.

$^1H$ NMR ($CDCl_3$, 400 MHz) δ 9.03 (br, 1H), 7.33 (d, J=8.0 Hz, 1H), 7.28 (t, J=8.0 Hz, 1H), 7.15 (d, J=8.8 Hz, 1H), 7.05 (t, J=7.6 Hz, 1H), 2.93 (t, J=7.6 Hz, 2H), 2.76 (t, J=8.0 Hz, 2H).

Example 10-2: 3-(2-nitrosophenyl)propionic Acid

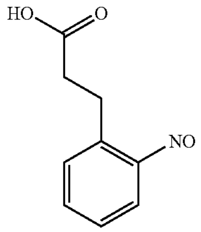

Sodium periodate (23.1 g, 107 mmol) was added to the mixture of Example 10-1 (8.8 g, 53 mmol) in tetrahydrofuran (120 mL) and water (30 mL) with an ice-water bath. The mixture was stirred at room temperature for 1 h. The reaction mixture was concentrated under reduced pressure to remove the organic solvent. The resulting residue was diluted with water (100 mL), and hydrochloric acid (2 M) was added to adjust pH to weak acidity. Then the mixture was extracted with ethyl acetate (450 mL). The combined organic phases were dried over anhydrous sodium sulfate, filtered and concentrated under reduced pressure. The crude product was triturated in ethyl acetate (100 mL) to afford the title compound (4.5 g, 46%) as a yellow solid.

MS (ESI): m/z=171.2 $[M+H]^+$.

Example 10-3: (E)-3-(2-((4-(Hydroxymethyl)phenyl)diazenyl)phenyl)propanoic Acid

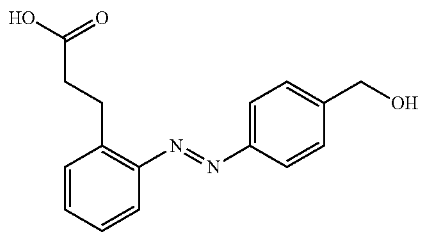 [SMILES: O=C(O)CCc1ccccc1/N=N/c1ccc(CO)cc1]

To a mixture of Example 10-2 (4.5 g, 25.1 mmol) and (4-aminophenyl)methanol (3.1 g, 25.1 mmol) in dichloromethane (150 mL), acetic acid (15 mL) was added. The mixture was stirred at room temperature for 48 h under nitrogen protection. LCMS indicated that starting materials were consumed. The reaction mixture was diluted with dichloromethane (100 mL), washed with water (100 mL*2) and saturated brine (100 mL) sequentially. The organic phase was dried over anhydrous sodium sulfate, concentrated under reduced pressure and the residue was purified by normal phase column chromatography (dichloromethane: methanol=94:6) and purified by triturated in ethyl acetate (30 mL) to afford the title compound (4.0 g, 56%) as a red solid.

MS (ESI): m/z=285.1 $[M+H]^+$.

Example 10-4: (E)-3-(2-((4-(4,7,10,10-tetramethyl-3,8-dioxo-2,9-dioxa-4,7-diazaundecyl)phenyl)diazenyl)phenyl)propanoic Acid

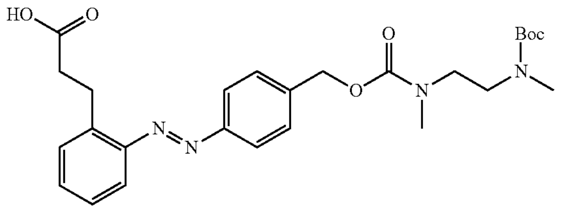 [SMILES: CN(CCN(C)C(=O)OC(C)(C)C)C(=O)OCc1ccc(/N=N/c2ccccc2CCC(=O)O)cc1]

To a mixture of Example 10-3 (3.7 g, 13.0 mmol) and bis(p-nitrophenyl)carbonate (4.752 g, 15.6 mmol) in dichloromethane (50 mL), diisopropylethylamine (3.361 g, 26.0 mmol) was added dropwise with an ice water bath. The reaction mixture was stirred at room temperature for 30 min, and then tert-butylmethyl (2-(methylamino)ethyl)carbamate (3.184 g, 16.9 mmol) was added dropwise to the reaction solution at 0° C. After addition was completed, the solution was reacted at room temperature for 1 h, and then warmed up to 40° C. and stirred for 2 h. LCMS indicated that starting materials were completely consumed. The reaction mixture was diluted with dichloromethane (200 mL) and washed with water (100 mL). The organic phase was dried over anhydrous sodium sulfate and concentrated under reduced pressure. The residue was purified by normal phase column chromatography (dichloromethane:methanol=10:1) to afford the target compound (1.1 g, 17%) as a yellow solid.

MS (ESI): m/z=521.1 $[M+Na]^+$.

Example 10-5: (E)-10-methoxy-9-((3-(2-((4-(4,7,10,10-tetramethyl-3,8-dioxo-2,9-dioxa-4,7-diazaundecyl)phenyl)diazenyl)phenyl)propanoyl)oxy)-5,6-dihydro-[1,3]dioxolo[4,5-g]isoquinolino[3,2-a]isoquinolin-7-ium

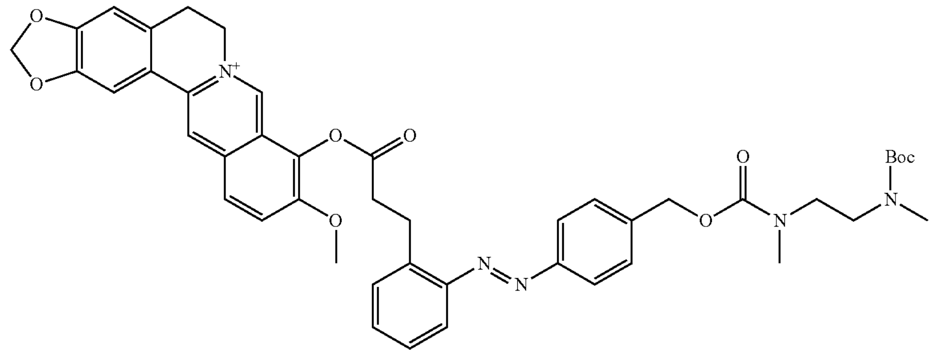 [SMILES: COc1ccc2cc3[n+](cc2c1OC(=O)CCc1ccccc1/N=N/c1ccc(COC(=O)N(C)CCN(C)C(=O)OC(C)(C)C)cc1)CCc1cc2c(cc1-3)OCO2]

To a mixture of Example 10-4 (650 mg, 1.3 mmol) and pyridine (412 mg, 5.2 mmol) in dichloromethane (30 mL), oxalyl chloride (486 mg, 1 mmol) was added dropwise at room temperature. The reaction mixture was stirred at room temperature for 30 min and LCMS indicated that starting materials were consumed. The reaction mixture was concentrated under reduced pressure, dried in vacuum by oil pump. The residue was dissolved in acetonitrile (5 mL) and then added dropwise to a mixture of Intermediate A-8 (420 mg, 1.3 mmol) and pyridine (412 mg, 5.2 mmol) in acetonitrile (30 mL). The reaction mixture was stirred at room temperature for 20 min and LCMS indicated that starting materials were consumed. The reaction mixture was concentrated under reduced pressure and diluted with dichloromethane (100 mL), washed with water (100 mL) and hydrochloric acid (1 N, 100 mL). The organic phase was dried over anhydrous sodium sulfate and concentrated under reduced pressure. The residue was purified by normal phase column chromatography (dichloromethane:methanol=92:8, containing 0.1% trifluoroacetic acid) to afford the target compound (217 mg, 21%) as a yellow oil.

MS (ESI): m/z=803.2 $[M+H]^+$.

Example 10: 9-((3-(2-((E)-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenyl)diazenyl)phenyl)propanoyl)oxy)-10-methoxy-5,6-dihydro-[1,3]dioxolo[4,5-g]isoquinolino[3,2-a]isoquinolin-7-ium

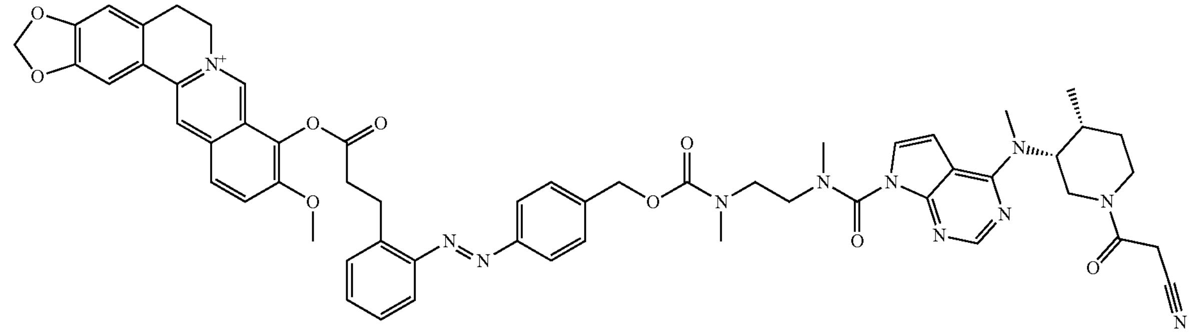 [SMILES: COc1ccc2cc3[n+](cc2c1OC(=O)CCc1ccccc1/N=N/c1ccc(COC(=O)N(C)CCN(C)C(=O)n2ccc4c(N(C)[C@H]5CN(C(=O)CC#N)CC[C@H]5C)ncnc42)cc1)CCc1cc2c(cc1-3)OCO2]

To a mixture of Example 10-5 (217 mg, 0.27 mmol) in dichloromethane (2 mL) was added trifluoroacetic acid (0.4 mL). The mixture was stirred at room temperature for 1 h. LCMS indicated that the reaction was completed. The reaction mixture was concentrated under reduced pressure, the resulting residue was dried in vacuum by oil pump and dissolved in N,N-dimethylformamide (1.5 mL) and cooled to 0° C. N,N-diisopropylethylamine (139 mg, 1.1 mmol) and Example 1-11 (258 mg, 0.54 mmol) were added and the mixture was stirred at room temperature for 0.5 h. After the reaction was quenched by hydrochloric acid (1 N), the reaction was purified by Prep-HPLC (gradient eluted by acetonitrile/water (containing 0.1% trifluoroacetic acid)) to afford the title compound (63.0 mg, 22.4%) as a yellow solid.

MS (ESI): m/z=1140.4 $[M]^+$.

$^1$H NMR (400 MHz, $CD_3OD$) δ 9.60-9.47 (m, 1H), 8.72-8.67 (m, 1H), 8.19-8.07 (m, 3H), 7.87-7.74 (m, 2H), 7.63-7.39 (m, 6H), 6.99-6.51 (m, 4H), 6.09 (s, 2H), 5.21-5.05 (m, 1H), 4.97-4.86 (m, 3H), 4.00-3.71 (m, 8H), 3.66-3.37 (m, 8H), 3.24-3.16 (m, 9H), 3.05-2.81 (m, 6H), 2.40-2.26 (m, 1H), 1.90-1.77 (m, 1H).

Example 11: (E)-9-((5-(5-((4-((((2-(4-(1-(3-(cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)(methyl)carbamoyl)oxy)methyl)phenyl)diazenyl)-2-hydroxybenzamido)pentanoyl)oxy)-10-methoxy-5,6-dihydro-[1,3]dioxolo[4,5-g]isoquinolino[3,2-a]isoquinolin-7-ium

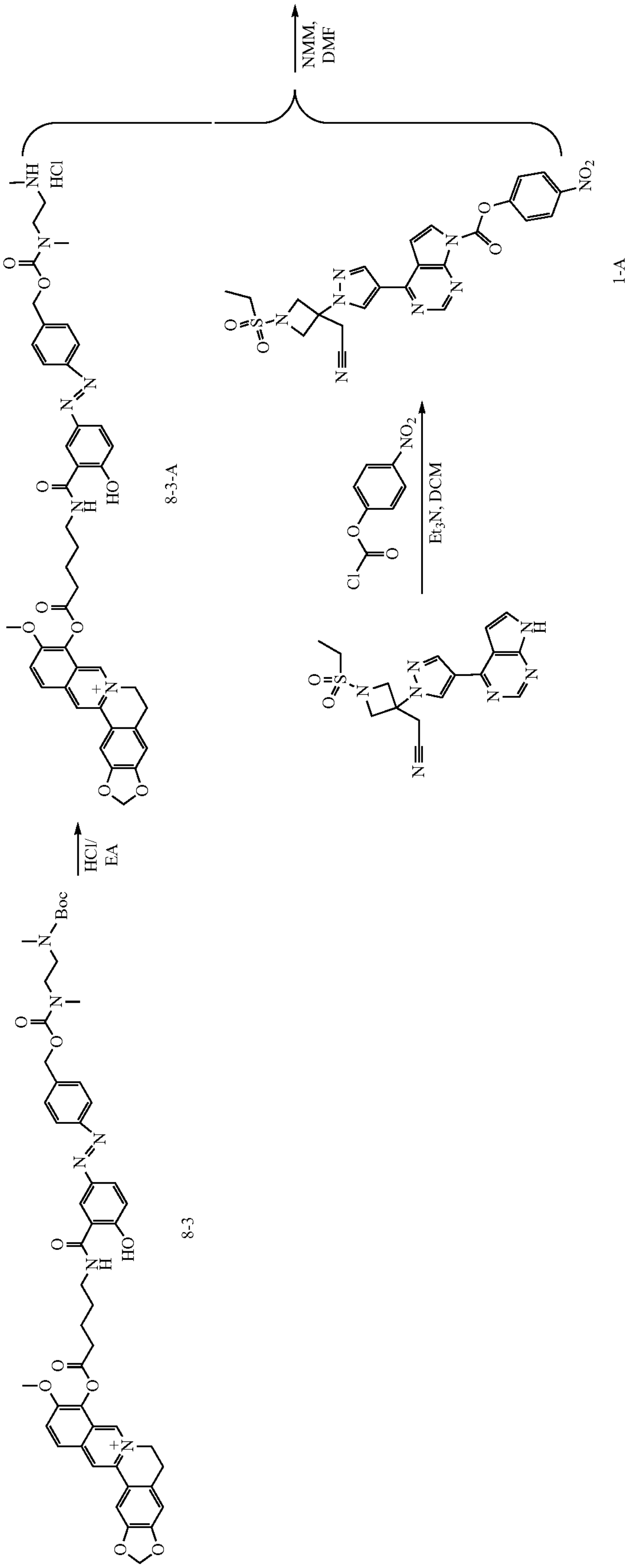
8-3
8-3-A
1-A

-continued
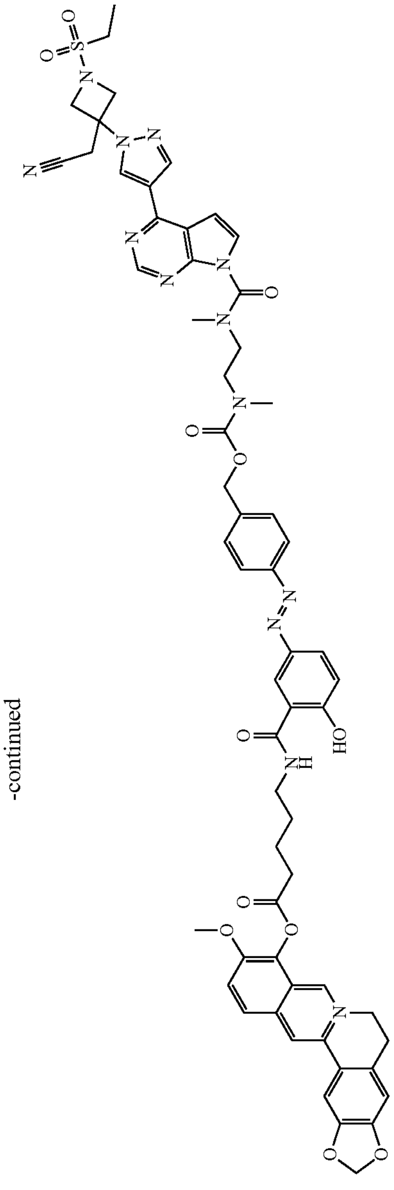
11

Example 8-3-A: (E)-9-((5-(2-hydroxy-5-((4-(((methyl(2-(methylamino)ethyl)carbamoyl)oxy)methyl)phenyl)diazenyl)benzamido)pentanoyl)oxy)-10-methoxy-5,6-dihydro-[1,3]dioxolo[4,5-g]isoquinolino[3,2-a]isoquinolin-7-iumhydrochloric acid

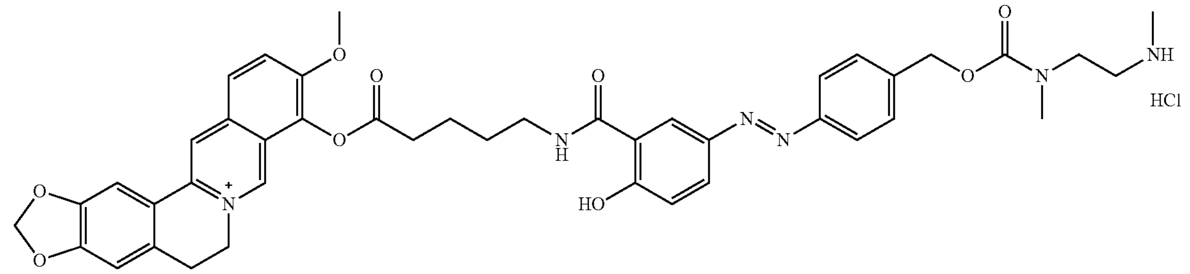 [SMILES: CNCCN(C)C(=O)OCc1ccc(/N=N/c2ccc(O)c(C(=O)NCCCCC(=O)Oc3c(OC)ccc4cc5[n+](cc34)CCc3cc4c(cc3-5)OCO4)c2)cc1 ; Cl]

To a solution of Example 8-3 (7.7 g, 7.13 mmol) in ethyl acetate (35 mL) was added hydrochloride ethyl acetate solution (4 N, 70 mL) at 0° C. The mixture was reacted at 25° C. for 1 h. After the reaction was completed as monitored by LCMS, the reaction mixture was filtered and the filter cake was rinsed with ethyl acetate to afford the title compound (6.8 g, 110%) as a red solid.

MS (ESI): m/z=789.3 $[M]^+$.

Example 1-A: 4-nitrophenyl 4-(1-(3-(cyanomethyl)-1-(ethylsulfonyl)azetidin-3-yl)-1H-pyrazol-4-yl)-7H-pyrrolo[2,3-d]pyrimidine-7-carboxylate

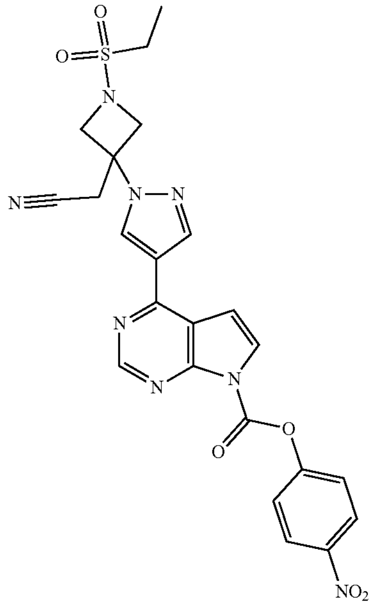 [SMILES: CCS(=O)(=O)N1CC(CC#N)(n2cc(-c3ncnc4c3ccn4C(=O)Oc3ccc([N+](=O)[O-])cc3)cn2)C1]

To a mixture of Baricitinib (100 mg, 0.27 mmol) and triethylamine (109 mg, 1.08 mmol) in dichloromethane (5 mL) was added 4-nitrophenyl carbonochloridate (108 mg, 0.54 mmol) at room temperature. The reaction mixture was stirred at room temperature for 1.5 h. LCMS indicated that starting materials were completely consumed. The reaction mixture was diluted with dichloromethane (50 mL), washed with water (50 mL) and brine (50 mL) successively, and the organic phase was dried with anhydrous sodium sulfate and concentrated under reduced pressure to give a crude product. The crude product was triturated in dichloromethane (5 mL), filtered and the filter cake was dried to give the title compound (100 mg, 85%) as a yellow solid.

MS (ESI): m/z=537.0 $[M+H]^+$.

Example 11: (E)-9-((5-(5-((4-((((2-(4-(1-(3-(cyanomethyl)-1-(ethylsulfonyl)azetidin-3-yl)-1H-pyrazol-4-yl)-N-methyl-7H-pyrrolo[2,3-d]pyrimidine-7-carboxamido)ethyl)(methyl)carbamoyl)oxy)methyl)phenyl)diazenyl)-2-hydroxybenzamido)pentanoyl)oxy)-10-methoxy-5,6-dihydro-[1,3]dioxolo[4,5g]-isoquinolino[3,2-a]isoquinolin-7-ium

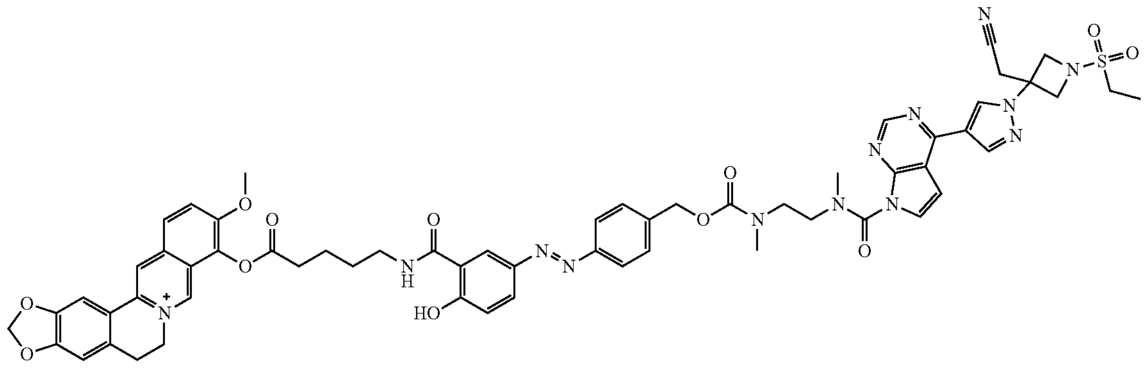 [SMILES: CCS(=O)(=O)N1CC(CC#N)(n2cc(-c3ncnc4c3ccn4C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)cn2)C1]

To a mixture of Example 8-3-A (118 mg, 0.15 mmol), N-methylmorpholine (19 mg, 0.18 mmol) in N,N-dimethylformamide (2 mL) was added Example 1-A (100 mg, 0.18 mmol). The mixture was stirred at room temperature for 2 h. LCMS indicated that starting materials were completely consumed. The reaction mixture was quenched with hydrochloric acid (1 N). The mixture was purified in Prep-HPLC (gradient eluted by acetonitrile/water (containing 0.1% trifluoroacetic acid)) to afford the title compound (93 mg, 42%) as a yellow solid.

MS (ESI): m/z=1186.4 $[M]^+$.

$^1$H NMR (400 MHz, $CD_3CN$) δ 9.37 (s, 1H), 8.98-8.55 (m, 4H), 8.18-8.02 (m, 4H), 7.66-7.33 (m, 6H), 7.04-6.88 (m, 3H), 6.12 (s, 2H), 5.29-5.09 (m, 1H), 4.77-4.55 (m, 5H), 4.28-4.22 (m, 3H), 4.02 (s, 3H), 3.77-3.46 (m, 9H), 3.12-2.91 (m, 14H), 1.34-1.31 (in, 5H).

Following compounds are provided by similar method of Example 11 by replacing corresponding starting materials. The reaction solvent for preparation of Example 1-A can be dichloromethane, N,N-dimethylformamide, etc., and the base can be triethylamine, 2,6-dimethylpyridine, etc. The solvent for the preparation of Example 11 can be N,N-dimethylformamide, N,N-dimethylacetamide, etc.

| | | |
|---|---|---|
| 12 | Compound structure | 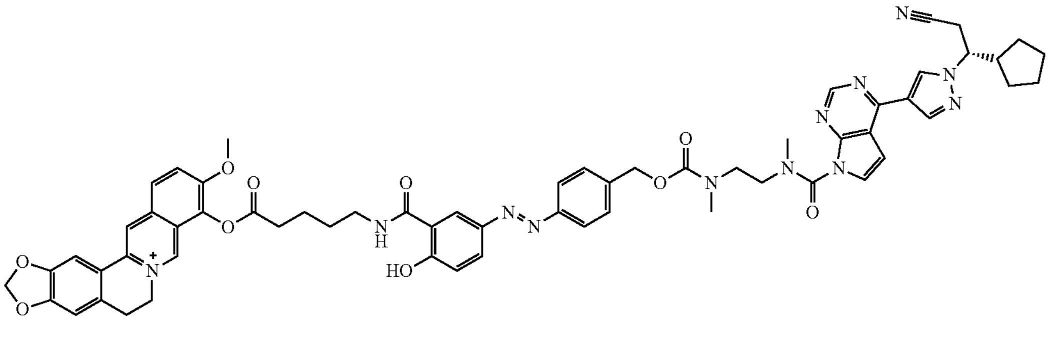 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn([C@H](CC#N)C7CCCC7)c6)ncnc54)cc2)ccc1O)CCc1cc2c(cc1-3)OCO2] |
| | LCMS, $^1$H NMR | MS (ESI): m/z = 1121.5 $[M]^+$. $^1$H NMR (400 MHZ, $CD_3CN$) δ 13.34 (s, 1H), 9.37-9.36 (m, 1H), 8.81-8.75 (m, 1H), 8.55-7.84 (m, 9H), 7.63-7.45 (m, 5H), 7.05-6.88 (m, 3H), 6.12 (s, 2H), 5.29-5.07 (m, 1H), 4.81-4.66 (m, 2H), 4.41-4.35 (m, 1H), 3.80-3.59 (m, 6H), 3.14-2.82 (m, 11H), 1.69-1.56 (m, 3H), 1.29-0.91 (m, 13H). |

-continued
13 Compound structure
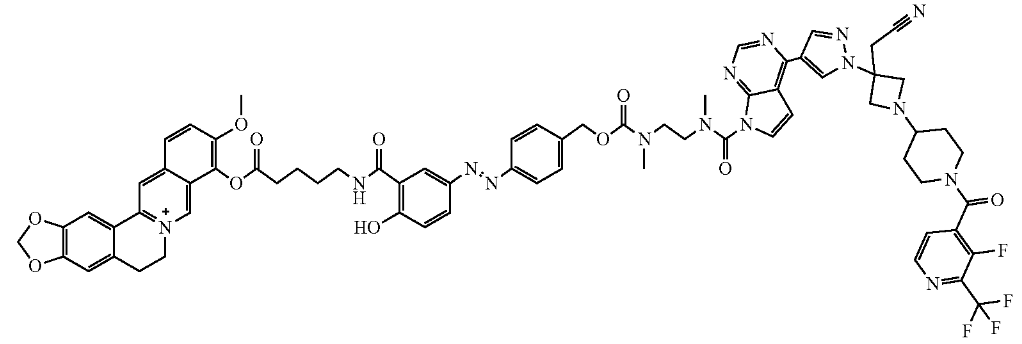 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn(C7(CC#N)CN(C8CCN(C(=O)c9ccnc(C(F)(F)F)c9F)CC8)C7)c6)ncnc54)cc2)ccc1O)CCc1cc2c(cc1-3)OCO2]
LCMS, $^1$H NMR
MS (ESI): m/z = 685.0 $[M/2]^+$
$^1$H NMR (400 MHZ, $CD_3CN$) δ 13.38 (s, 1H), 9.38 (s, 1H), 8.87-8.78 (m, 1H), 8.61-8.55 (m, 3H), 8.35-8.29 (m, 2H), 8.11-8.05 (m, 4H), 7.6373-6.86 (m, 10H), 6.12 (s, 2H), 5.2-4.48 (m, 8H), 4.03 (s, 3H), 3.67-3.44 (m, 9H), 3.19-3.14 (m, 2H), 2.94-2.90 (m, 11H), 2.14-2.06 (m, 4H), 1.83-1.64 (m, 4H), 1.50-1.44 (m, 3H).
14 Compound structure
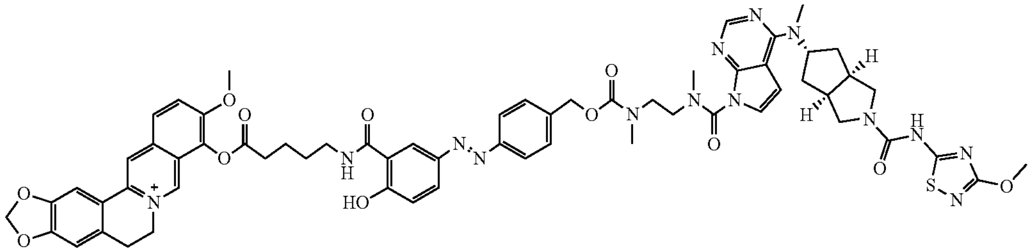 [SMILES: COc1nsc(NC(=O)N2C[C@H]3C[C@H](N(C)c4ncnc5c4ccn5C(=O)N(C)CCN(C)C(=O)OCc4ccc(/N=N/c5ccc(O)c(C(=O)NCCCCC(=O)Oc6c(OC)ccc7cc8[n+](cc67)CCc6cc7c(cc6-8)OCO7)c5)cc4)C[C@H]3C2)n1]
LCMS, $^1$H NMR
MS (ESI): m/z = 615.5 $[M/2]^+$.
$^1$H NMR (400 MHZ, $CD_3CN$) δ 13.38 (s, 1H), 9.40 (d, 4.8 Hz, 1H), 8.57 (s, 1H), 8.31-8.14 (m, 2H), 8.05-7.91 (m, 4H), 7.71-6.73 (m,13H), 6.13 (s, 2H), 5.23-5.01 (m, 3H), 4.80-4.77 (m, 2H), 4.04 (s, 3H), 3.91-3.90 (m, 3H), 3.64-2.90 (m, 25H), 1.92-1.79 (m, 5H), 1.29-1.21 (m, 1H).
15 Compound structure
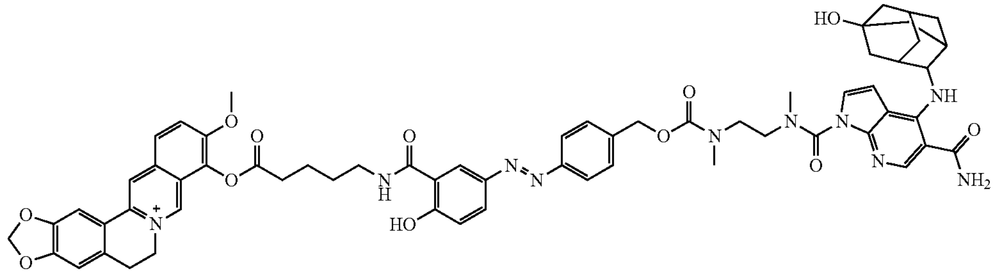 [SMILES: COc1ccc2cc3[n+](cc2c1OC(=O)CCCCNC(=O)c1cc(/N=N/c2ccc(COC(=O)N(C)CCN(C)C(=O)n4ccc5c(NC6C7CC8CC6CC(O)(C8)C7)c(C(N)=O)cnc54)cc2)ccc1O)CCc1cc2c(cc1-3)OCO2]
LCMS, $^1$H NMR
MS (ESI): m/z = 1141.4 $[M]^+$.
$^1$H NMR (400 MHZ, $CD_3CN$) δ 12.88 (s, 1H), 10.73-10.57 (m, 1H), 9.42-9.39 (m, 1H), 8.56-8.06 (m, 6H), 7.56-6.88 (m, 7H), 6.47-6.28 (m, 1H), 6.12 (s, 2H), 4.04 (s, 3H), 3.99-3.58 (m, 6H), 3.17-2.91 (m, 9H), 2.06-1.96 (m, 3H), 1.83-1.46 (m, 10H).

-continued
16 Compound structure
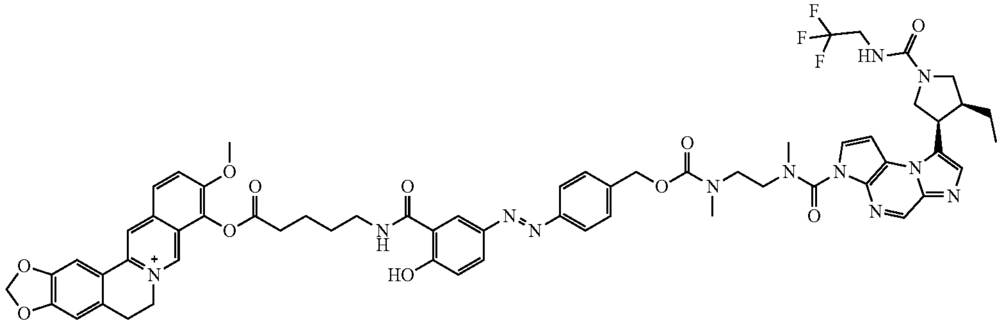 [SMILES: CC[C@@H]1CN(C(=O)NCC(F)(F)F)C[C@@H]1c1cnc2cnc3c(ccn3C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)n12]
LCMS, $^1$H NMR
MS (ESI): m/z = 1195.4 $[M]^+$.
$^1$H NMR (400 MHZ, $CD_3CN$) δ 13.50 (s, 1H), 9.40 (s, 1H), 8.92 (s, 1H), 8.56-6.89 (m, 14H), 6.12 (s, 2H), 5.67 (t, J = 6.0 Hz, 1H), 5.31-4.98 (m, 1H), 4.78 (t, J = 6.4 Hz, 2H), 4.03 (s, 3H), 3.97-3.13 (m, 11H), 2.94-2.91 (m, 10H), 1.93-1.89 (m, 2H), 1.23-0.66 (m, 6H).
17 Compound structure
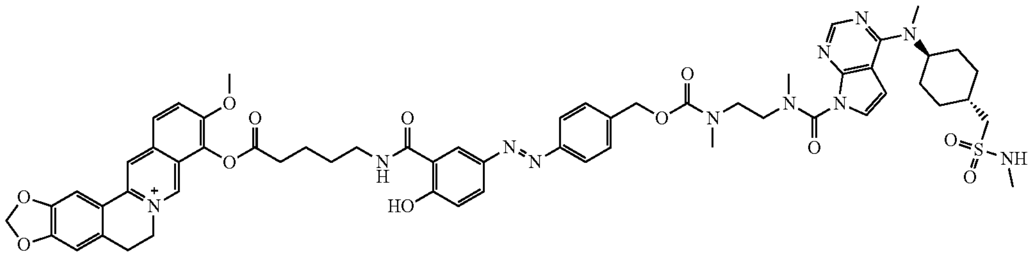 [SMILES: CNS(=O)(=O)C[C@H]1CC[C@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)CC1]
LCMS, $^1$H NMR
MS (ESI): m/z = 1152.4 $[M]^+$.
$^1$H NMR (400 MHZ, $CD_3CN$) δ 13.39 (s, 1H), 9.41 (s, 1H), 8.58 (s, 1H), 8.35-7.77 (m, 8H), 7.51-6.60 (m, 7H), 6.12 (s, 2H), 5.30-5.13 (m, 3H), 4.78 (t, J = 6.4 Hz, 2H), 4.49-4.36 (m, 2H), 4.04 (s, 3H), 3.63-3.55 (m, 5H), 3.17-2.91 (m, 14H), 2.79 (s, 3H), 2.13-1.23 (m, 12H).
18 Compound structure
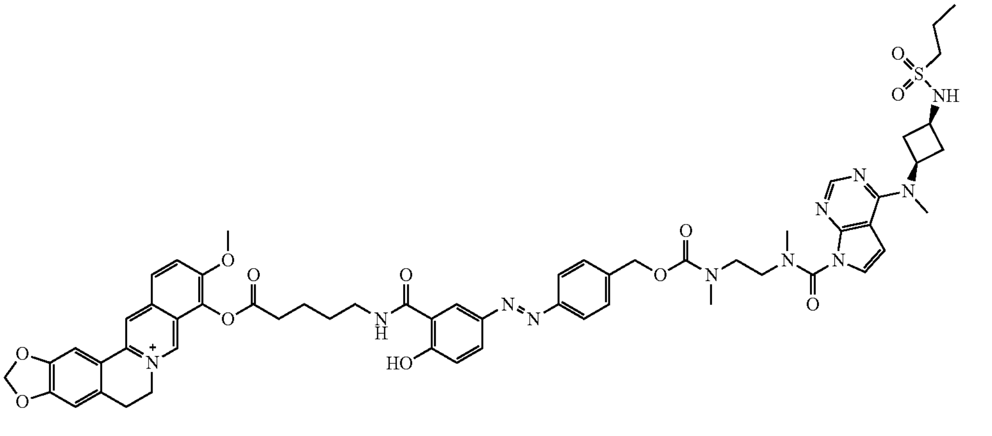 [SMILES: CCCS(=O)(=O)N[C@H]1C[C@@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)C1]
LCMS, $^1$H NMR
MS (ESI): m/z = 1138.4 $[M]^+$.
$^1$H NMR (400 MHZ, $CD_3CN$) δ 13.45 (s, 1H), 9.40 (s, 1H), 8.57 (s, 1H), 8.34-8.30 (m, 2H), 8.29-7.44 (m, 10H), 7.16-6.63 (m, 4H), 6.12 (s, 2H), 5.80-5.68 (m, 1H), 5.26-5.12 (m, 1H), 4.79-4.61 (m, 4H), 4.04 (s, 3H), 3.60-3.55 (m, 6H), 3.22-3.14 (m, 6H), 2.97-2.56 (m, 10H), 2.31-2.18 (m, 3H), 1.90-1.80 (m, 2H), 1.79-1.71 (m, 3H), 1.05-1.01 (m, 3H).

Biological Test 1: Assay of Codrug in the Lumen Contents of the Duodenum or Colon of Mice (Lumen Content Ex Vivo)

C57 BL/6 male mice (6-8 weeks of age) were dissected after $CO_2$ euthanasia. Duodenal and colonic segments were taken and placed in 1.5 ml centrifuge tubes, and PBS solution was simultaneously added. The intestine segments were cut longitudinally, shaken to release the intestinal contents, and mixed upside down. Dimethyl sulfoxide solution of each example compound was prepared separately, 20 μl of each of the above dimethyl sulfoxide solution was added into 1 ml of solution of duodenal or colonic contents in PBS, mixed upside-down repeatedly and placed in a 37° C. water bath. Samples were collected at 0 h, 1 h, 4 h, 16 h, and 20 h by adding quenching acetonitrile, vortexed and centrifuged for 10 minutes. The supernatant was taken and 10 μl of the internal standard compound (Intermediate D) was added. The amounts (ng) of the example compounds, Berberrubine and Tofacitinib were determined by liquid chromatography mass spectrometry and quantified by standard curve, and the results are shown in Table 1. The results showed that the codrug compounds of the present invention were able to release active ingredients in the intestine after administration.

that the codrug compound, Tofacitinib and Berberrubine were all restricted mainly within intestinal tissues with only very low drug exposure in plasma.

Figure 6:
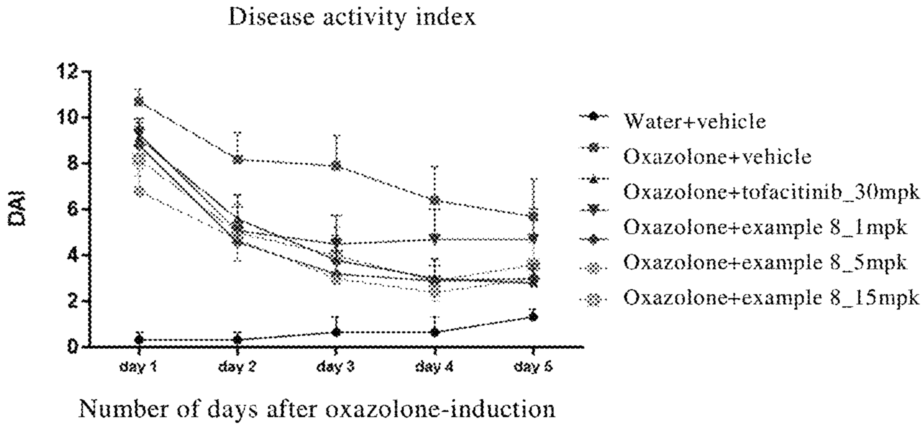
FIG. 6 shows the changing diagram of disease activity index score after the mice were administered with compound of example 8 in the oxazolone-induced colitis mouse model.

Biological Test 3: Efficacy Study of Codrug Compounds in Oxazolone-Induced Colitis Model in Mice $C_{57}$BL/6 mice was used to establish an oxazolone-induced colitis model according to the method of Heller et al. On the first day, the skin on the back of the mouse was shaved (2 cm×2 cm), and 150 μl of 3% oxazolone solution (dissolved in a 4:1 mixture of acetone and olive oil) was applied for pre-sensitization. The mice were randomly grouped on the $6^{th}$ day after pre-sensitization. The corresponding example compounds were given by oral gavage (120 mg/kg), while the blank control group and model group were given vehicle solvent, and the dosing volume was 10 mL/kg. The test group was intracolonically injected with 50 ul of 1.2% oxazolone solution on the next day, while blank control group was administrated with pure water. Oral gavage dosing of the test article was continued for 4 days, and the Disease Activity Index (DAI) scores were recorded daily. The results are shown in FIG. 6, compared with the model group, the administration of codrug compounds significantly improved the Disease Activity Index scores.

TABLE 1

The respective release of Berberrubine, Tofacitinib, SHR0302 and Upadacitinib from examples 1, 8, 14, and 16 in different intestinal lumen contents with time

| | | Intestine segment | | | | | | | | | |
|---|---|---|---|---|---|---|---|---|---|---|---|
| | | Duodenum | | | | | Colon | | | | |
| | | Time point | | | | | | | | | |
| No. | Check item | 0 hour | 1 hour | 4 hours | 16 hours | 20 hours | 0 hour | 1 hour | 4 hours | 16 hours | 20 hours |
| Example 1 | Berberrubine (ng) | N.D. | 25.5 | 42.7 | 34.0 | N.D. | N.D. | 55.5 | 53.0 | 138.0 | N.D. |
| | Tofacitinib (ng) | N.D. | 135.0 | 540.0 | 1168.8 | N.D. | N.D. | 284.5 | 643.0 | 962.0 | N.D. |
| Example 8 | Berberrubine (ng) | N.D. | 170.6 | 364.7 | 418.6 | N.D. | N.D. | 275.0 | 357.0 | 894.0 | N.D. |
| | Tofacitinib (ng) | N.D. | 145.8 | 164.0 | 698.7 | N.D. | N.D. | 444.0 | 679.0 | 644.5 | N.D. |
| Example 14 | Berberrubine (ng) | 15.4 | 347.5 | 334.1 | N.D. | 1198.8 | 36.2 | 198.2 | 239.1 | N.D. | 718.8 |
| | SHR0302 (ng) | 0.0 | 0.0 | 29.2 | N.D. | 595.6 | 0.0 | 34.2 | 112.8 | N.D. | 390.2 |
| Example 16 | Berberrubine (ng) | 18.8 | 347.4 | 675.4 | N.D. | 1344.9 | 87.1 | 223.2 | 318.9 | N.D. | 288.7 |
| | Upadacitinib (ng) | 0.0 | 0.0 | 125.8 | N.D. | 1734.8 | 0.0 | 171.4 | 721.0 | N.D. | 2387.7 |

N.D. means none-detected

Biological Test 2: Pharmacokinetic Experiments of Codrug Compounds in Mice

The test compounds were given orally (P0.15 mg/kg) to CD-1 mice, and blood and tissue samples from various segments of the gastrointestinal tract were collected at different time points. LC-MS/MS was used to determine the concentrations of the example codrug compounds, as well as the released Tofacitinib and Berberrubine in the plasma of the mice. Animals were approximately 6-8 weeks age at the start of the dosing experiment. Times of blood and tissue sample collection were: 0.5, 1, 2, 4, 8 and 24 hours after administration. Methods for the analysis of biological sample and sample detection were established.

The results are shown in FIGS. 1-5. The results showed that the example codrug compounds were able to release Tofacitinib and Berberrubine in the intestine of mice, and All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A codrug compound of formula I, wherein the codrug compound is formed by coupling the first drug molecule, the second drug molecule and a linker precursor:

$$D_1\text{-linker-}D_2; \qquad \text{I}$$

wherein, $D_1$ is a first drug group; and the first drug group is a structural fragment in the first drug molecule which can be connected to the linker, and the first drug group is a berberine analog of formula II, formula III, or formula IV:

formula II

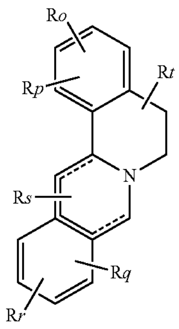

formula III

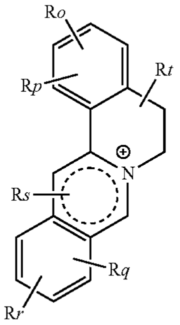

formula IV

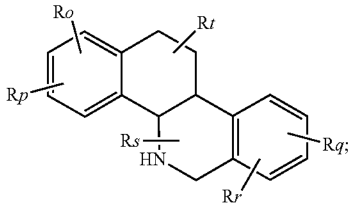

wherein

Ro, Rp, Rq, Rr, Rs and Rt are each independently selected from the group consisting of H, substituted or unsubstituted $C_1$-$C_4$ alkyl, and substituted or unsubstituted $C_1$-$C_4$ alkoxy; or two of Ro, Rp, Rq, Rr, Rs and Rt on two adjacent atoms together with the atoms to which they are attached form a 5-7 membered heterocyclic ring; wherein substituted means that one or more hydrogen atoms of the group is independently replaced by a substituent selected from the group consisting of halogen, $C_1$-$C_4$ alkyl and phenyl;

$D_2$ is a second drug group; and the second drug group is a structural fragment in the second drug molecule which can be connected to the linker, wherein the second drug molecule is a JAK family inhibitor selected from the group consisting of Tofacitinib, Ruxolitinib, Oclacitinib, Baricitinib, Peficitinib, Abrocitinib, Filgotinib, Upadacitinib, Delgocitinib, Itacitinib, Fedratinib, Decernotinib, SHR-0302, AZD-4205, ASN-002, BMS-986165, PF-06700841, PF-06651600, R-348, INCB-52793, ATI-501, ATI-502, NS-018, KL-130008, and deuterated derivatives of any of the foregoing, or the second drug molecule is selected from the group consisting of:

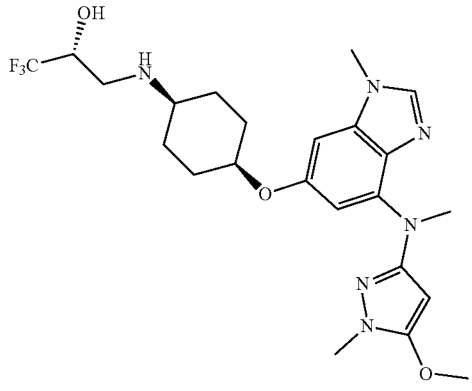

,

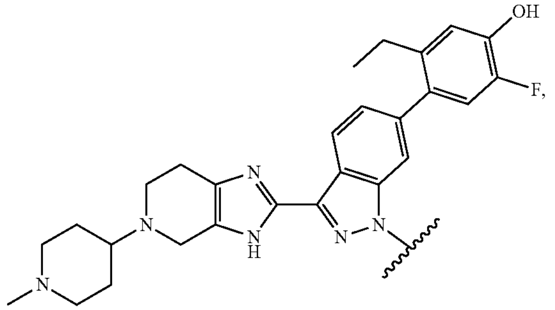

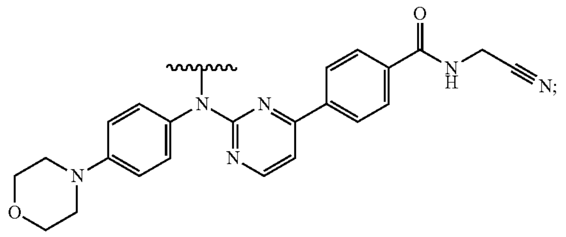

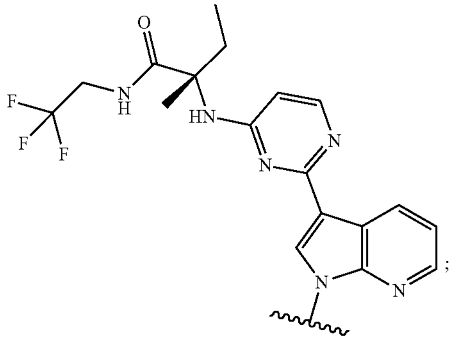

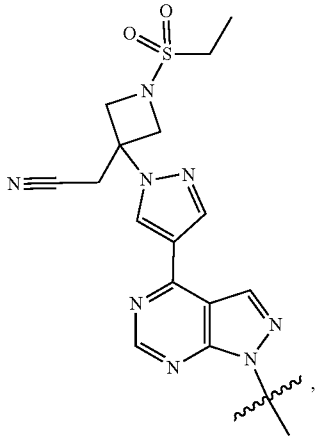

and

-continued
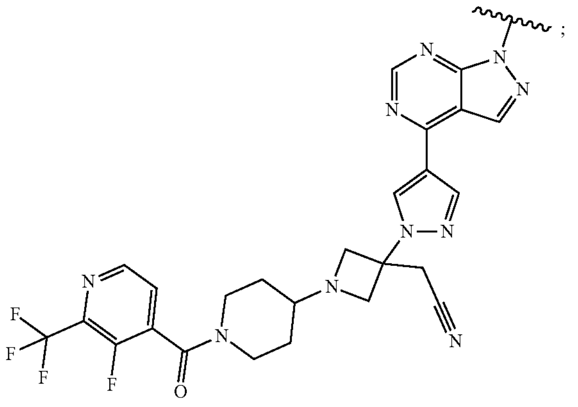
and the linker has a structure of (a), (b), or (c), wherein in each formula, $J_1$ connects to the first drug group, and $J_2$ connects to the second drug group;
(a)
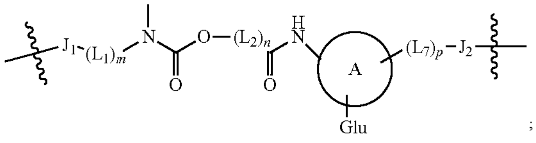
Glu has a structure selected from the group consisting of:
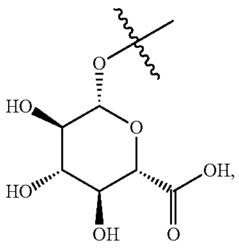
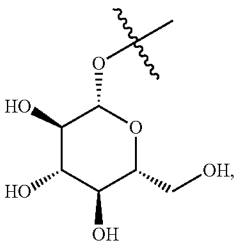
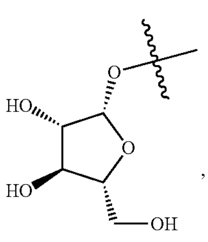
,
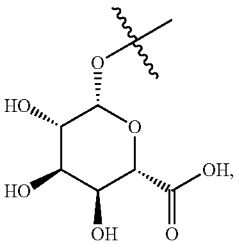
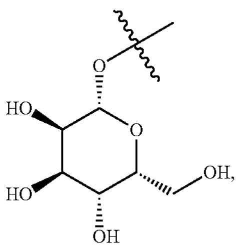
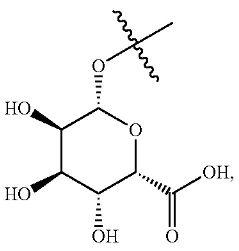
-continued
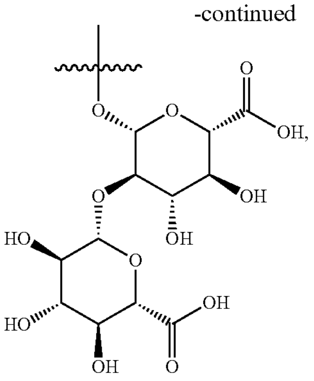
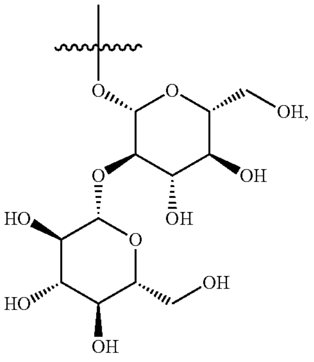
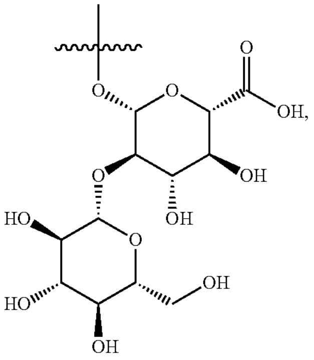
and
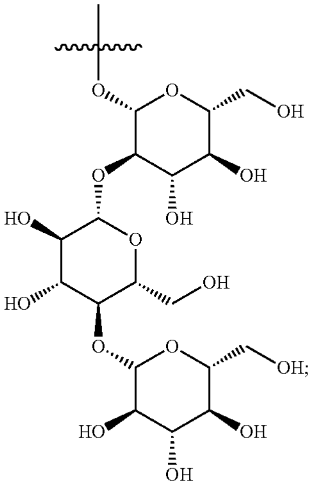
wherein the A ring is selected from the group consisting of $C_6$-$C_{10}$ aryl, 5-10 membered heteroaryl, and 3-12 membered heterocyclic group;

(b)

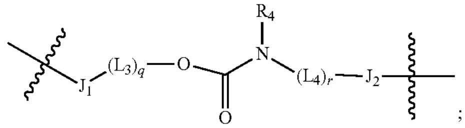

;

wherein, $R_4$ is selected from the group consisting of H, $C_{1-6}$ alkyl, $C_{1-6}$ alkyoxy-$C_{1-4}$ alkylene-$C_{3-12}$ cycloalkyl, and $C_{3-12}$ cycloalkyl-$C_{1-4}$ alkylene-;

(c)

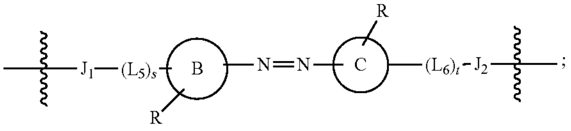

;

wherein the B-ring and C-ring are independently selected from the group consisting of $C_6$-$C_{10}$ aryl, 5-10 membered heteroaryl, and 3-12 membered heterocyclic group;

in the above formulas (a), (b) and (c), $J_1$ and $J_2$ are each independently —$(Y)_z$—, and each Y is selected from the group consisting of —NH—, —C(O)—, —CH═CH—, —$NH(CH_2)$—, —NHC(O)—, —$CH_2$—, —$OCH_2CH_2O$—, —O—, —S—, —$P(O)_2$ O—, —$S(O)_2$—, —S(O)—, —C(O)NH—, and —N═N—; and each Y can independently be substituted by one or more R, with the proviso that the combination of each Y forms a chemically stable structure;

each $L_1$, $L_2$, $L_3$, $L_4$, $L_5$, $L_6$ and $L_7$ is independently selected from the group consisting of $C_1$-$C_8$alkylene, $C_{1-6}$ alkylene-O—$C_{1-4}$ alkylene (—$CH_2$—O—$CH_2$—), $C_{2-6}$ alkenyl, $C_{2-6}$ alkynyl, $C_{3-6}$ cycloalkyl, $C_6$-$C_{10}$ arylidene, 5-10 membered heteroarylidene, 3-12 membered heterocyclylene group, —NH—, —C(O)—, —CH═CH—, —$NH(CH_2)$—, —NHC(O)—, —$CH_2$—, —$OCH_2CH_2O$—, —O—, —S—, —$P(O)_2$ O—, —$S(O)_2$—, —S(O)—, —C(O)NH—, —N═N—, and —$C(O)NH(CH_2)(1-4)$-NHC(O)—; with the proviso that the combination of $L_1$, $L_2$, $L_3$, $L_4$, $L_5$, $L_6$ and $L_7$ forms a stable divalent structure;

each Y, $L_1$, $L_2$, $L_3$, $L_4$, $L_5$, $L_6$ and $L_7$ is independently optionally substituted by one or more R, wherein each R is independently selected from the group consisting of —OH, $C_1$-$C_4$ alkyl, halogen, cyano, nitro, —$OR_4$, $C_{1-6}$ haloalkyl, sulfonate group, formyl, carboxyl, and —$COOR_4$; with the proviso that each Y, $L_1$, $L_2$, $L_3$, $L_4$, $L_5$, $L_6$ and $L_7$ together form a chemically stable structure;

m, n, p, q, r, s and t are each independently 0, 1, 2, 3, 4, 5, 6, 7 or 8; and z is 0, 1, 2, 3, 4, 5 or 6.

2. The codrug compound of claim 1, wherein the second drug molecule is Tofacitinib, Ruxolitinib, Oclacitinib, Baricitinib, Peficitinib, Abrocitinib, Filgotinib, Upadacitinib, Delgocitinib, Itacitinib, Fedratinib, Decernotinib, SHR-0302, AZD-4205, ASN-002, BMS-986165, PF-06700841, PF-06651600, R-348, INCB-52793, ATI-501, ATI-502, NS-018, KL-130008, or a deuterated derivative of any of the foregoing.

3. The codrug compound of claim 1, wherein the first drug group is selected from the group consisting of:

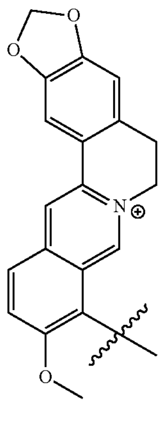

,

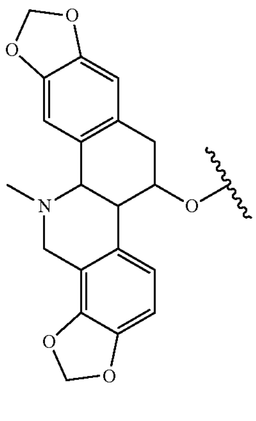

,

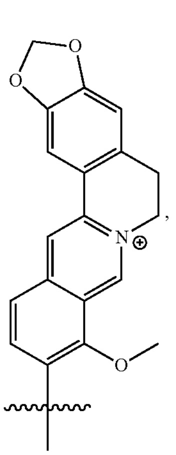

,

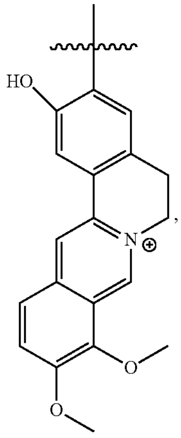

,

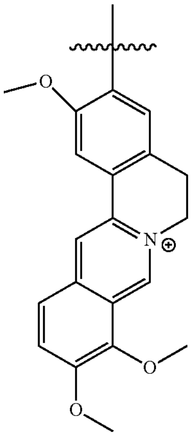

, and

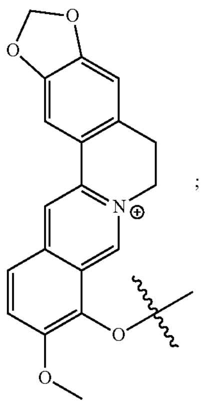 [SMILES: *Oc1c(OC)ccc2cc3[n+](cc12)CCc1cc2c(cc1-3)OCO2]

;

or the first drug group is a group formed by losing one hydrogen atom in a drug molecular selected from the group consisting of:

-continued
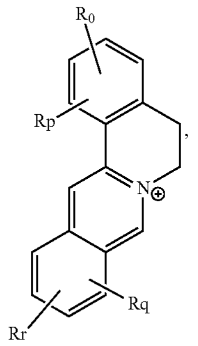
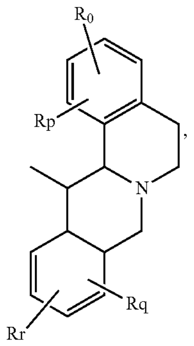
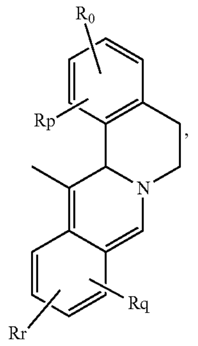
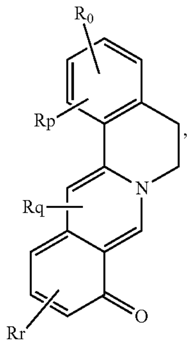
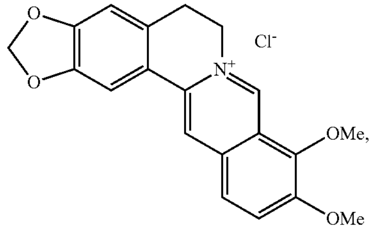
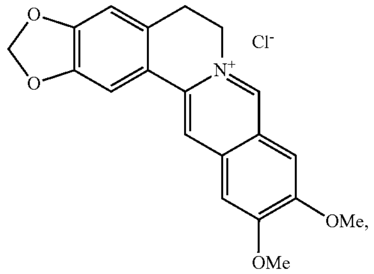
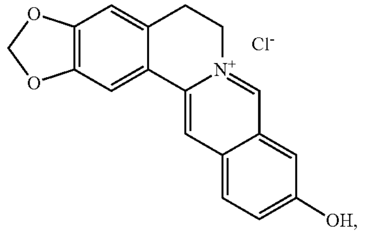
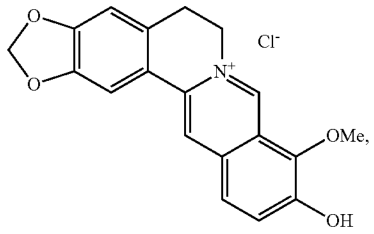
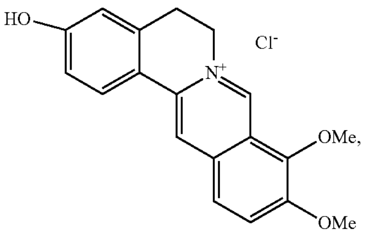
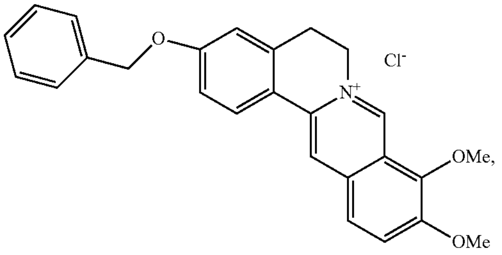
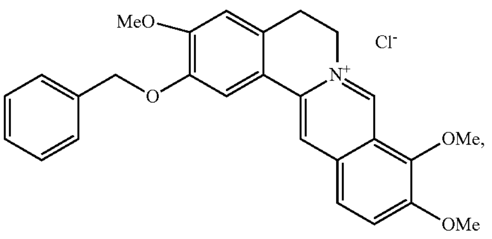
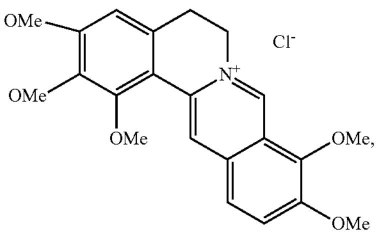
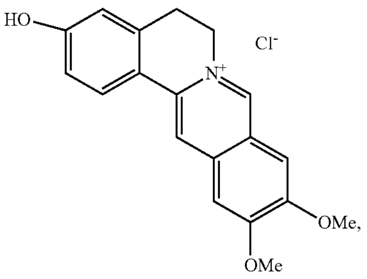
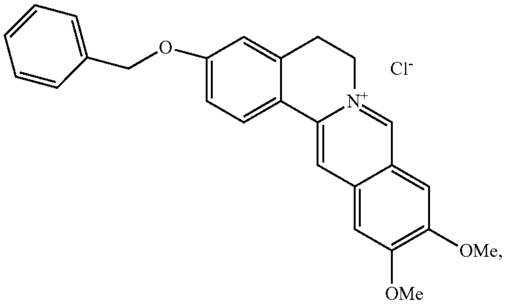

-continued
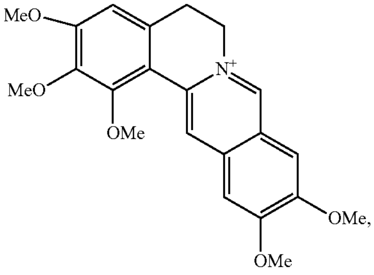
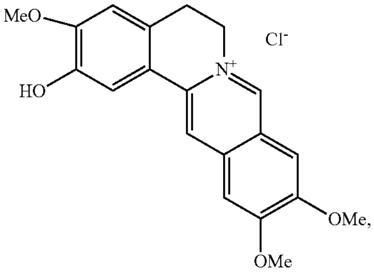
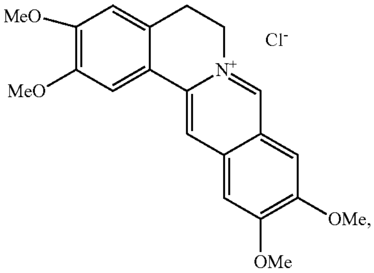
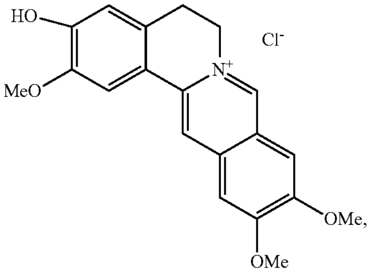
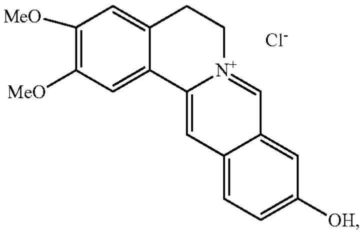
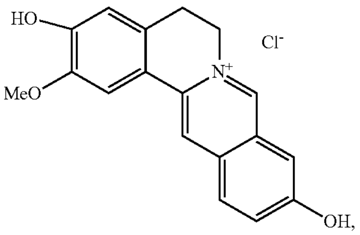
and
-continued
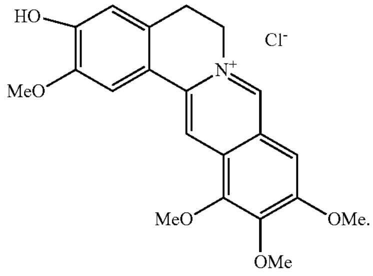
4. The codrug compound of claim 1, wherein the first drug group has the structure shown in the following formula:
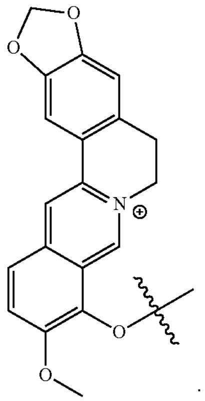
5. The codrug compound of claim 1, wherein the second drug group is selected from the group consisting of:
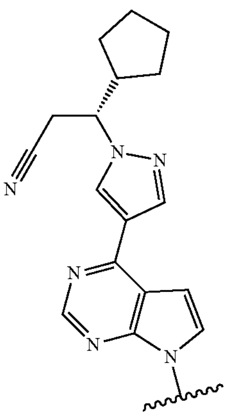
,
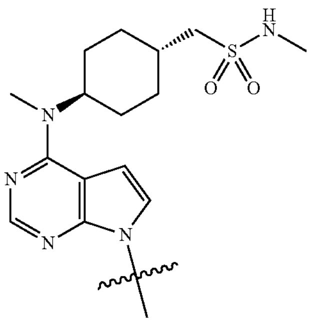
, -continued
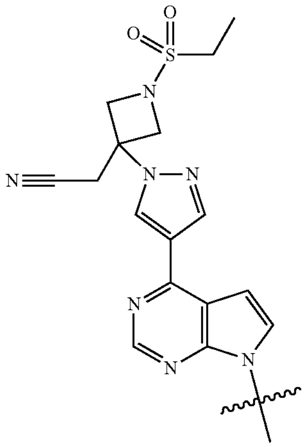
,
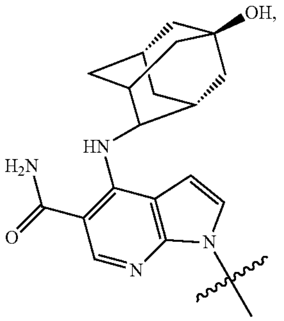
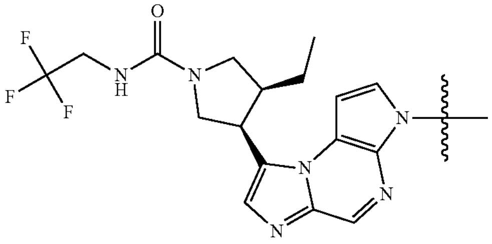
,
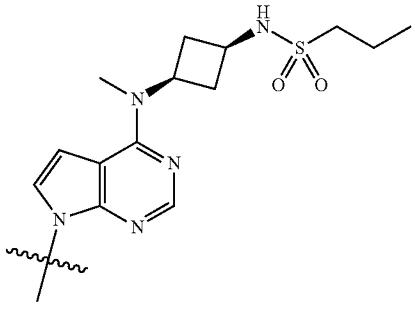
,
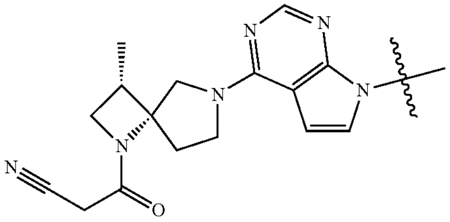
,
-continued
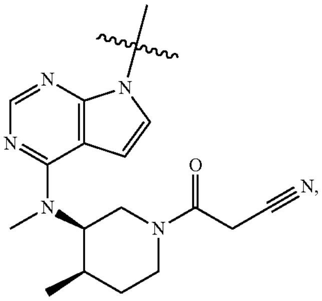
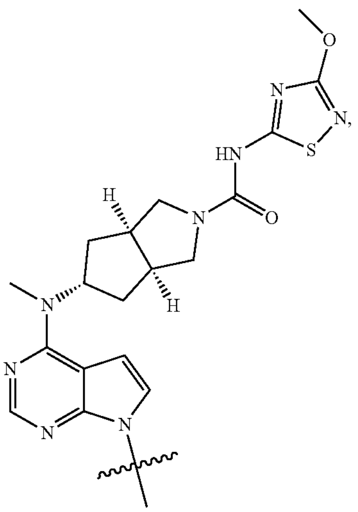
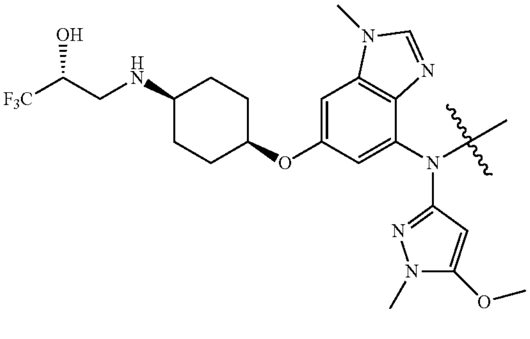
,
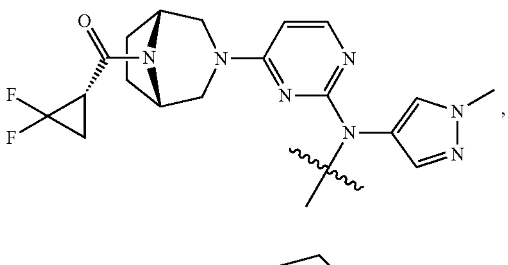
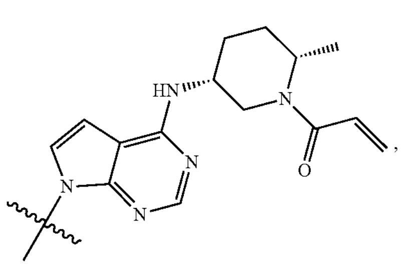

-continued
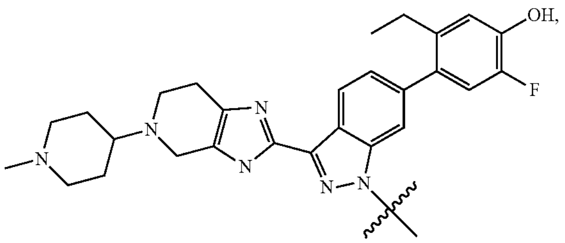
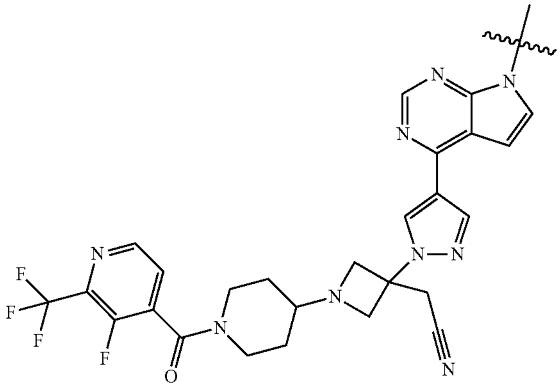
,
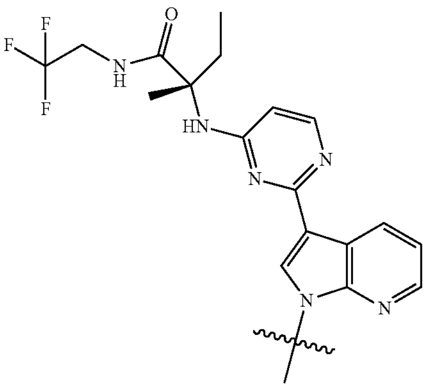
,
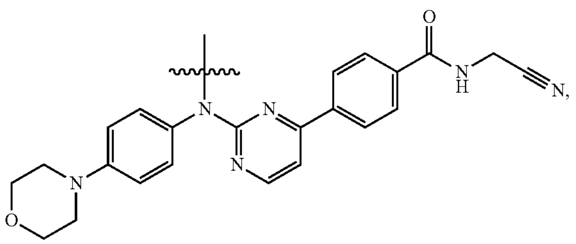
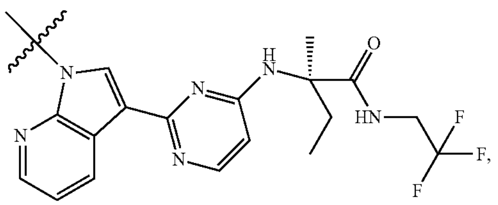
-continued
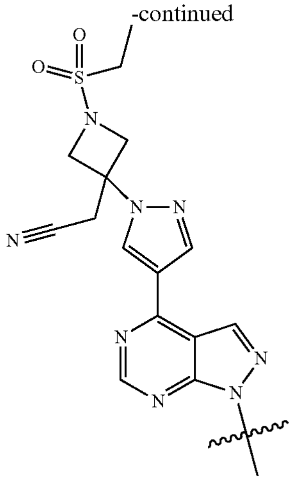
, and
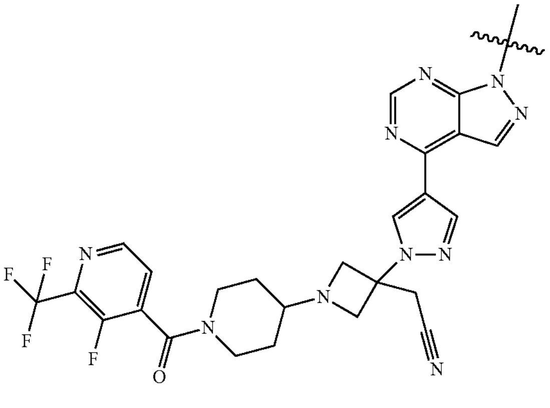
.
6. The codrug compound of claim 1, wherein the second drug group is selected from the group consisting of:
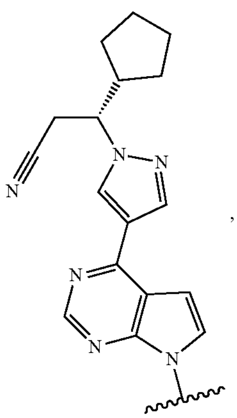
,
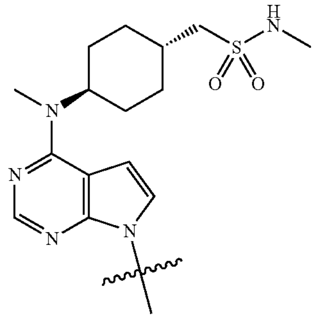
, -continued
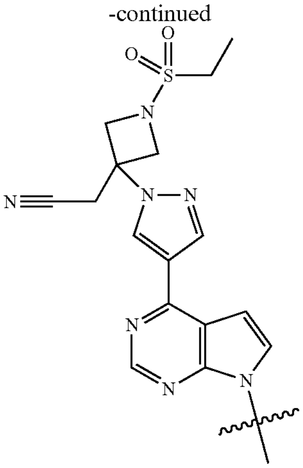
,
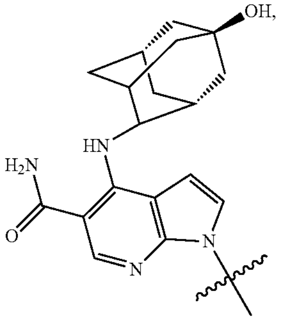
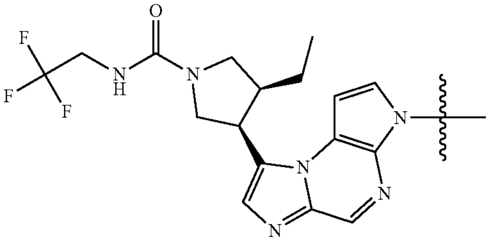
,
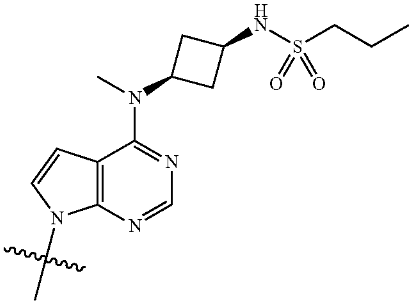
,
-continued
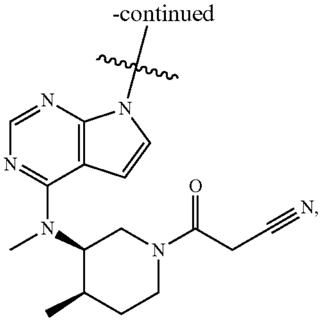
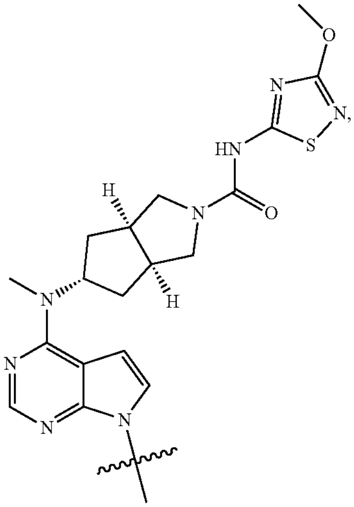
and
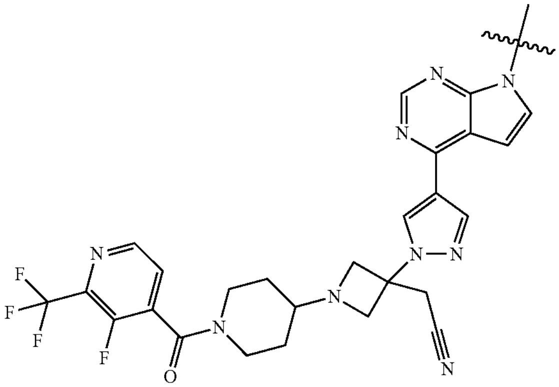
.
7. The codrug compound of claim 1, wherein the linker is selected group (A), (B), or (C):
Group (A) has a structure of $-L_a-L-$, where $L_a$ has a structure selected from the group consisting of:
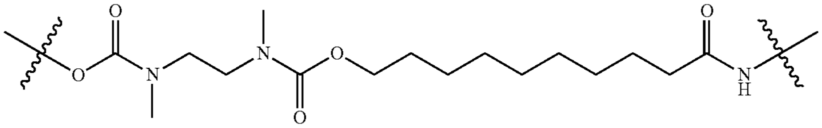
,
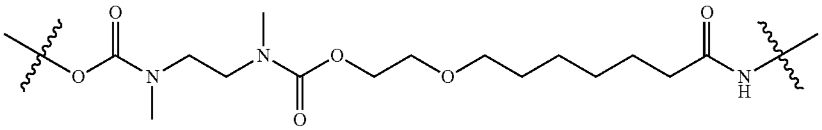
, -continued
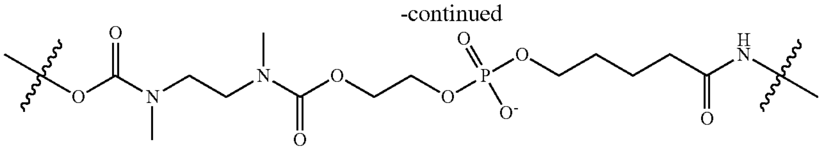
,
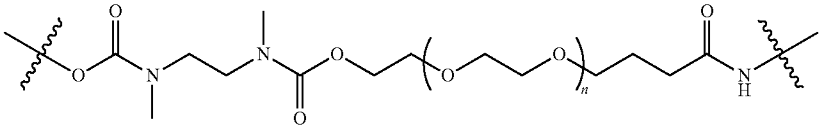
,
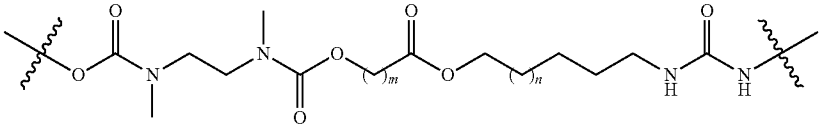
,
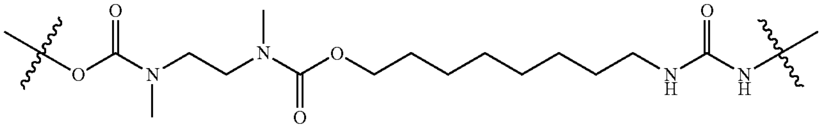
, and
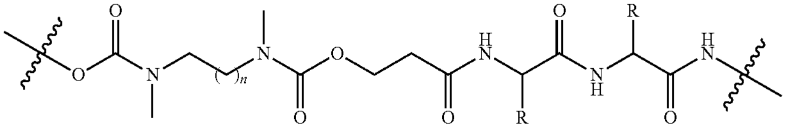
;
and L has the structure shown below, wherein * is the connection site of L to $L_a$:
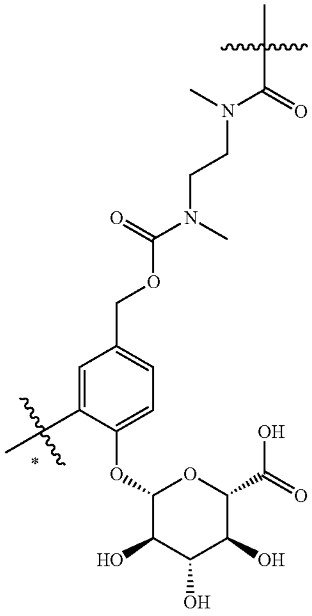 [SMILES: *C(=O)N(C)CCN(C)C(=O)OCc1ccc(O[C@@H]2O[C@H](C(=O)O)[C@@H](O)[C@H](O)[C@H]2O)c(*)c1]
Group (B):
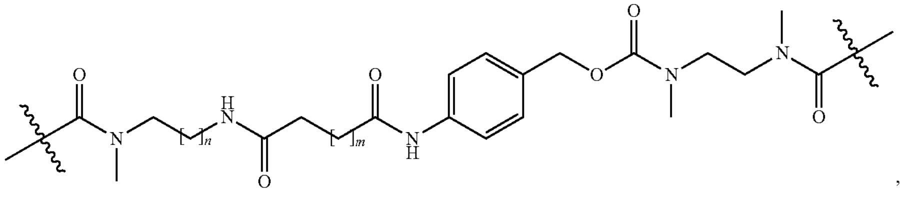
, -continued
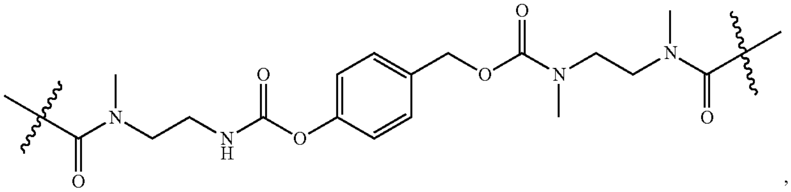
,
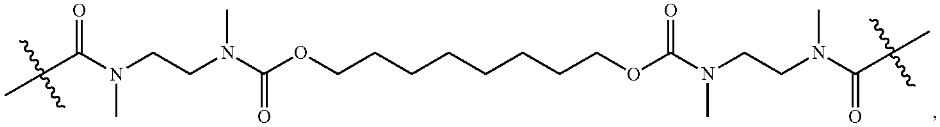
,
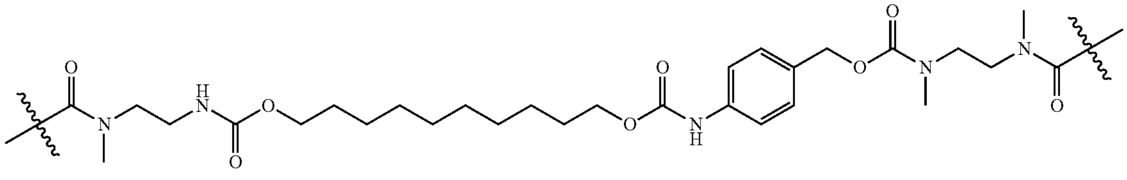
Group (C):
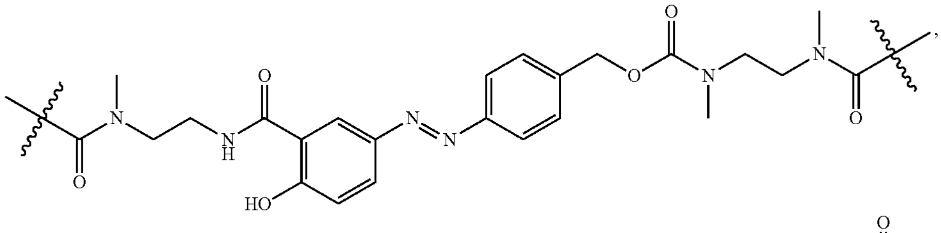
,
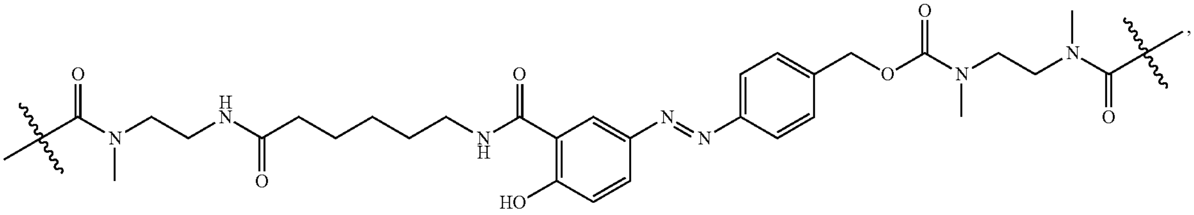
,
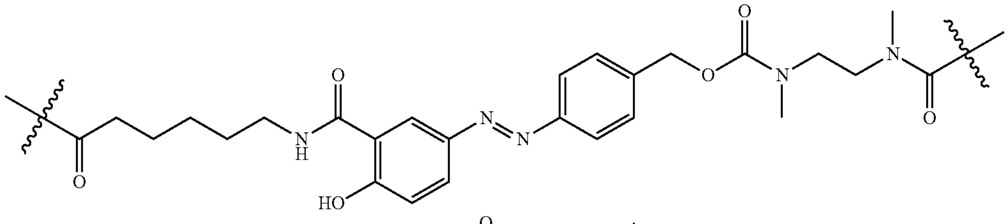
,
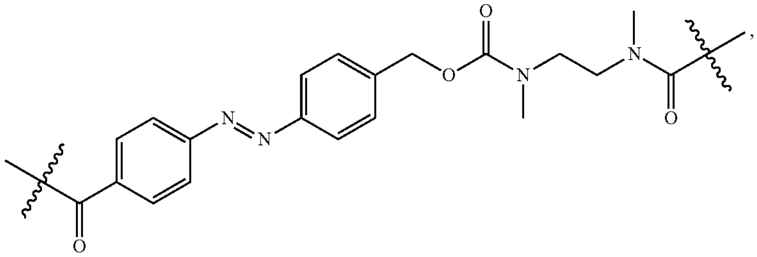
,
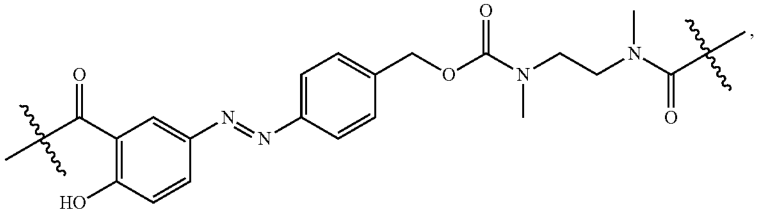
, -continued
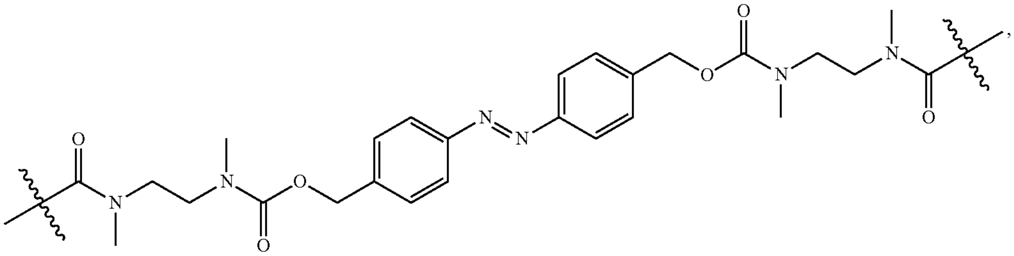
,
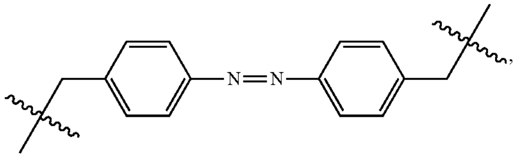
,
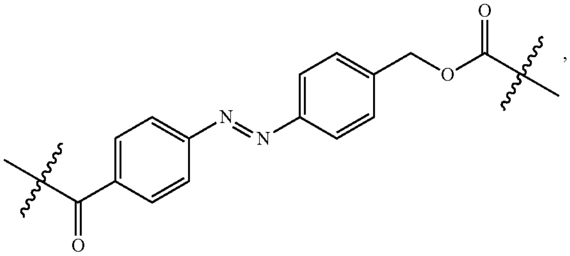
,
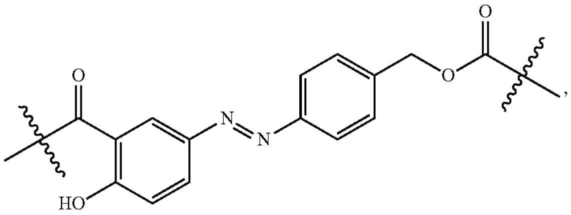
,
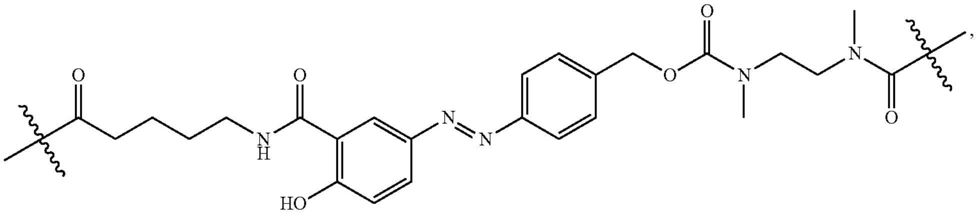
,
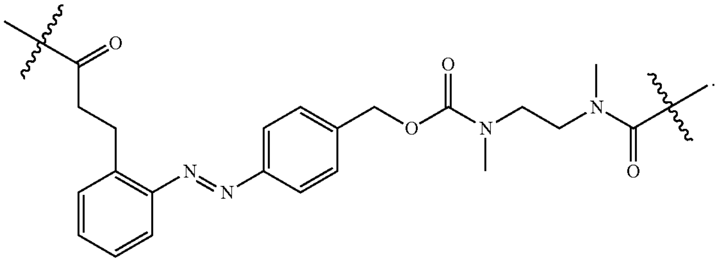
.

8. The compound of formula I according to claim 1, wherein the compound is selected from the following group:
| No. | Structure |
|---|---|
| 1 | 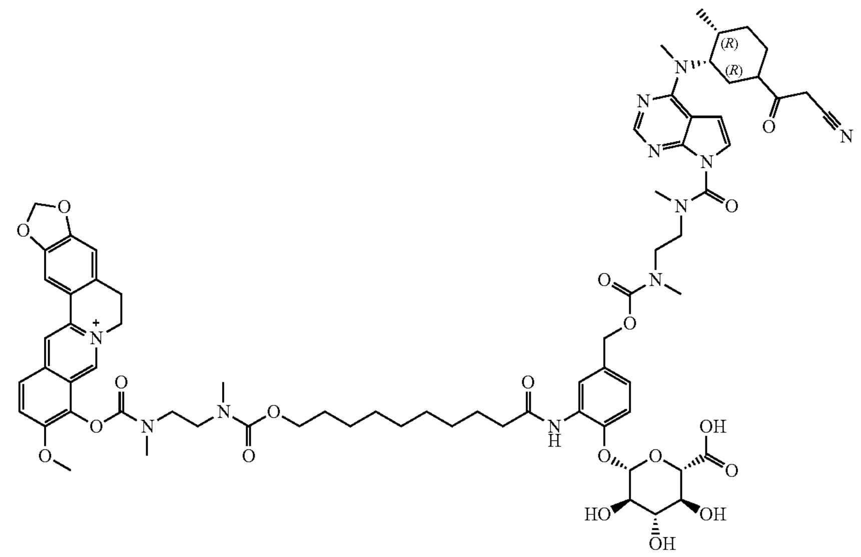 |
| 2 | 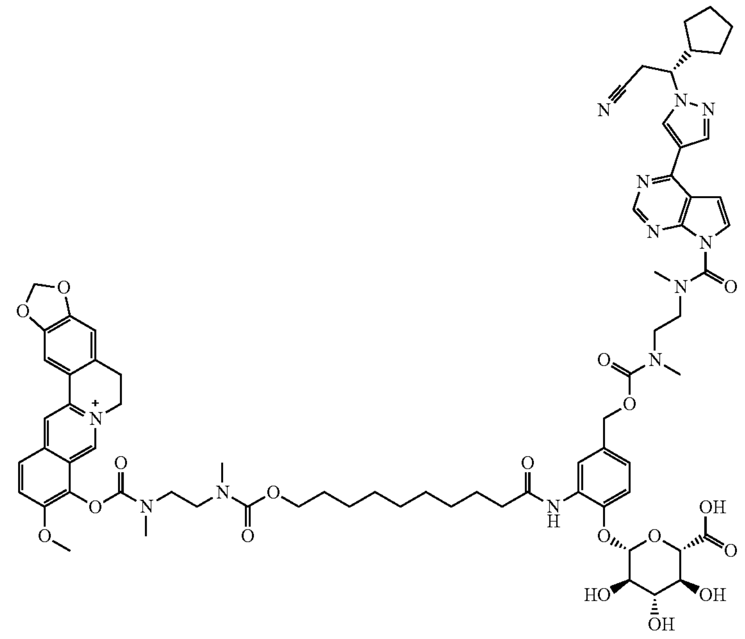 [SMILES: COc1ccc2cc3[n+](cc2c1OC(=O)N(C)CCN(C)C(=O)OCCCCCCCCCC(=O)Nc1cc(COC(=O)N(C)CCN(C)C(=O)n2ccc4c(-c5cnn([C@H](CC#N)C6CCCC6)c5)ncnc42)ccc1O[C@@H]1O[C@H](C(=O)O)[C@@H](O)[C@H](O)[C@H]1O)CCc1cc2c(cc1-3)OCO2] |

-continued
| No. | Structure |
| --- | --- |
| 3 | 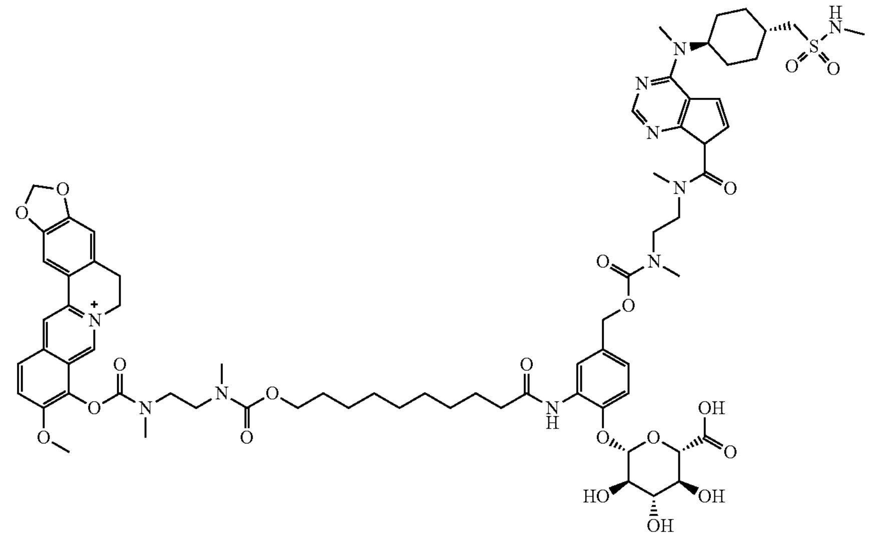 [SMILES: CNS(=O)(=O)C[C@H]1CC[C@H](N(C)c2ncnc3c2C=CC3C(=O)N(C)CCN(C)C(=O)OCc2ccc(O[C@@H]3O[C@H](C(=O)O)[C@@H](O)[C@H](O)[C@H]3O)c(NC(=O)CCCCCCCCCOC(=O)N(C)CCN(C)C(=O)Oc3c(OC)ccc4cc5[n+](cc34)CCc3cc4c(cc3-5)OCO4)c2)CC1] |
| 4A | 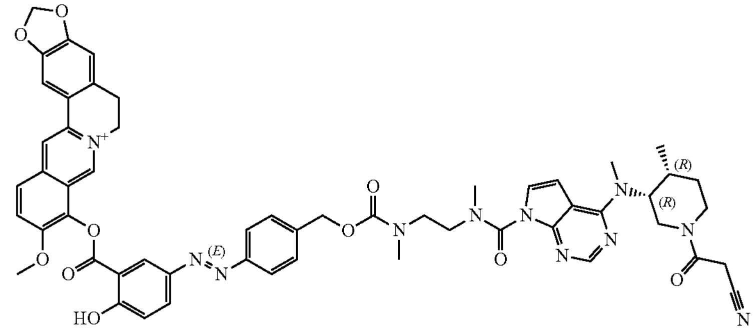 |
| 4B | 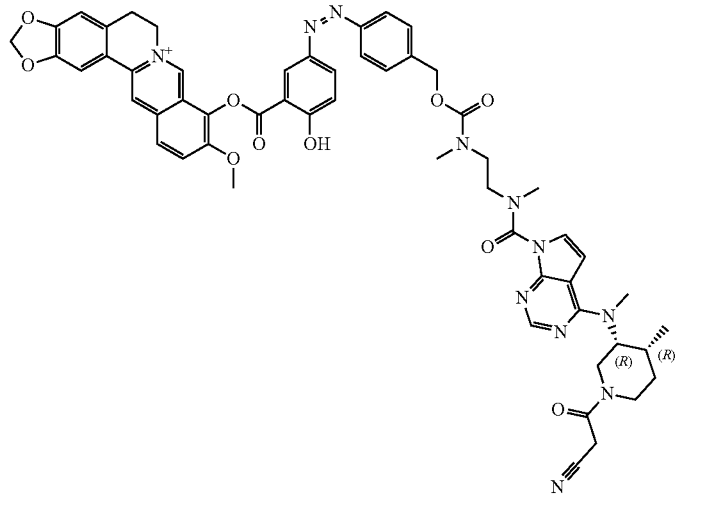 |

-continued
| No. | Structure |
| --- | --- |
| 5 | 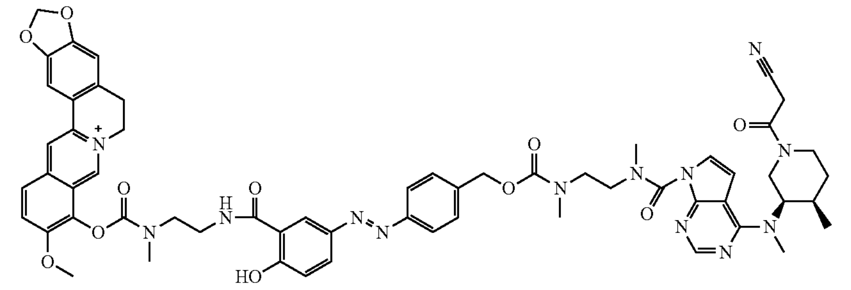 [SMILES: COc1ccc2cc3[n+](cc2c1OC(=O)N(C)CCNC(=O)c1cc(/N=N/c2ccc(COC(=O)N(C)CCN(C)C(=O)n4ccc5c(N(C)[C@H]6CN(C(=O)CC#N)CC[C@H]6C)ncnc54)cc2)ccc1O)CCc1cc2c(cc1-3)OCO2] |
| 6 | 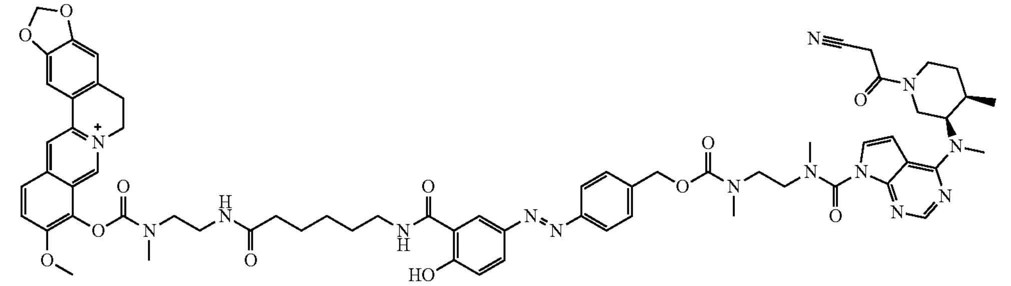 [SMILES: COc1ccc2cc3[n+](cc2c1OC(=O)N(C)CCNC(=O)CCCCCNC(=O)c1cc(/N=N/c2ccc(COC(=O)N(C)CCN(C)C(=O)n4ccc5c(N(C)[C@H]6CN(C(=O)CC#N)CC[C@H]6C)ncnc54)cc2)ccc1O)CCc1cc2c(cc1-3)OCO2] |
| 7 | 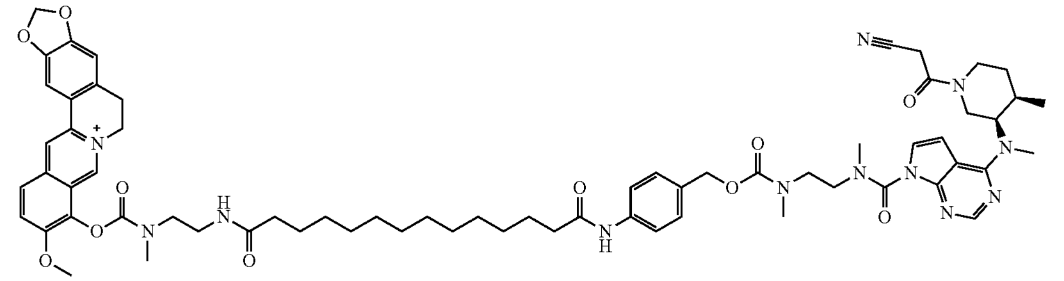 [SMILES: COc1ccc2cc3[n+](cc2c1OC(=O)N(C)CCNC(=O)CCCCCCCCCCCCC(=O)Nc1ccc(COC(=O)N(C)CCN(C)C(=O)n2ccc4c(N(C)[C@H]5CN(C(=O)CC#N)CC[C@H]5C)ncnc42)cc1)CCc1cc2c(cc1-3)OCO2] |
| 8 | 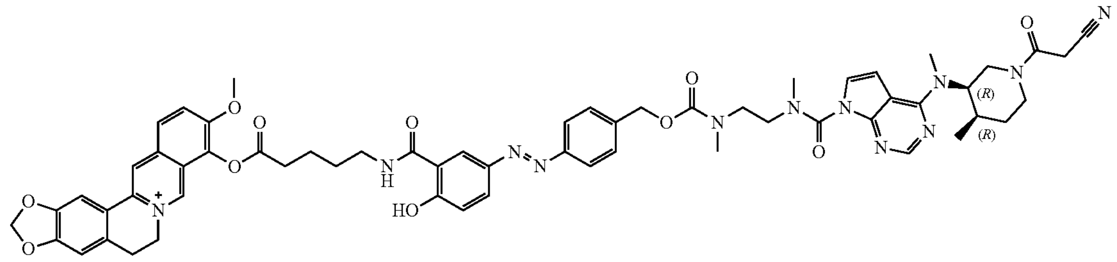 |
| 9 | 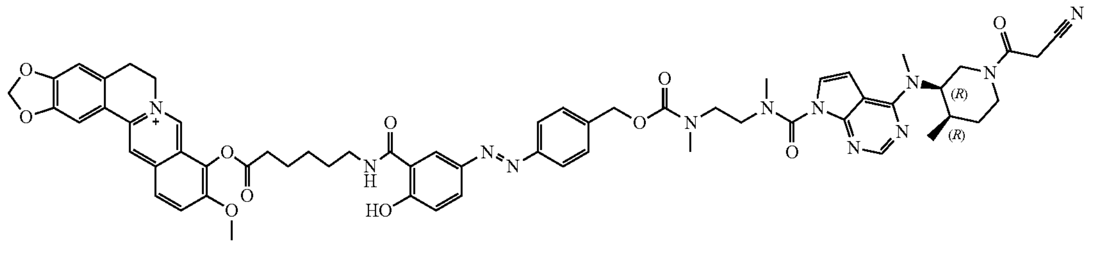 |

-continued
| No. | Structure |
| --- | --- |
| 10 | 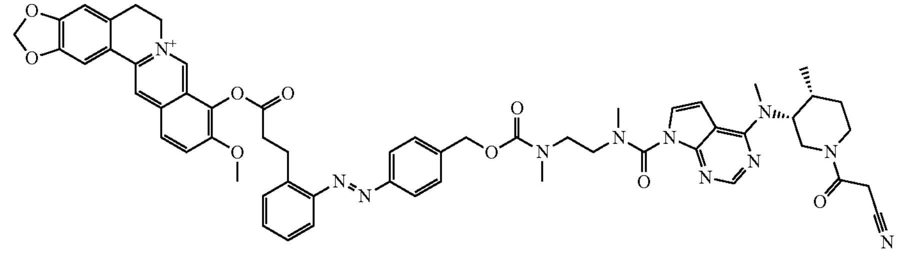 [SMILES: COc1ccc2cc3[n+](cc2c1OC(=O)CCc1ccccc1/N=N/c1ccc(COC(=O)N(C)CCN(C)C(=O)n2ccc4c(N(C)[C@H]5CN(C(=O)CC#N)CC[C@H]5C)ncnc42)cc1)CCc1cc2c(cc1-3)OCO2] |
| 11 | 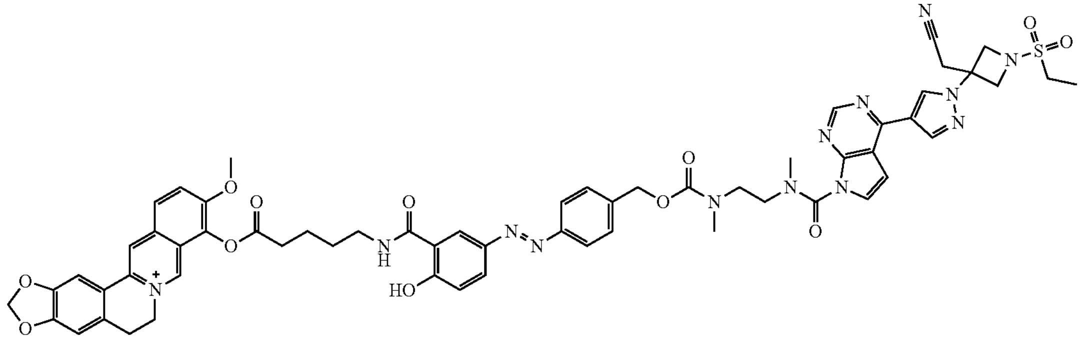 [SMILES: CCS(=O)(=O)N1CC(CC#N)(n2cc(-c3ncnc4c3ccn4C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)cn2)C1] |
| 12 | 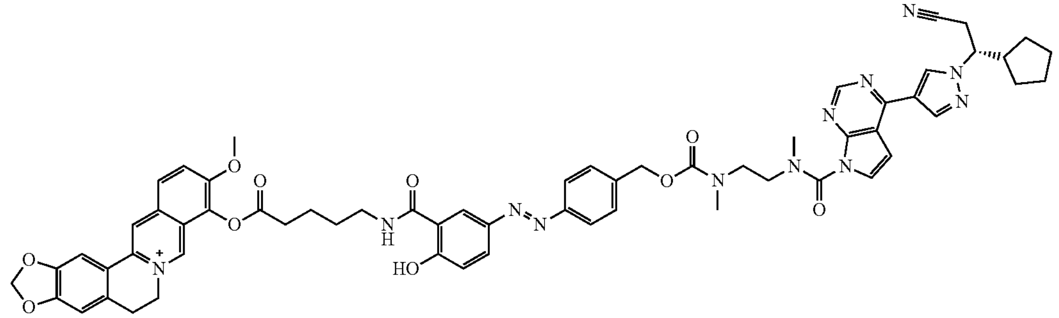 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn([C@H](CC#N)C7CCCC7)c6)ncnc54)cc2)ccc1O)CCc1cc2c(cc1-3)OCO2] |
| 13 | 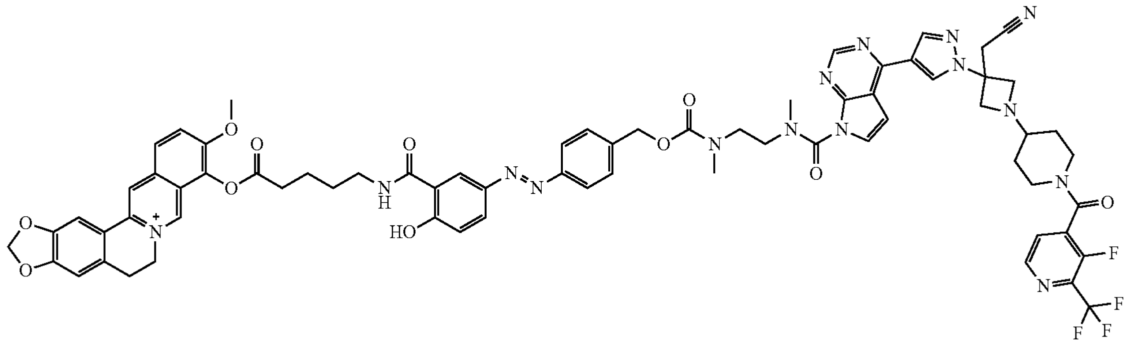 [SMILES: COc1ccc2cc3[n+](cc2c1OC(=O)CCCCNC(=O)c1cc(/N=N/c2ccc(COC(=O)N(C)CCN(C)C(=O)n4ccc5c(-c6cnn(C7(CC#N)CN(C8CCN(C(=O)c9ccnc(C(F)(F)F)c9F)CC8)C7)c6)ncnc54)cc2)ccc1O)CCc1cc2c(cc1-3)OCO2] |
| 14 | 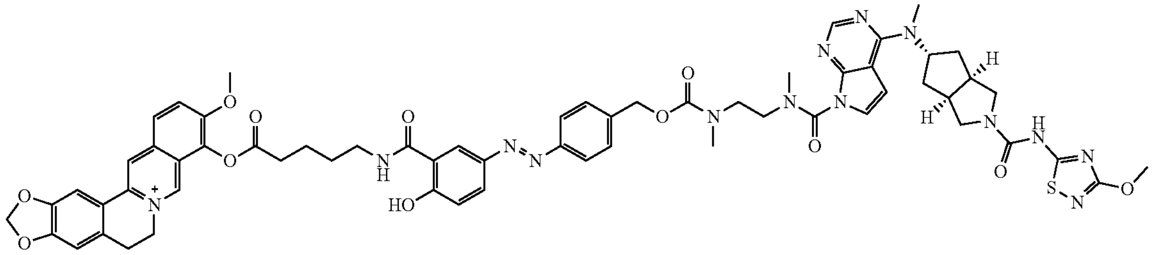 [SMILES: COc1nsc(NC(=O)N2C[C@H]3C[C@H](N(C)c4ncnc5c4ccn5C(=O)N(C)CCN(C)C(=O)OCc4ccc(/N=N/c5ccc(O)c(C(=O)NCCCCC(=O)Oc6c(OC)ccc7cc8[n+](cc67)CCc6cc7c(cc6-8)OCO7)c5)cc4)C[C@H]3C2)n1] |

-continued

| No. | Structure |
|---|---|
| 15 | 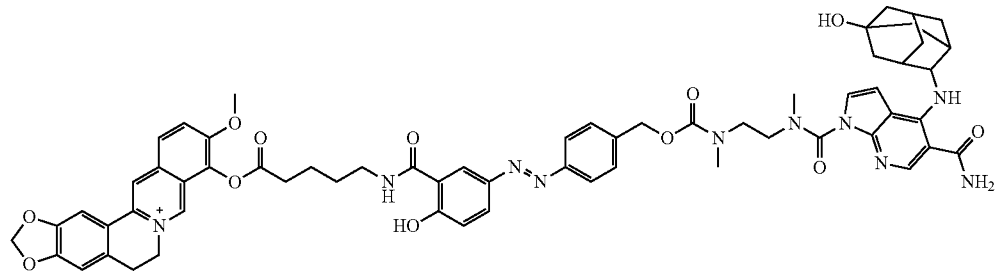 [SMILES: COc1ccc2cc3[n+](cc2c1OC(=O)CCCCNC(=O)c1cc(/N=N/c2ccc(COC(=O)N(C)CCN(C)C(=O)n4ccc5c(NC6C7CC8CC6CC(O)(C8)C7)c(C(N)=O)cnc54)cc2)ccc1O)CCc1cc2c(cc1-3)OCO2] |
| 16 | 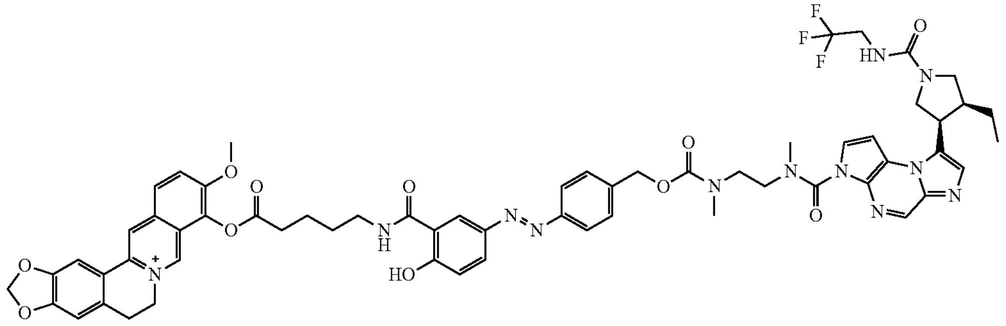 [SMILES: CC[C@@H]1CN(C(=O)NCC(F)(F)F)C[C@@H]1c1cnc2cnc3c(ccn3C(=O)N(C)CCN(C)C(=O)OCc3ccc(/N=N/c4ccc(O)c(C(=O)NCCCCC(=O)Oc5c(OC)ccc6cc7[n+](cc56)CCc5cc6c(cc5-7)OCO6)c4)cc3)n12] |
| 17 | 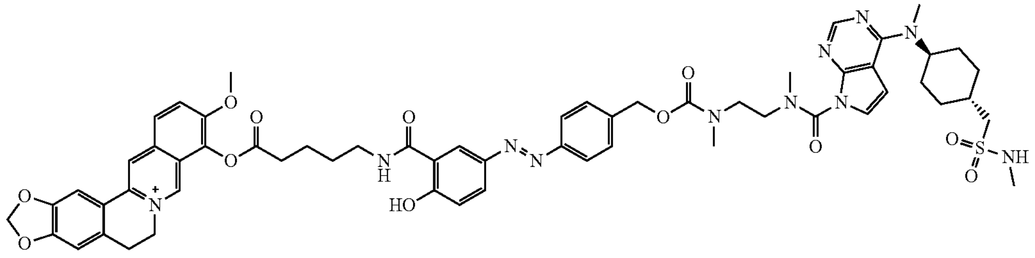 [SMILES: CNS(=O)(=O)C[C@H]1CC[C@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)CC1] |
| 18 | 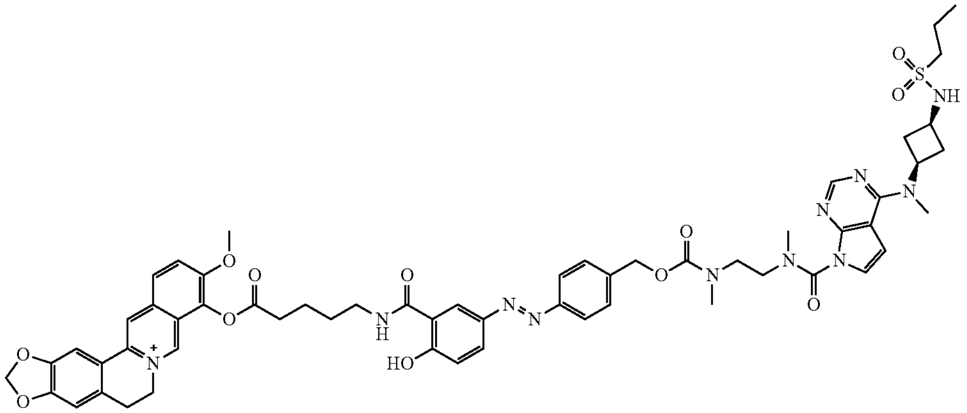 [SMILES: CCCS(=O)(=O)N[C@H]1C[C@@H](N(C)c2ncnc3c2ccn3C(=O)N(C)CCN(C)C(=O)OCc2ccc(/N=N/c3ccc(O)c(C(=O)NCCCCC(=O)Oc4c(OC)ccc5cc6[n+](cc45)CCc4cc5c(cc4-6)OCO5)c3)cc2)C1] |

9. A pharmaceutical composition, comprising a therapeutically effective amount of a compound of claim 1, or a stereoisomer, a racemate, or a pharmaceutically acceptable salt thereof, and pharmaceutically acceptable excipients.

10. The pharmaceutical composition of claim 9, wherein the pharmaceutical composition is an enteric-coated preparation.

11. A method of treating a disease, comprising administering a therapeutically effective amount of the pharmaceutical composition of claim 9 to a subject in need thereof, wherein the disease is selected from the group consisting of: gastrointestinal inflammatory diseases, gastroenteritis caused by radiotherapy or chemotherapy, gastrointestinal autoimmune diseases, peptic ulcer, irritable bowel syndrome, gastric cancer, esophageal cancer, and colon cancer.

12. A method of treating a gastrointestinal functional disorder comprising administering to a subject in need thereof a codrug compound or a pharmaceutically acceptable salt thereof according to claim 1, or a pharmaceutical composition of claim 9, wherein the gastrointestinal functional disorder is gastrointestinal inflammatory disease.

13. The method of claim 12, wherein the gastrointestinal functional disorder is selected from the group consisting of ulcerative colitis, Crohn's disease, and colitis associated with immune checkpoint inhibitor therapy.

14. The method of claim 11, wherein the disease is selected from the group consisting of: ulcerative colon inflammation, Crohn's disease, colitis associated with immune checkpoint inhibitor therapy, collagenous colitis, lymphocytic colitis, pouchitis, acute/chronic gastritis, acute/chronic appendicitis, graft-versus-host disease, celiac sprue, and autoimmune bowel disease.

* * * * *